(12) United States Patent
Su et al.

(10) Patent No.: US 12,139,508 B2
(45) Date of Patent: Nov. 12, 2024

(54) STEROID DERIVATIVE REGULATORS, METHOD FOR PREPARING THE SAME, AND USES THEREOF

(71) Applicants: JIANGSU HANSOH PHARMACEUTICAL GROUP CO., LTD., Jiangsu (CN); SHANGHAI HANSOH BIOMEDICAL CO., LTD., Shanghai (CN)

(72) Inventors: Yidong Su, Jiangsu (CN); Haining Deng, Jiangsu (CN); Xiaopo Chen, Jiangsu (CN); Rudi Bao, Jiangsu (CN); Fujun Zhang, Jiangsu (CN)

(73) Assignees: Jiangsu Hansoh Pharmaceutical Group Co., Ltd., Jiangsu (CN); Shanghai Hansoh Biomedical Co., Ltd., Shanghai (CN)

( * ) Notice: Subject to any disclaimer, the term of this patent is extended or adjusted under 35 U.S.C. 154(b) by 460 days.

(21) Appl. No.: 16/969,133

(22) PCT Filed: Jan. 31, 2019

(86) PCT No.: PCT/CN2019/074134
§ 371 (c)(1),
(2) Date: Aug. 11, 2020

(87) PCT Pub. No.: WO2019/154257
PCT Pub. Date: Aug. 15, 2019

(65) Prior Publication Data
US 2021/0139530 A1  May 13, 2021

(30) Foreign Application Priority Data

Feb. 11, 2018 (CN) .......................... 201810141153.6
Mar. 5, 2018 (CN) .......................... 201810180543.4
May 21, 2018 (CN) .......................... 201810491114.9
Jul. 13, 2018 (CN) .......................... 201810771964.4
Nov. 23, 2018 (CN) .......................... 201811408081.3

(51) Int. Cl.
| | | |
|---|---|---|
| C07J 43/00 | (2006.01) | |
| C07J 1/00 | (2006.01) | |
| C07J 7/00 | (2006.01) | |
| C07J 9/00 | (2006.01) | |
| C07J 41/00 | (2006.01) | |

(52) U.S. Cl.
CPC .............. *C07J 43/003* (2013.01); *C07J 1/00* (2013.01); *C07J 7/009* (2013.01); *C07J 9/00* (2013.01); *C07J 41/0094* (2013.01)

(58) Field of Classification Search
CPC .... C07J 43/003; C07J 41/0094; C07J 53/008; C07J 7/009; C07J 5/0015; C07J 41/005
See application file for complete search history.

(56) References Cited

FOREIGN PATENT DOCUMENTS

| | | |
|---|---|---|
| CN | 104136452 A | 11/2014 |
| CN | 105339381 A | 2/2016 |
| WO | 1993003732 A1 | 3/1993 |
| WO | 2003077919 A1 | 9/2003 |
| WO | 2014169831 A1 | 10/2014 |
| WO | 2014169833 A1 | 10/2014 |
| WO | 2016061537 A1 | 4/2016 |

OTHER PUBLICATIONS

Botella et al., Neuroactive steroids. 2. 3alpha-hydroxy-3beta-methyl-21-(4-cyano-1H-pyrazol-1'-yl)-19-nor-5beta-pregnan-20 (SAGE-217): A clinical next generation neuroactive steroid positive allosteric modulator of the (gamma-aminobutyric acid)A receptor. J Medicinal Chemistry, pp. 7810-7819, (Year: 2017).*
Lociuro et al., On Cardioactive Steroids. XVII. The Synthesis of gamma-isobufalin. Tetrahedron, vol. 44(1), pp. 35-40 (Year: 1988).*
Anderson, A., et al., "Conformationally constrained anesthetic steroids that modulate GABA(A) receptors," J. Med. Chem. vol. 43, No. 22, Oct. 18, 2000 pp. 4118-4121.
Galofre, M., et al., "GABAA receptor and cell membrane potential as functional endpoints in cultured neurons to evaluate chemicals for human acute toxicity," Neurotoxicology and Teratology, vol. 32, Feb. 10, 2009, pp. 52-54.
Veleiro, A.S., et al., "Synthesis and GABAA receptor activity of a 6, 19-Oxido analogue of pregnanolone," Biorganic & Medicinal Chemistry Letters, vol. 13, Dec. 31, 2003, pp. 343-345.
International Search Report issued May 7, 2019 in International Application No. PCT/CN2019/074134.
Written Opinion issued May 7, 2019 in International Application No. PCT/CN2019/074134.

* cited by examiner

*Primary Examiner* — Barbara P Badio
(74) *Attorney, Agent, or Firm* — Ice Miller LLP

(57) ABSTRACT

Steroid derivative regulators, a method for preparing the same, and uses thereof are described. Specifically, a compound of formula (I), a preparation method therefor, a pharmaceutical composition containing the compound, and uses thereof as a regulator the of $GABA_A$ receptor for treating depression, convulsion, Parkinson's disease, and nervous system diseases are described, wherein the substituents of the formula (I) are as defined in the description.

3 Claims, No Drawings

STEROID DERIVATIVE REGULATORS, METHOD FOR PREPARING THE SAME, AND USES THEREOF

CROSS-REFERENCE TO RELATED APPLICATION

This application is a Section 371 of International Application No. PCT/CN2019/074134 filed Jan. 31, 2019, which was published in the Chinese Language Aug. 15, 2019, under International Publication No. WO 2019/154257, which claims priority under 35 U.S.C. § 119(b) to Chinese Patent Application No. 201810141153.6 filed Feb. 11, 2018, Chinese Patent Application No. 201810180543.4 filed Mar. 5, 2018, Chinese Patent Application No. 201810491114.9 filed May 21, 2018, Chinese Patent Application No. 201810771964.4 filed Jul. 13, 2018 and Chinese Patent Application No. 201811408081.3 filed Nov. 23, 2018.

FIELD OF THE INVENTION

The present invention belongs to the field of drug synthesis, and in particular relates to a steroid derivative regulator, a method for preparing the same, and a use thereof.

BACKGROUND OF THE INVENTION $GABA_A$ receptor is a chemically-gated channel on the cell membrane and belongs to ionic receptors. $GABA_A$ receptor is widely distributed in the nervous system, and can bind to inhibitory neurotransmitter GABA (gamma-aminobutyric acid), leading to the opening of chloride channels and inhibition of neurons. $GABA_A$ receptor regulator (tetrahydroprogesterone) is a positive regulator of $GABA_A$ receptor. The binding of tetrahydroprogesterone to intrasynaptic $GABA_A$ receptor regulator can increase the opening frequency of chloride channel on the receptor and the influx of chloride ion, thereby increasing the Phasic current, producing a rapid inhibitory effect, reducing nerve excitability, and providing an anti-anxiety and anti-depression effect. The binding of tetrahydroprogesterone to extrasynaptic $GABA_A$ receptor provides a continuous chloride ion current, and mediates a lasting and sustained inhibitory effect. Tetrahydroprogesterone can also increase the content of brain derived neurotrophic factor (BDNF), promote the regeneration of hippocampal neurons, and provide a neuroprotective effect, thereby improving anxiety and depression symptoms; but the specific mechanism of action is not clear yet.

Major depressive disorder (MDD) is a common, chronic and recurrent disease. The burden and adverse consequence caused by it are becoming more and more serious. In the past 40 years, the research and clinical application of antidepressants have greatly developed. However, most antidepressants (fluoxetine, paroxetine, sertraline, fluvoxamine, citalopram, etc.) take 2 to 4 weeks to have an effect. The clinical treatment of major depressive disorder patients, especially patients with suicidal tendency, often needs to be prompt and rapid, thus there is an urgent need to develop fast-acting antidepressants.

In the past two decades, there has been little innovation in the research and development of depression treatments. The development goal of $GABA_A$ receptor regulator is to change the expectation of patients by changing the treatment regimen of MDD. If successfully developed, the $GABA_A$ receptor regulator may become the first drug that provides a truly new mechanism of action for the treatment of depression in more than two decades. At present, foreign pharmaceutical companies, including Sage Therapeutics and Marinus etc., are doing their best to develop $GABA_A$ receptor regulators.

Published patent applications related to $GABA_A$ receptor regulators include: WO2003077919, WO2014169833, WO2016061537, WO2015180679, and WO2015027227.

$GABA_A$ receptor regulators, as a popular target in the pharmaceutical industry, currently have a good application prospect.

First, $GABA_A$ receptor regulators can be applied to major depressive disorder (MDD). The annual incidence of MDD in China is about 2%, thus there is a huge market potential.

Second, existing antidepressants take a long time, commonly 3 to 4 weeks, to have an effect, have a high failure rate up to 40%, and require long-term medication. $GABA_A$ receptor regulators can provide a significant antidepressant effect within 24 hours, and the effect can last for several days to two weeks.

Third, $GABA_A$ receptor regulators can meet the treatment need of MDD patients with oral administration once a day.

SUMMARY OF THE INVENTION

The objective of the present invention is to provide a compound of formula (I), a stereoisomer thereof, or a pharmaceutically acceptable salt thereof, wherein the structure of the compound of formula (I) is as follows:

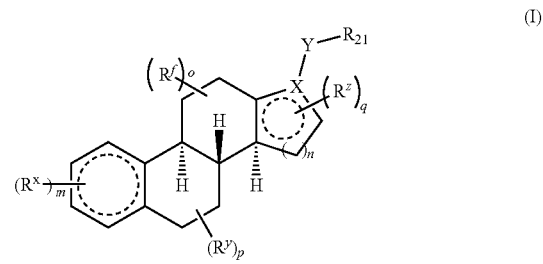

wherein:
X is selected from the group consisting of —$CR_{17}$— and —N—;
Y is selected from the group consisting of —$CR_{23}R_{24}$—, —$S(CH_2)_{n1}$—, —$P(CH_2)_{n1}$—, —$O(CH_2)_{n1}$—, —$(CH_2)_{n1}NR_{22}$—,

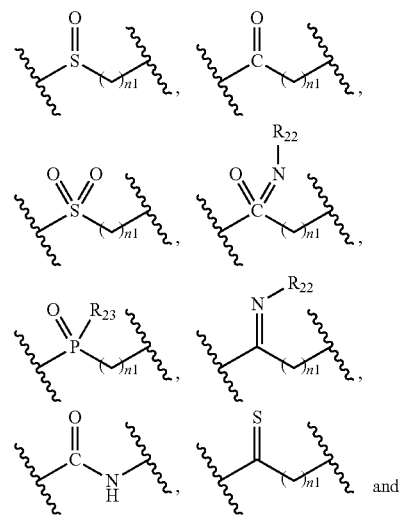

and

-continued

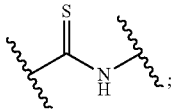

$R^x$, $R^y$, $R^z$ and $R^f$ are identical or different and are each independently selected from the group consisting of hydrogen atom, deuterium atom, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, $-(CH_2)_{n1}R_{23}$, $-(CH_2)_{n1}OR_{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}NR_{23}R_{24}$, $-(CH_2)_{n1}C(O)NR_{23}R_{24}$, $-(CH_2)_{n1}NR_{23}C(O)R_{24}$ and $-(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, thiol, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{25}$, $-(CH_2)_{n1}OR_{25}$, $-(CH_2)_{n1}SR_{25}$, $-(CH_2)_{n1}C(O)R_{25}$, $-(CH_2)_{n1}C(O)OR_{25}$, $-(CH_2)_{n1}S(O)_{m1}R_{25}$, $-(CH_2)_{n1}NR_{25}R_{26}$, $-(CH_2)_{n1}C(O)NR_{25}R_{26}$, $-(CH_2)_{n1}C(O)NHR_{25}$, $-(CH_2)_{n1}NR_{25}C(O)R_{26}$ and $-(CH_2)_{n1}NR_{25}S(O)_{m1}R_{26}$;

or, any two adjacent or non-adjacent groups of $R^x$, $R^y$, $R^z$ and $R^f$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{23}$, $-(CH_2)_{n1}OR_{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}NR_{23}R_{24}$, $-(CH_2)_{n1}C(O)NR_{23}R_{24}$, $-(CH_2)_{n1}NR_{23}C(O)R_{24}$ and $-(CH_2)_{n1}NR_{23}S(O)_{m1}R_{24}$;

or, any two adjacent groups of $R^x$, $R^y$, $R^z$ and $R^f$ are absent and can form a double bond;

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, $-(CH_2)_{n1}R_{23}$, $-(CH_2)_{n1}OR_{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}NR_{23}R_{24}$, $-(CH_2)_{n1}C(O)NR_{23}R_{24}$, $-(CH_2)_{n1}NR_{23}C(O)R_{24}$ and $-(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{25}$, $-(CH_2)_{n1}OR_{25}$, $-(CH_2)_{n1}SR_{25}$, $-(CH_2)_{n1}C(O)R_{25}$, $-(CH_2)_{n1}C(O)OR_{25}$, $-(CH_2)_{n1}S(O)_{m1}R_{25}$, $-(CH_2)_{n1}NR_{25}R_{26}$, $-(CH_2)_{n1}C(O)NR_{25}R_{26}$, $-(CH_2)_{n1}C(O)NHR_{25}$, $-(CH_2)_{n1}NR_{25}C(O)R_{26}$ and $-(CH_2)_{n1}NR_{25}S(O)_{m1}R_{26}$;

when X is $-CR_{17}-$, $R_{17}$ is selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

or, $R_{17}$ and any group of $R^x$, $R^y$, $R^z$ and R can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{23}$, $-(CH_2)_{n1}OR_{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}NR_{23}R_{24}$, $-(CH_2)_{n1}C(O)NR_{23}R_{24}$, $-(CH_2)_{n1}NR_{23}C(O)R_{24}$ and $-(CH_2)_{n1}NR_{23}S(O)_{m1}R_{24}$;

$R_{22}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, $-(CH_2)_{n1}R_{23}$, $-(CH_2)_{n1}OR_{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}NR_{23}R_{24}$, $-(CH_2)_{n1}C(O)NR_{23}R_{24}$, $-(CH_2)_{n1}NR_{23}C(O)R_{24}$ and $-(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{25}$, $-(CH_2)_{n1}OR_{25}$, $-(CH_2)_{n1}SR_{25}$, $-(CH_2)_{n1}C(O)R_{25}$, $-(CH_2)_{n1}C(O)OR_{25}$, $-(CH_2)_{n1}S(O)_{m1}R_{25}$, $-(CH_2)_{n1}NR_{25}R_{26}$, $-(CH_2)_{n1}C(O)NR_{25}R_{26}$, $-(CH_2)_{n1}C(O)NHR_{25}$, $-(CH_2)_{n1}NR_{25}C(O)R_{26}$ and $-(CH_2)_{n1}NR_{25}S(O)_{m1}R_{26}$;

$R_{23}$, $R_{24}$, $R_{25}$ and $R_{26}$ are identical or different and are each independently selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

m is an integer of 0, 1, 3, 4, 5, 6, 7, 8, 9 or 10;
n is an integer of 0, 1, 2 or 3;
o is an integer of 0, 1, 2, 3, 4 or 5;
p is an integer of 0, 1, 2, 3, 4, 5 or 6;
q is an integer of 0, 1, 2, 3, 4, 5 or 6;
$m_1$ is an integer of 0, 1 or 2; and
$n_1$ is an integer of 0, 1, 2, 3, 4 or 5.

In a preferred embodiment of the present invention, the compound of formula (I) is a compound of formula (I-A), a stereoisomer thereof, or a pharmaceutically acceptable salt thereof:

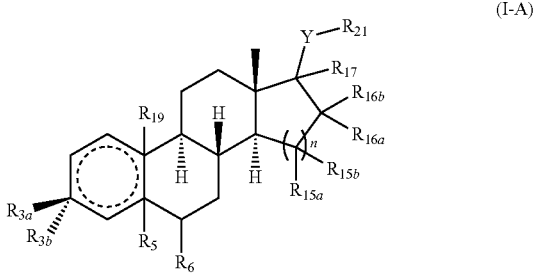

(I-A)

wherein:

Y is selected from the group consisting of —S(CH$_2$)$_{n1}$—,

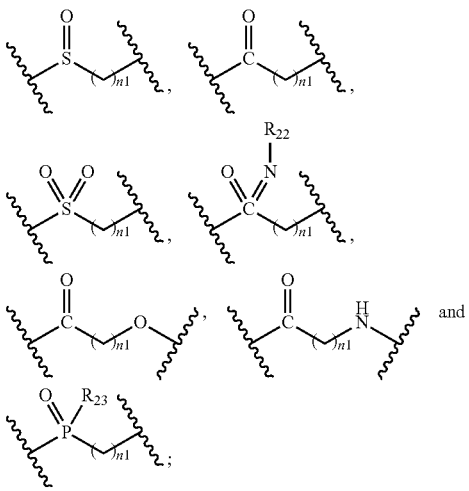

$R_{3a}$ and $R_{3b}$ are identical or different and are each independently selected from the group consisting of hydrogen atom, deuterium atom, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$S(O)NR$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{23}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, thiol, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

$R_5$, $R_6$, $R_{15a}$, $R_{15b}$, $R_{16a}$, $R_{16b}$ and $R_{19}$ are identical or different and are each independently selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$S(O)NR$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{23}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

or, any two adjacent or non-adjacent groups of $R_5$, $R_6$, $R_{15a}$, $R_{15b}$, $R_{16a}$, $R_{16b}$ and $R_{19}$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

$R_{17}$ is selected from the group consisting of hydrogen atom, deuterium atom, alkyl, deuterated alkyl, haloalkyl, hydroxy, amino, alkenyl, alkynyl, cycloalkyl, heterocyclyl, aryl and heteroaryl, wherein the alkyl, cycloalkyl, heterocyclyl, aryl and heteroaryl are each optionally further substituted by one or more substituents selected from the group consisting of deuterium atom, substituted or unsubstituted alkyl, halogen, hydroxy, substituted or unsubstituted amino, oxo, nitro, cyano, alkenyl, alkynyl, alkoxy, hydroxyalkyl, substituted or unsubstituted cycloalkyl, substituted or unsubstituted heterocyclyl, substituted or unsubstituted aryl and substituted or unsubstituted heteroaryl;

or, $R_{17}$ and any group of $R_{16a}$ and $R_{16b}$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$;

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}NR_{23}R_{24}$, —$(CH_2)_{n1}C(O)NR_{23}R_{24}$, —$(CH_2)_{n1}NR_{23}C(O)R_{24}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

n is an integer of 0, 1, 2 or 3;

$R_{22}$-$R_{26}$, $m_1$ and $n_1$ are as defined in the compound of formula (I).

In a preferred embodiment of the present invention, the compound of formula (I) is a compound of formula (II), a stereoisomer thereof, or a pharmaceutically acceptable salt thereof:

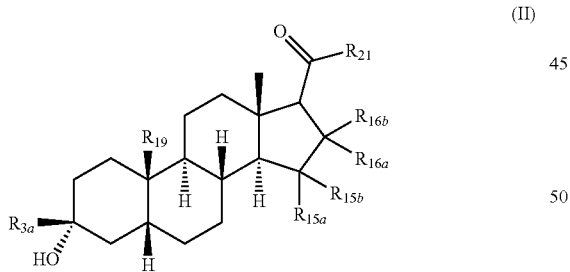

(II)

wherein:

$R_{3a}$ is selected from the group consisting of hydrogen atom, deuterium atom, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)(NR_{23})R_{24}$, —$(CH_2)_{n1}NR_{23}R_{24}$, —$(CH_2)_{n1}C(O)NR_{23}R_{24}$, —$(CH_2)_{n1}NR_{23}C(O)R_{23}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, thiol, oxo, nitro, cyano, hydroxy, alkenyl, alkynyl, alkoxy, haloalkoxy, hydroxyalkyl, cycloalkyl, heterocyclyl, aryl, heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

$R_{15a}$, $R_{15b}$, $R_{16a}$ and $R_{16b}$ are identical or different and are each independently selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)(NR_{23})R_{24}$, —$(CH_2)_{n1}NR_{23}R_{24}$, —$(CH_2)_{n1}C(O)NR_{23}R_{24}$, —$(CH_2)_{n1}NR_{23}C(O)R_{23}$ and —$(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl, heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$, and $R_{15a}$, $R_{15b}$, $R_{16a}$ and $R_{16b}$ are not hydrogen at the same time;

or, any two adjacent or non-adjacent groups of $R_{15a}$, $R_{15b}$, $R_{16a}$ and $R_{16b}$ can be bonded to form a cycloalkyl, heterocyclyl, aryl or heteroaryl, wherein the cycloalkyl, heterocyclyl, aryl or heteroaryl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl, heteroaryl, —$(CH_2)_{n1}R_{25}$, —$(CH_2)_{n1}OR_{25}$, —$(CH_2)_{n1}SR_{25}$, —$(CH_2)_{n1}C(O)R_{25}$, —$(CH_2)_{n1}C(O)OR_{25}$, —$(CH_2)_{n1}S(O)_{m1}R_{25}$, —$(CH_2)_{n1}NR_{25}R_{26}$, —$(CH_2)_{n1}C(O)NR_{25}R_{26}$, —$(CH_2)_{n1}C(O)NHR_{25}$, —$(CH_2)_{n1}NR_{25}C(O)R_{26}$ and —$(CH_2)_{n1}NR_{25}S(O)_{m1}R_{26}$;

$R_{19}$ is selected from the group consisting of hydrogen atom, deuterium atom, alkyl, deuterated alkyl, haloalkyl, alkoxy, haloalkoxy, halogen, amino, thiol, nitro, hydroxy, cyano, alkenyl, alkynyl, cycloalkyl, heterocyclyl, aryl, heteroaryl, —$(CH_2)_{n1}R_{23}$, —$(CH_2)_{n1}OR_{23}$, —$(CH_2)_{n1}SR_{23}$, —$(CH_2)_{n1}C(O)R_{23}$, —$(CH_2)_{n1}C(O)OR_{23}$, —$(CH_2)_{n1}S(O)_{m1}R_{23}$, —$(CH_2)_{n1}S(O)(NR_{23})R_{24}$, —$(CH_2)_{n1}NR_{23}R_{24}$, —$(CH_2)_{n1}C(O)NR_{23}R_{24}$, —$(CH_2)_{n1}NR_{23}C(O)R_{23}$ and —$(CH_2)_{n1}NR_{23}S(O)_{m1}R_{24}$;

$R_{21}$, $R_{23}$-$R_{26}$, $m_1$ and $n_1$ are as defined in the compound of formula (I).

In a preferred embodiment of the present invention, the compound of formula (I) is a compound of formula (III), a stereoisomer thereof, or a pharmaceutically acceptable salt thereof:

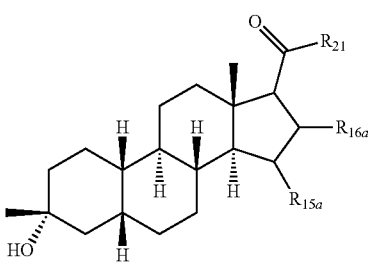

(III)

wherein:

R$_{15a}$, R$_{16a}$ and R$_{21}$ are as defined in the compound of formula (II).

In a preferred embodiment of the present invention, the compound of formula (I) is a compound of formula (IV), a stereoisomer thereof, or a pharmaceutically acceptable salt thereof:

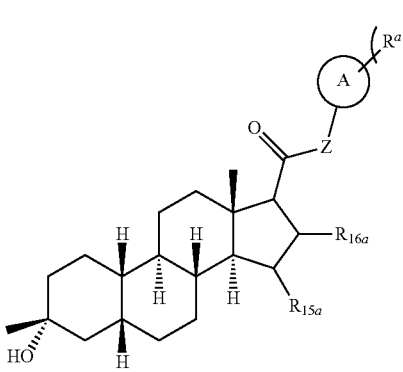

(IV)

wherein:

Z is selected from the group consisting of —CR$_{23}$R$_{24}$—, —(CH$_2$)$_{n1}$NR$_{23}$— and —(CH$_2$)$_{n1}$O(CH$_2$)$_{n2}$—, and preferably methylene;

ring A is selected from the group consisting of cycloalkyl, heterocyclyl, aryl and heteroaryl, wherein the cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl, heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

each R$_a$ is identical or different and each is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$S(O)(NR$_{23}$)R$_{24}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{23}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl, heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

R$_{15a}$ is selected from the group consisting of hydrogen atom, alkyl, haloalkyl, alkoxy, halogen, amino, hydroxy, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$S(O)$_{m1}$R$_{23}$ and —(CH$_2$)$_{n1}$NR$_{23}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl;

R$_{16a}$ is selected from the group consisting of hydrogen atom, alkyl, haloalkyl, alkoxy, halogen, amino, hydroxy, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$S(O)$_{m1}$R$_{23}$ and —(CH$_2$)$_{n1}$NR$_{23}$R$_{24}$;

or, R$_{15a}$ and R$_{16a}$ can form a cycloalkyl or heterocyclyl, wherein the cycloalkyl or heterocyclyl is optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl, and R$_{15a}$ and R$_{16a}$ are not hydrogen at the same time;

R$_{23}$ and R$_{24}$ are each selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl and heteroaryl, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl, heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

R$_{25}$-R$_{26}$, m$_1$, n$_1$ and x are as defined in the compound of formula (II).

In a preferred embodiment of the present invention, the compound of formula (I) is a compound of formula (IV-A), a stereoisomer thereof, or a pharmaceutically acceptable salt thereof:

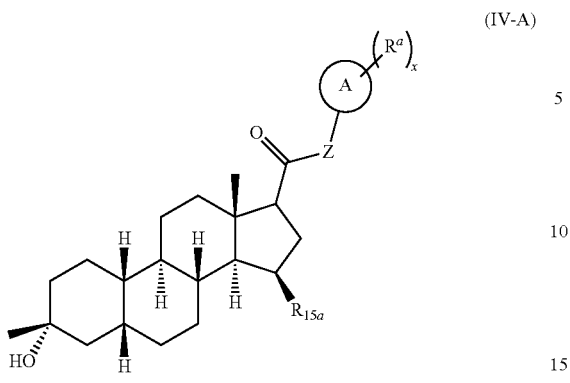

(IV-A)

$R_{15a}$ is selected from the group consisting of hydrogen atom, alkyl, haloalkyl, alkoxy, halogen, amino, hydroxy, cycloalkyl, heterocyclyl, aryl, heteroaryl, $-(CH_2)_{n1}R_{23}$, $-(CH_2)_{n1}OR_{23}$, $-(CH_2)_{n1}SR_{23}$, $-(CH_2)_{n1}S(O)_{m1}R_{23}$ and $-(CH_2)_{n1}NR_{23}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, cycloalkyl, heterocyclyl, aryl and heteroaryl;

ring A, $R^a$ and x are as defined in the compound of formula (IV).

In a preferred embodiment of the present invention, the compound of formula (I) is a compound of formula (V), a stereoisomer thereof, or a pharmaceutically acceptable salt thereof:

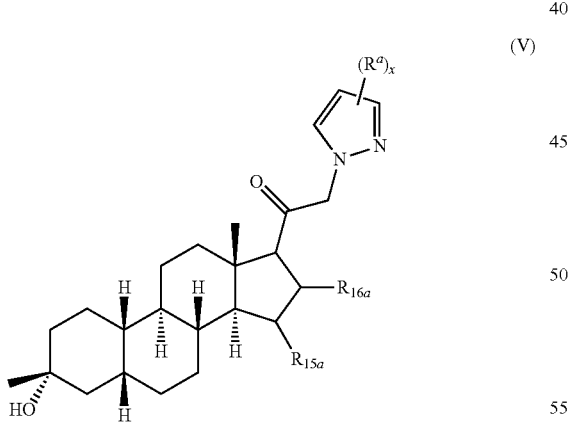

(V)

wherein:

$R_{15a}$, $R_{16a}$, $R^a$ and x are as defined in the compound of formula (IV).

In a preferred embodiment of the present invention, the compound of formula (I) is a compound of formula (V-A), a stereoisomer thereof, or a pharmaceutically acceptable salt thereof:

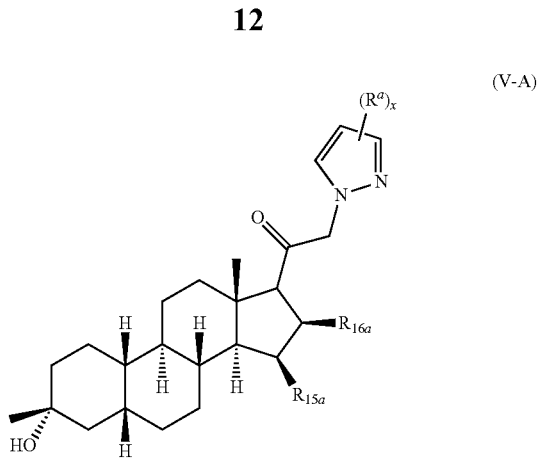

(V-A)

wherein:

$R_{15a}$, $R_{16a}$, $R^a$ and x are as defined in the compound of formula (V).

In a preferred embodiment of the present invention, the compound of formula (I) is a compound of formula (VI), a stereoisomer thereof, or a pharmaceutically acceptable salt thereof:

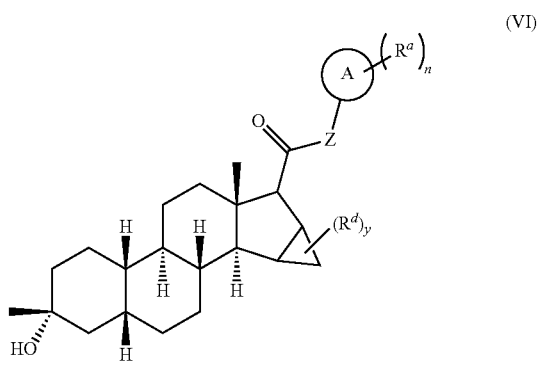

(VI)

wherein:

each $R^d$ is identical or different and each is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, $-(CH_2)_{n1}R_{23}$, $-(CH_2)_{n1}OR^{23}$, $-(CH_2)_{n1}SR_{23}$, $-(CH_2)_{n1}C(O)R_{23}$, $-(CH_2)_{n1}C(O)OR_{23}$, $-(CH_2)_{n1}S(O)_{m1}R_{23}$, $-(CH_2)_{n1}S(O)(NR_{23})R_{24}$, $-(CH_2)_{n1}NR_{23}R_{24}$, $-(CH_2)_{n1}C(O)NR_{23}R_{24}$, $-(CH_2)_{n1}NR_{23}C(O)R_{23}$ and $-(CH_2)_{n1}NR_{23}S(O)_{m1}R_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, $-(CH_2)_{n1}R_{25}$, $-(CH_2)_{n1}OR^{25}$, $-(CH_2)_{n1}SR_{25}$, $-(CH_2)_{n1}C(O)R_{25}$, $-(CH_2)_{n1}C(O)OR_{25}$, $-(CH_2)_{n1}S(O)_{m1}R_{25}$, $-(CH_2)_{n1}NR_{25}R_{26}$, $-(CH_2)_{n1}C(O)NR_{25}R_{26}$, $-(CH_2)_{n1}C(O)NHR_{25}$, $-(CH_2)_{n1}NR_{25}C(O)R_{26}$ and $-(CH_2)_{n1}NR_{25}S(O)_{m1}R_{26}$;

y is an integer of 0, 1, 3 or 4;

ring A, Z, $R^a$, $R_{23}$-$R_{26}$, $m_1$, $n_1$ and x are as defined in the compound of formula (IV).

In a preferred embodiment of the present invention, the compound of formula (I) is a compound of formula (VI-A), a stereoisomer thereof, or a pharmaceutically acceptable salt thereof:

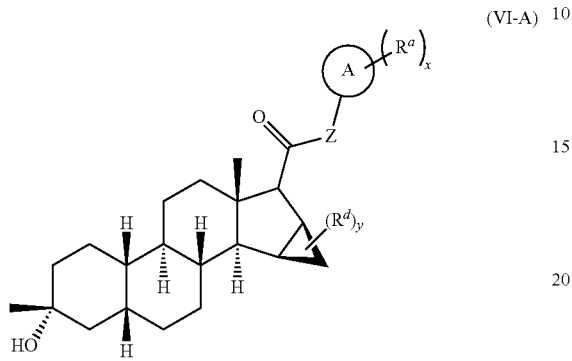

(VI-A)

wherein:

ring A, Z, $R^a$, $R^d$, $R_{23}$-$R_{26}$, $m_1$, $n_1$, x and y are as defined in the compound of formula (VI).

In a preferred embodiment of the present invention, the compound of formula (I) is a compound of formula (VII), a stereoisomer thereof, or a pharmaceutically acceptable salt thereof:

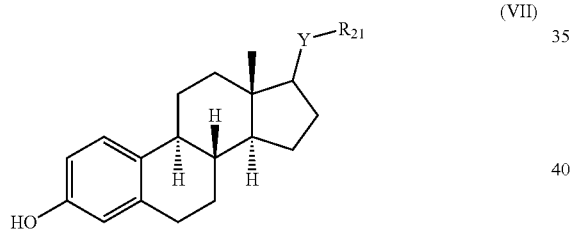

(VII)

wherein:

Y is selected from the group consisting of —S(CH$_2$)$_{n1}$—,

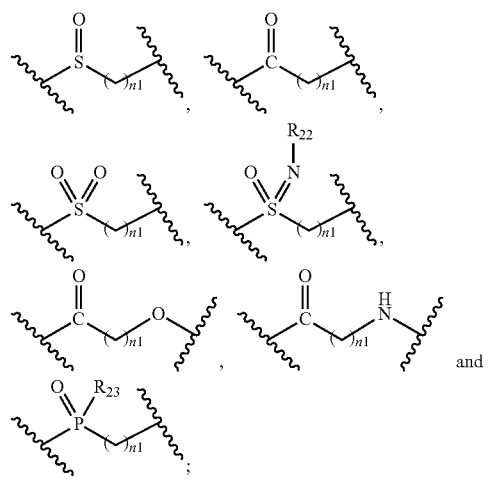

and $R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

$R_{22}$-$R_{26}$, $m_1$ and $n_1$ are as defined in the compound of formula (I).

In a preferred embodiment of the present invention, the compound of formula (I) is a compound of formula (VIII), a stereoisomer thereof, or a pharmaceutically acceptable salt thereof:

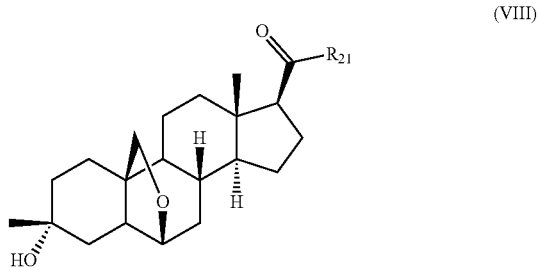

(VIII)

wherein:

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

$R_{23}$-$R_{26}$, $m_1$ and $n_1$ are as defined in the compound of formula (I).

In a preferred embodiment of the present invention, the compound of formula (I) is a compound of formula (IX), a stereoisomer thereof, or a pharmaceutically acceptable salt thereof:

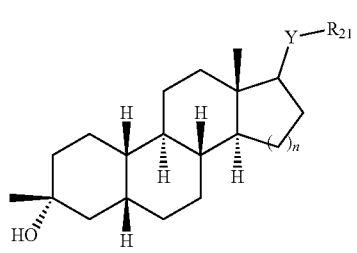
(IX)

wherein:
Y is selected from the group consisting of —S(CH$_2$)$_{n1}$—,

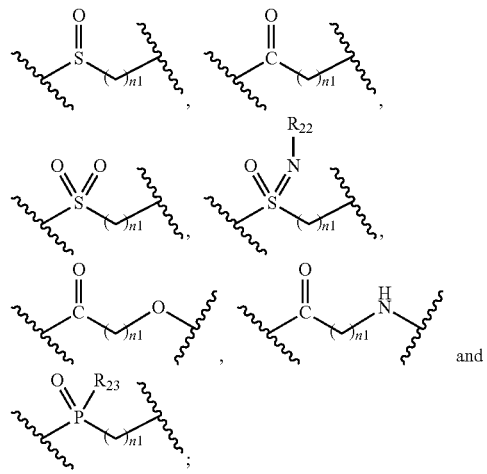

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$; and n is an integer of 0, 1 or 2;

$R_{22}$-$R_{26}$, $m_1$ and $n_1$ are as defined in the compound of formula (I).

In a preferred embodiment of the present invention, the compound of formula (I) is a compound of formula (X), a stereoisomer thereof, or a pharmaceutically acceptable salt thereof:

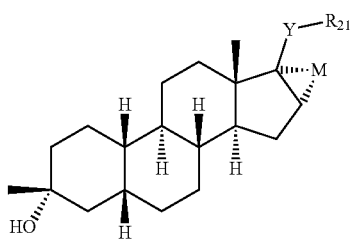
(X)

wherein:
M is selected from the group consisting of —CR$_{23}$— and oxygen;
Y is selected from the group consisting of —S(CH$_2$)$_{n1}$—,

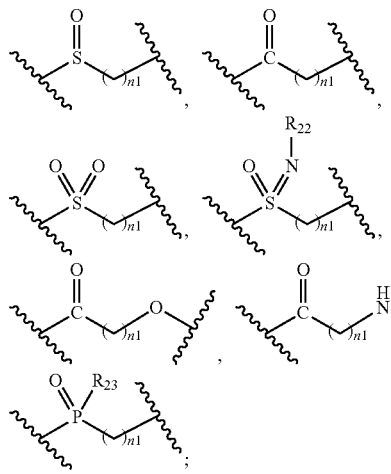

$R_{21}$ is selected from the group consisting of hydrogen atom, deuterium atom, alkyl, deuterated alkyl, haloalkyl, alkoxy, haloalkoxy, halogen, amino, nitro, hydroxy, cyano, alkenyl, alkynyl, cycloalkyl, heterocyclyl, aryl, heteroaryl, —(CH$_2$)$_{n1}$R$_{23}$, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$S(O)$_{m1}$R$_{23}$, —(CH$_2$)$_{n1}$NR$_{23}$R$_{24}$, —(CH$_2$)$_{n1}$C(O)NR$_{23}$R$_{24}$, —(CH$_2$)$_{n1}$NR$_{23}$C(O)R$_{24}$ and —(CH$_2$)$_{n1}$NR$_{23}$S(O)$_{m1}$R$_{24}$, wherein the alkyl, haloalkyl, cycloalkyl, heterocyclyl, aryl and heteroaryl are each optionally further substituted by one or more substituents selected from the group consisting of deuterium atom, alkyl, haloalkyl, halogen, amino, oxo, nitro, cyano, hydroxy, alkenyl, alkynyl, alkoxy, haloalkoxy, hydroxyalkyl, substituted or unsubstituted cycloalkyl, substituted or unsubstituted heterocyclyl, substituted or unsubstituted aryl, substituted or unsubstituted heteroaryl, —(CH$_2$)$_{n1}$R$_{25}$, —(CH$_2$)$_{n1}$OR$_{25}$, —(CH$_2$)$_{n1}$SR$_{25}$, —(CH$_2$)$_{n1}$C(O)R$_{25}$, —(CH$_2$)$_{n1}$C(O)OR$_{25}$, —(CH$_2$)$_{n1}$S(O)$_{m1}$R$_{25}$, —(CH$_2$)$_{n1}$NR$_{25}$R$_{26}$, —(CH$_2$)$_{n1}$C(O)NR$_{25}$R$_{26}$, —(CH$_2$)$_{n1}$C(O)NHR$_{25}$, —(CH$_2$)$_{n1}$NR$_{25}$C(O)R$_{26}$ and —(CH$_2$)$_{n1}$NR$_{25}$S(O)$_{m1}$R$_{26}$;

$R_{22}$-$R_{26}$, $m_1$ and $n_1$ are as defined in the compound of formula (I).

In a preferred embodiment of the present invention, in the compound of formula (IV-1), formula (IV-B), formula (IV-2), formula (IV-3), formula (IV-5), formula (V), formula (V-A), formula (IX) or formula (IX-A), the stereoisomer thereof or the pharmaceutically acceptable salt thereof, the ring A is selected from the group consisting of:

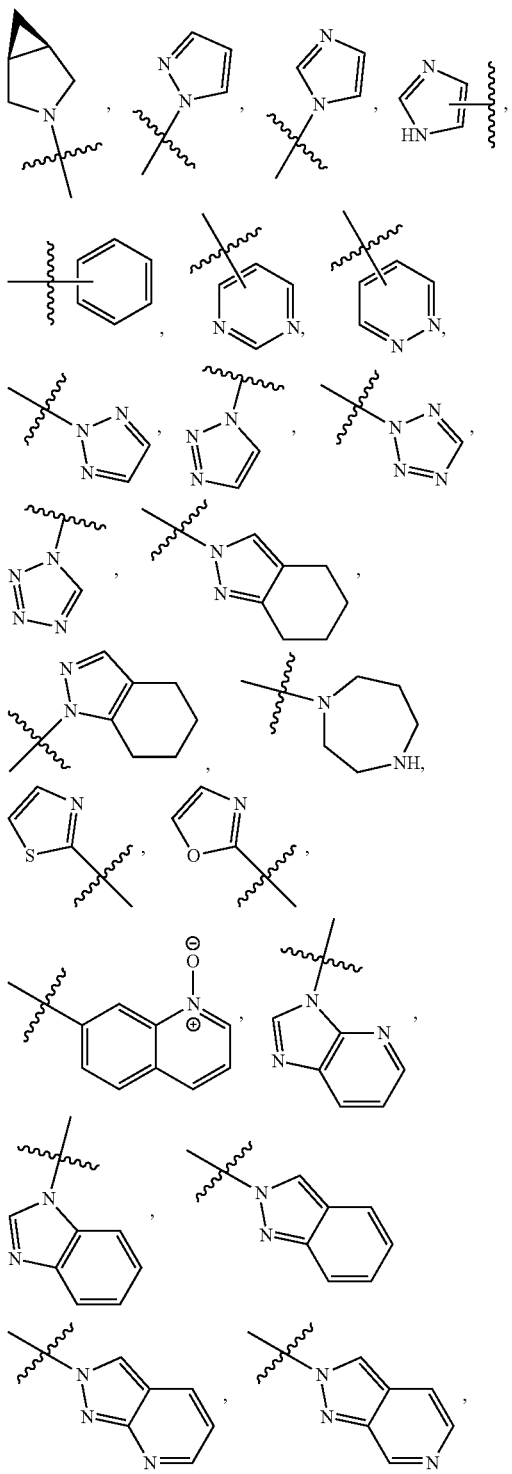

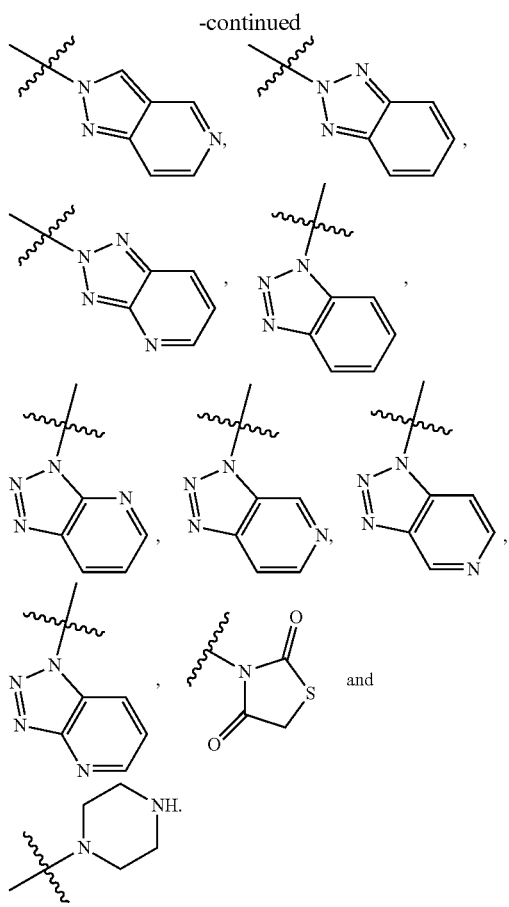

In a preferred embodiment of the present invention, the compound of any formula, the stereoisomer thereof or the pharmaceutically acceptable salt thereof,
wherein:
Z is selected from the group consisting of —CH$_2$—, —CH$_2$NH—, —CH$_2$O—, —CH$_2$—, —NH— and —NHSO$_2$—;
Y is selected from the group consisting of —C(O)—, —C(O)CH$_2$—, —C(O)O—, —C(O)CH$_2$NH—, —C(O)CH$_2$O—, —SCH$_2$—, —S(O)CH$_2$—, —S(O)$_2$CH$_2$—, —P(O)R$_{23}$—, —C(O)NH— and —C(O)NHSO$_2$—; R$^a$ is selected from the group consisting of hydrogen atom, halogen, amino, cyano, nitro, C$_{1-6}$ alkyl, C$_{2-6}$ alkynyl, C$_{3-6}$ cycloalkyl, C$_{1-6}$ haloalkyl, C$_{3-8}$ halocycloalkyl, C$_{1-6}$ alkoxy, C$_{1-6}$ hydroxyalkyl, —(CH$_2$)$_{n1}$OR$_{23}$, —(CH$_2$)$_{n1}$SR$_{23}$, —(CH$_2$)$_{n1}$C(O)R$_{23}$, —(CH$_2$)$_{n1}$C(O)OR$_{23}$, —(CH$_2$)$_{n1}$C(O)NR$_{23}$R$_{24}$ and —(CH$_2$)$_{n1}$S(O)$_{m1}$R$_{23}$, wherein the C$_{1-6}$ alkyl, C$_{2-6}$ alkynyl, C$_{3-6}$ cycloalkyl, C$_{1-6}$ haloalkyl, C$_{3-6}$ halocycloalkyl, C$_{1-6}$ alkoxy and C$_{1-6}$ hydroxyalkyl are each optionally further substituted by one or more substituents selected from the group consisting of hydrogen atom, halogen, cyano, hydroxy, C$_{1-6}$ alkyl, C$_{3-6}$ cycloalkyl and 3 to 6 membered heterocyclyl;
R$^d$ is selected from the group consisting of hydrogen atom, halogen, amino, cyano, nitro, C$_{1-6}$ alkyl, C$_{2-6}$ alkynyl, C$_{3-6}$ cycloalkyl, C$_{1-6}$ haloalkyl, C$_{3-8}$ halocycloalkyl, C$_{1-6}$ alkoxy and C$_{1-6}$ hydroxy alkyl;
R$_{23}$ and R$_{24}$ are identical or different and are each independently selected from the group consisting of C$_{1-6}$ alkyl, C$_{3-8}$ cycloalkyl and 3 to 8 membered heterocyclyl, wherein the $C_{1-6}$ alkyl, $C_{3-8}$ cycloalkyl and 3 to 8 membered heterocyclyl are each optionally further substituted by one or more substituents selected from the group consisting of deuterium atom, halogen, hydroxy, $C_{1-3}$ alkyl, amino, oxo, nitro, cyano, $C_{2-6}$ alkenyl, $C_{2-6}$ alkynyl, $C_{1-6}$ alkoxy, $C_{1-6}$ hydroxyalkyl, $C_{3-8}$ cycloalkyl, $-(CH_2)_{n1}NR_{25}R_{26}$, 3 to 8 membered heterocyclyl, 6 to 10 membered aryl and 5 to 12 membered heteroaryl.

In a preferred embodiment of the present invention, the compound of any formula, a stereoisomer thereof or a pharmaceutically acceptable salt thereof, wherein:

$R_{15a}$ is selected from the group consisting of hydrogen atom, $C_{1-6}$ alkyl, $C_{1-6}$ haloalkyl, $C_{1-6}$ alkoxy, halogen, amino, hydroxy, $C_{3-8}$ cycloalkyl, $C_{3-8}$ halocycloalkyl, 3 to 8 membered heterocyclyl, 6 to 10 membered aryl, 5 to 12 membered heteroaryl, $-(CH_2)_{n1}R_{23}$, $-(CH_2)_{n1}OR_{23}$, $-(CH_2)_{n1}C(O)OR_{23}$, $-(CH_2)_{n1}SR_{23}$, $-(CH_2)_{n1}S(O)_{m1}R_{23}$ and $-(CH_2)_{n1}NR_{23}R_{24}$, wherein the $C_{1-6}$ alkyl, $C_{1-6}$ haloalkyl, $C_{1-6}$ alkoxy, $C_{3-8}$ cycloalkyl, $C_{3-8}$ halocycloalkyl, 3 to 8 membered heterocyclyl, 6 to 10 membered aryl and 5 to 12 membered heteroaryl are each optionally further substituted by one or more substituents selected from the group consisting of hydrogen atom, halogen, cyano, hydroxy, nitro, $C_{1-6}$ alkyl, $C_{1-6}$ haloalkyl, $C_{3-6}$ cycloalkyl, $-(CH_2)_{n1}NR_{25}R_{26}$ and 3 to 6 membered heterocyclyl;

$R_{16a}$ is selected from the group consisting of hydrogen atom, halogen, cyano, $C_{1-6}$ alkyl and $C_{1-6}$ haloalkyl;

or, $R_{15a}$ and $R_{16a}$ can form a $C_{3-8}$ cycloalkyl, wherein the $C_{3-8}$ cycloalkyl is optionally further substituted by one or more substituents selected from the group consisting of hydrogen atom, $C_{1-6}$ alkyl, $C_{1-6}$ haloalkyl and halogen, and $R_{15a}$ and $R_{16a}$ are not hydrogen at the same time;

$R_{23}$ and $R_{24}$ are identical or different and are each independently selected from the group consisting of hydrogen atom, $C_{1-6}$ alkyl, $C_{3-8}$ cycloalkyl and 3 to 8 membered heterocyclyl, wherein the $C_{1-6}$ alkyl, $C_{3-8}$ cycloalkyl and 3 to 8 membered heterocyclyl are each optionally further substituted by one or more substituents selected from the group consisting of deuterium atom, halogen, hydroxy, $C_{1-3}$ alkyl, amino, oxo, nitro, cyano, $C_{2-6}$ alkenyl, $C_{2-6}$ alkynyl, $C_{1-6}$ alkoxy, $C_{1-6}$ hydroxyalkyl, $C_{3-8}$ cycloalkyl, $-(CH_2)_{n1}NR_{25}R_{26}$, 3 to 8 membered heterocyclyl, 6 to 10 membered aryl and 5 to 12 membered heteroaryl.

In a preferred embodiment of the present invention, the compound of formula (I), or the stereoisomer thereof, is selected from the group consisting of:

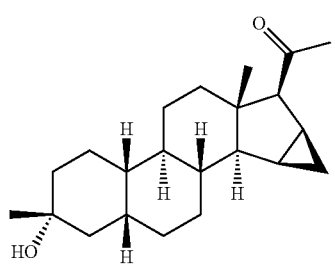

1

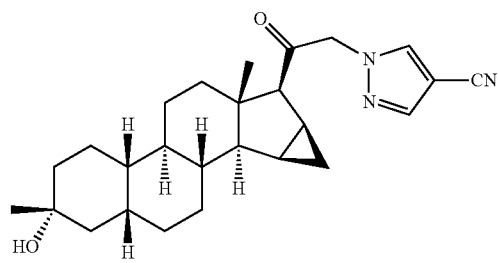

2

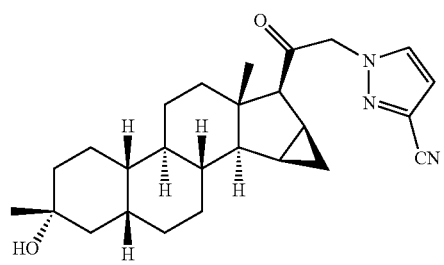

3

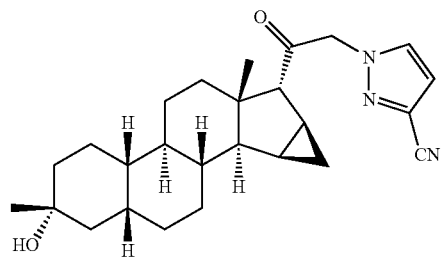

4

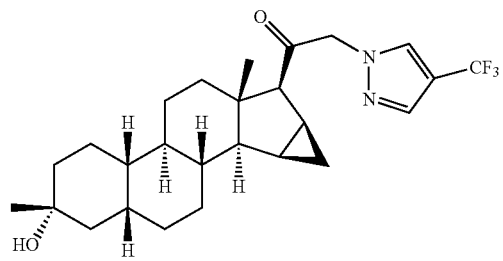

5

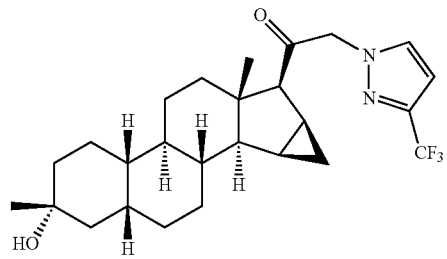

6

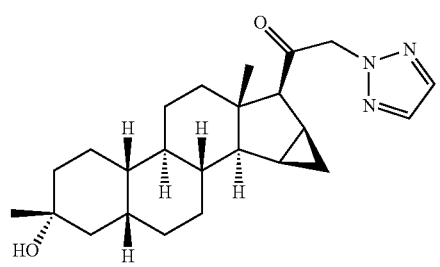

7

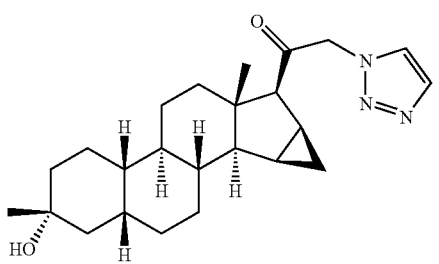
8
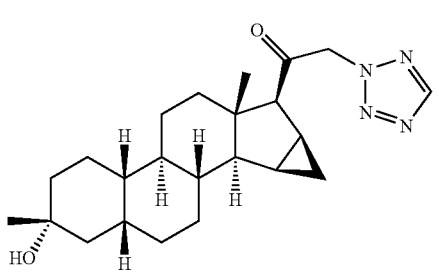
9
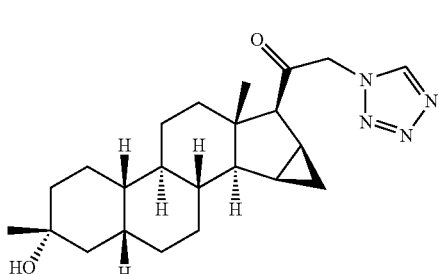
10
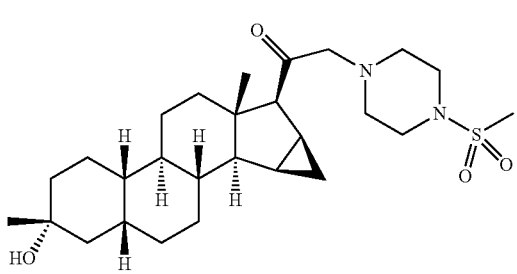
11
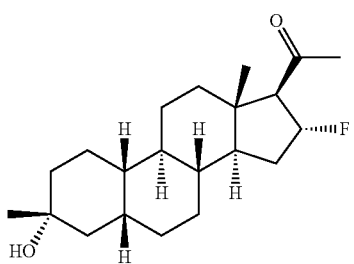
12
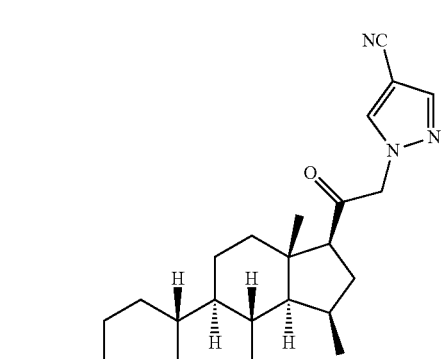
13
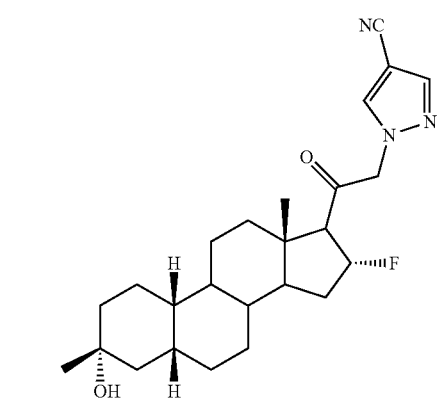
14
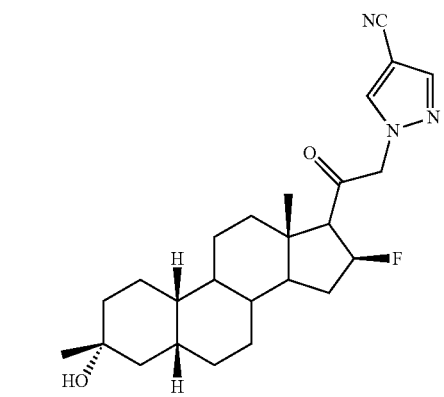
15
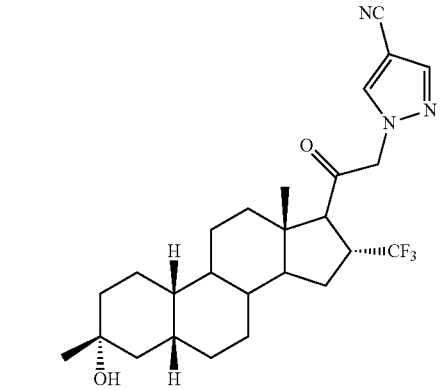
16

17
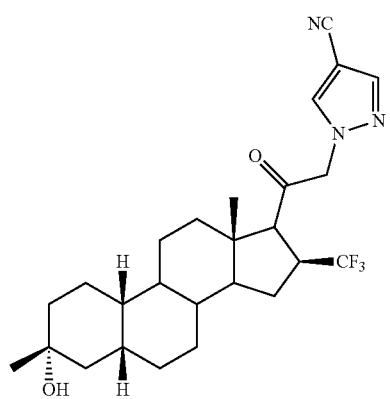
18
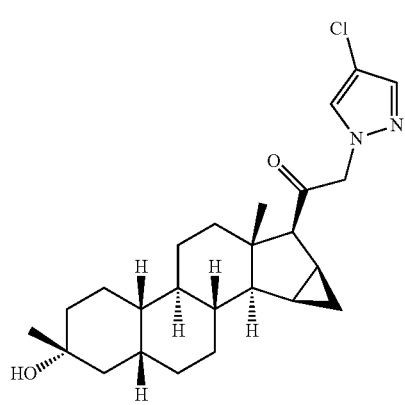
19
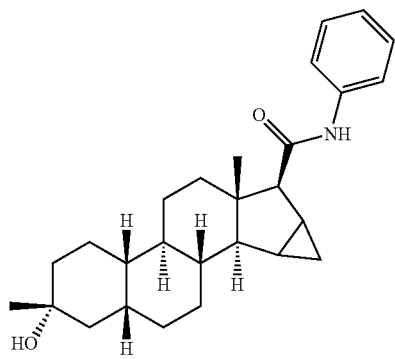
20
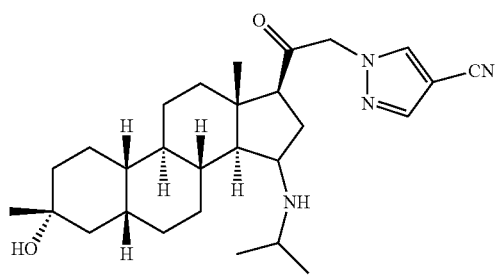
21
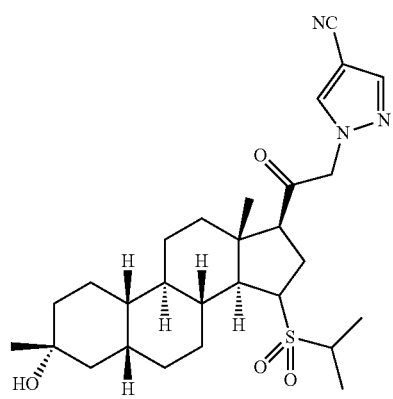
22
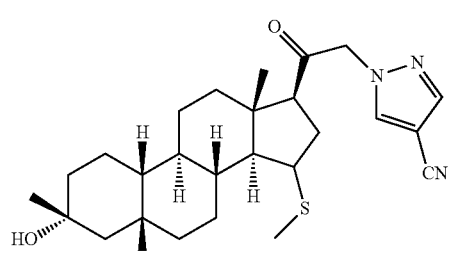
23
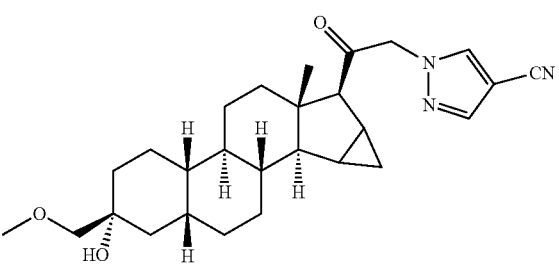
24
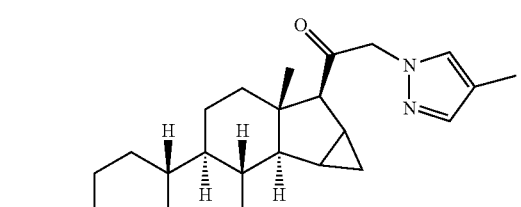
25
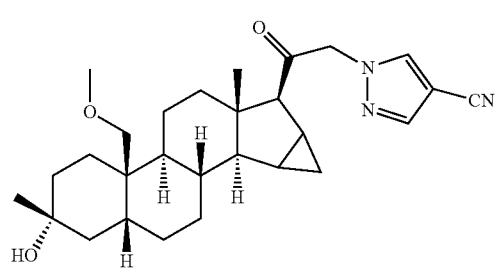

25
-continued
26
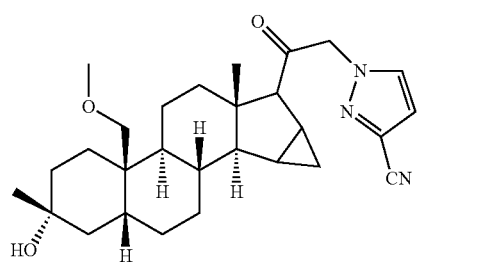
27
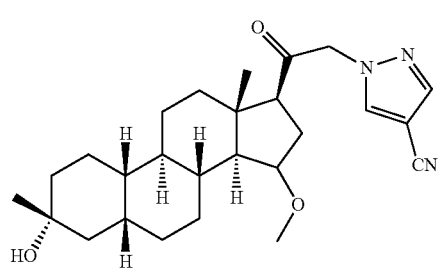
28
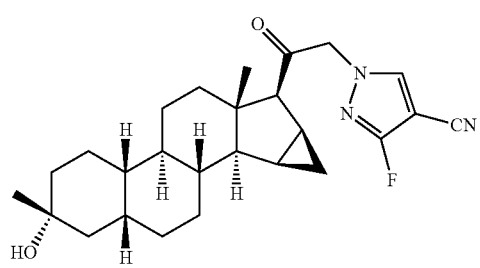
29
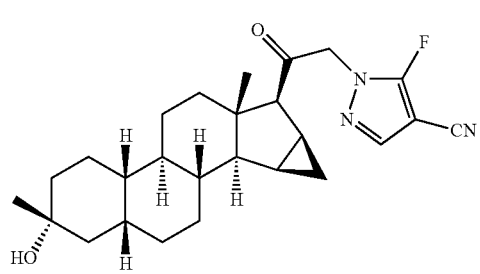
30
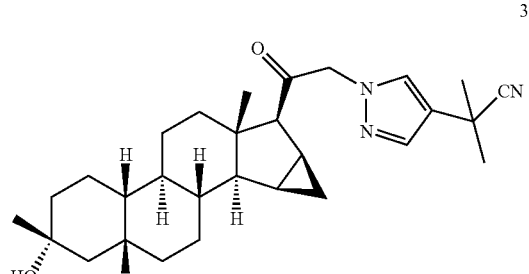
31
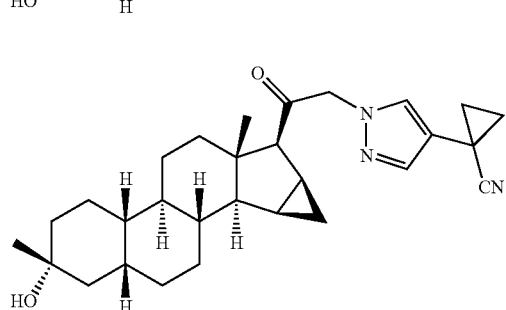
26
-continued
32
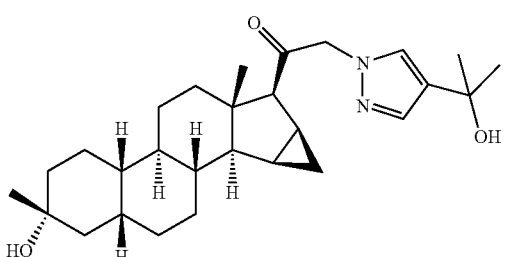
33
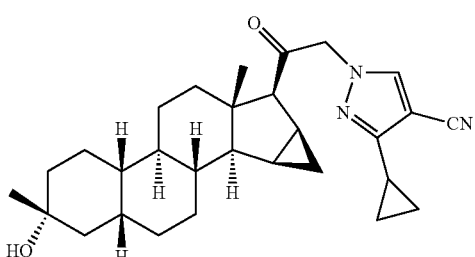
34
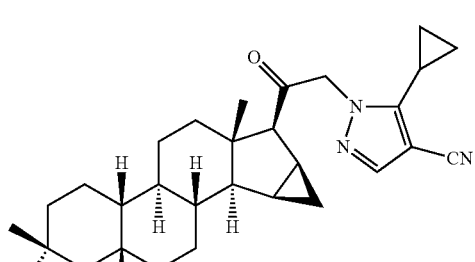
35
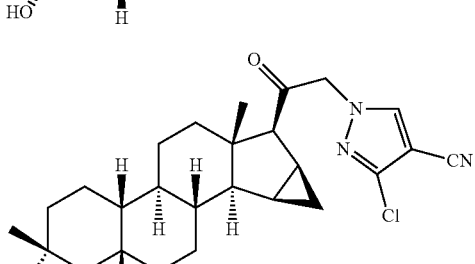
36
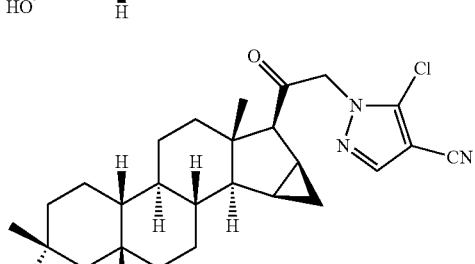
37A
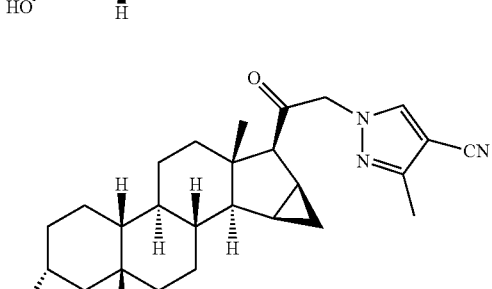

27
-continued
37B
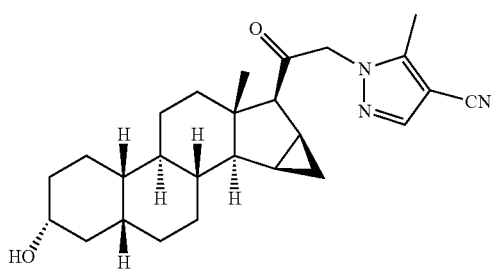
38
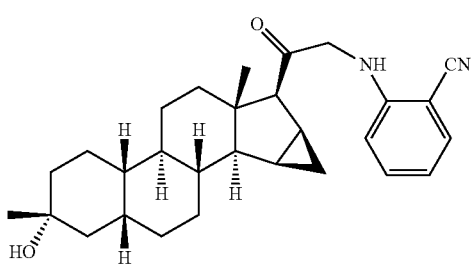
39
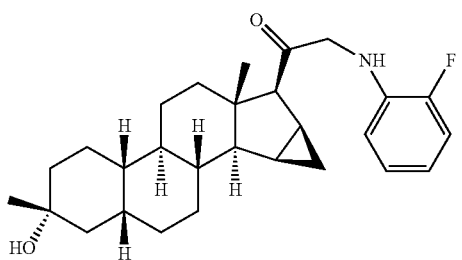
40
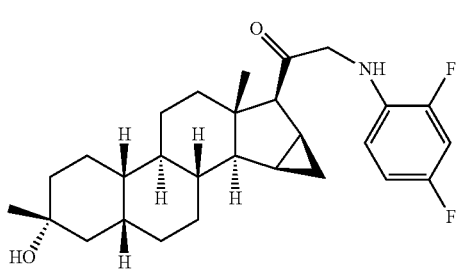
41
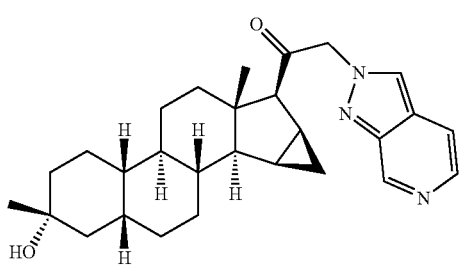
42
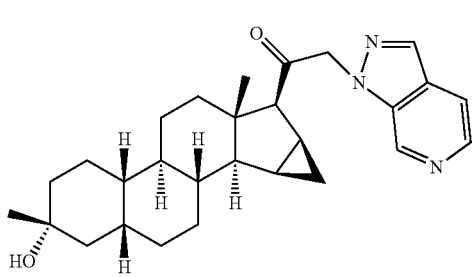
28
-continued
43
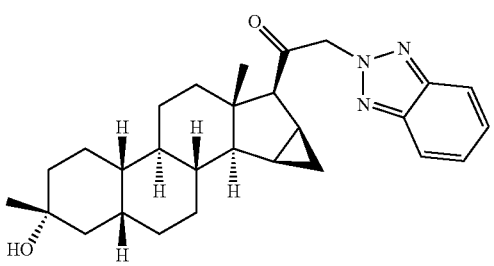
44
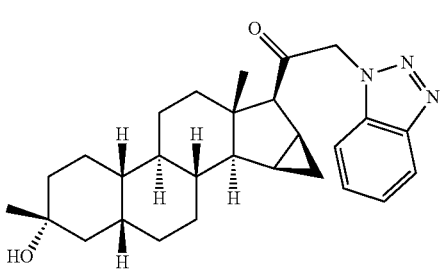
45
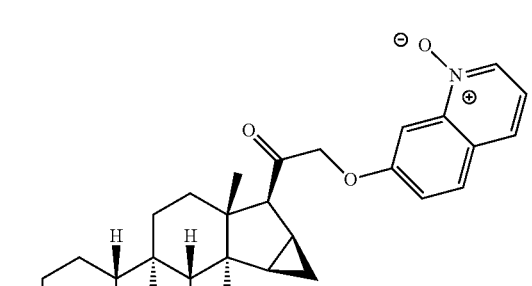
46
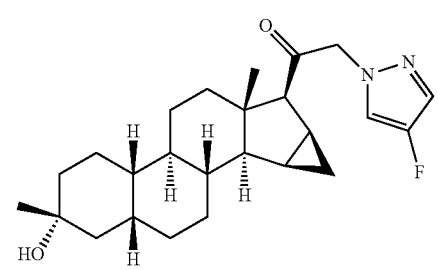
47
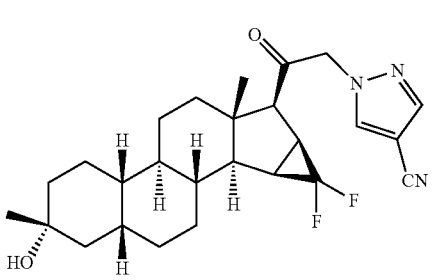

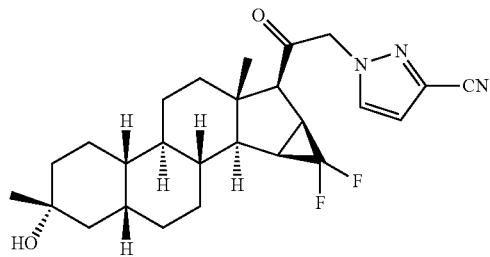
48
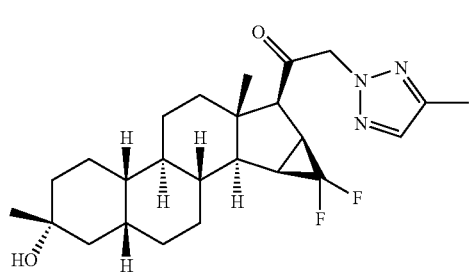
49
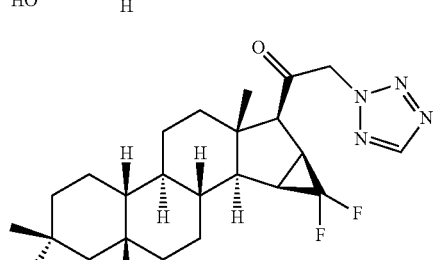
50
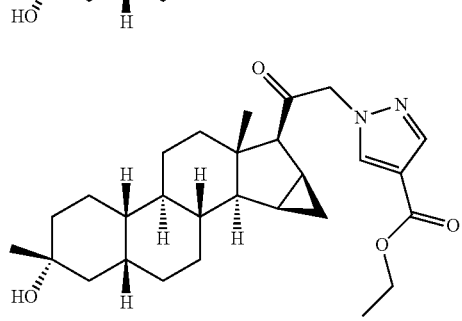
51
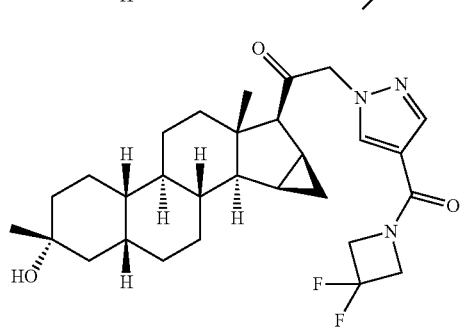
52
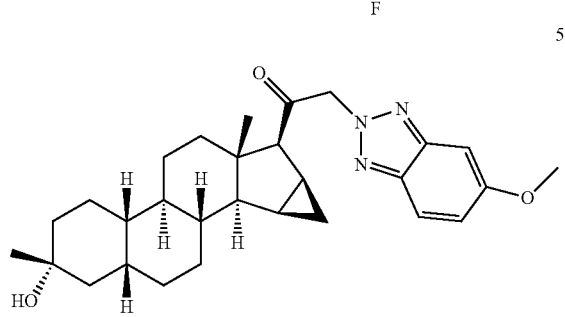
53
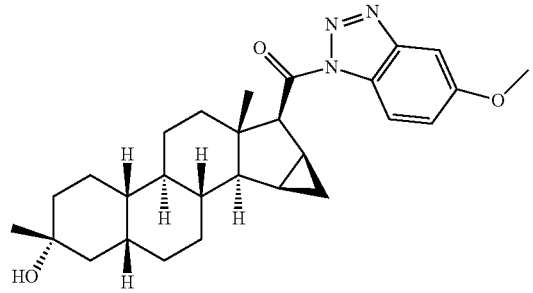
54A
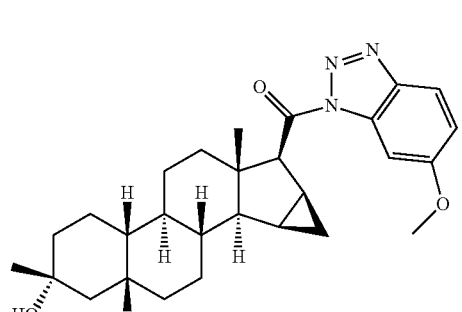
54B
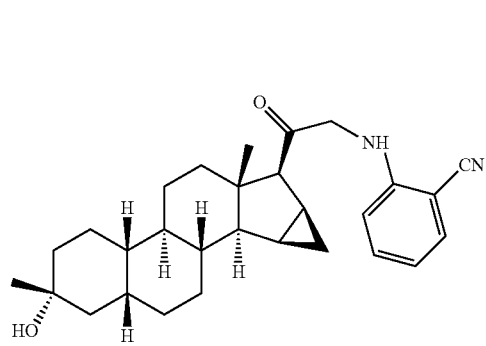
55
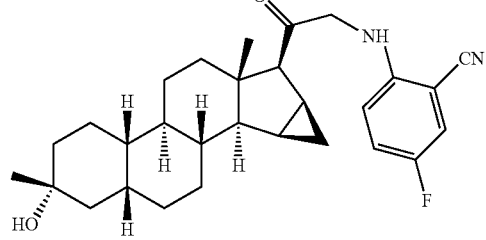
56
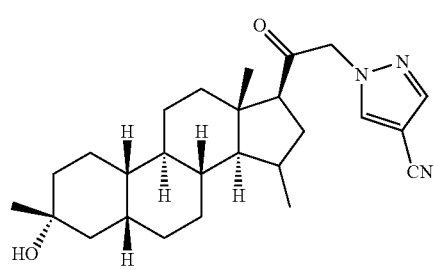
57

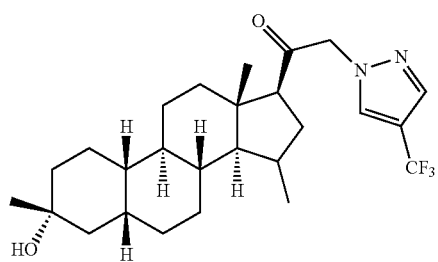
58
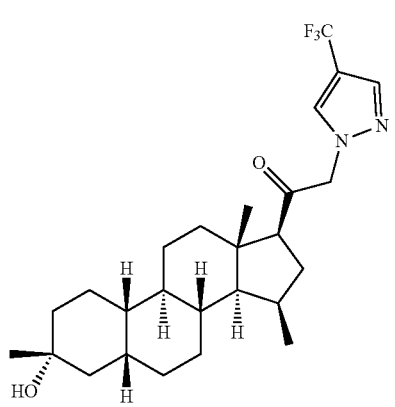
59
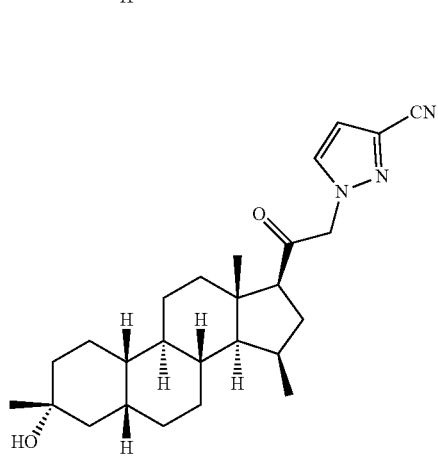
60
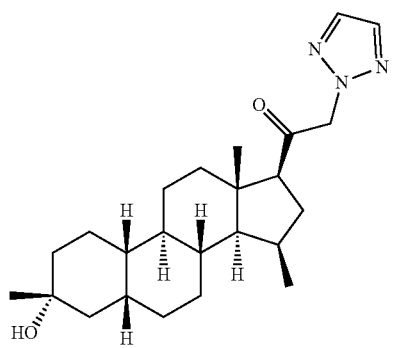
61
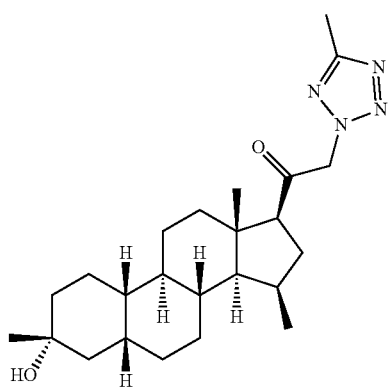
62
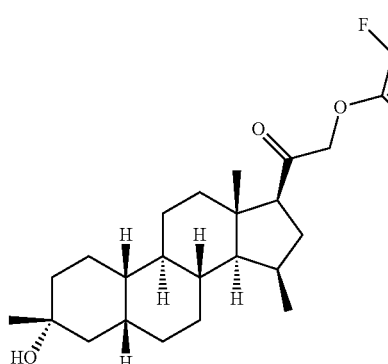
63
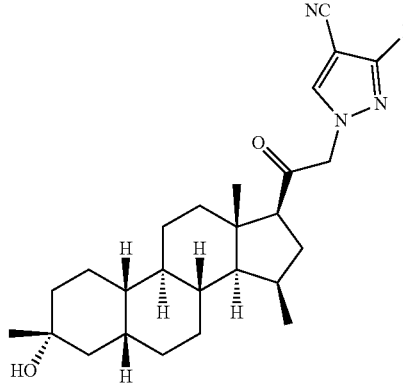
64
65

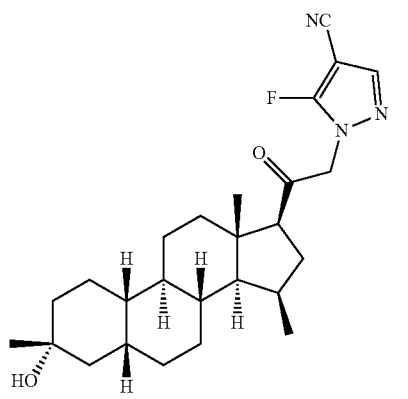
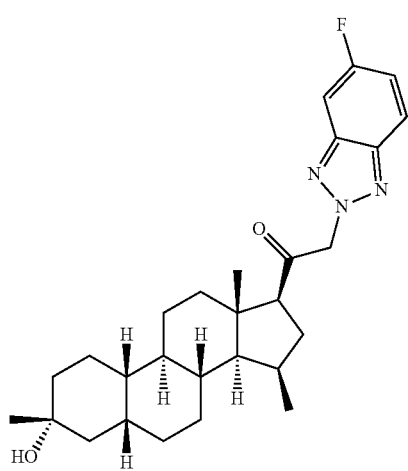
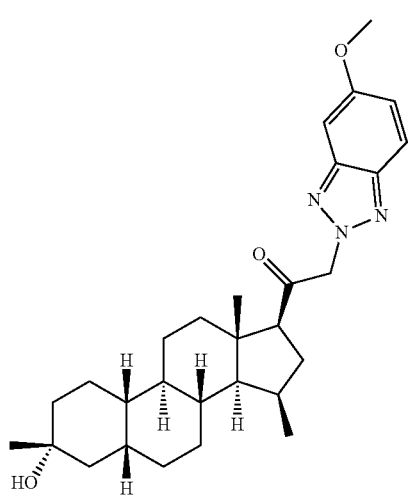
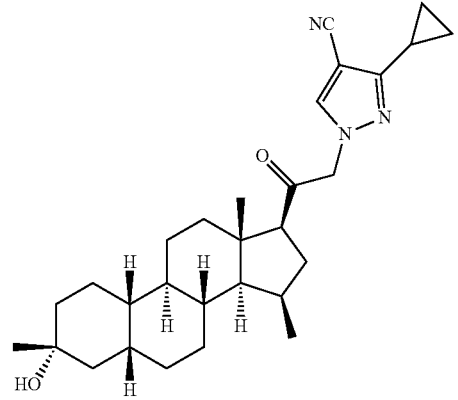
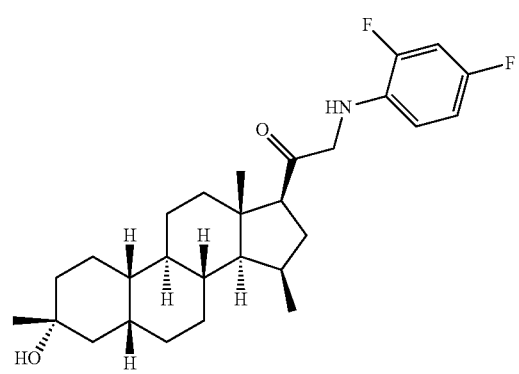
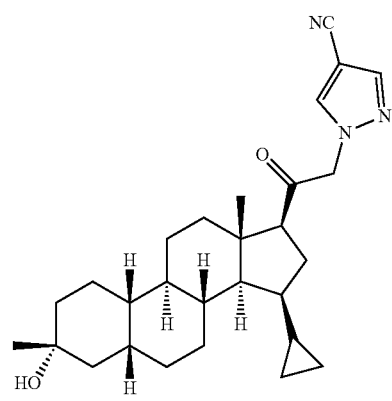
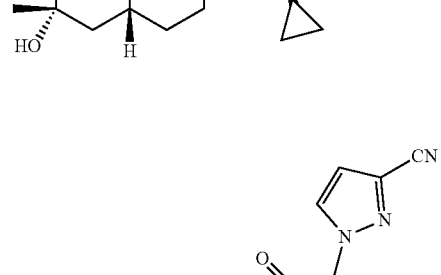
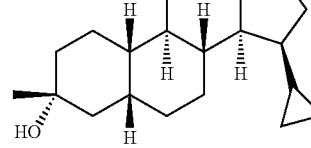

73
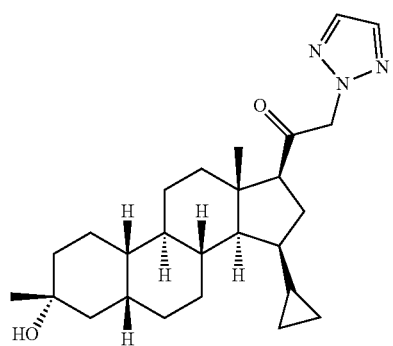
74
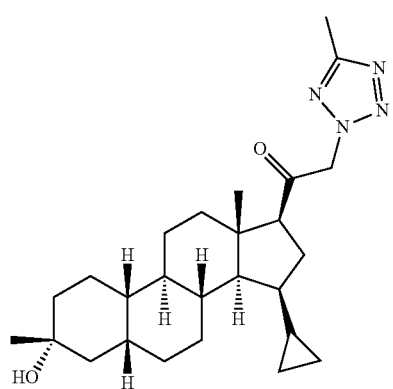
75
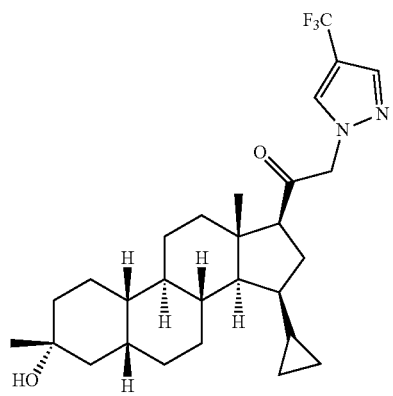
76
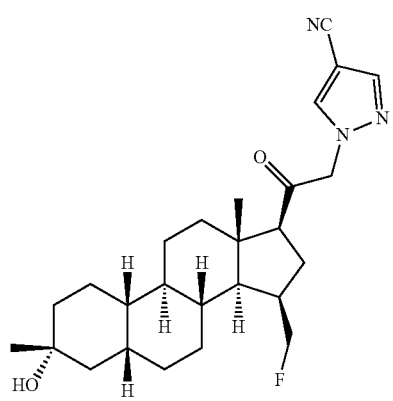
77
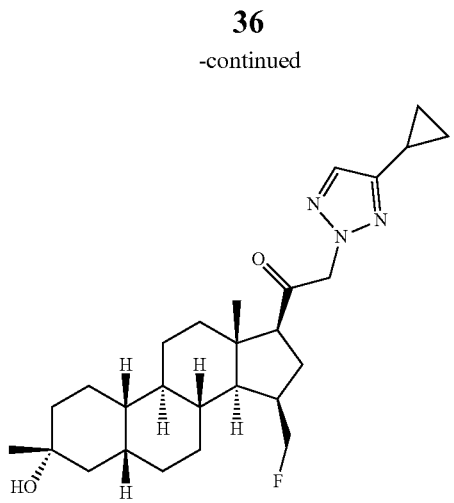
78
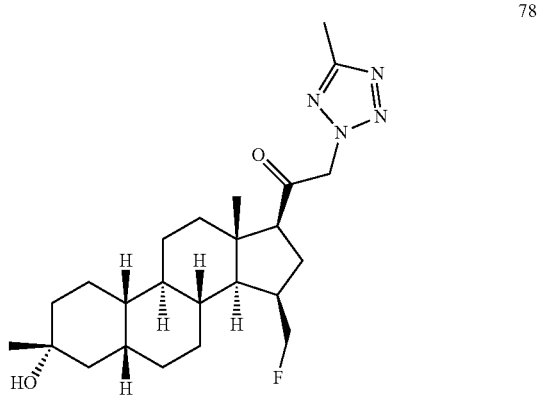
79
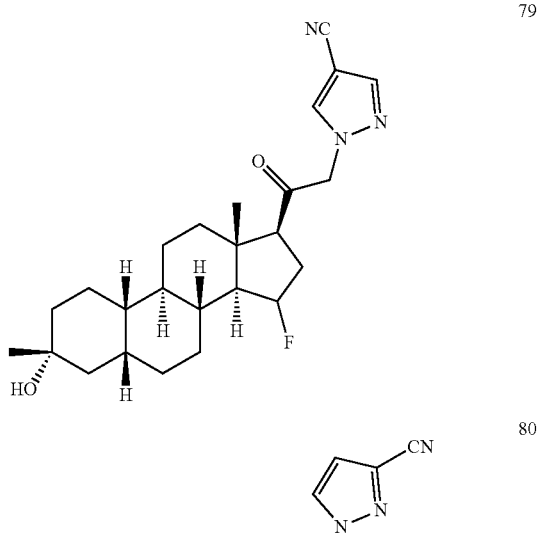
80
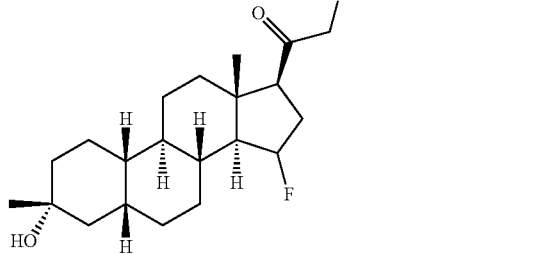

81
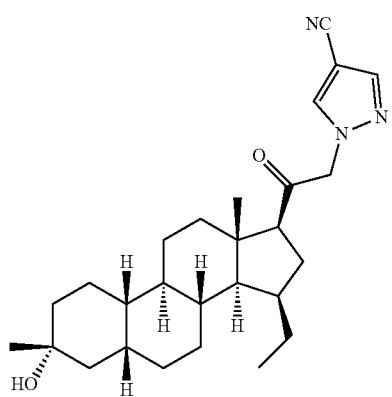
82
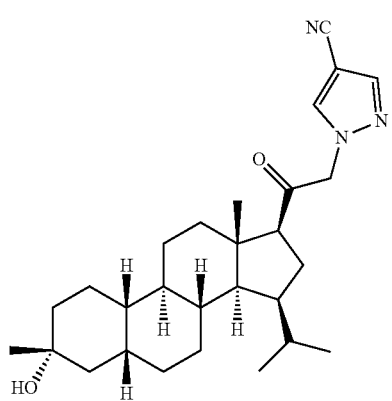
83
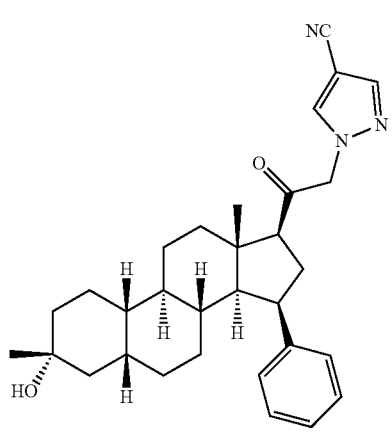
84
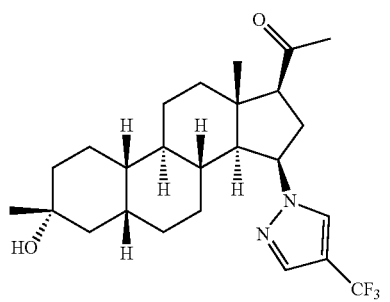
85
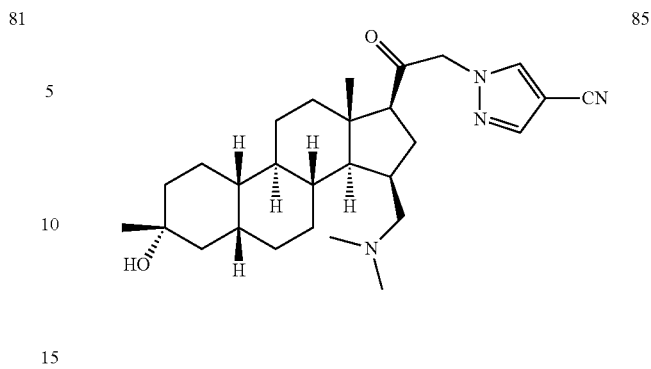
86
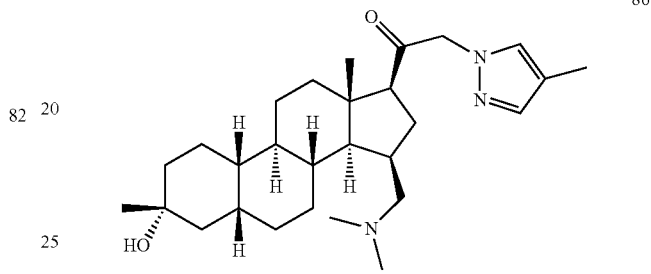
87
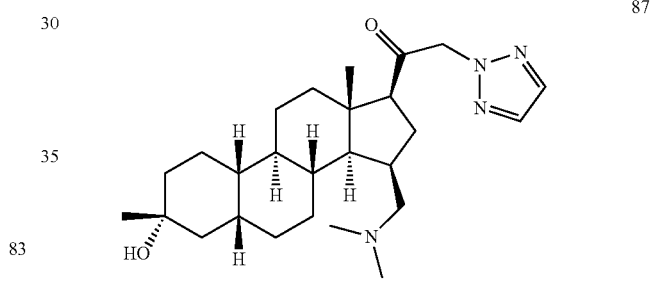
88
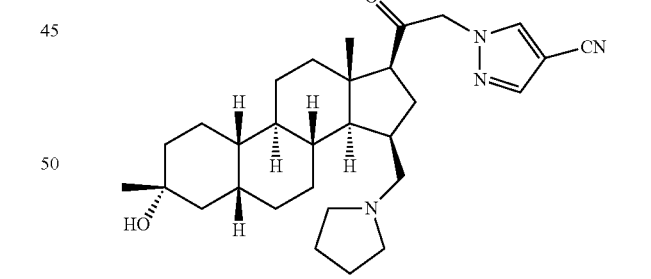
89
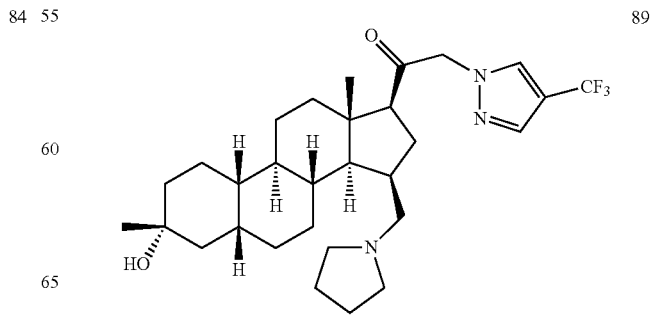

90
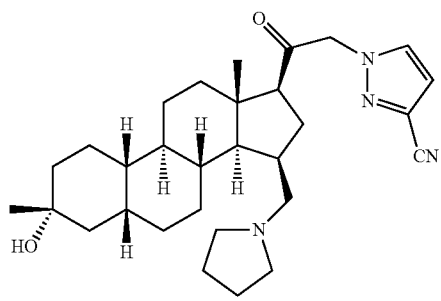
94
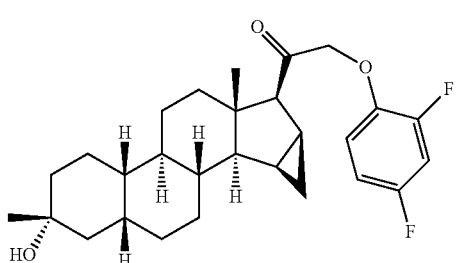
91
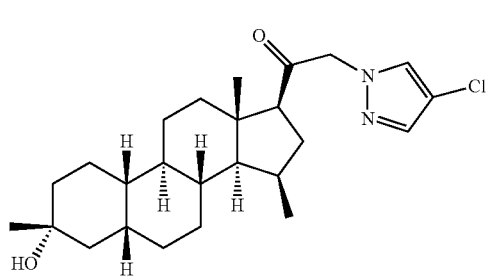
95
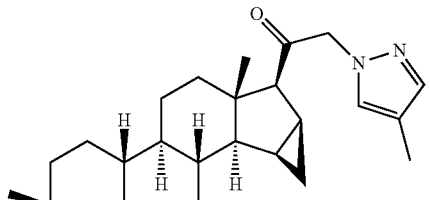
92
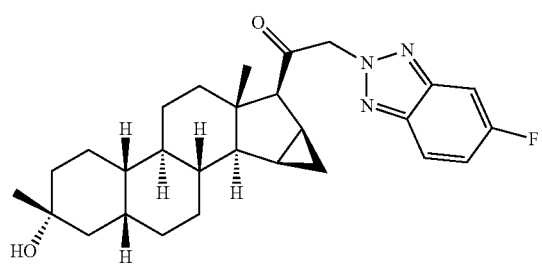
96
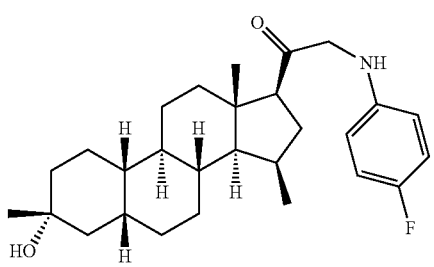
93A
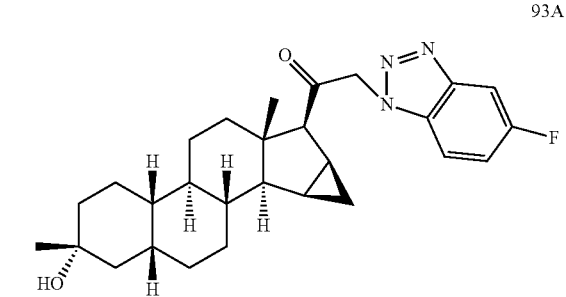
97
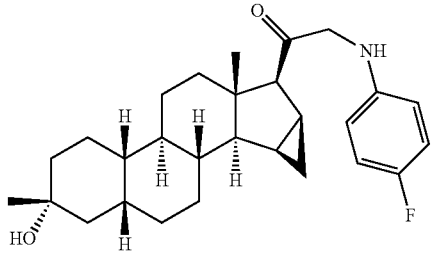
93B
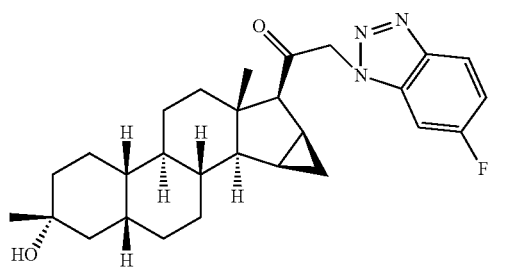
98
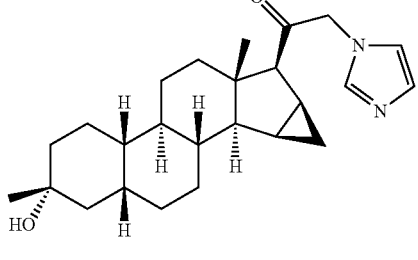

99
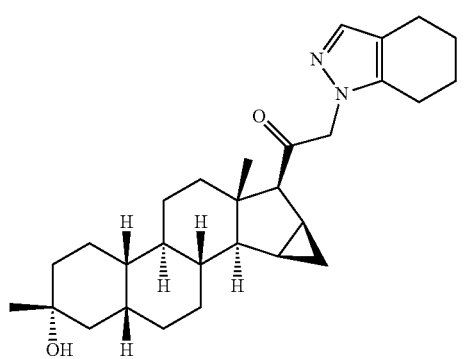
100
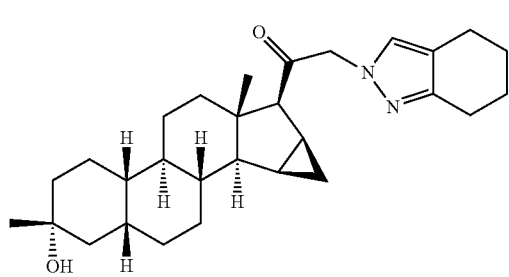
101
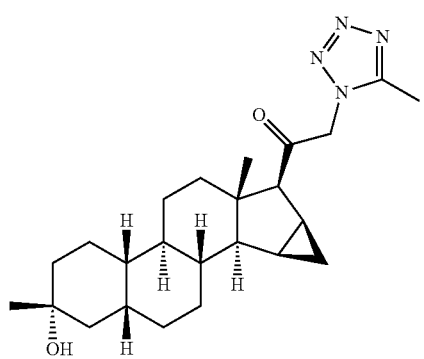
102
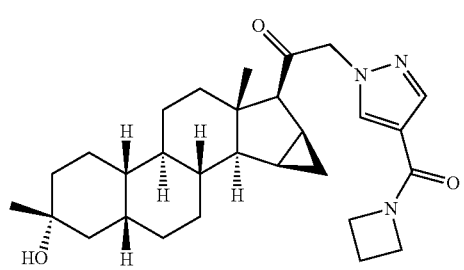
103
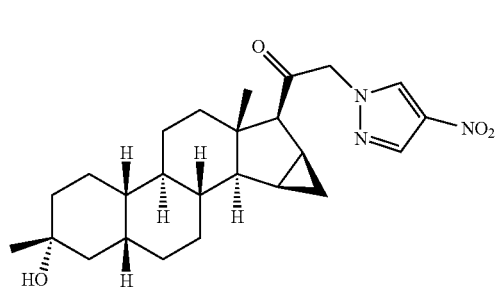
104
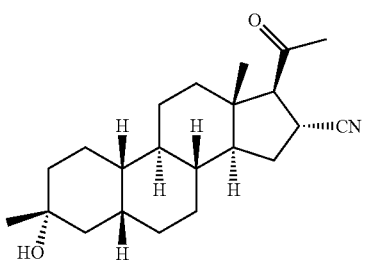
105
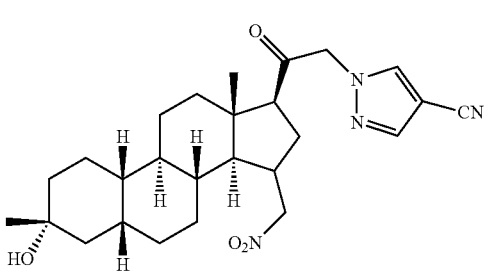
106
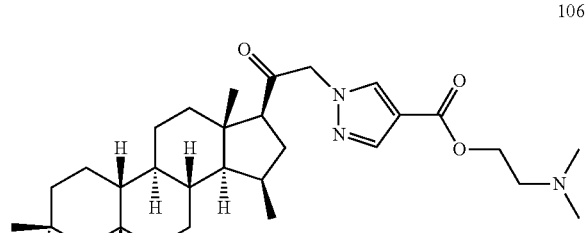
107
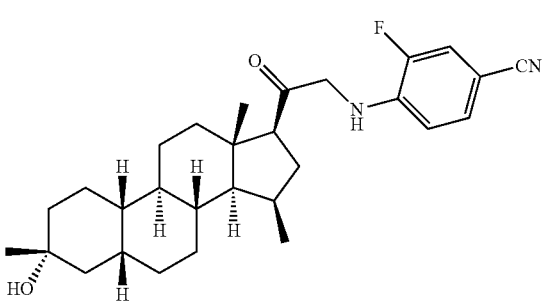
108
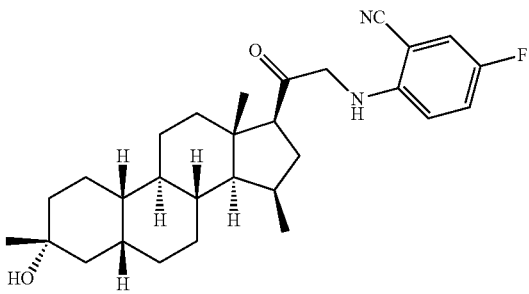

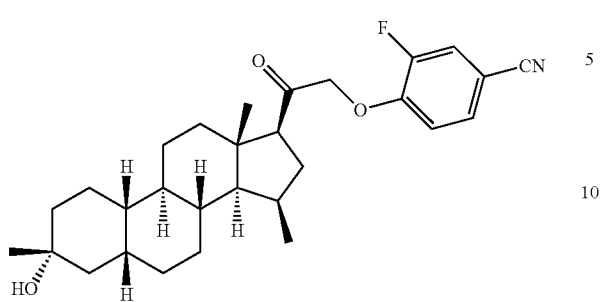
109
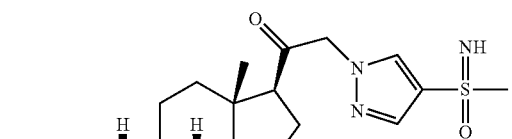
114
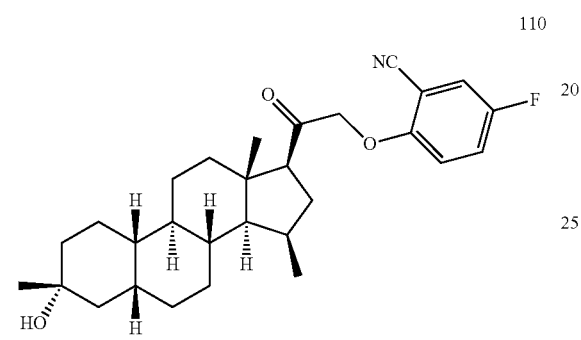
110
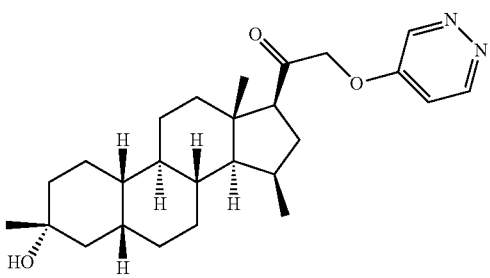
115
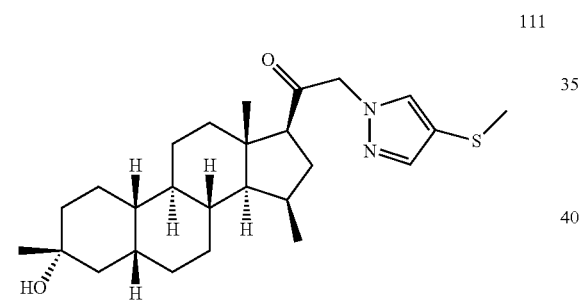
111
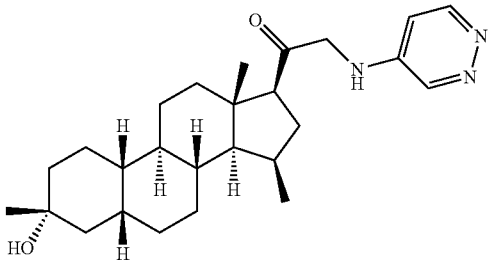
116
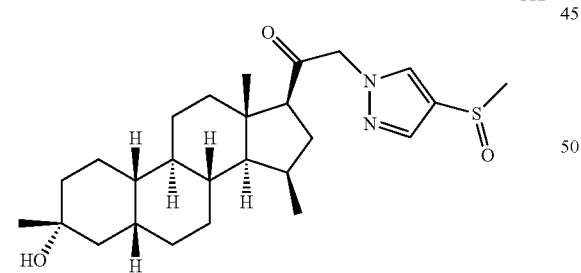
112
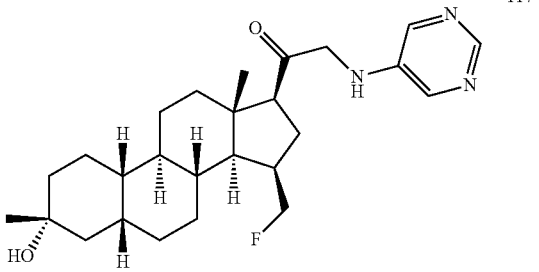
117
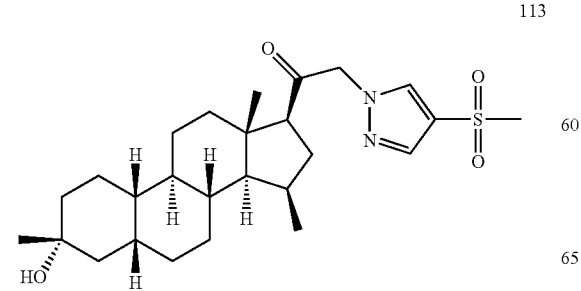
113
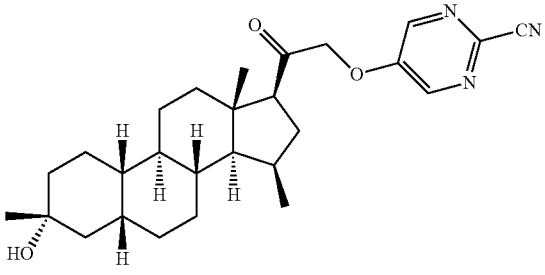
118

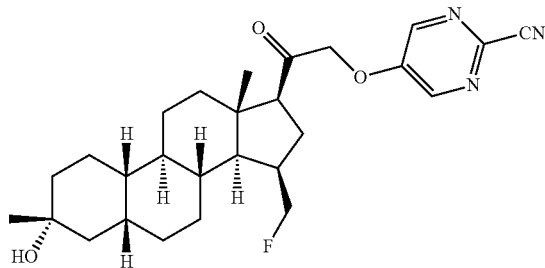
119
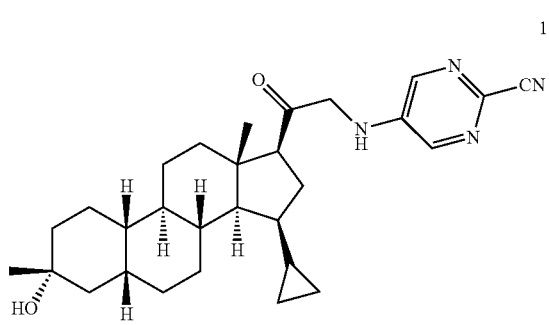
120
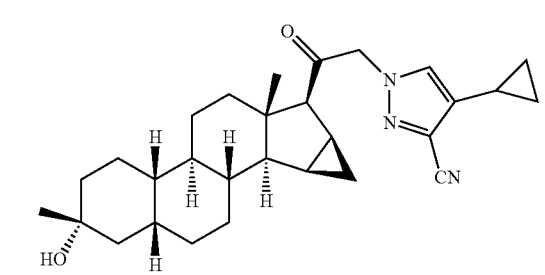
121
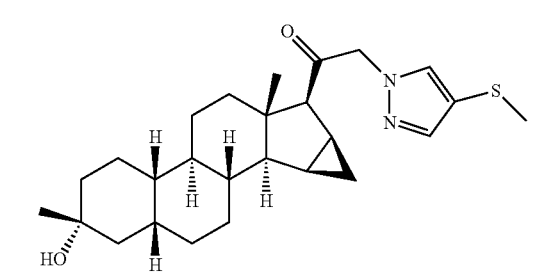
122
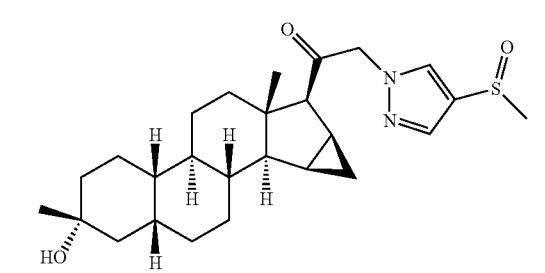
123
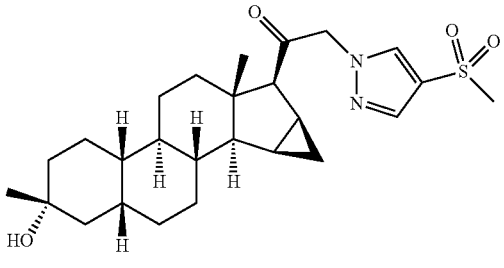
124
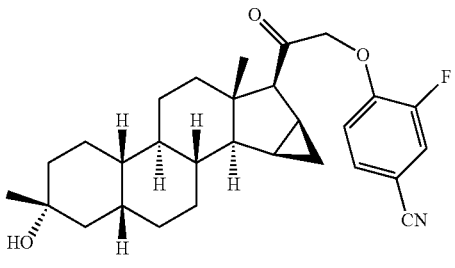
125
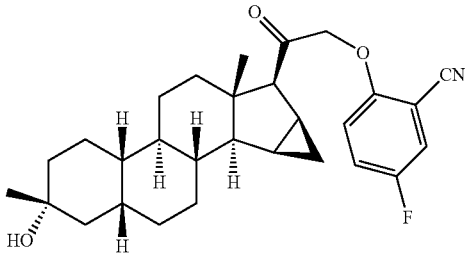
126
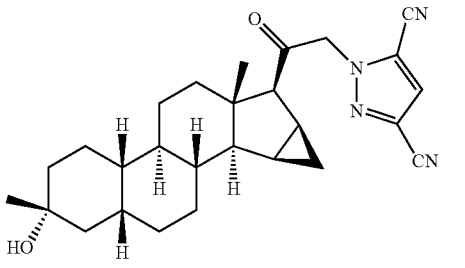
127
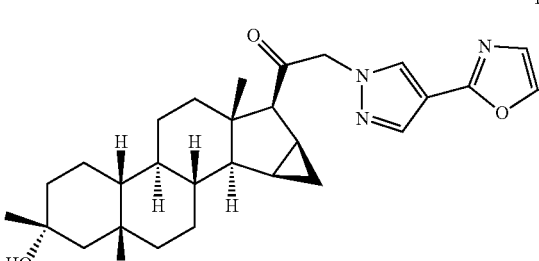
128
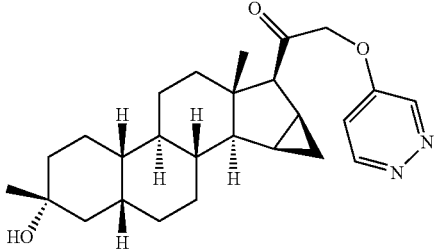
129

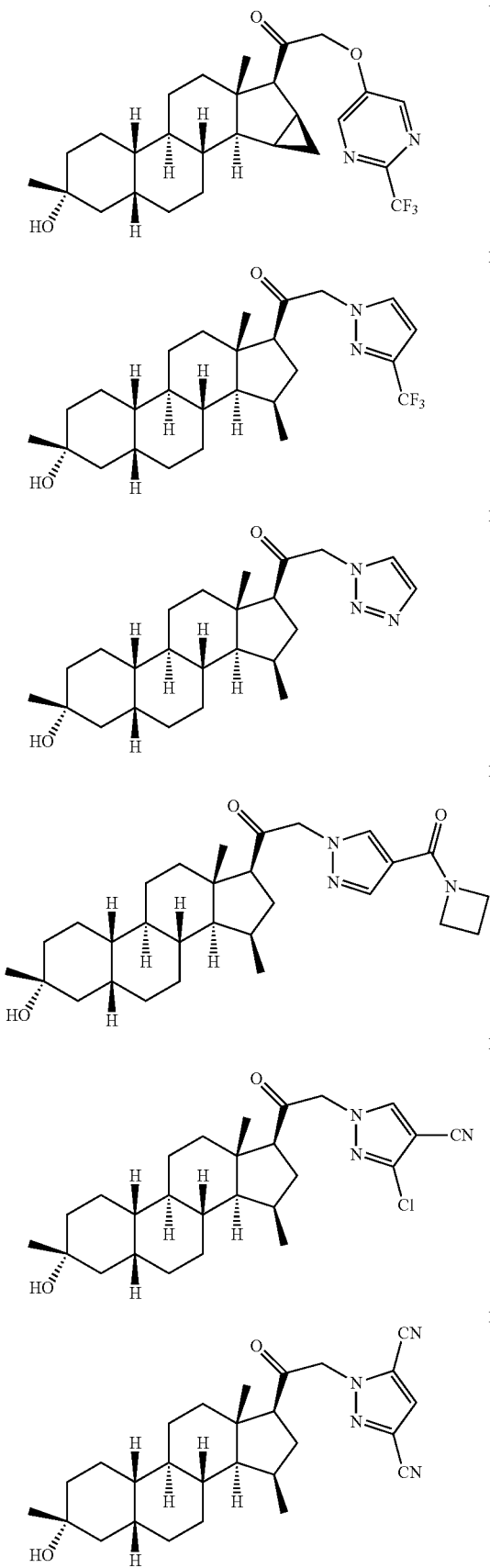
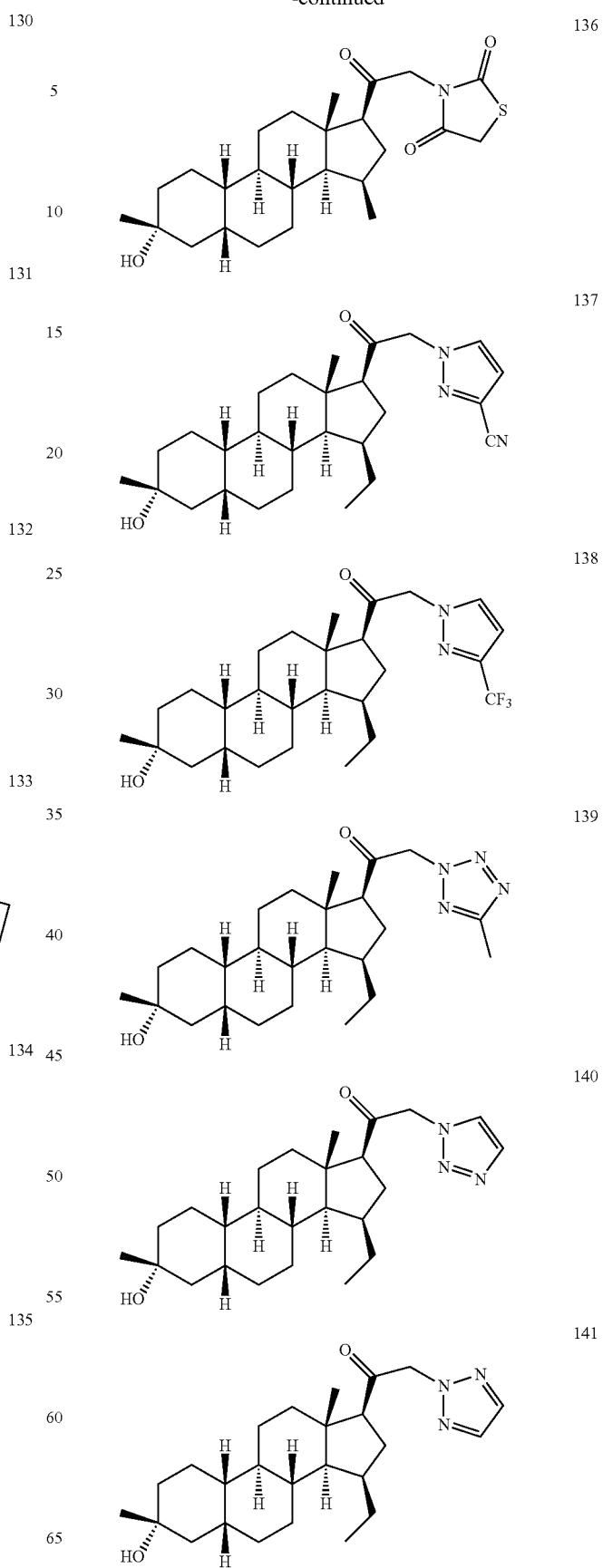

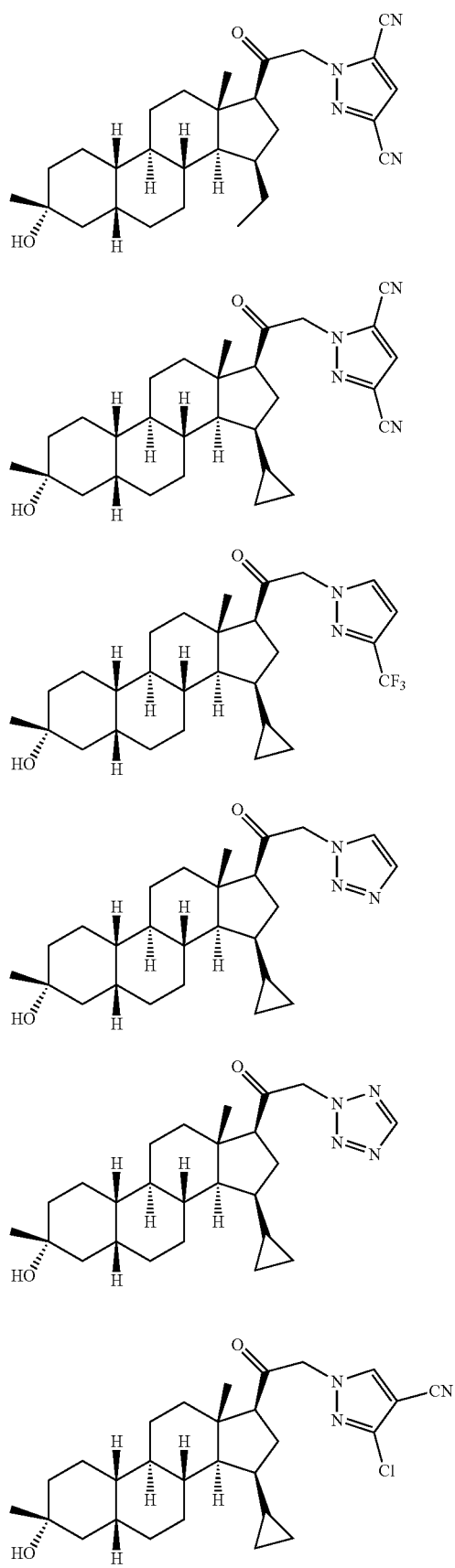
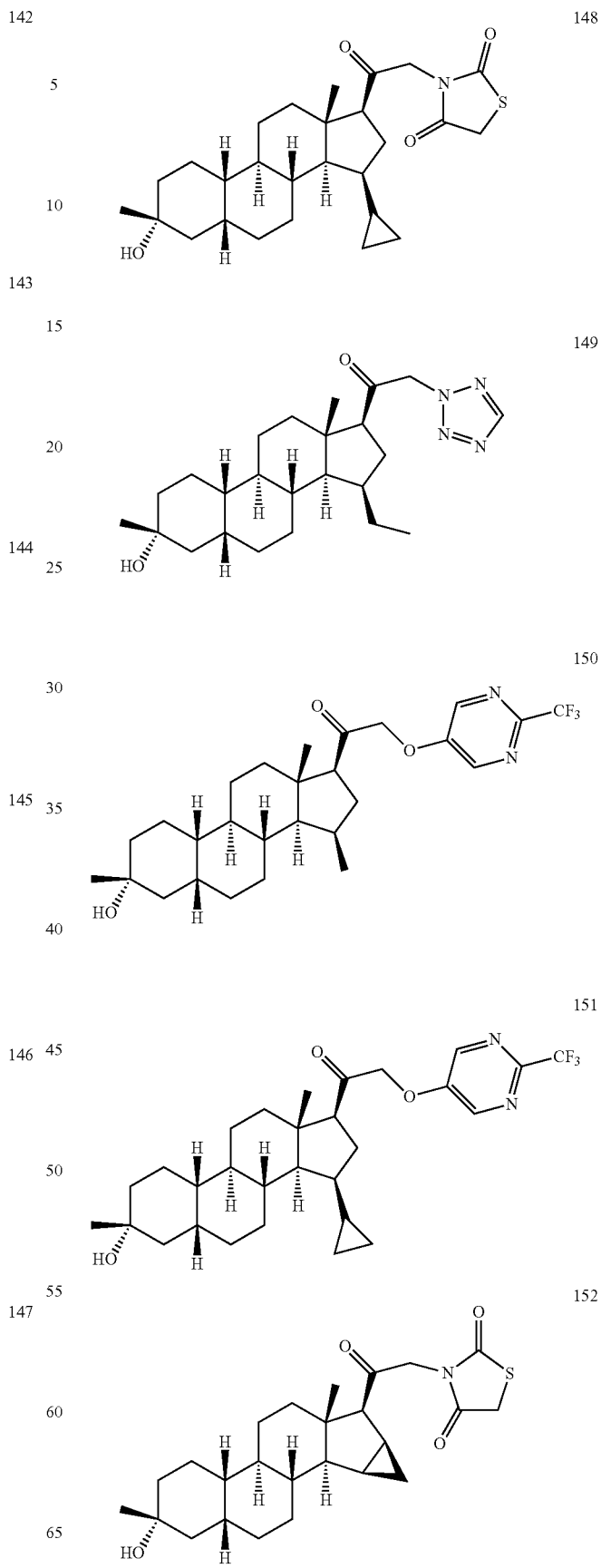

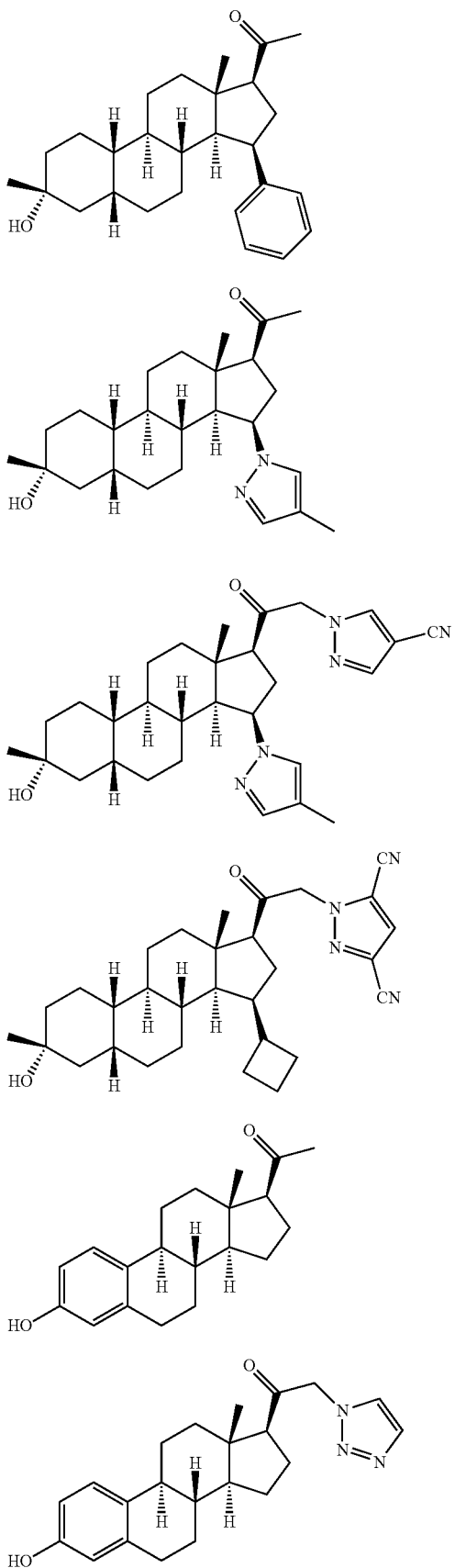
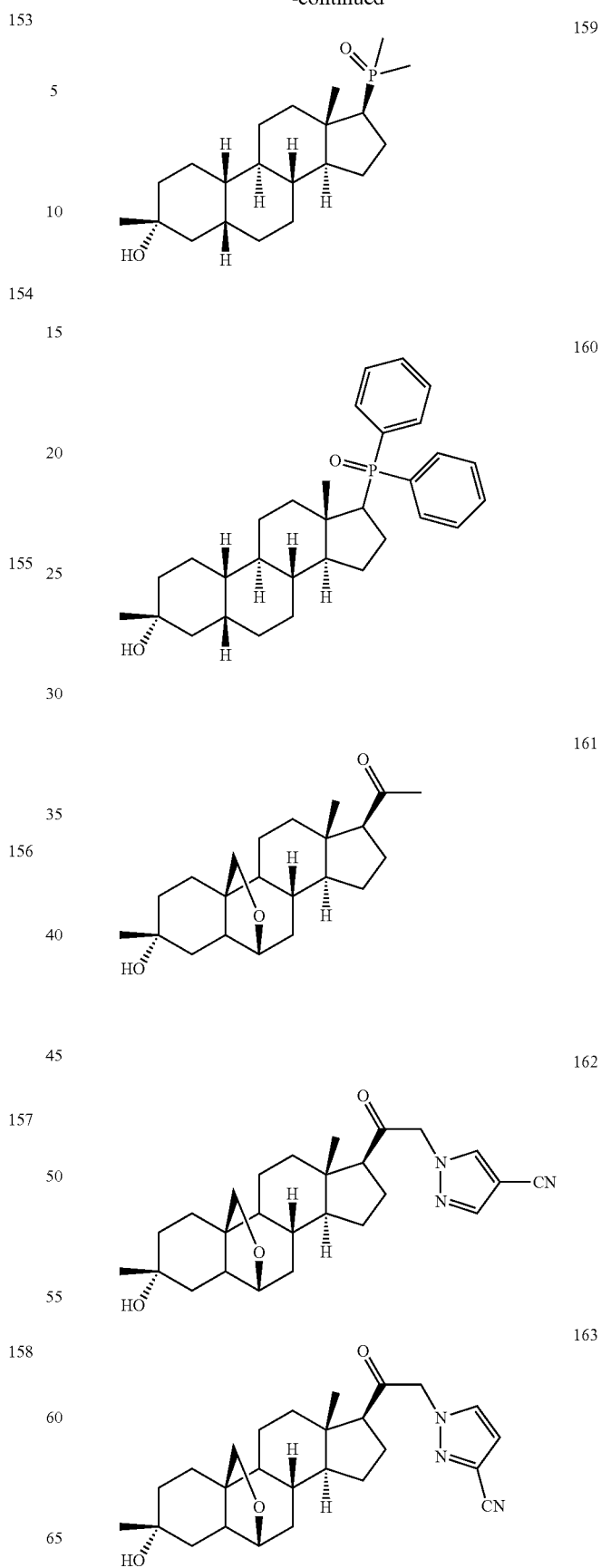

53
-continued
164
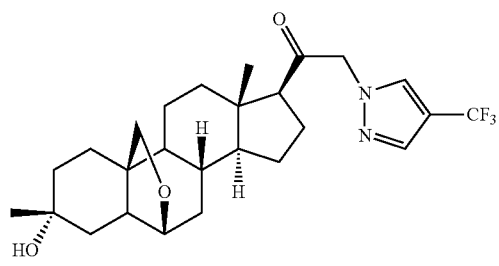
165
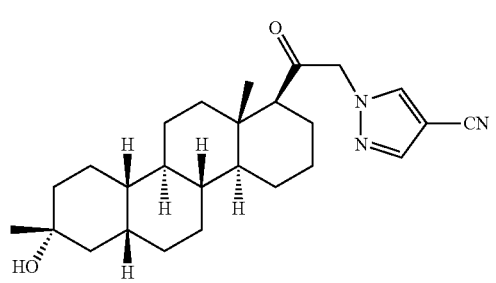
166
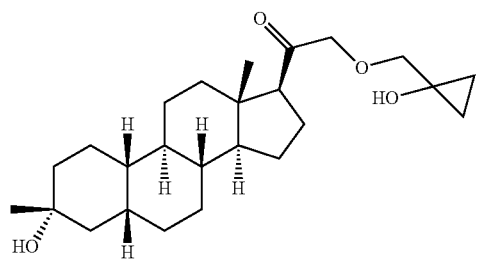
167
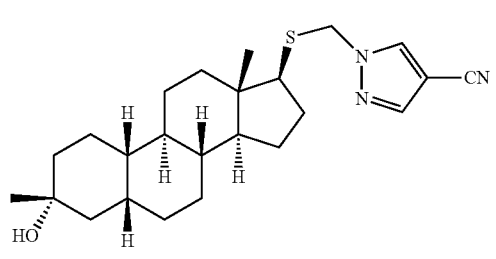
168
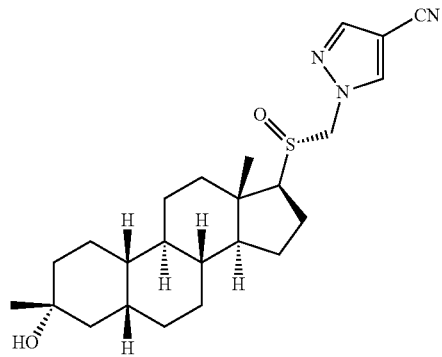
54
-continued
169
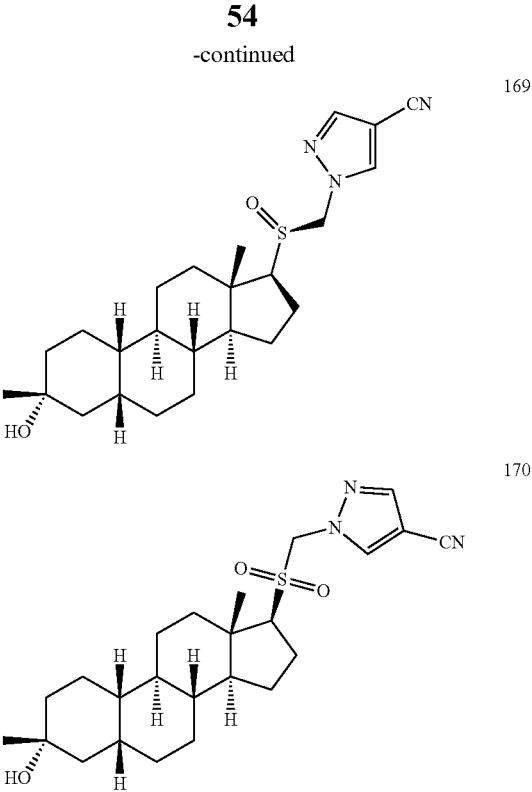
170
171
172
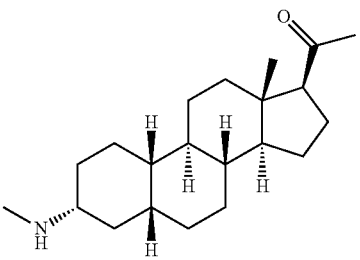
173
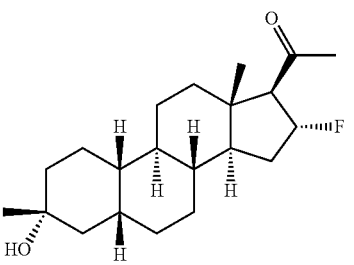

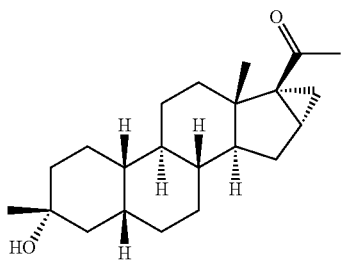

174

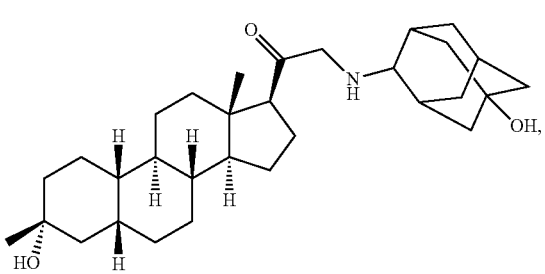

179 or the pharmaceutically acceptable salt thereof.

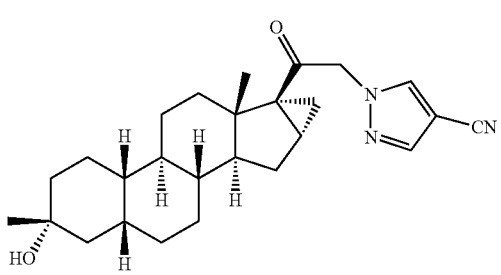

175

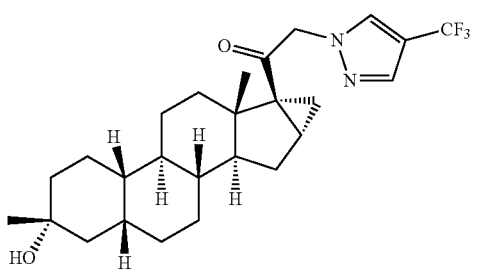

176

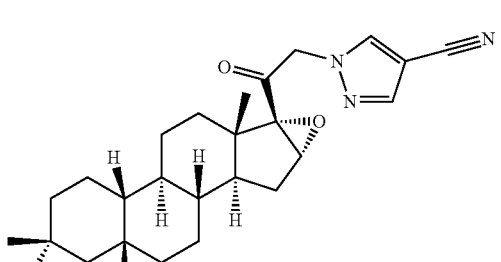

177

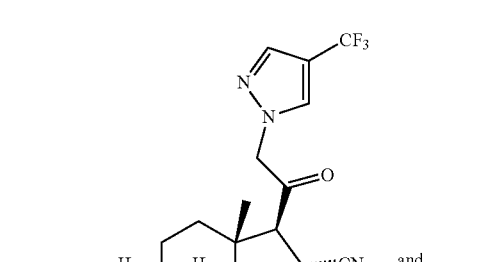

178 and

The present invention further relates to a pharmaceutical composition comprising a therapeutically effective amount of any one of the compound of formula (I), the stereoisomer thereof, or the pharmaceutically acceptable salt thereof, and one or more pharmaceutically acceptable carriers, diluents or excipients.

The present invention further relates to a use of any one of the compound of formula (I), the stereoisomer thereof, or the pharmaceutically acceptable salt thereof, or the pharmaceutical composition comprising the same in the preparation of a $GABA_A$ receptor regulator medicament.

The present invention further relates to a use of the compound of formula (I), the stereoisomer thereof, or the pharmaceutically acceptable salt thereof, or the pharmaceutical composition comprising the same in the preparation of a medicament for treating a Central Nervous System (CNS)-related disease, wherein the CNS-related disease is selected from the group consisting of sleep disorder, mood disorder, schizophrenia spectrum disorder, spasmodic disorder, memory disorder and/or cognitive disorder, dyskinesia, personality disorder, autism spectrum disorder, pain, traumatic brain injury, vascular disease, substance abuse disorder and/or withdrawal syndrome or tinnitus.

The present invention further relates to the compound of formula (I), the stereoisomer thereof, or the pharmaceutically acceptable salt thereof, or the pharmaceutical composition comprising the same for use in treating a CNS-related disease.

The present invention also relates to a method for preventing and/or treating a CNS-related disease, comprising administering to a patient a therapeutically effective amount of the compound of formula (I), the stereoisomer thereof, or the pharmaceutically acceptable salt thereof, or the pharmaceutical composition comprising the same.

Definitions

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 8 carbon atoms, more preferably an alkyl having 1 to 6 carbon atoms, and most preferably an alkyl having 1 to 3 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The alkyl of present invention is preferably selected from the group consisting of methyl, ethyl, isopropyl, tert-butyl, haloalkyl, deuterated alkyl, alkoxy-substituted alkyl and hydroxy-substituted alkyl.

The term "alkylene" refers to an alkyl of which a hydrogen atom is further substituted, for example, "methylene" refers to —CH$_2$—, "ethylene" refers to —(CH$_2$)$_2$—, "propylene" refers to —(CH$_2$)$_3$—, "butylene" refers to —(CH$_2$)$_4$— and the like. The term "alkenyl" refers to an alkyl as defined above that consists of at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, further preferably 3 to 8 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring. The cycloalkyl is preferably cyclopropyl.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably a 6 to 14 membered spiro cycloalkyl, and more preferably a 7 to 10 membered spiro cycloalkyl. According to the number of the spiro atoms shared between the rings, the spiro cycloalkyl can be divided into a mono-spiro cycloalkyl, a di-spiro cycloalkyl, or a poly-spiro cycloalkyl, and the spiro cycloalkyl is preferably a mono-spiro cycloalkyl or di-spiro cycloalkyl, and more preferably a 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

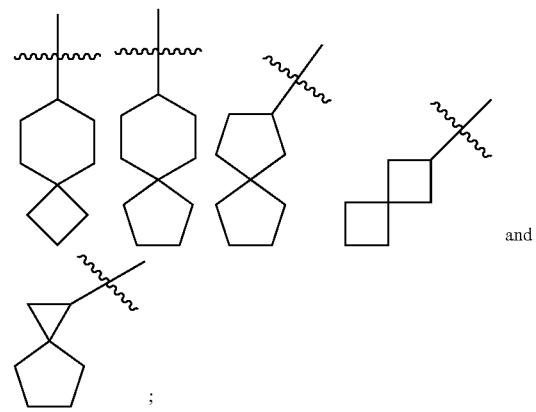

and also include spiro cycloalkyl in which a cycloalkyl and a heterocyclyl are connected through one spiro atom, non-limiting examples thereof include:

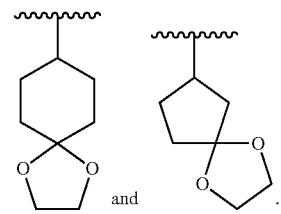 [SMILES: *C1CCC2(CC1)OCCO2 ; *C1CCC2(C1)OCCO2]

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated π-electron system. The fused cycloalkyl is preferably a 6 to 14 membered fused cycloalkyl, and more preferably a 7 to 10 membered fused cycloalkyl. According to the number of membered rings, the fused cycloalkyl can be divided into a bicyclic, tricyclic, tetracyclic or polycyclic fused cycloalkyl, and the fused cycloalkyl is preferably a bicyclic or tricyclic fused cycloalkyl, and more preferably a 5-membered/5-membered, or 5-membered/6-membered bicyclic fused cycloalkyl. Non-limiting examples of fused cycloalkyl include:

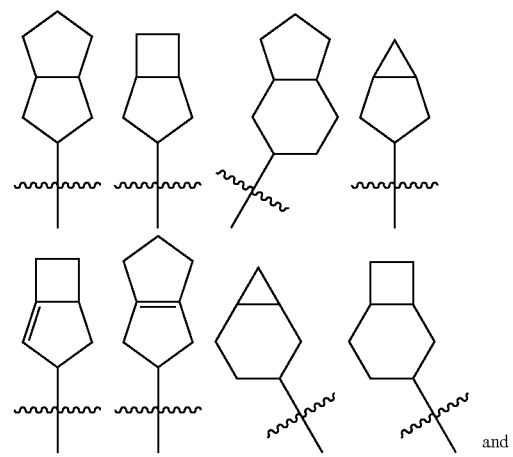

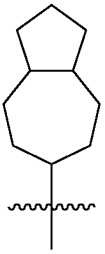

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated 2-electron system. The bridged cycloalkyl is preferably a 6 to 14 membered bridged cycloalkyl, and more preferably a 7 to 10 membered bridged cycloalkyl. According to the number of membered rings, the bridged cycloalkyl can be divided into a bicyclic, tricyclic, tetracyclic or polycyclic bridged cycloalkyl, and the bridged cycloalkyl is preferably a bicyclic, tricyclic or tetracyclic bridged cycloalkyl, and more preferably a bicyclic or tricyclic bridged cycloalkyl. Non-limiting examples of bridged cycloalkyl include:

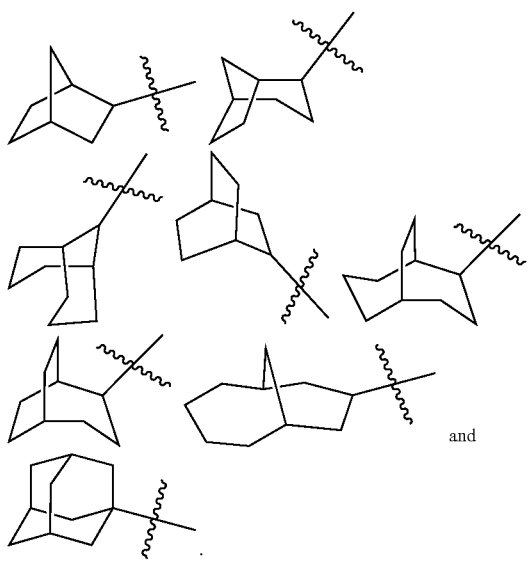

and

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "heterocyclyl" refers to a 3 to 20 membered saturated or partially unsaturated monocyclic or polycyclic hydrocarbon group, wherein one or more ring atoms are heteroatoms selected from the group consisting of N, O and S(O)$_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 10 ring atoms; and most preferably 3 to 8 ring atoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl, 1,4-diazacyclyl and the like, and preferably tetrahydrofuranyl, pyrazolidinyl, morpholinyl, 1,4-diazacyclyl, piperazinyl and pyranyl. Polycyclic heterocyclyl includes a heterocyclyl having a spiro ring, fused ring or bridged ring. The heterocyclyl having a spiro ring, fused ring or bridged ring is optionally bonded to other group via a single bond, or further bonded to other cycloalkyl, heterocyclyl, aryl and heteroaryl via any two or more atoms on the ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and S(O)$_m$ (wherein m is an integer of 0 to 2), with the remaining ring atoms being carbon atoms, where the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

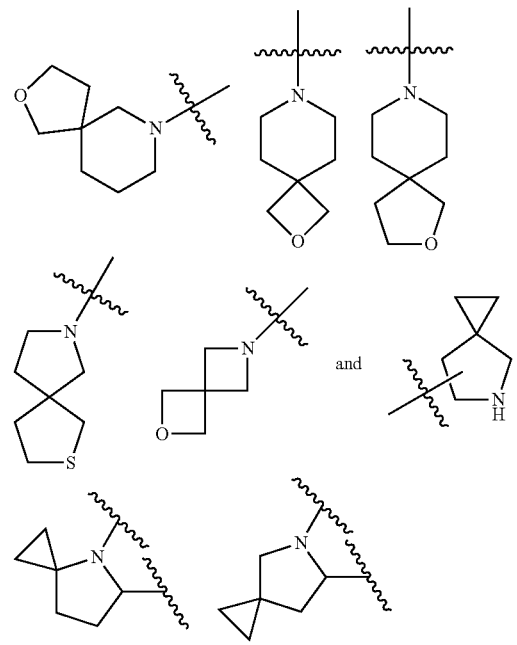

and

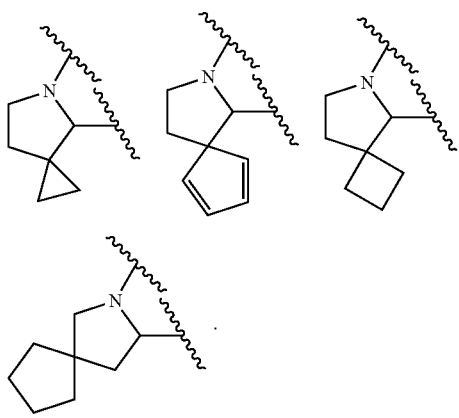

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and $S(O)_m$ (wherein m is an integer of 0 to 2), with the remaining ring atoms being carbon atoms. The fused heterocyclyl is preferably a 6 to 14 membered fused heterocyclyl, and more preferably a 7 to 10 membered fused heterocyclyl. According to the number of membered rings, the fused heterocyclyl can be divided into a bicyclic, tricyclic, tetracyclic or polycyclic fused heterocyclyl, and preferably a bicyclic or tricyclic fused heterocyclyl, and more preferably a 5-membered/5-membered or 5-membered/6-membered bicyclic fused heterocyclyl. Non-limiting examples of fused heterocyclyl include:

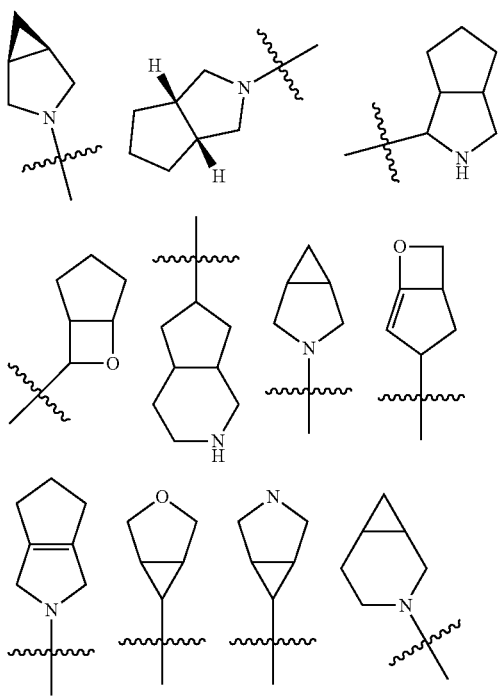

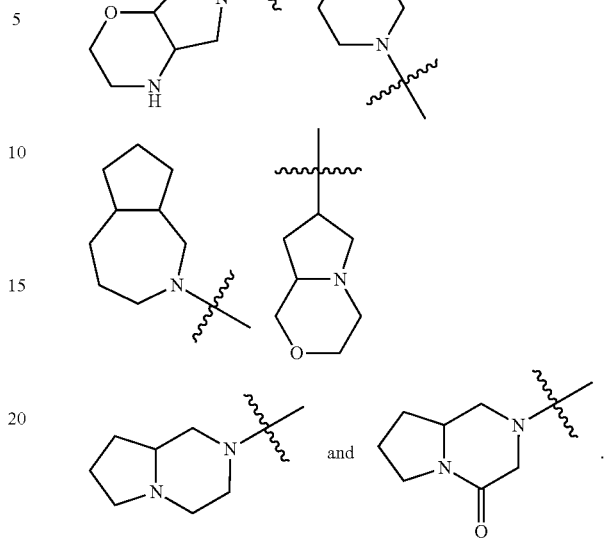

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and $S(O)_m$ (wherein m is an integer of 0 to 2), with the remaining ring atoms being carbon atoms. The bridged heterocyclyl is preferably a 6 to 14 membered bridged heterocyclyl, and more preferably a 7 to 10 membered bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

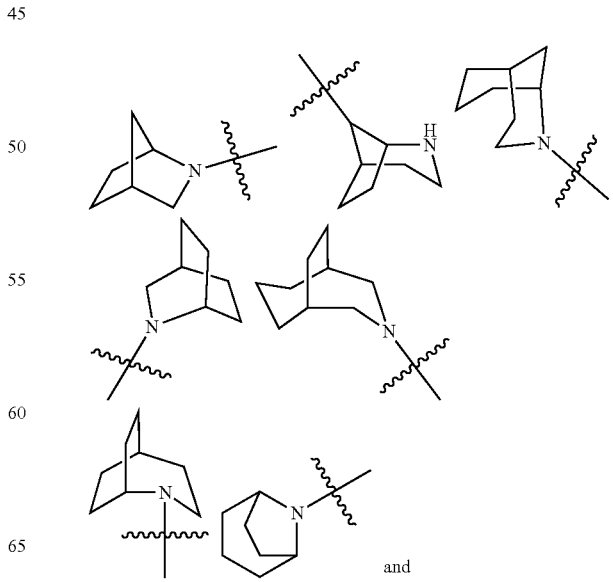

-continued

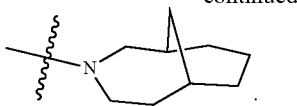

The heterocyclyl ring can be fused to the ring of aryl, heteroaryl or cycloalkyl, wherein the ring bound to the parent structure is heterocyclyl. Non-limiting examples thereof include:

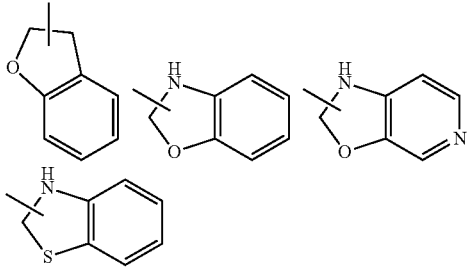

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy and alkoxycarbonyl.

The term "aryl" refers to a 6 to 14 membered all-carbon monocyclic ring or polycyclic fused ring (i.e. each ring in the system shares an adjacent pair of carbon atoms with another ring in the system) having a conjugated 21-electron system, preferably a 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. Non-limiting examples thereof include:

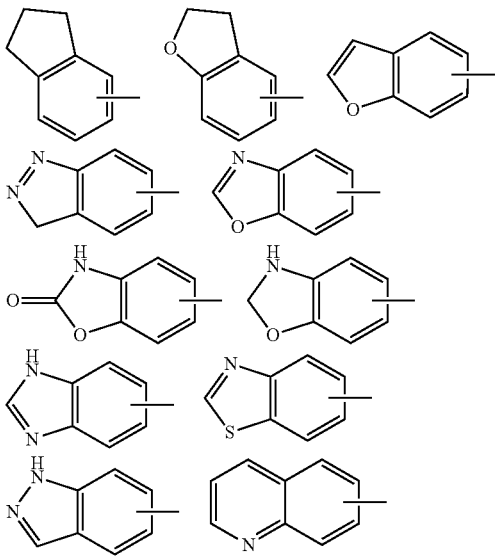

-continued

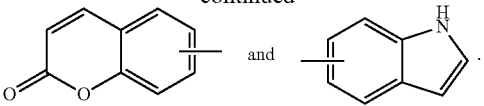

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 12 membered heteroaromatic system having 1 to 4 heteroatoms selected from the group consisting of O, S and N. The heteroaryl is preferably a 5 to 10 membered heteroaryl, and more preferably a 5 or 6 membered heteroaryl, for example imidazolyl, furyl, thienyl, thiazolyl, pyrazolyl, oxazolyl, pyrrolyl, triazolyl, tetrazolyl, pyridyl, pyrimidinyl, thiadiazolyl, pyrazinyl and the like, preferably triazolyl, tetrazolyl, thienyl, imidazolyl, pyrazolyl, pyridazinyl, pyrimidinyl, thiazolyl, oxazolyl, isoxazolyl or pyrimidinyl, and more preferably triazolyl, tetrazolyl, pyrazolyl, pyridyl, pyridazinyl, pyrimidinyl, thiazolyl, oxazolyl, isoxazolyl or imidazolyl. The heteroaryl ring can be fused to the ring of aryl, heterocyclyl or cycloalkyl, wherein the ring bound to the parent structure is heteroaryl ring. Non-limiting examples thereof include:

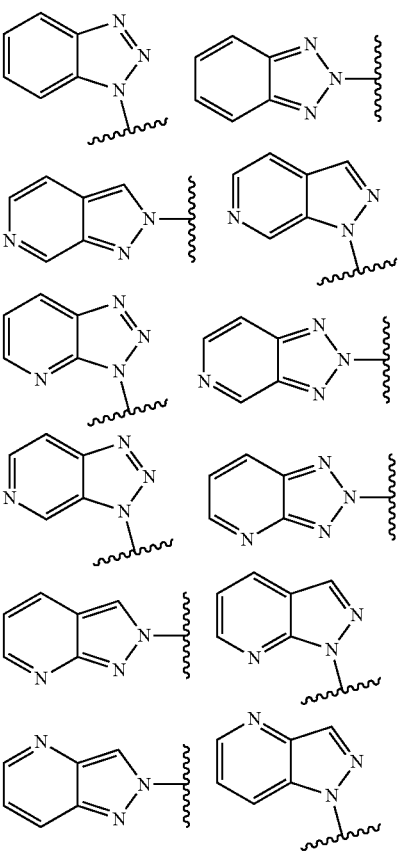

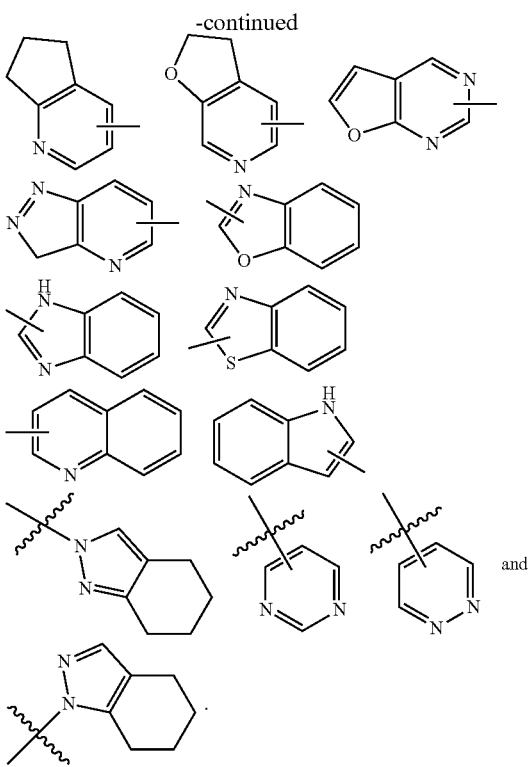

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "alkoxy" refers to an —O-(alkyl) or an —O-(unsubstituted cycloalkyl) group, wherein the alkyl is as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl group substituted by hydroxy(s), wherein the alkyl is as defined above.

"Alkenyl" refers to a chain alkenyl, also known as alkene group, which is a straight or branched chain group comprising 2 to 20 carbon atoms, preferably an alkenyl having 2 to 8 carbon atoms, more preferably an alkenyl having 2 to 6 carbon atoms, and most preferably an alkenyl having 2 to 3 carbon atoms. The alkenyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy or alkoxycarbonyl.

"Alkynyl" refers to (CH≡C—), which is a straight or branched chain group comprising 2 to 20 carbon atoms, preferably an alkynyl having 2 to 8 carbon atoms, more preferably an alkynyl having 2 to 6 carbon atoms, and most preferably an alkynyl having 2 to 3 carbon atoms. The alkynyl can be further substituted by other related group, for example alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

"Hydroxy" refers to an —OH group.
"Halogen" refers to fluorine, chlorine, bromine or iodine.
"Amino" refers to a —NH$_2$ group.
"Cyano" refers to a —CN group.
"Nitro" refers to a —NO$_2$ group.
"Carboxy" refers to a —C(O)OH group.
"THF" refers to tetrahydrofuran.
"EtOAc" refers to ethyl acetate.
"MeOH" refers to methanol.
"DMF" refers to N,N-dimethylformamide.
"DIPEA" refers to diisopropylethylamine.
"TFA" refers to trifluoroacetic acid.
"MeCN" refers to acetonitrile.
"DMA" refers to N,N-dimethylacetamide.
"Et$_2$O" refers to diethyl ether.
"DCE" refers to 1,2-dichloroethane.
"DIPEA" refers to N,N-diisopropylethylamine.
"NBS" refers to N-bromosuccinimide.
"NIS" refers to N-iodosuccinimide.
"Cbz-Cl" refers to benzyl chloroformate.
"Pd$_2$(dba)$_3$" refers to tris(dibenzylideneacetone)dipalladium.
"Dppf" refers to 1,1'-bisdiphenylphosphinoferrocene.
"HATU" refers to 2-(7-azabenzotriazol-1-yl)-N,N,N',N'-tetramethyluronium hexafluorophosphate.
"KHMDS" refers to potassium hexamethyldisilazide.
"LiHMDS" refers to lithium bis(trimethylsilyl)amide.
"MeLi" refers to methyl lithium.
"n-BuLi" refers to n-butyl lithium.
"NaBH(OAc)$_3$" refers to sodium triacetoxyborohydride.

Different expressions such as "X is selected from the group consisting of A, B or C", "X is selected from the group consisting of A, B and C", "X is A, B or C", "X is A, B and C" and the like, express the same meaning, that is, X can be any one or more of A, B and C.

The hydrogen atom of the present invention can be substituted by its isotope deuterium. Any of the hydrogen atoms in the compounds of the examples of the present invention can also be substituted by deuterium atom.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without excessive efforts. For example, the combination of amino or hydroxy having free hydrogen and carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to exert biological activity.

A "pharmaceutically acceptable salt" refers to a salt of the compound of the present invention, which is safe and effective in mammals and has the desired biological activity.

DETAILED DESCRIPTION OF THE INVENTION

The present invention will be further described with reference to the following examples, but the examples should not be considered as limiting the scope of the present invention.

EXAMPLES

The structures of the compounds of the present invention were identified by nuclear magnetic resonance (NMR) and/or liquid chromatography-mass spectrometry (LC-MS). NMR shifts (δ) are given in parts per million (ppm). NMR was determined by a Bruker AVANCE-400 machine. The solvents for determination were deuterated-dimethyl sulfoxide (DMSO-$d_6$), deuterated-methanol ($CD_3OD$) and deuterated-chloroform ($CDCl_3$), and the internal standard was tetramethylsilane (TMS).

Liquid chromatography-mass spectrometry (LC-MS) was determined on an Agilent 1200 Infinity Series mass spectrometer. High performance liquid chromatography (HPLC) was determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm. Yantai Huanghai 200 to 300 mesh silica gel was generally used as a carrier for column chromatography.

The raw materials used in the examples of the present invention are known and commercially available, or can be synthesized by adopting or according to known methods in the art.

Unless otherwise stated, all reactions of the present invention were carried out under continuous magnetic stirring under a dry nitrogen or argon atmosphere, the solvent was dry, and the reaction temperature was in degrees celsius.

Example 1

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)ethan-1-one

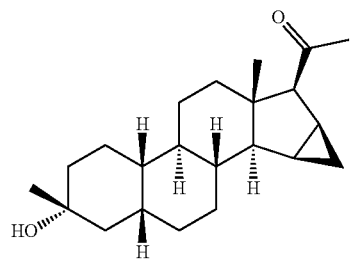

Step 1: Preparation of (3R,5R,8R,9R,10S,13S,14S)-3-hydroxy-3,13-dimethyl-16-(phenylsulfinyl)hexadecahydro-17H-cyclopenta[a]phenanthren-17-one

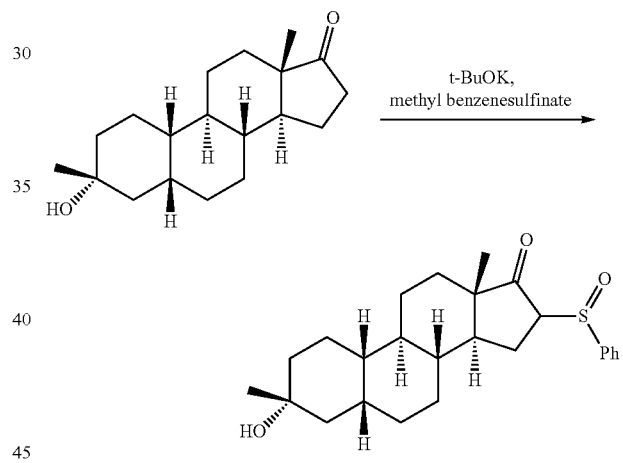

Potassium tert-butoxide (2.3 g, 20.7 mmol) was dissolved in anhydrous tetrahydrofuran (200 mL), and the reaction system was purged with nitrogen. (3R,5R,8R,9R,10S,13S,14S)-3-Hydroxy-3,13-dimethylhexadecahydro-17H-cyclopenta[a]phenanthren-17-one (3 g, 10.3 mmol) was added to the above solution to obtain an orange solution, which was then stirred at 25° C. for 10 minutes. Methyl benzenesulfinate (3.2 g, 20.7 mmol) was added, and then the reaction solution was stirred at 30° C. for half an hour. Water (100 mL) was added to the reaction solution to quench the reaction, and the aqueous phase was extracted with ethyl acetate (100 mL×3). The organic phases were combined, dried over anhydrous sodium sulfate, filtrated and concentrated. The resulting crude product was purified by column chromatography (petroleum ether/ethyl acetate: 50/1-3/1) to obtain (3R,5R,8R,9R,10S,13S,14S)-3-hydroxy-3,13-dimethyl-16-(phenylsulfinyl)hexadecahydro-17H-cyclopenta[a]phenanthren-17-one (3.5 g, yield: 82%).

Step 2: Preparation of (3R,5R,8R,9R,10S,13S,14S)-3-hydroxy-3,13-dimethyl-1,2,3,4,5,6,7,8,9,10,11,12,13,14-tetradecahydro-17H-cyclopenta[a]phenanthren-17-one

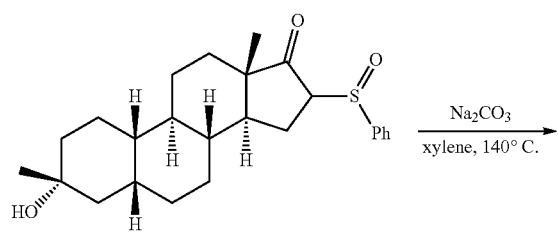

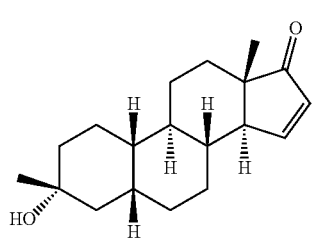

(3R,5R,8R,9R,10S,13S,14S)-3-Hydroxy-3,13-dimethyl-16-(phenylsulfinyl)hexadecahydro-17H-cyclopenta[a]phenanthren-17-one (3.5 g, 8.5 mmol) was dissolved in xylene (50 mL), and the reaction system was purged with nitrogen. Sodium carbonate (24.7 g, 0.17 mol) was added, and then the reaction solution was stirred at 140° C. overnight. The reaction solution was filtrated, and the organic phase was concentrated. The resulting crude product was purified by column chromatography (petroleum ether/ethyl acetate: 50/1-3/1) to obtain (3R,5R,8R,9R,10S,13S,14S)-3-hydroxy-3,13-dimethyl-1,2,3,4,5,6,7,8,9,10,11,12,13,14-tetradecahydro-17H-cyclopenta[a]phenanthren-17-one (1.5 g, yield: 62%).

$^1$H NMR (400 MHz, CDCl$_3$) δ 7.53 (dd, J=5.9, 1.2 Hz, 1H), 6.03 (dd, J=6.0, 3.2 Hz, 1H), 2.42-2.33 (m, 1H), 1.90-1.79 (m, 4H), 1.76-1.66 (m, 2H), 1.58-1.48 (m, 5H), 1.47-1.37 (m, 4H), 1.36-1.23 (m, 7H), 1.08 (s, 3H).

Step 3: Preparation of (2R,4aS,4bR,6aS,7aS,8aS,8bR,8cR,10aR)-2-hydroxy-2,6a-dimethylhexadecahydrocyclopropa[4,5]cyclopenta[1,2-a]phenanthren-7(1H)-one

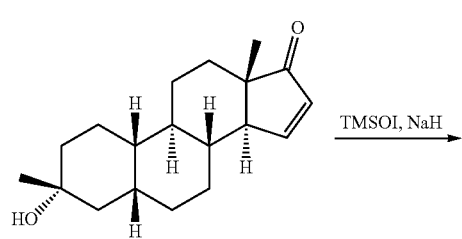

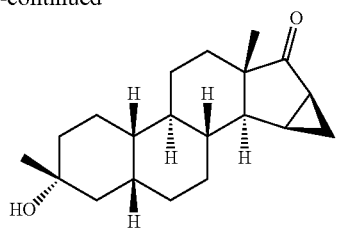

Trimethyl sulfoxide (0.92 g, 4.2 mmol) was dissolved in anhydrous dimethyl sulfoxide (10 mL), and the reaction system was purged with nitrogen. Sodium hydride (168 mg, 4.2 mmol) was added, and then the reaction solution was stirred for 1 hour. A solution of (3R,5R,8R,9R,10S,13S,14S)-3-hydroxy-3,13-dimethyl-1,2,3,4,5,6,7,8,9,10,11,12,13,14-tetradecahydro-17H-cyclopenta[a]phenanthren-17-one (1.0 g, 3.5 mmol) in dimethyl sulfoxide (5 mL) was added, and then the reaction solution was stirred at room temperature overnight. Water (50 mL) was added to the reaction solution to quench the reaction, and the aqueous phase was extracted with ethyl acetate (50 mL×3). The organic phases were combined, dried over anhydrous sodium sulfate, filtrated and concentrated. The resulting crude product was purified by column chromatography (petroleum ether/ethyl acetate: 50/1-3/1) to obtain (2R,4aS,4bR,6aS,7aS,8aS,8bR,8cR,10aR)-2-hydroxy-2,6a-dimethylhexadecahydrocyclopropa[4,5]cyclopenta[1,2-a]phenanthren-7(1H)-one (0.75 g, yield: 71%).

$^1$H NMR (400 MHz, CDCl$_3$) δ 2.06-2.00 (m, 1H), 1.97-1.91 (m, 1H), 1.88-1.79 (m, 3H), 1.78-1.67 (m, 6H), 1.63-1.54 (m, 2H), 1.48-1.39 (m, 3H), 1.37-1.25 (m, 9H), 1.15-1.05 (m, 2H), 0.96 (s, 3H).

Step 4: Preparation of (2R,4aS,4bR,6aS,7aS,8aR,8bR,8cR,10aR)-7-ethylidene-2,6a-dimethyloctadecahydrocyclopropa[4,5]cyclopenta[1,2-a]phenanthren-2-ol

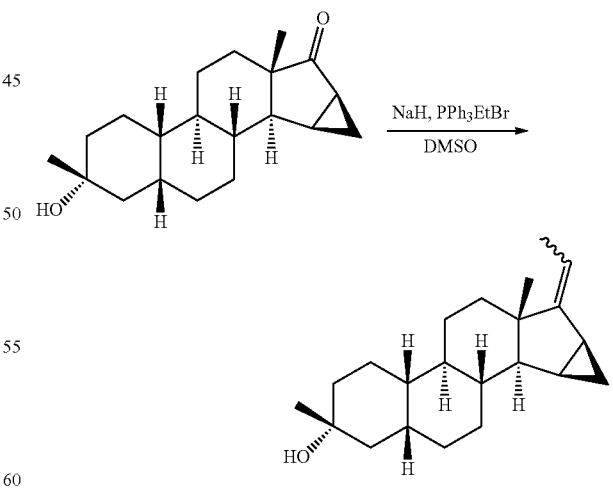

PPh$_3$EtBr (14.8 g, 40 mmol) was dissolved in anhydrous dimethyl sulfoxide (50 mL), and the reaction system was purged with nitrogen. Sodium hydride (1.6 g, 40 mmol) was added, and then the reaction solution was stirred at room temperature for 1 hour. (2R,4aS,4bR,6aS,7aS,8aS,8bR,8cR,10aR)-2-Hydroxy-2,6a-dimethylhexadecahydrocyclopropa

[4,5]cyclopenta[1,2-a]phenanthren-7(1H)-one (0.6 g, 2.0 mmol) was added, and then the reaction solution was stirred at 100° C. overnight. The reaction solution was cooled to room temperature. Water (200 mL) was added to the reaction solution to quench the reaction, and the aqueous phase was extracted with ethyl acetate (200 mL×2). The organic phases were combined, dried over anhydrous sodium sulfate, filtrated and concentrated. The resulting crude product was purified by column chromatography (petroleum ether/ethyl acetate: 50/1-3/1) to obtain (2R,4aS,4bR,6aS,7aS,8aR,8bR,8cR,10aR)-7-ethylidene-2,6a-dimethyloctadecahydrocyclopropa[4,5]cyclopenta[1,2-a]phenanthren-2-ol (0.5 g, yield: 81%).

Step 5: Preparation of (2R,4aS,4bR,6aS,7aS,8aR,8bR,8cR,10aR)-7-(1-hydroxyethyl)-2,6a-dimethyl-octadecahydrocyclopropa[4,5]cyclopenta[1,2-a]phenanthren-2-ol

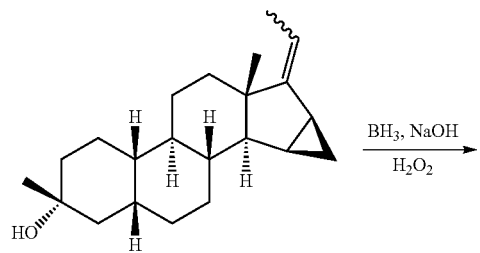

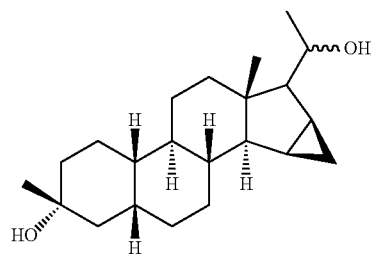

(2R,4aS,4bR,6aS,7aS,8aR,8bR,8cR,10aR)-7-Ethylidene-2,6a-dimethyloctadecahydrocyclopropa[4,5]cyclopenta[1,2-a]phenanthren-2-ol (0.4 g, 1.3 mmol) was dissolved in anhydrous tetrahydrofuran (10 mL). The solution was cooled to 0° C., and then BH$_3$/THF (12.7 mL, 12.7 mmol) was added dropwise. The reaction solution was stirred at room temperature for 3 hours, and TLC showed that the reaction was completed. The reaction solution was cooled to 0° C., and then 3 M aqueous NaOH solution (4 mL) was slowly added, followed by the addition of H$_2$O$_2$ (3 mL). The reaction solution was stirred at room temperature for 2 hours, and TLC showed that the reaction was completed. Ethyl acetate (50 mL) was added, and then the reaction solution was washed with saturated aqueous Na$_2$S$_2$O$_3$ solution (30 mL) and water (30 mL) successively. The organic phase was dried over anhydrous sodium sulfate, filtrated and concentrated to obtain the crude product (0.4 g, yield: 100%, crude), which was used directly in the next step.

Step 6: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

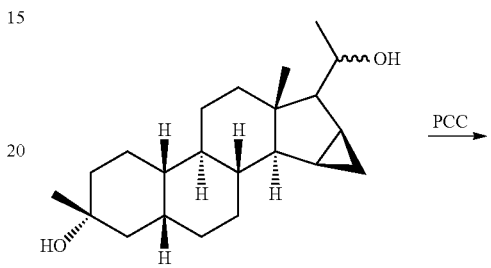

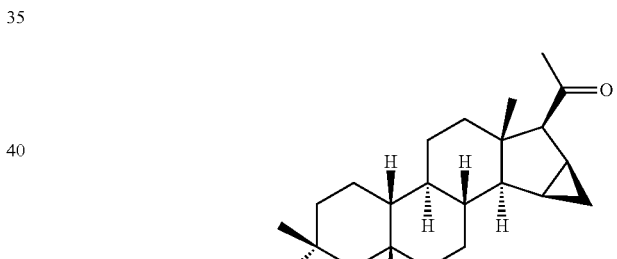

28

(2R,4aS,4bR,6aS,7aS,8aR,8bR,8cR,10aR)-7-(1-Hydroxyethyl)-2,6a-dimethyloctadecahydrocyclopropa[4,5]cyclopenta[1,2-a]phenanthren-2-ol (0.4 g, 1.2 mmol) was dissolved in dichloromethane (20 mL). PCC (0.52 g, 40 mmol) was added, and then the reaction solution was stirred at room temperature for 2 hours. The reaction solution was filtrated, and the organic phase was concentrated. The resulting crude product was purified by column chromatography (petroleum ether/ethyl acetate: 50/1-3/1) to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (0.35 g, yield: 83%).

$^1$H NMR (400 MHz, CDCl$_3$) δ 2.74 (d, J=4.1 Hz, 1H), 2.21 (s, 3H), 1.97-1.91 (m, 1H), 1.87-1.62 (m, 7H), 1.56-1.50 (m, 1H), 1.44-1.21 (m, 15H), 1.12-1.00 (m, 1H), 0.90-0.83 (m, 1H), 0.72 (s, 3H), 0.44-0.36 (m, 1H).

Example 2

Preparation of 1-(2-((2R,4aS,4bR,6aS,7S,7aS,8aR, 8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

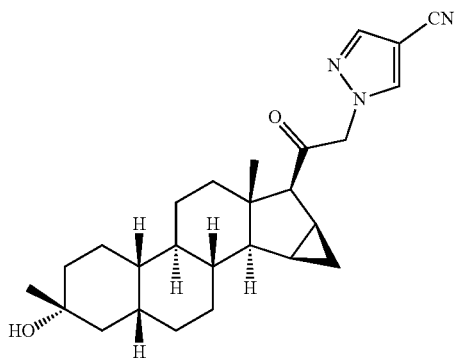

Step 1: Preparation of 2-bromo-1-((2R,4aS,4bR, 6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

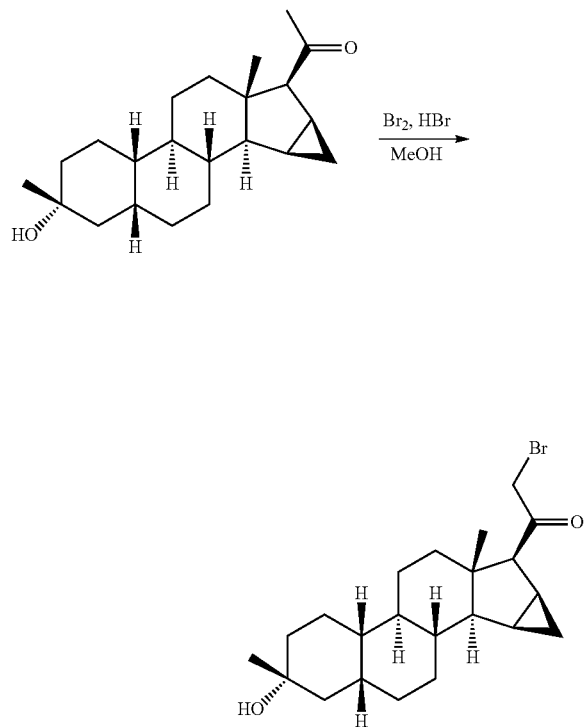

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)ethan-1-one (70 mg, 0.21 mmol) was dissolved in methanol (3 mL). A drop of hydrogen bromide was added to the solution, followed by the addition of liquid bromine (41 mg, 0.25 mmol), and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (87 mg, yield: 100%, crude), which was used directly in the next step.

Step 2: Preparation of 1-(2-((2R,4aS,4bR,6aS,7S, 7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

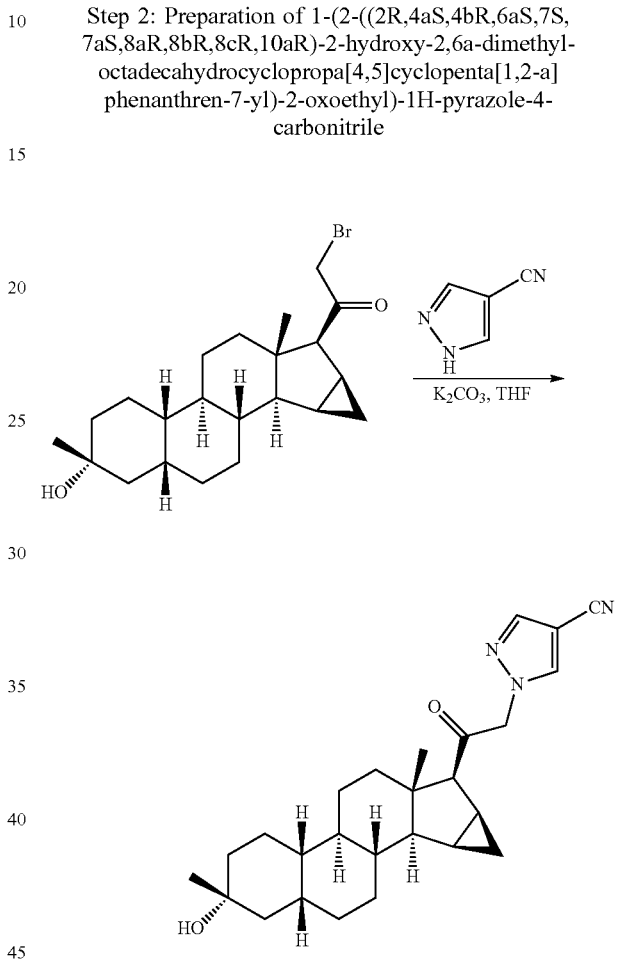

2-Bromo-1-((2R,4aS,4bR,6aS,7S,7aS,8aR,8bR,8cR, 10aR)-2-hydroxy-2,6a-dimethyloctadecahydrocyclopropa[4,5]cyclopenta[1,2-a]phenanthren-7-yl)ethan-1-one (87 mg, 0.21 mmol), 1H-pyrazole-4-carbonitrile (59 mg, 0.64 mmol) and potassium carbonate (145 mg, 1.05 mmol) were dissolved in tetrahydrofuran (2 mL), and the resulting reaction solution was stirred at room temperature overnight. The reaction solution was filtrated, and the filtrate was concentrated. The resulting crude product was purified by high performance liquid chromatography to obtain 1-(2-((2R, 4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (33 mg, yield: 37%).

MS m/z (ESI): 404.2 [M−H$_2$O+H]$^+$.

$^1$H NMR (400 MHz, CDCl$_3$) δ 7.88 (s, 1H), 7.82 (s, 1H), 5.24-5.13 (m, 2H), 2.84 (d, J=2.7 Hz, 1H), 1.98-1.92 (m, 1H), 1.87-1.77 (m, 4H), 1.76-1.66 (m, 3H), 1.57-1.51 (m, 1H), 1.46-1.24 (m, 15H), 1.12-1.02 (m, 1H), 1.00-0.96 (m, 1H), 0.78 (s, 3H), 0.54-0.46 (m, 1H).

Example 3 and Example 4

Preparation of 1-(2-((2R,4aS,4bR,6aS,7S,7aS,8aR,8bR,8cR,10aR)-2-hydroxy-2,6a-dimethyloctadeca-hydrocyclopropa[4,5]cyclopenta[1,2-a]phenanthren-7-yl)-2-oxoethyl)-1H-pyrazole-3-carbonitrile (3) 1-(2-((2R,4aS,4bR,6aS,7R,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-3-carbonitrile (4)

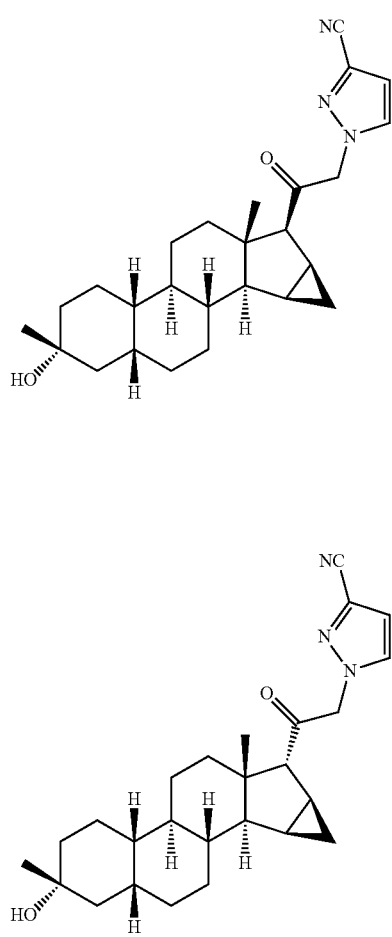

3

4

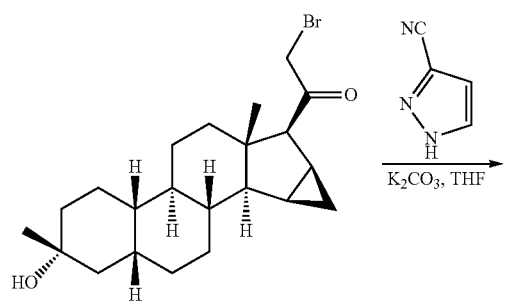

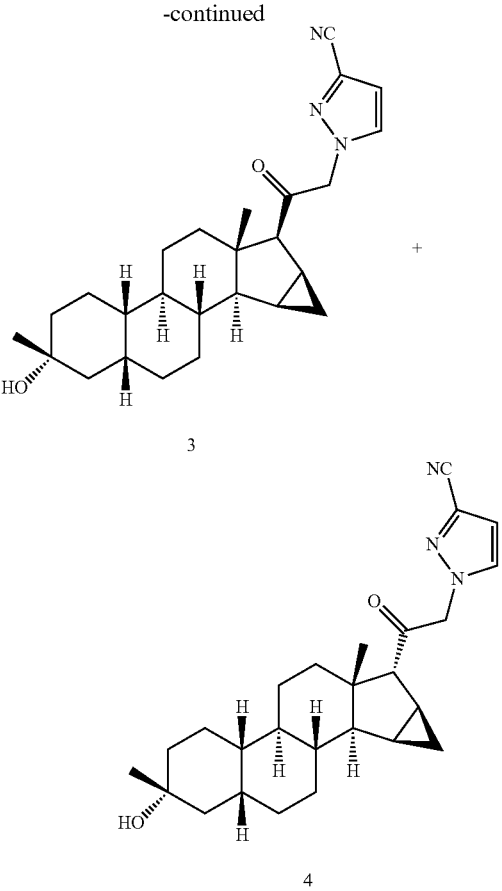

3

4

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.19 mmol), 1H-pyrazole-3-carbonitrile (55 mg, 0.58 mmol) and potassium carbonate (131 mg, 0.95 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-3-carbonitrile (34.7 mg, yield: 42%) and 1-(2-((2R,4aS,4bR,6aS,7R,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-3-carbonitrile (3.7 mg, yield: 4.5%).

Example 3

MS m/z (ESI): 404.2 [M−H$_2$O+H]$^+$ $^1$H NMR (400 MHz, CDCl$_3$) δ 7.50 (d, J=2.4 Hz, 1H), 6.74 (d, J=2.4 Hz, 1H), 5.29-5.13 (m, 2H), 2.83 (d, J=2.9 Hz, 1H), 1.97-1.92 (m, 1H), 1.86-1.79 (m, 4H), 1.73-1.64 (m, 3H), 1.58-1.52 (m, 1H), 1.43-1.27 (m, 15H), 1.12-0.96 (m, 2H), 0.79 (s, 3H), 0.53-0.44 (m, 1H).

Example 4

MS m/z (ESI): 404.2 [M−H$_2$O+H]$^+$.

$^1$H NMR (400 MHz, CDCl$_3$) δ 7.52 (d, J=2.4 Hz, 1H), 6.75 (d, J=2.4 Hz, 1H), 5.11-4.96 (m, 2H), 2.92 (s, 1H), 1.93-1.87 (m, 1H), 1.82-1.74 (m, 2H), 1.72-1.62 (m, 4H), 1.51 (s, 1H), 1.46-1.24 (m, 15H), 1.18-1.09 (m, 2H), 1.04 (s, 3H), 0.89-0.84 (m, 1H), 0.46-0.40 (m, 1H).

Example 5

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one

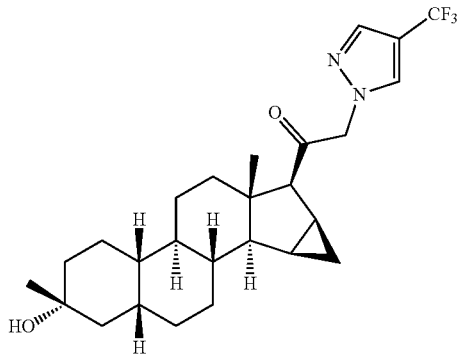

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one

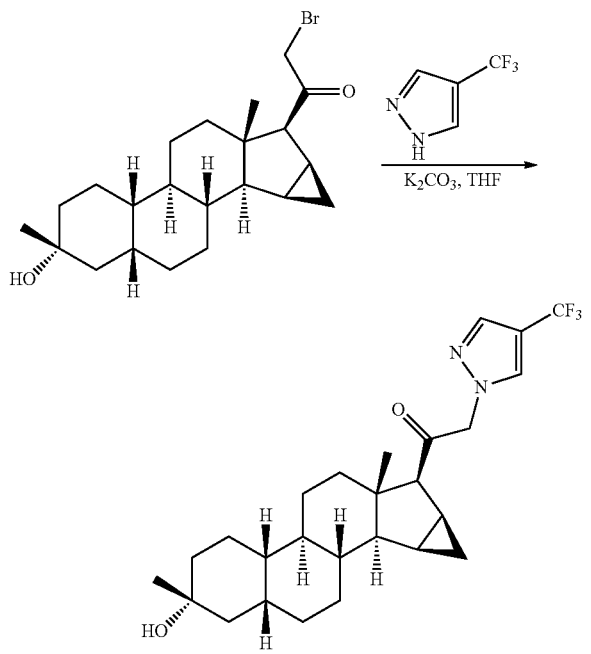

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (60 mg, 0.15 mmol), 4-(trifluoromethyl)-1H-pyrazole (60 mg, 0.44 mmol) and potassium carbonate (104 mg, 0.75 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(trifluoromethyl)-1H-pyrazol-1-yl)ethan-1-one (22.2 mg, yield: 33%).

MS m/z (ESI): 465.3 [M+H]$^+$.

$^1$H NMR (400 MHz, CDCl$_3$) δ 7.74 (s, 1H), 7.73 (s, 1H), 5.25-5.09 (m, 2H), 2.83 (d, J=3.6 Hz, 1H), 2.00-1.91 (m, 1H), 1.89-1.79 (m, 4H), 1.78-1.65 (m, 3H), 1.58-1.52 (m, 1H), 1.47-1.22 (m, 15H), 1.15-0.95 (m, 2H), 0.79 (s, 3H), 0.52-0.44 (m, 1H).

Example 6

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one

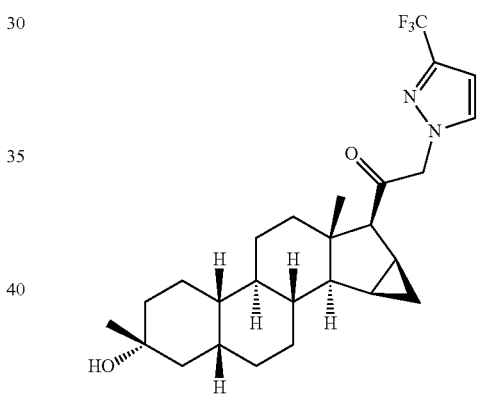

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one

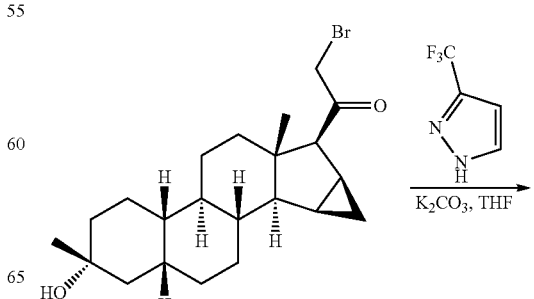

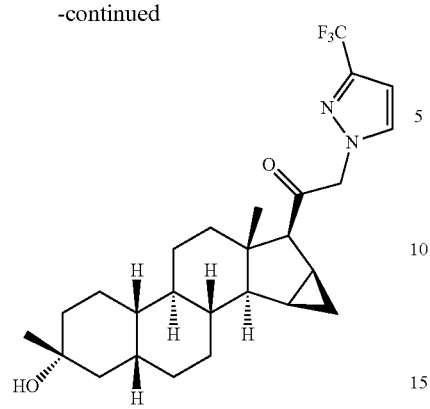

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.2 mmol), 3-(trifluoromethyl)-1H-pyrazole (80 mg, 0.6 mmol) and potassium carbonate (138 mg, 1.0 mmol) were dissolved in tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(3-(trifluoromethyl)-1H-pyrazol-1-yl)ethan-1-one (17 mg, yield: 18%).

MS m/z (ESI): 447.3 [M−H$_2$O+H]$^+$.

$^1$H NMR (400 MHz, CDCl$_3$) δ 7.49 (d, J=1.9 Hz, 1H), 6.60 (d, J=1.9 Hz, 1H), 5.27-5.13 (m, 2H), 2.83 (d, J=3.7 Hz, 1H), 1.99-1.90 (m, 1H), 1.89-1.76 (m, 4H), 1.75-1.61 (m, 3H), 1.58-1.50 (m, 1H), 1.50-1.21 (m, 15H), 1.13-0.96 (m, 2H), 0.79 (s, 3H), 0.52-0.45 (m, 1H).

Example 7 and Example 8

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(2H-1,2,3-triazol-2-yl)ethan-1-one (7)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-1,2,3-triazol-1-yl)ethan-1-one (8)

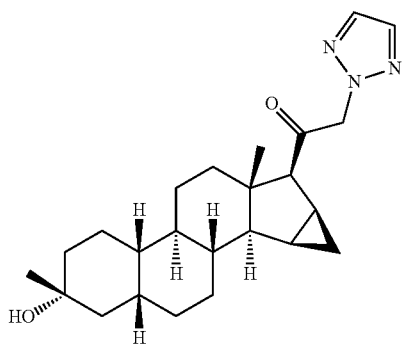

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-1,2,3-triazol-2-yl)ethan-1-one (7) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-1,2,3-triazol-1-yl)ethan-1-one (8)

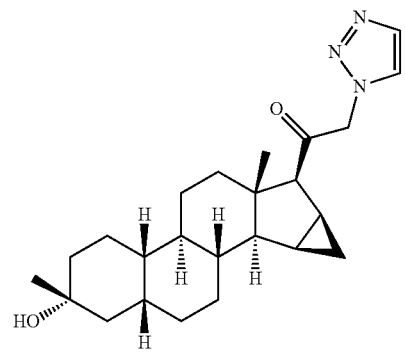

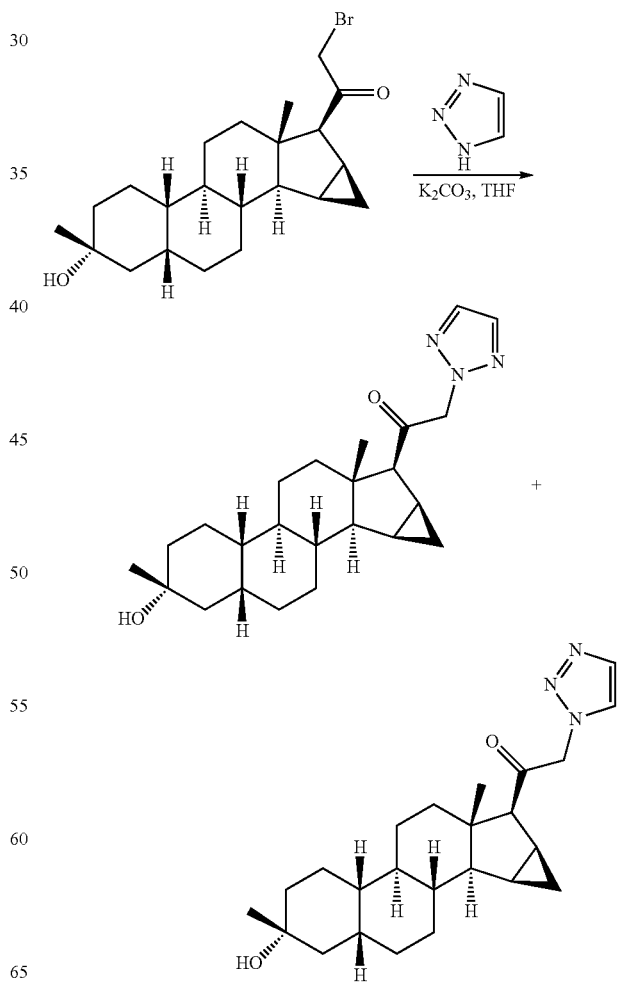

2-Bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (80 mg, 0.19 mmol), 1H-1,2,3-triazole (40 mg, 0.58 mmol) and potassium carbonate (131 mg, 0.95 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-1,2,3-triazol-2-yl)ethan-1-one (7) (9.2 mg, yield: 12%) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-1,2,3-triazol-1-yl)ethan-1-one (8) (17.8 mg, yield: 23%).

Example 7

MS m/z (ESI): 380.3 [M−H$_2$O+H]$^+$.

$^1$H NMR (400 MHz, CDCl$_3$) δ 7.69 (s, 2H), 5.55-5.36 (m, 2H), 2.82 (d, J=4.1 Hz, 1H), 1.99-1.92 (m, 1H), 1.87-1.74 (m, 4H), 1.73-1.52 (m, 5H), 1.47-1.26 (m, 14H), 1.14-0.98 (m, 2H), 0.84 (s, 3H), 0.52-0.43 (m, 1H).

Example 8

MS m/z (ESI): 398.3 [M+H]$^+$.

$^1$H NMR (400 MHz, CDCl$_3$) δ 7.76 (s, 1H), 7.66 (s, 1H), 5.52-5.35 (m, 2H), 2.87 (d, J=3.9 Hz, 1H), 2.02-1.92 (m, 1H), 1.89-1.78 (m, 4H), 1.76-1.65 (m, 3H), 1.59-1.52 (m, 1H), 1.48-1.23 (m, 15H), 1.15-0.98 (m, 2H), 0.80 (s, 3H), 0.56-0.45 (m, 1H).

Example 9 and Example 10

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(2H-tetrazol-2-yl)ethan-1-one (9)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-tetrazol-1-yl)ethan-1-one (10)

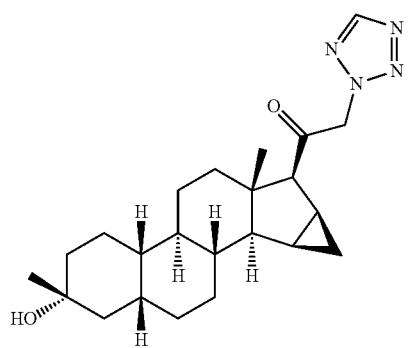

9

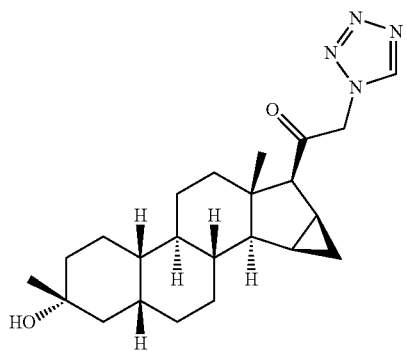

10

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-tetrazol-2-yl)ethan-1-one (9) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-tetrazol-1-yl)ethan-1-one (10)

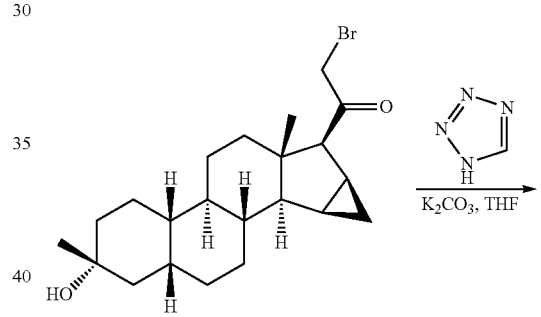

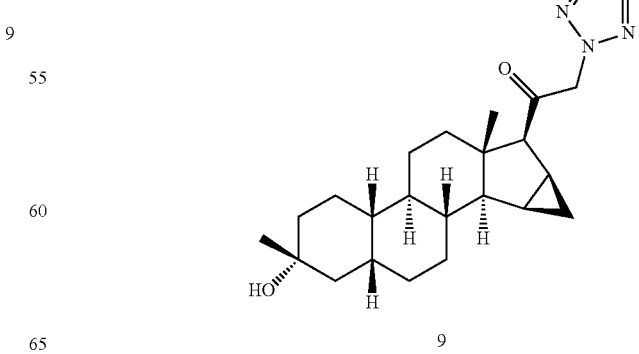

9

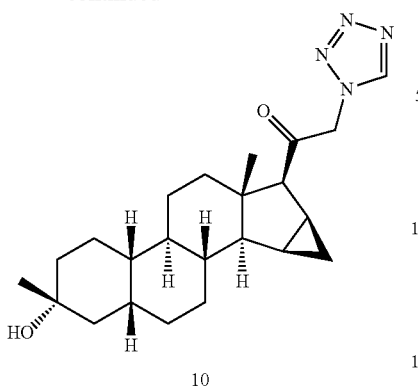

2-Bromo-1-((2R,4aS,4bR,6aS,7S,7aS,8aR,8bR,8cR, 10aR)-2-hydroxy-2,6a-dimethyloctadecahydrocyclopropa [4,5]cyclopenta[1,2-a]phenanthren-7-yl)ethan-1-one (50 mg, 0.12 mmol), 1H-tetrazole (26 mg, 0.37 mmol) and potassium carbonate (83 mg, 0.6 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS,4bR,6aS,7S, 7aS,8aR,8bR,8cR,10aR)-2-hydroxy-2,6a-dimethylocta-decahydrocyclopropa[4,5]cyclopenta[1,2-a]phenanthren-7-yl)-2-(2H-tetrazol-2-yl)ethan-1-one (9) (11.6 mg, yield: 24%) and 1-((2R,4aS,4bR,6aS,7S,7aS,8aR,8bR,8cR,10aR)-2-hydroxy-2,6a-dimethyloctadecahydrocyclopropa[4,5]cy-clopenta[1,2-a]phenanthren-7-yl)-2-(1H-tetrazol-1-yl) ethan-1-one (10) (4.4 mg, yield: 9%).

Example 9

MS m/z (ESI): 381.2 [M−H$_2$O+H]$^+$ $^1$H NMR (400 MHz, CDCl$_3$) δ 8.58 (s, 1H), 5.74-5.62 (m, 2H), 2.88 (d, J=3.8 Hz, 1H), 1.97-1.91 (m, 1H), 1.87-1.79 (m, 4H), 1.75-1.64 (m, 3H), 1.58-1.55 (m, 1H), 1.45-1.35 (m, 7H), 1.34-1.24 (m, 8H), 1.14-1.01 (m, 2H), 0.85 (s, 3H), 0.56-0.48 (m, 1H).

Example 10

MS m/z (ESI): 399.3 [M+H]$^+$ $^1$H NMR (400 MHz, CDCl$_3$) δ 8.77 (s, 1H), 5.57-5.39 (m, 2H), 2.90 (s, 1H), 2.00-1.91 (m, 1H), 1.88-1.79 (m, 4H), 1.76-1.65 (m, 3H), 1.59-1.56 (m, 1H), 1.46-1.37 (m, 7H), 1.35-1.24 (m, 8H), 1.13-0.99 (m, 2H), 0.79 (s, 3H), 0.58-0.49 (m, 1H).

Example 11

1-((2R,4aS,4bR,6aS,7S,7aS,8aR,8bR,8cR,10aR)-2-Hydroxy-2,6a-dimethyloctadecahydrocyclopropa[4, 5]cyclopenta[1,2-a]phenanthren-7-yl)-2-(4-(methyl-sulfonyl)piperazin-1-yl)ethan-1-one

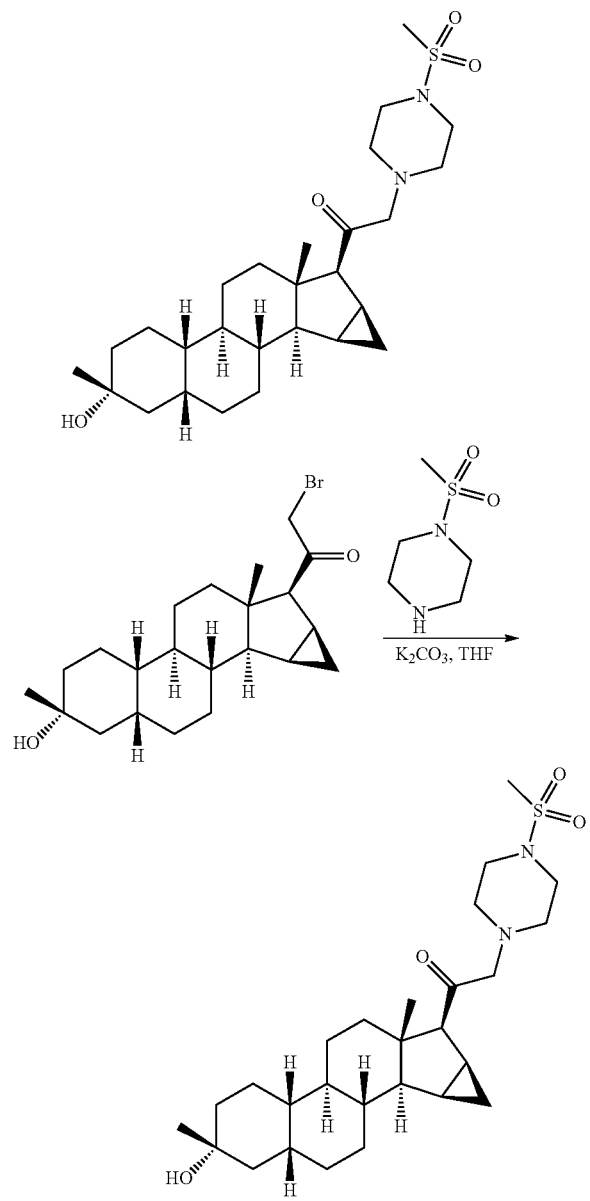

2-Bromo-1-((2R,4aS,4bR,6aS,7S,7aS,8aR,8bR,8cR, 10aR)-2-hydroxy-2,6a-dimethyloctadecahydrocyclopropa [4,5]cyclopenta[1,2-a]phenanthren-7-yl)ethan-1-one (50 mg, 0.12 mmol), 1-(methylsulfonyl)piperazine (60 mg, 0.36 mmol) and potassium carbonate (83 mg, 0.6 mmol) were dissolved in tetrahydrofuran (3 mL), and the resulting reaction solution was stirred at room temperature overnight. The reaction solution was filtrated, and the filtrate was concentrated. The resulting crude product was purified by high performance liquid chromatography to obtain 1-((2R,4aS, 4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)piperazin-1-yl)ethan-1-one (13.7 mg, yield: 23%).

MS m/z (ESI): 493.2 [M+H]+.

1H NMR (400 MHz, CDCl3) δ 3.63 (br, 2H), 3.47 (br, 4H), 2.93 (br, 4H), 2.82 (s, 3H), 2.73 (s, 1H), 1.90-1.88 (m, 1H), 1.86-1.81 (m, 2H), 1.81-1.70 (m, 3H), 1.70-1.64 (m, 2H), 1.57-1.50 (m, 1H), 1.41 (s, 5H), 1.34-1.22 (m, 10H), 1.12-0.99 (m, 1H), 0.92-0.85 (m, 1H), 0.73 (s, 3H), 0.49-0.39 (m, 1H).

Example 12

1-((3R,8R,9R,10S,13S,14S,16R,17S)-16-Fluoro-3-hydroxy-3,13-dimethylhexadecahydro-1H-cyclopenta[a]phenanthren-17-yl)ethan-1-one

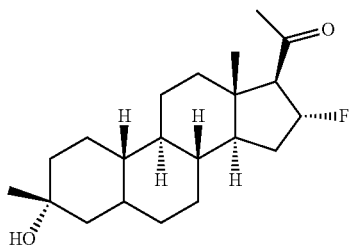

Step 1: Preparation of (3R,5R,8R,9R,10S,13S,14S,16R)-16-fluoro-3-hydroxy-3,13-dimethylhexadecahydro-17H-cyclopenta[a]phenanthren-17-one

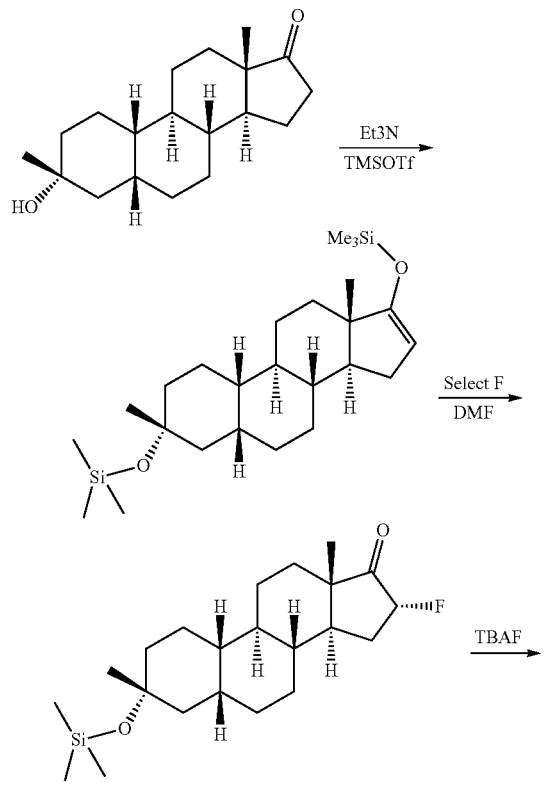

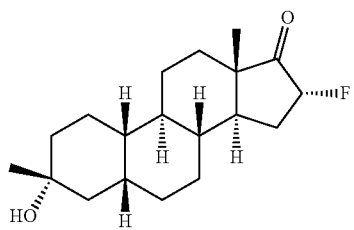

Trimethylsilyl triflate (5.6 mL, 31.0 mmol) was added dropwise to a solution of (3R,5R,8R,9R,10S,13S,14S)-3-hydroxy-3,13-dimethylhexadecahydro-17H-cyclopenta[a]phenanthren-17-one (3 g, 10.3 mmol) and triethylamine (36.0 mL, 258.2 mmol) in toluene (45 mL), and the resulting reaction solution was heated to reflux for 2 hours. The reaction solution was cooled, washed with saturated sodium bicarbonate, and extracted with n-hexane. The organic phase was concentrated to dryness to obtain the crude product (((3R,5R,8R,9R,10S,13S,14S)-3,13-dimethyl-2,3,4,5,6,7,8,9,10,11,12,13,14,15-tetradecahydro-1H-cyclopenta[a]phenanthrene-3,17-diyl)bis(oxy))bis(trimethylsilane). A selective fluorine reagent (4.0 g, 11.4 mmol) was added to a solution of (((3R,5R,8R,9R,10S,13S,14S)-3,13-dimethyl-2,3,4,5,6,7,8,9,10,11,12,13,14,15-tetradecahydro-1H-cyclopenta[a]phenanthrene-3,17-diyl)bis(oxy))bis(trimethylsilane) in N,N-dimethylformamide (25 mL), and the resulting reaction solution was stirred at room temperature for 2 hours to obtain (3R,5R,8R,9R,10S,13S,14S,16R)-16-fluoro-3,13-dimethyl-3-((trimethylsilyl)oxy)hexadecahydro-17H-cyclopenta[a]phenanthren-17-one. A solution of tetrabutylammonium fluoride in tetrahydrofuran (11.4 mL, 1 M) was added, and the resulting reaction solution was stirred at room temperature overnight. The reaction solution was extracted with ethyl acetate, and washed with saturated saline three times. The organic phase was concentrated to dryness, and the resulting crude product was purified by column chromatography (petroleum ether:ethyl acetate=6:4) to obtain (3R,5R,8R,9R,10S,13S,14S,16R)-16-fluoro-3-hydroxy-3,13-dimethylhexadecahydro-17H-cyclopenta[a]phenanthren-17-one (2.0 g, yield: 50.9%).

1H NMR (400 MHz, CDCl3) δ 5.09 (dd, J=50.6, 7.5 Hz, 1H), 2.18-1.58 (m, 10H), 1.54-1.01 (m, 14H), 0.92 (s, 3H).

19F NMR (376 MHz, CDCl3) δ -192.59.

Step 2: Preparation of (3R,5R,8R,9R,10S,13S,14S,16R)-17-ethylidene-16-fluoro-3,13-dimethylhexadecahydro-1H-cyclopenta[a]phenanthren-3-ol

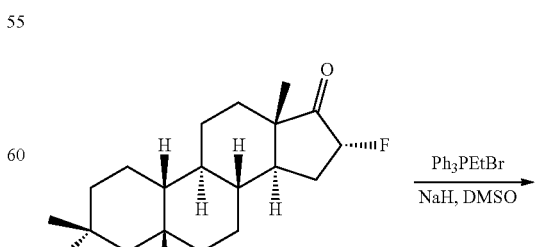

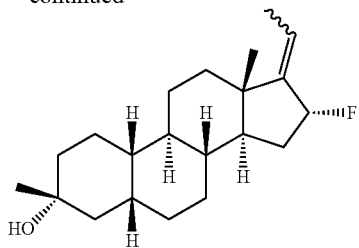

Sodium hydride (123 mg, 3.08 mmol, 60% w/w) was added to a solution of ethyltriphenylphosphonium bromide (1.2 g, 3.24 mmol) in dimethyl sulfoxide (20 mL) in batches under a nitrogen atmosphere, and the resulting reaction solution was stirred at room temperature for 1 hour. (3R,5R,8R,9R,10S,13S,14S,16R)-16-Fluoro-3-hydroxy-3,13-dimethylhexadecahydro-17H-cyclopenta[a]phenanthren-17-one (200 mg, 0.65 mmol) was added, and the reaction solution was heated to 70° C. under a nitrogen atmosphere overnight. The reaction solution was cooled, and saturated saline was added. 1 N hydrochloric acid was added to adjust pH to 6, and the reaction solution was extracted with ethyl acetate. The organic phase was washed with saturated saline, and concentrated to dryness to obtain a crude product. The crude product was purified by column chromatography (petroleum ether:ethyl acetate=7:3) to obtain (3R,5R,8R,9R,10S,13S,14S,16R)-17-ethylidene-16-fluoro-3,13-dimethylhexadecahydro-1H-cyclopenta[a]phenanthren-3-ol (80 mg, yield: 38.5%).

$^1$H NMR (400 MHz, CDCl$_3$) δ 5.71-5.59 (m, 1H), 5.12 (dt, J=57.2, 7.0 Hz, 1H), 2.27-2.11 (m, 2H), 1.92-1.24 (m, 21H), 1.22-1.09 (m, 4H), 1.06 (s, 3H).

$^{19}$F NMR (376 MHz, CDCl$_3$) δ −153.69.

Step 3: Preparation of (3R,8R,9R,10S,13S,14S,16R,17S)-16-fluoro-17-(1-hydroxyethyl)-3,13-dimethylhexadecahydro-1H-cyclopenta[a]phenanthren-3-ol

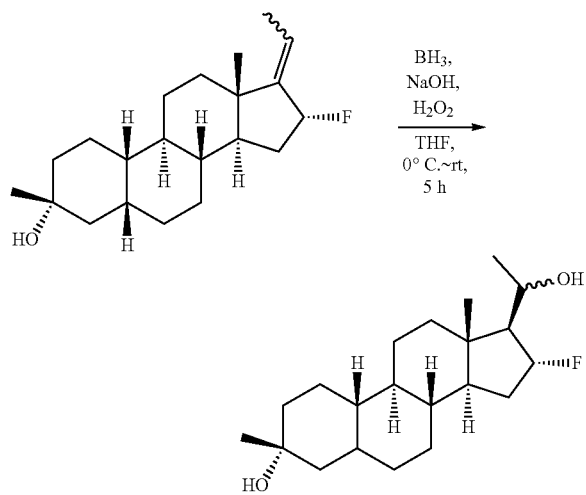

(3R,5R,8R,9R,10S,13S,14S,16R)-17-Ethylidene-16-fluoro-3,13-dimethylhexadecahydro-1H-cyclopenta[a]phenanthren-3-ol (80 mg, 0.25 mmol) was dissolved in anhydrous tetrahydrofuran (50 mL). A solution of borane in tetrahydrofuran (1 M, 2.5 mL) was added dropwise at room temperature, and the resulting reaction solution was stirred at room temperature for 1 hour. The reaction solution was cooled with ice water, and sodium hydroxide solution (3 M, 1 mL) was slowly added dropwise to release a large amount of gas. Hydrogen peroxide (25%, 0.58 mL) was slowly added dropwise, and then the reaction solution was stirred at room temperature for 2 hours. The reaction solution was extracted with ethyl acetate, washed with sodium thiosulfate solution and saturated saline, and dried to obtain (3R,8R,9R,10S,13S,14S,16R,17S)-16-fluoro-17-(1-hydroxyethyl)-3,13-dimethylhexadecahydro-1H-cyclopenta[a]phenanthren-3-ol (80 mg), which was used directly in the next step.

$^1$H NMR (400 MHz, CDCl$_3$) δ 5.47-5.16 (m, 1H), 4.22-4.05 (m, 1H), 2.42-2.17 (m, 1H), 1.94-0.93 (m, 27H), 0.87 (s, 3H).

$^{19}$F NMR (376 MHz, CDCl$_3$) δ −178.27.

Step 4: Preparation of 1-((3R,8R,9R,10S,13S,14S,16R,17S)-16-fluoro-3-hydroxy-3,13-dimethylhexadecahydro-1H-cyclopenta[a]phenanthren-17-yl)ethan-1-one

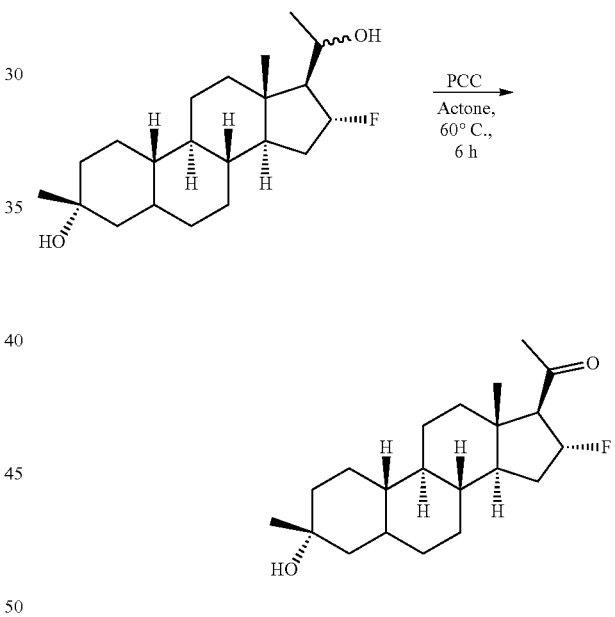

Pyridinium chlorochromate (102 mg, 0.47 mmol) was added to a solution of (3R,8R,9R,10S,13S,14S,16R,17S)-16-fluoro-17-(1-hydroxyethyl)-3,13-dimethylhexadecahydro-1H-cyclopenta[a]phenanthren-3-ol (80 mg) in acetone (2 mL), and the resulting reaction solution was reacted at 60° C. for 6 hours. The reaction solution was concentrated to dryness, and the resulting residue was purified by column chromatography (petroleum ether:ethyl acetate=5:2) to obtain 1-((3R,8R,9R,10S,13S,14S,16R,17S)-16-fluoro-3-hydroxy-3,13-dimethylhexadecahydro-1H-cyclopenta[a]phenanthren-17-yl)ethan-1-one (22 mg, yield: 25%).

$^1$H NMR (400 MHz, CDCl$_3$) δ 5.64-5.35 (m, 1H), 2.44-2.09 (m, 6H), 1.97-1.75 (m, 4H), 1.74-1.00 (m, 20H), 0.98-0.68 (m, 2H).

$^{19}$F NMR (376 MHz, CDCl$_3$) δ −168.20.

Example 13

1-(2-((3R,5R,8R,9R,10S,13S,14S,15R)-3-Hydroxy-3,13,15-trimethylhexadecahydro-1H-cyclopenta[a]phenanthren-17-yl)-2-oxoethyl)-1H-pyrazole-4-carbonitrile

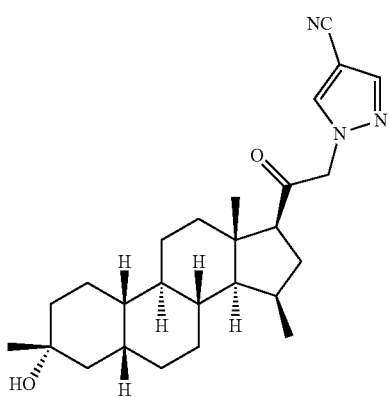

Step 1: (3R,5R,8R,9R,10S,13S,14S,15R)-3-Hydroxy-3,13,15-trimethylhexadecahydro-17H-cyclopenta[a]phenanthren-17-one

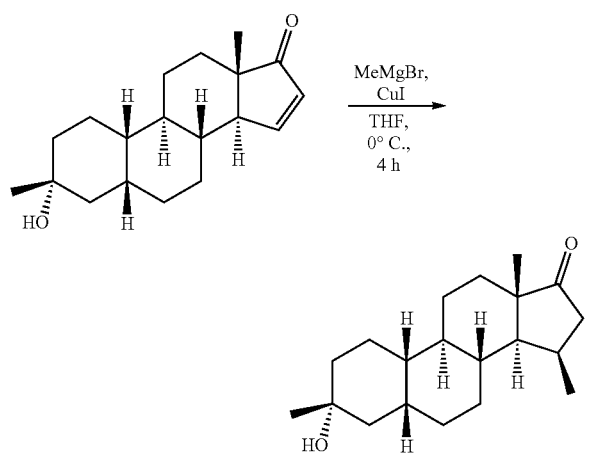

3.0 M methylmagnesium bromide (8.5 mL, 25.5 mmol) and 20 mL of anhydrous tetrahydrofuran were added to a dry 100 mL round bottom flask. The reaction system was purged with nitrogen, and cooled to 0° C. Cuprous iodide (3.94 g, 20.7 mmol) was added, and then the reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (2 g, 6.9 mmol) was dissolved in 10 ml of anhydrous tetrahydrofuran, and the resulting solution was slowly added dropwise to the reaction system. The reaction solution was stirred for 3 hours, and TLC showed that the reaction was completed. Saturated ammonium chloride solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (petroleum ether:ethyl acetate=2:1) to obtain (3R,5R,8R,9R,10S,13S,14S,15R)-3-hydroxy-3,13,15-trimethylhexadecahydro-17H-cyclopenta[a]phenanthren-17-one (1.56 g, yield: 75%).

$^1$H NMR (400 MHz, CDCl$_3$) δ 2.51-2.42 (m, 2H), 2.24 (d, J=17.6 Hz, 1H), 1.89-1.63 (m, 7H), 1.54-1.18 (m, 16H), 1.10 (d, J=7.6 Hz, 3H), 1.03 (s, 3H).

Step 2: (3R,5R,8R,9R,10S,13S,14S,15R,E)-17-Ethylidene-3,13,15-trimethylhexadecahydro-1H-cyclopenta[a]phenanthren-3-ol

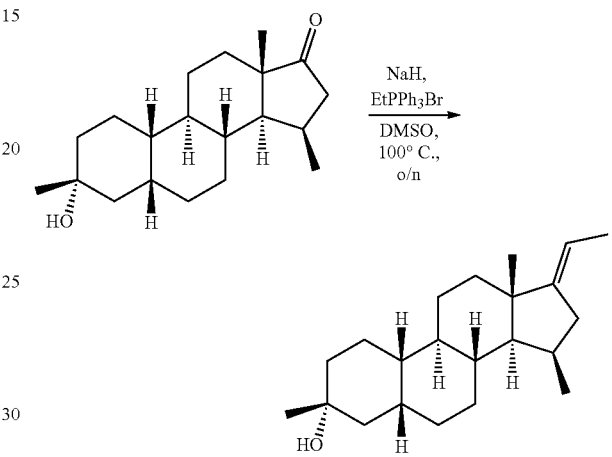

Ethyltriphenylphosphonium bromide (18.5 g, 50 mmol) was dissolved in anhydrous dimethyl sulfoxide (50 mL), and the reaction system was purged with nitrogen. Sodium hydride (2.0 g, 50 mmol) was added, and then the reaction solution was stirred at room temperature for 1 hour. (3R,5R,8R,9R,10S,13S,14S,15R)-3-Hydroxy-3,13,15-trimethylhexadecahydro-17H-cyclopenta[a]phenanthren-17-one (1.52 g, 5 mmol) was added, and then the reaction solution was stirred at 100° C. overnight. The reaction solution was cooled to room temperature. Water (200 mL) was added to the reaction solution to quench the reaction, and the aqueous phase was extracted with ethyl acetate (200 mL×2). The organic phases were combined, dried over anhydrous sodium sulfate, filtrated and concentrated. The resulting crude product was purified by column chromatography (petroleum ether/ethyl acetate: 50/1-3/1) to obtain (3R,5R,8R,9R,10S,13S,14S,15R,E)-17-ethylidene-3,13,15-trimethylhexadecahydro-1H-cyclopenta[a]phenanthren-3-ol (1.37 g, yield: 86%).

Step 3: (3R,5R,8R,9R,10S,13S,14S,15R,17S)-17-((R)-1-Hydroxyethyl)-3,13,15-trimethylhexadecahydro-1H-cyclopenta[a]phenanthren-3-ol

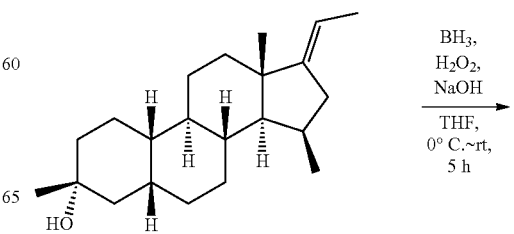

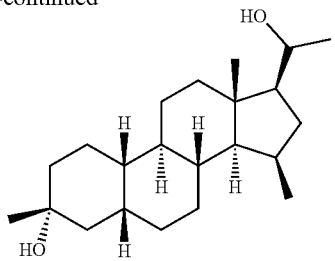

(3R,5R,8R,9R,10S,13S,14S,15R,E)-17-Ethylidene-3,13,15-trimethylhexadecahydro-1H-cyclopenta[a]phenanthren-3-ol (1.37 g, 4.33 mmol) was dissolved in anhydrous tetrahydrofuran (50 mL). The solution was cooled to 0° C., and then BH$_3$/THF (43 mL, 43 mmol) was added dropwise. The reaction solution was stirred at room temperature for 3 hours, and TLC showed that the reaction was completed. The reaction solution was cooled to 0° C., and then 3 M aqueous NaOH solution (40 mL) was slowly added, followed by the addition of H$_2$O$_2$ (30 mL). The reaction solution was stirred at room temperature for 2 hours, and TLC showed that the reaction was completed. Ethyl acetate (50 mL) was added, and then the reaction solution was washed with saturated aqueous Na$_2$S$_2$O$_3$ solution (30 mL) and water (30 mL) successively. The organic phase was dried over anhydrous sodium sulfate, filtrated and concentrated to obtain the crude product (1.37 g), which was used directly in the next step.

Step 4: 1-((3R,5R,8R,9R,10S,13S,14S,15R,17S)-3-Hydroxy-3,13,15-trimethylhexadecahydro-1H-cyclopenta[a]phenanthren-17-yl)ethan-1-one

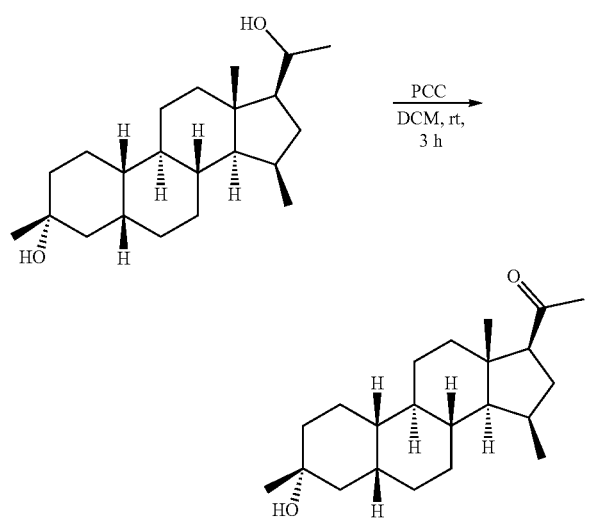

(3R,5R,8R,9R,10S,13S,14S,15R,17S)-17-((R)-1-Hydroxyethyl)-3,13,15-trimethyl hexadecahydro-1H-cyclopenta[a]phenanthren-3-ol (1.37 g, crude) was dissolved in dichloromethane (30 mL). PCC (1.8 g, 8.66 mmol) was added, and then the reaction solution was stirred at room temperature for 2 hours. The reaction solution was filtrated, and the organic phase was concentrated. The resulting crude product was purified by column chromatography (petroleum ether/ethyl acetate: 1/1) to obtain 1-((3R,5R,8R,9R,10S,13S,14S,15R,17S)-3-hydroxy-3,13,15-trimethylhexadecahydro-1H-cyclopenta[a]phenanthren-17-yl)ethan-1-one (780 mg, yield of two steps: 54.3%).

$^1$H NMR (400 MHz, CDCl$_3$) δ 2.49 (dd, J=8.8, 10.4 Hz, 1H), 2.14-2.03 (m, 5H), 1.95-1.79 (m, 5H), 1.69-1.06 (m, 18H), 0.96 (d, J=7.2 Hz, 3H), 0.78 (s, 3H).

Step 5: 2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one

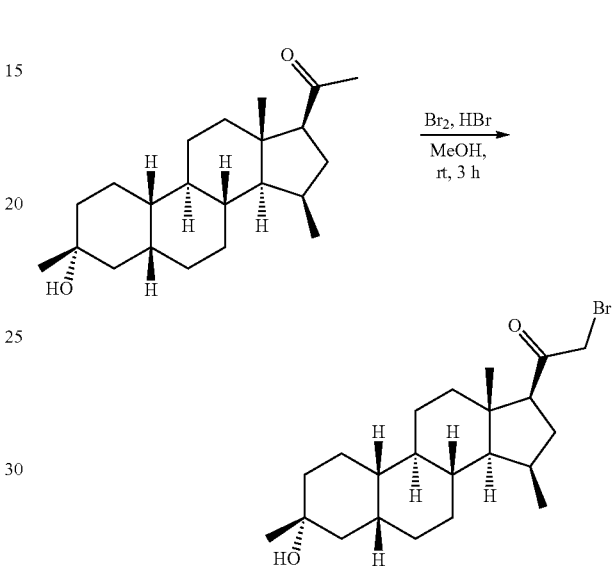

1-((3R,5R,8R,9R,10S,13S,14S,15R,17S)-3-Hydroxy-3,13,15-trimethylhexadecahydro-1H-cyclopenta[a]phenanthren-17-yl)ethan-1-one (333 mg, 1 mmol) was dissolved in methanol (10 mL). A drop of hydrogen bromide was added to the solution, followed by the addition of liquid bromine (176 mg, 1.1 mmol) was added, and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (413 mg, crude), which was used directly in the next step.

Step 6: 1-(2-((3R,5R,8R,9R,10S,13S,14S,15R)-3-Hydroxy-3,13,15-trimethylhexadecahydro-1H-cyclopenta[a]phenanthren-17-yl)-2-oxoethyl)-1H-pyrazole-4-carbonitrile

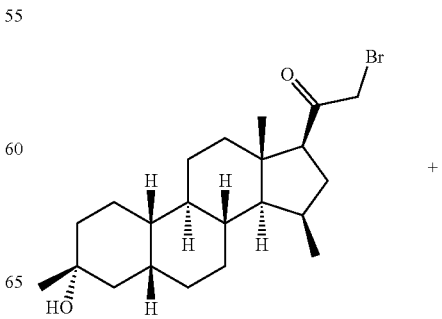

93

-continued

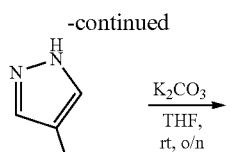

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 1H-pyrazole-4-carbonitrile (28 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-(2-((3R,5R,8R,9R,10S,13S,14S,15R)-3-hydroxy-3,13,15-trimethylhexadecahydro-1H-cyclopenta[a]phenanthren-17-yl)-2-oxoethyl)-1H-pyrazole-4-carbonitrile (41 mg, yield: 48%).

$^1$H NMR (400 MHz, CDCl$_3$) δ 7.86 (s, 1H), 7.81 (s, 1H), 5.01 (d, J=17.9 Hz, 1H), 4.90 (d, J=17.9 Hz, 1H), 2.62-2.48 (m, 1H), 2.30-2.06 (m, 3H), 2.04-1.75 (m, 7H), 1.75-1.04 (m, 15H), 0.99 (d, J=7.1 Hz, 3H), 0.84 (s, 3H).

MS m/z (ESI): 424.6 [M+H]$^+$.

94

Example 14 and Example 15

1-(2-((3R,5R,10S,13S,16R)-16-Fluoro-3-hydroxy-3,13-dimethylhexadecahydro-1H-cyclopenta[a]phenanthren-17-yl)-2-oxoethyl)-1H-pyrazole-4-carbonitrile (14) 1-(2-((3R,5R,10S,13S,16S)-16-Fluoro-3-hydroxy-3,13-dimethylhexadecahydro-1H-cyclopenta[a]phenanthren-17-yl)-2-oxoethyl)-1H-pyrazole-4-carbonitrile (15)

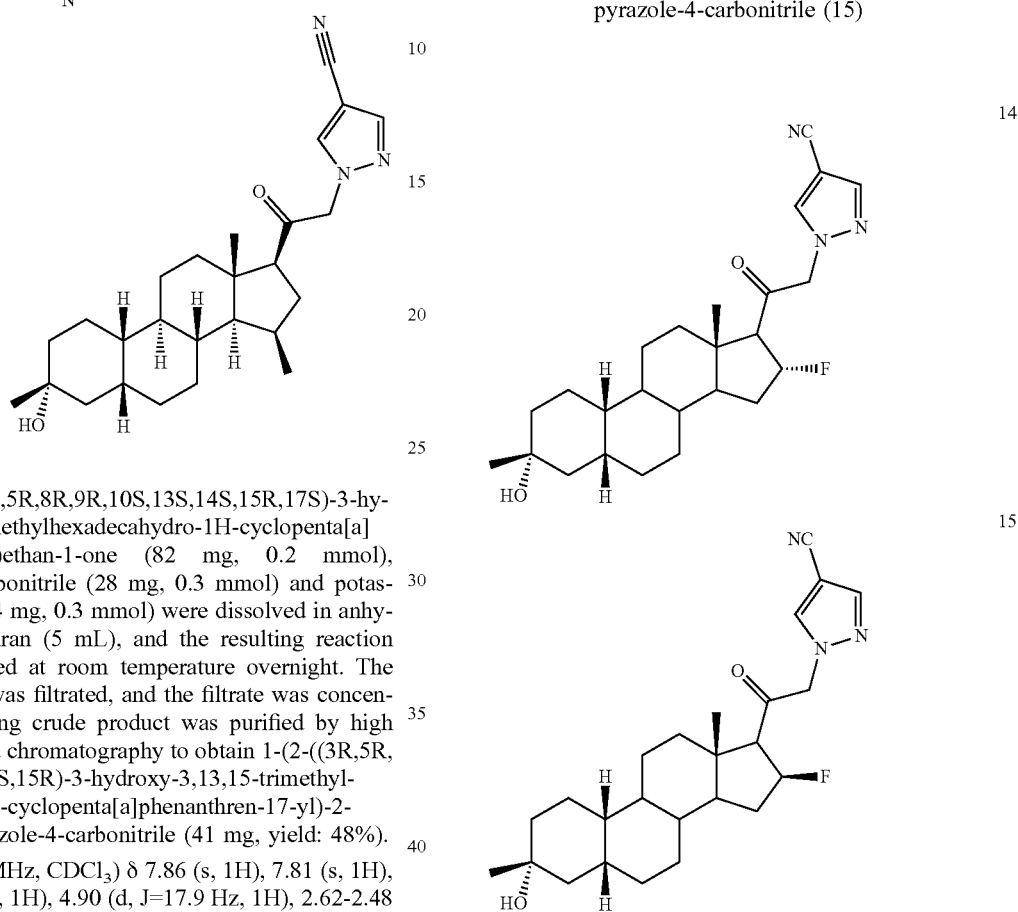

Example 14 and Example 15 were synthesized by the following specific scheme:

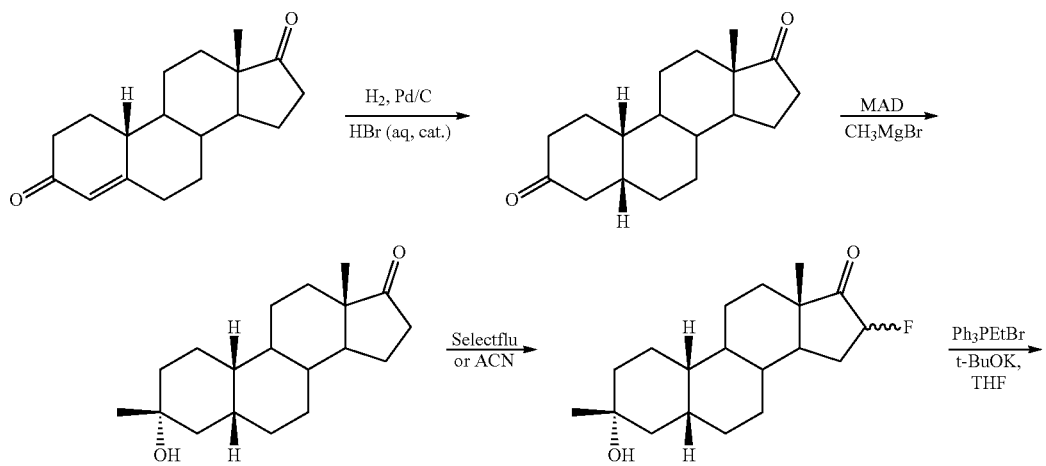

95 96
-continued
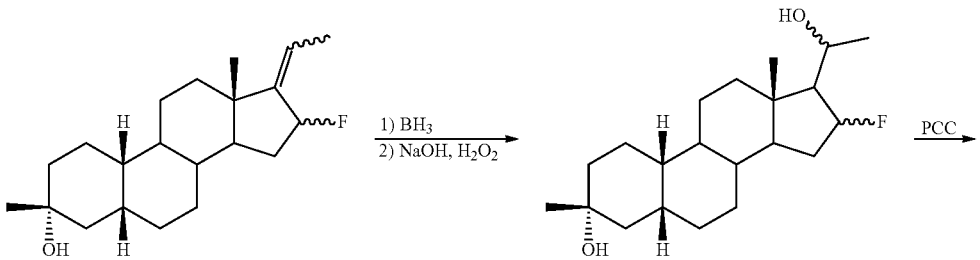
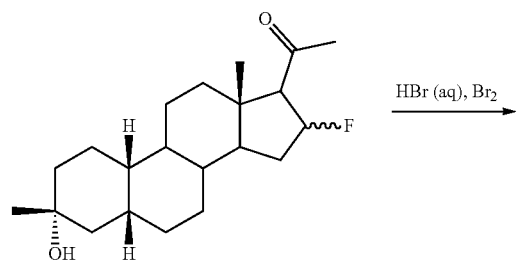
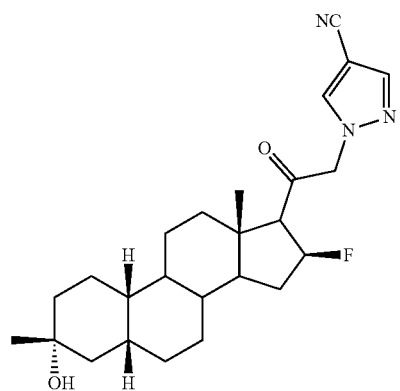
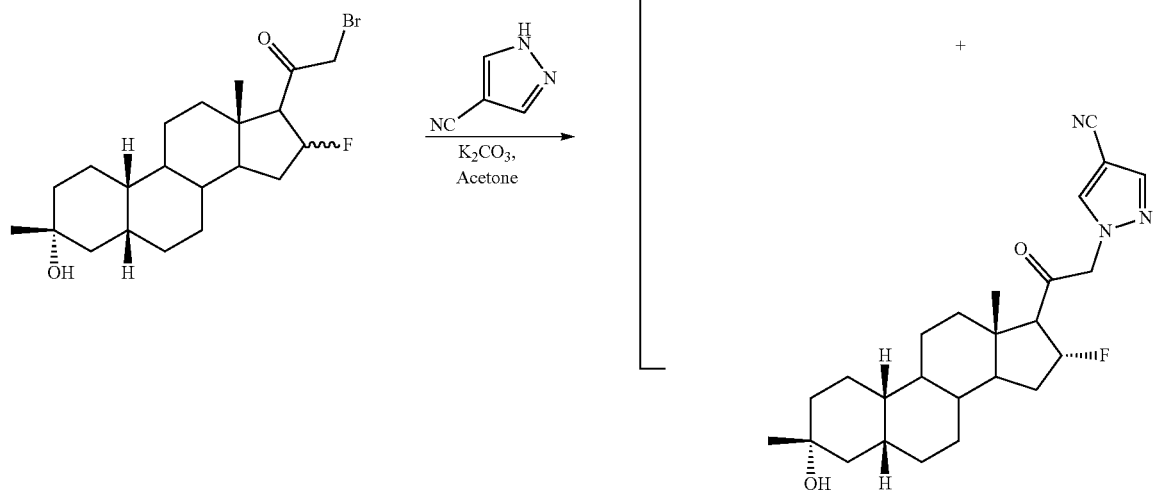

Example 14: MS m/z (ESI): 428.3 [M+1]+.
Example 15: MS m/z (ESI): 428.3 [M+1]+.

Example 16 and Example 17

1-(2-((3R,5R,10S,13S,16R)-3-Hydroxy-3,13-dimethyl-16-(trifluoromethyl)hexadecahydro-1H-cyclopenta[a]phenanthren-17-yl)-2-oxoethyl)-1H-pyrazole-4-carbonitrile (16)

1-(2-((3R,5R,10S,13S,16S)-3-Hydroxy-3,13-dimethyl-16-(trifluoromethyl)hexadecahydro-1H-cyclopenta[a]phenanthren-17-yl)-2-oxoethyl)-1H-pyrazole-4-carbonitrile (17)

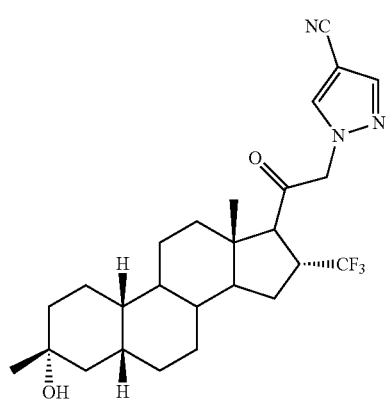

16

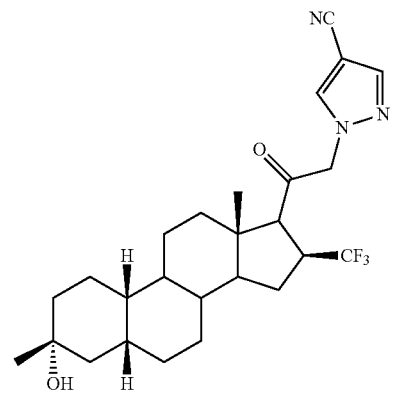

17

Example 16 and Example 17 were synthesized by the following specific scheme:

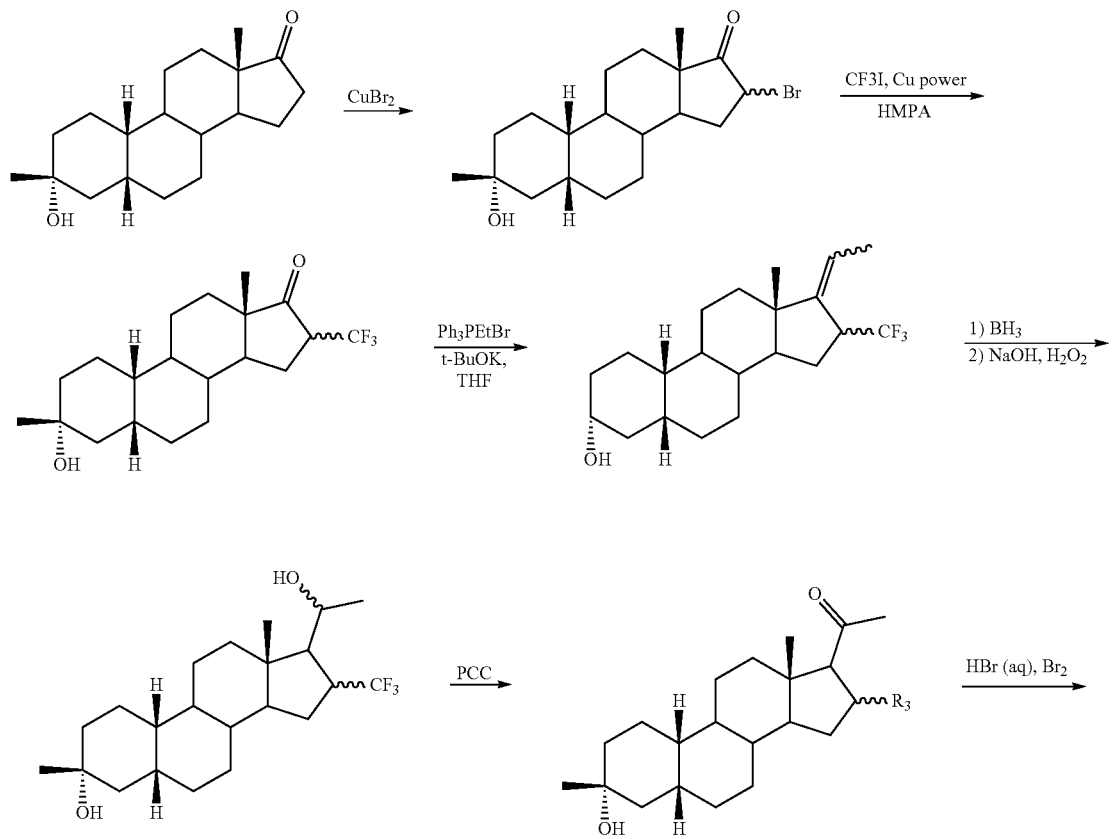

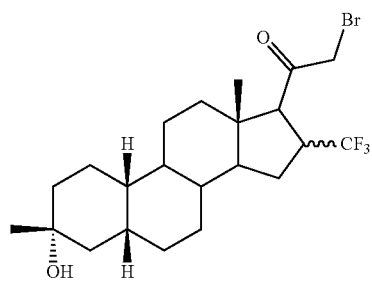 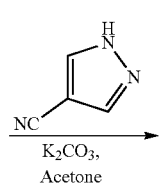 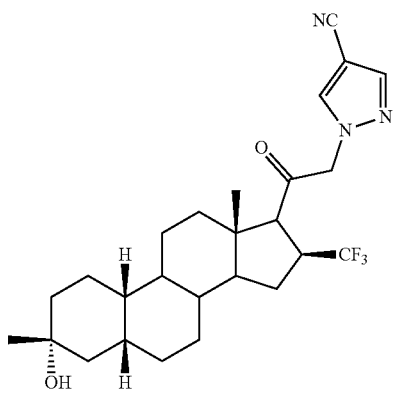

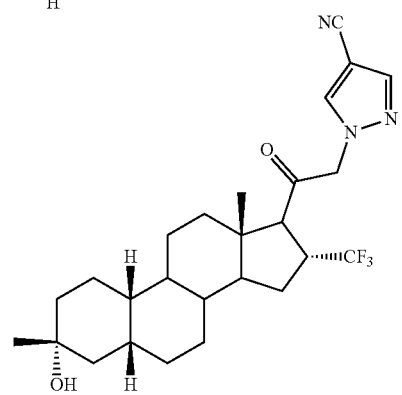

Example 16: MS m/z (ESI): 478.3 [M+1]⁺.
Example 17: MS m/z (ESI): 478.3 [M+1]⁺.

Example 18

2-(4-Chloro-1H-pyrazol-1-yl)-1-((2R,4aS,4bR,6aS, 7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

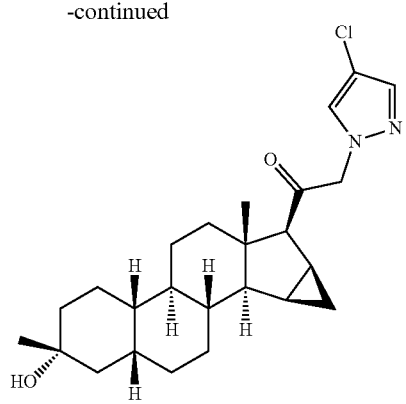

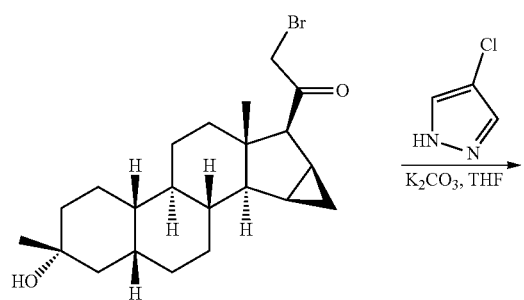

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a] phenanthren-7-yl)ethan-1-one and 4-chloro-1H-pyrazole were used as the starting materials, accordingly, 2-(4-chloro-1H-pyrazol-1-yl)-1-((2R,4aS,4bR,6aS,7S,7aS,8aR,8bR, 8cR,10aR)-2-hydroxy-2,6a-dimethyloctadecahydrocyclopropa[4,5]cyclopenta[1,2-a]phenanthren-7-yl)ethan-1-one (21.9 mg, yield: 26%) was obtained.

MS m/z (ESI): 431.2 [M+H]⁺

$^1$H NMR (400 MHz, CDCl₃) δ 7.45 (d, J=11.8 Hz, 2H), 5.17-5.01 (m, 2H), 2.81 (d, J=3.5 Hz, 1H), 1.99-1.91 (m, 1H), 1.86-1.79 (m, 3H), 1.77-1.62 (m, 3H), 1.57-1.49 (m, 3H), 1.44-1.20 (m, 14H), 1.12-0.96 (m, 2H), 0.78 (s, 3H), 0.51-0.44 (m, 1H).

101

Example 19

(2R,4aS,4bR,6aS,7S,8bR,8cR,10aR)-2-Hydroxy-2,
6a-dimethyl-N-phenyloctadecahydrocyclopropa[4,5]
cyclopenta[1,2-a]phenanthrene-7-carboxamide

102

Example 20

1-(2-((3R,5R,8R,9R,10S,13S,14S,17S)-3-Hydroxy-
15-(isopropylamino)-3,13-dimethylhexadecahydro-
1H-cyclopenta[a]phenanthren-17-yl)-2-oxoethyl)-
1H-pyrazole-4-carbonitrile

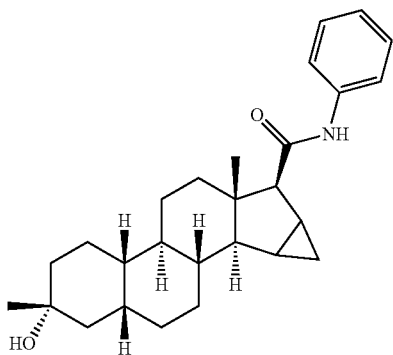

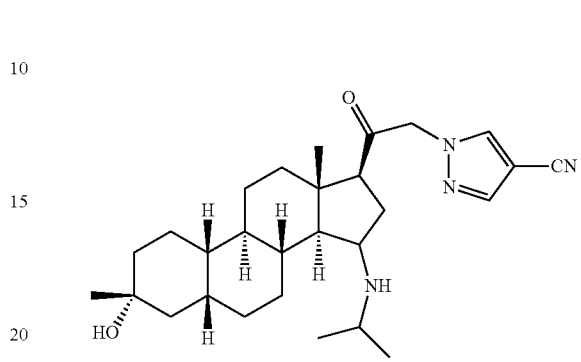

Example 19 was synthesized by the following specific scheme:

Example 20 was synthesized by the following specific scheme:

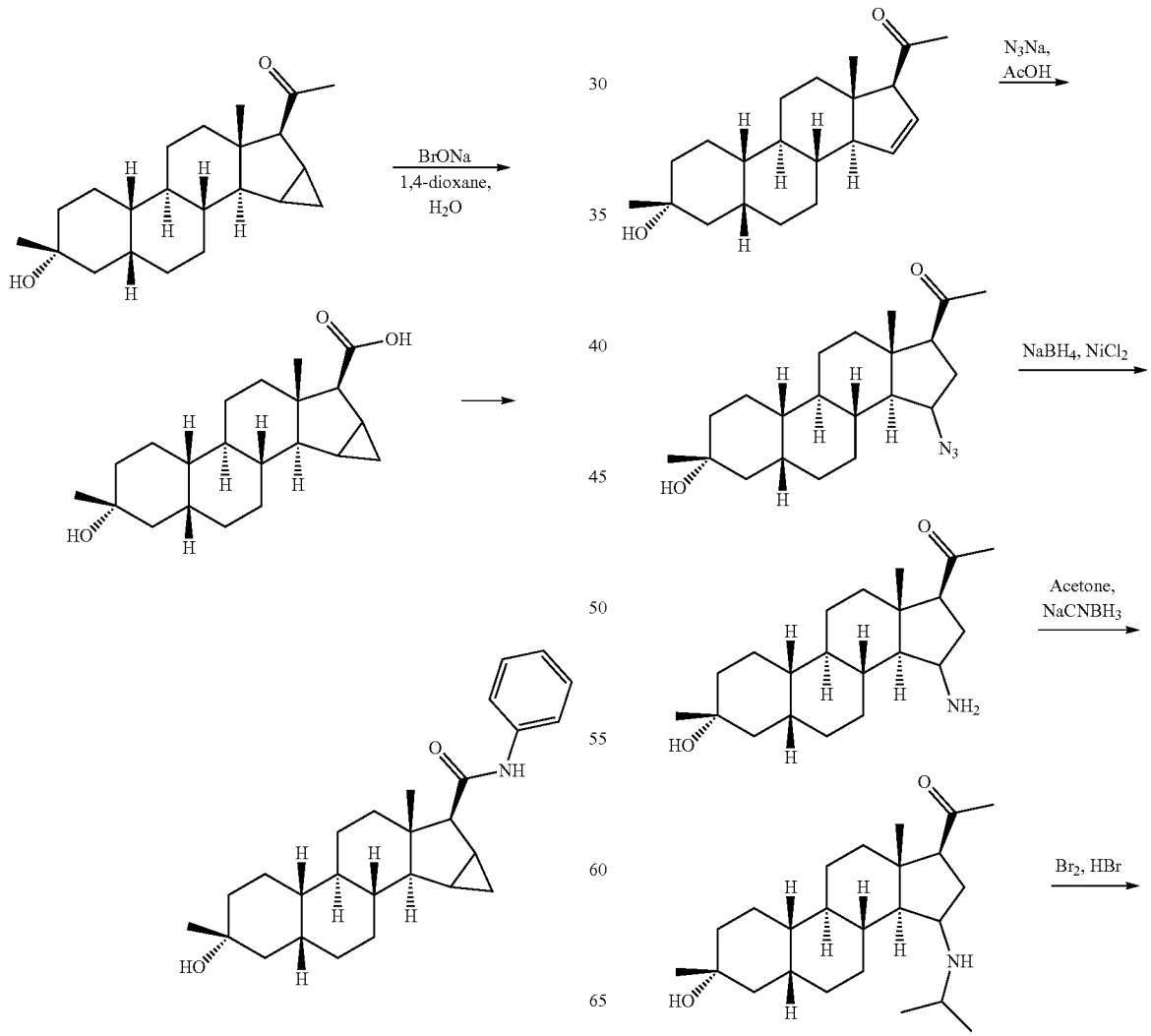

MS m/z (ESI): 408.3 [M+1]$^+$.

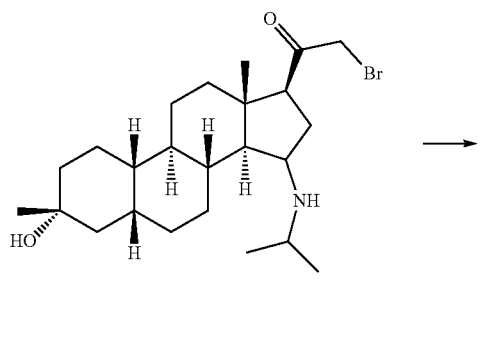
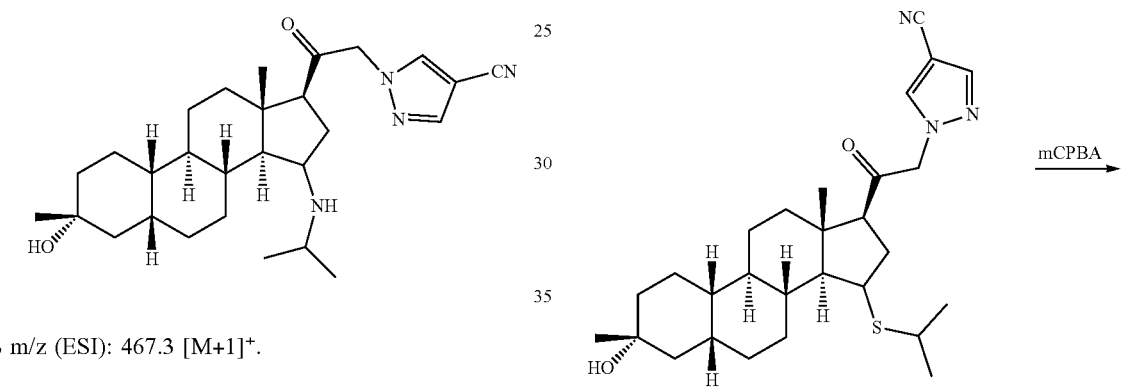
MS m/z (ESI): 467.3 [M+1]⁺.
Example 21
1-(2-((3R,5R,8R,9R,10S,13R,14S,17S)-3-Hydroxy-15-(isopropylsulfonyl)-3,13-dimethylhexadeca-hydro-1H-cyclopenta[a]phenanthren-17-yl)-2-oxo-ethyl)-1H-pyrazole-4-carbonitrile
Example 21 was synthesized by the following specific scheme:
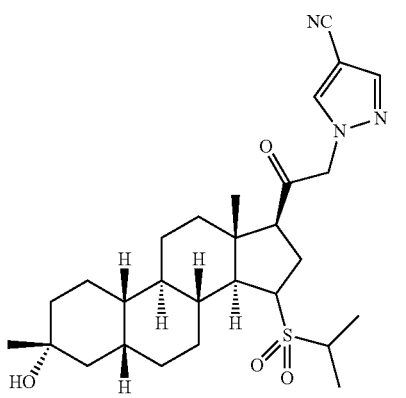
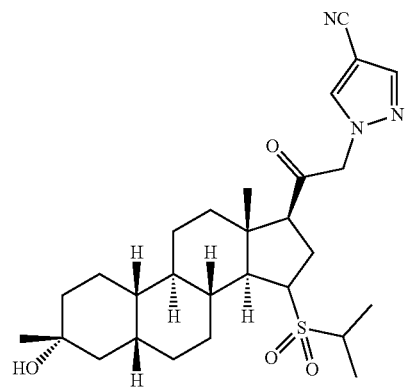
MS m/z (ESI): 516.3 [M+1]⁺.

Example 23
1-(2-((2R,4aS,4bR,6aS,7S,8bR,8cR,10aR)-2-Hydroxy-2-(methoxymethyl)-6a-methyloctadecahydrocyclopropa[4,5]cyclopenta[1,2-a]phenanthren-7-yl)-2-oxoethyl)-1H-pyrazole-4-carbonitrile
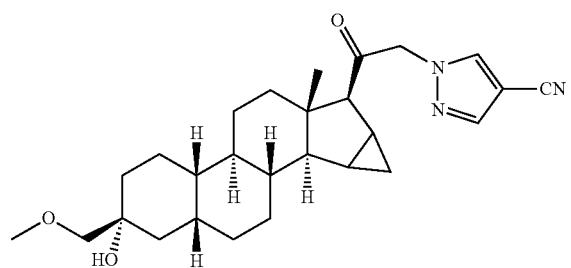
Example 23 was synthesized by the following specific scheme:
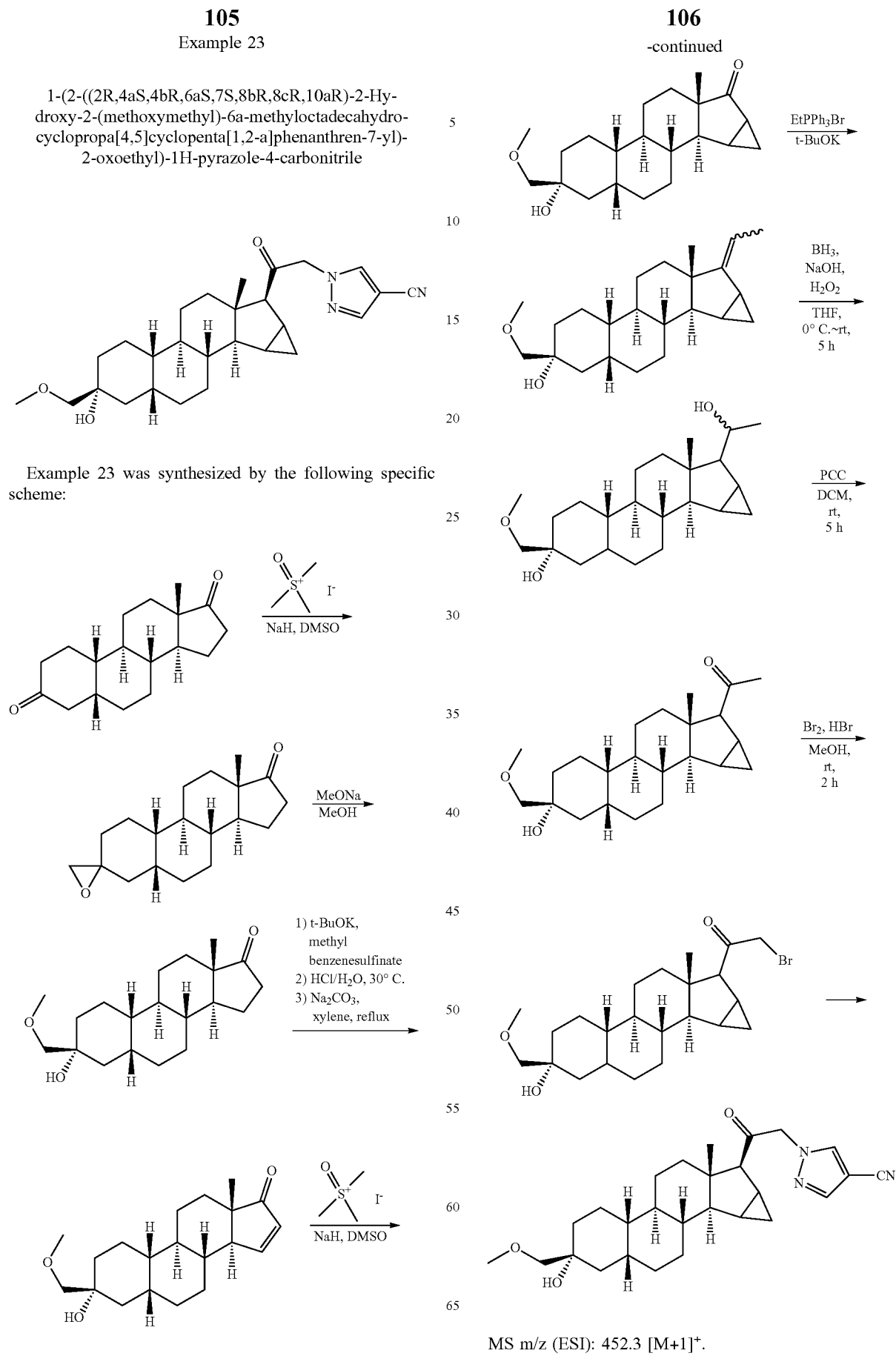
MS m/z (ESI): 452.3 [M+1]$^+$.

Example 24

1-((2R,4aS,4bR,6aS,7S,8bR,8cR,10aR)-2-Hydroxy-2-(methoxymethyl)-6a-methyloctadecahydrocyclopropa[4,5]cyclopenta[1,2-a]phenanthren-7-yl)-2-(4-methyl-1H-pyrazol-1-yl)ethan-1-one

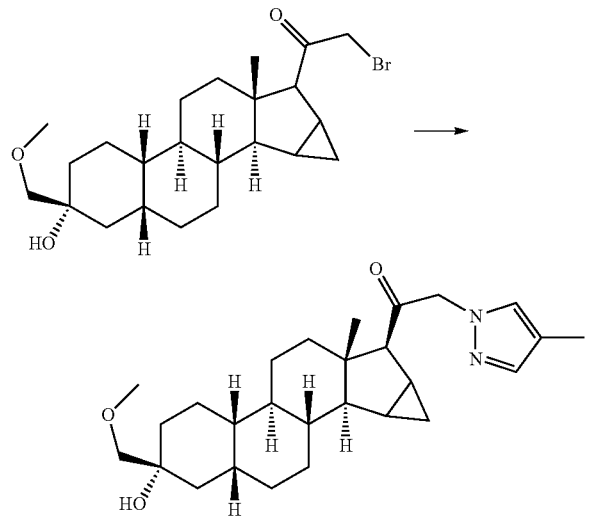

MS m/z (ESI): 441.3 [M+1]⁺.

Example 25

1-(2-((2R,4aR,4bS,6aS,8bS,8cR,10aR)-2-Hydroxymethyl-4a-(methoxymethyl)-2,6a-dimethyloctadecahydrocyclopropa[4,5]cyclopenta[1,2-a]phenanthren-7-yl)-2-oxoethyl)-1H-pyrazole-4-carbonitrile

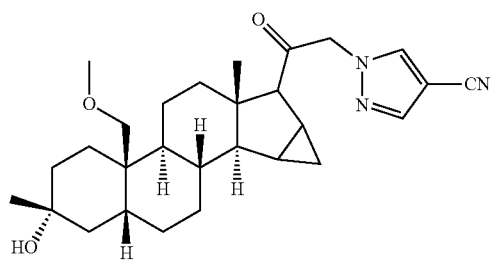

Example 25 was synthesized by the following specific scheme:

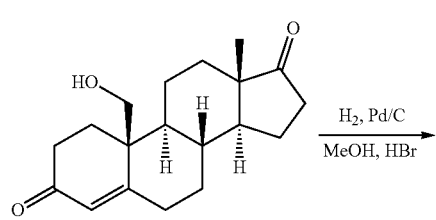

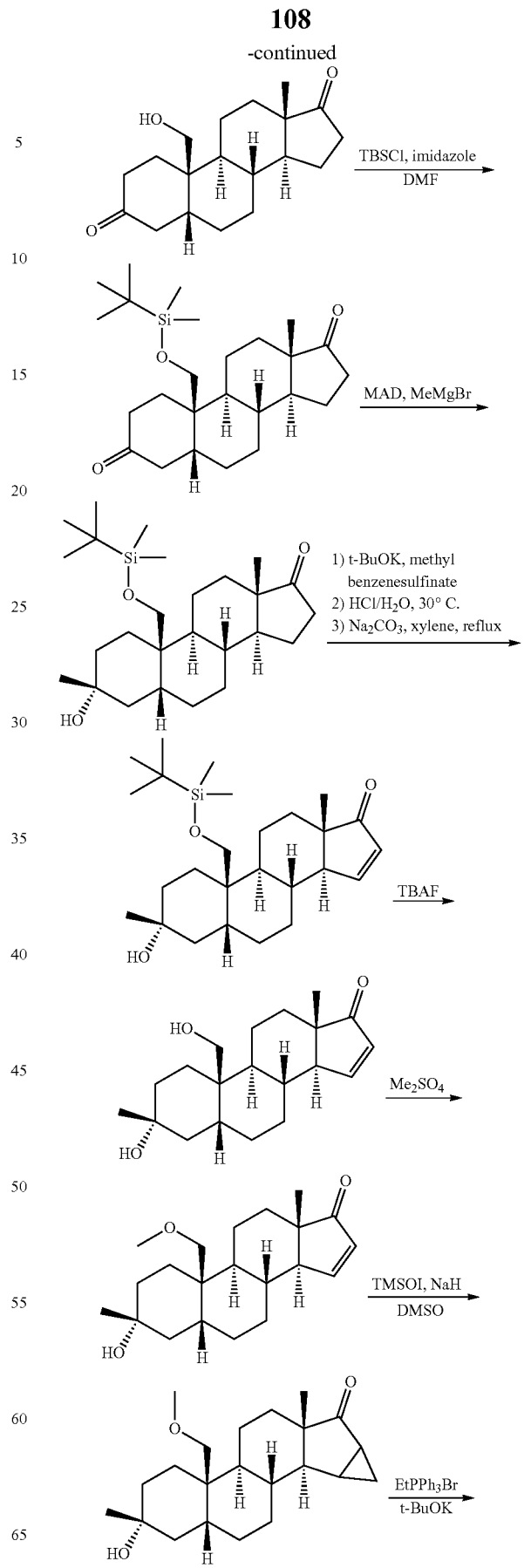

109
-continued
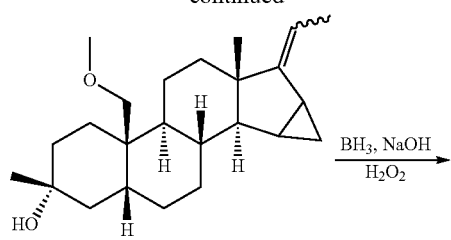
BH₃, NaOH
─────────→
H₂O₂
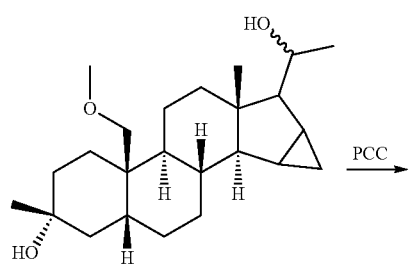
PCC →
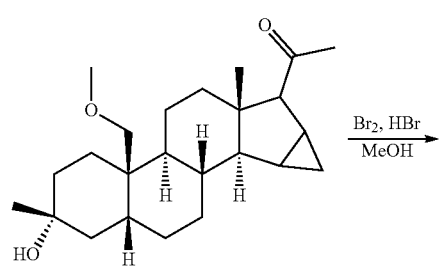
Br₂, HBr
─────────→
MeOH
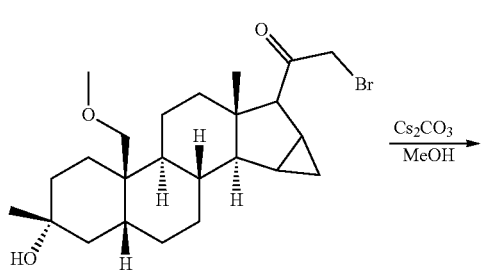
Cs₂CO₃
─────────→
MeCN
110
Example 26
1-(2-((2R,4aR,4bS,6aS,8bS,8cR,10aR)-2-Hydroxymethyl-4a-(methoxymethyl)-2,6a-dimethyloctadecahydrocyclopropa[4,5]cyclopenta[1,2-a]phenanthren-7-yl)-2-oxoethyl)-1H-pyrazole-3-carbonitrile
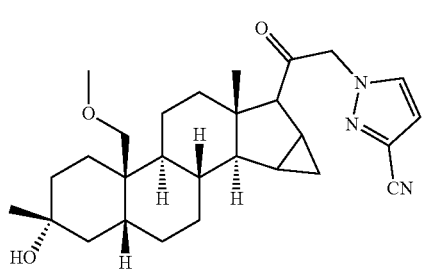
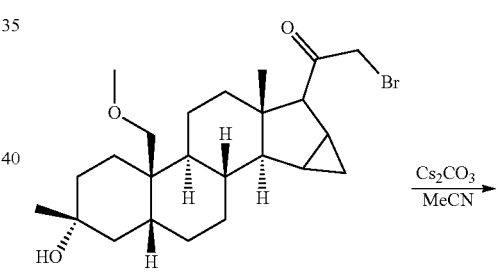
Cs₂CO₃
─────────→
MeCN
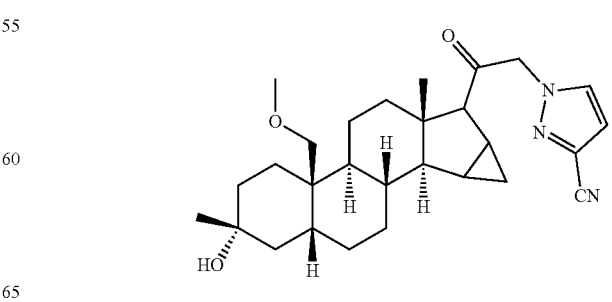
MS m/z (ESI): 466.3 [M+1]⁺.
MS m/z (ESI): 466.3 [M+1]⁺.

Example 33 and Example 34

3-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (33)

5-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (34)

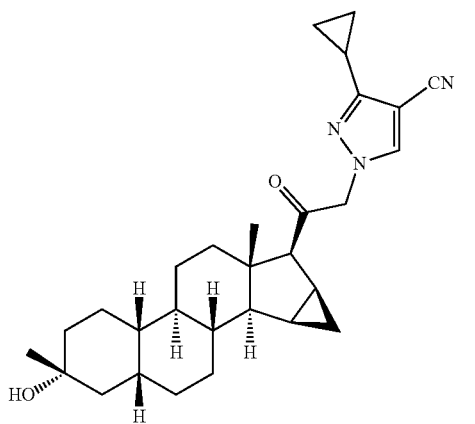

33

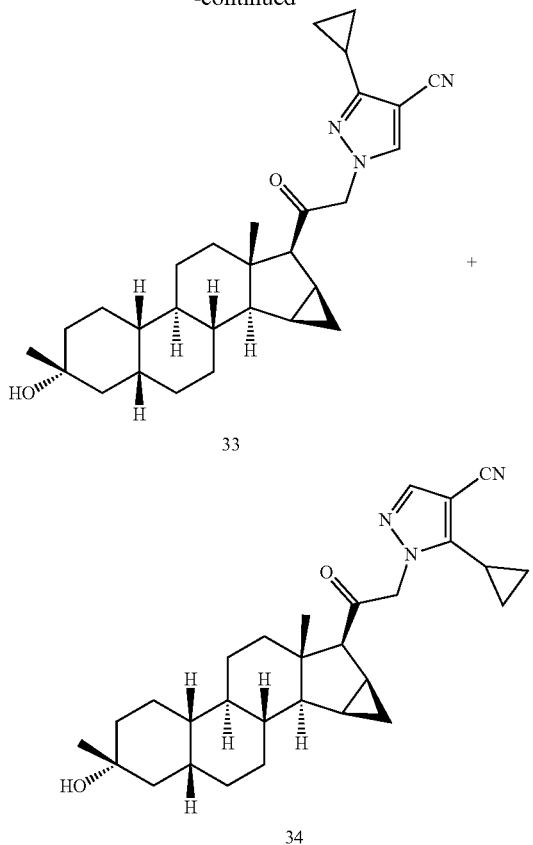

34

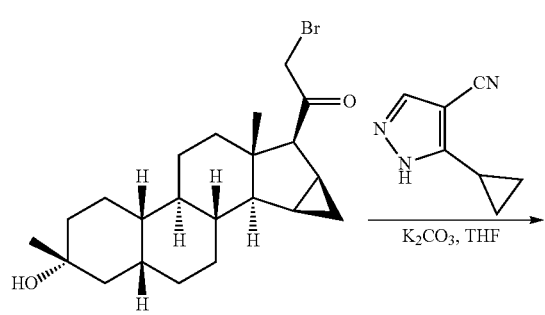

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 5-cyclopropyl-1H-pyrazole-4-carbonitrile were used as the starting materials, accordingly, 3-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (33) (19.2 mg, yield: 21%) and 5-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile (34) (3.0 mg, yield: 3.3%) were obtained.

Example 33

MS m/z (ESI): 462.3 [M+H]$^+$ $^1$H NMR (400 MHz, CDCl$_3$) δ 7.73 (s, 1H), 5.14-4.98 (m, 2H), 2.80 (d, J=2.2 Hz, 1H), 2.05-1.89 (m, 2H), 1.86-1.78 (m, 4H), 1.75-1.64 (m, 3H), 1.58-1.52 (m, 2H), 1.46-1.33 (m, 7H), 1.33-1.20 (m, 7H), 1.14-0.92 (m, 6H), 0.76 (s, 3H), 0.53-0.43 (m, 1H).

Example 34

MS m/z (ESI): 462.3 [M+H]$^+$ $^1$H NMR (400 MHz, CDCl$_3$) δ 7.69 (s, 1H), 5.33-5.13 (m, 2H), 2.85 (d, J=3.8 Hz, 1H), 2.00-1.92 (m, 1H), 1.86-1.79 (m, 3H), 1.76-1.62 (m, 4H), 1.60-1.51 (m, 2H), 1.45-1.34 (m, 7H), 1.34-1.22 (m, 7H), 1.17-0.94 (m, 7H), 0.81 (s, 3H), 0.54-0.45 (m, 1H).

Example 37A and Example 37B 1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)-3-methyl-1H-pyrazole-4-carbonitrile (37A)

1-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)-5-methyl-1H-pyrazole-4-carbonitrile (37B)

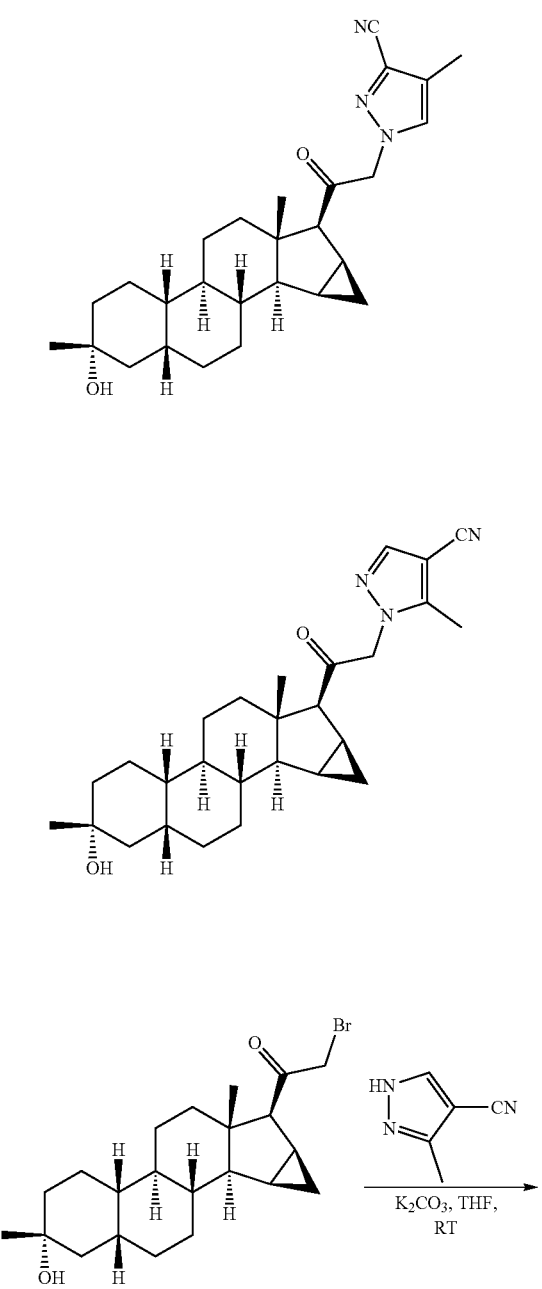

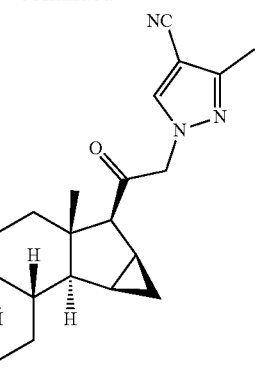

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 3-methyl-1H-pyrazole-4-carbonitrile were used as the starting materials, accordingly, a mixture of Example 37A and Example 37B (approximately 3:1) (25.9 mg, white solid, yield: 39.3%) was obtained. The mixture was further separated by preparative chromatography to obtain 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-3-methyl-1H-pyrazole-4-carbonitrile (37A) and 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-5-methyl-1H-pyrazole-4-carbonitrile (37B).

Example 37A: MS m/z (ESI): 436.3 [M+H]$^+$
Example 37B: MS m/z (ESI): 436.3 [M+H]$^+$

Example 40

2-((2,4-Difluorophenyl)amino)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

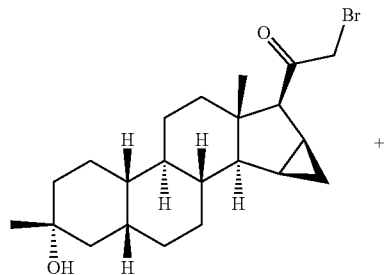

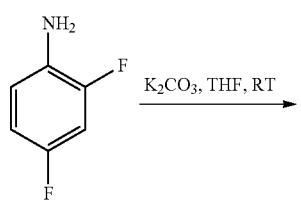

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 2,4-difluoroaniline were used as the starting materials, accordingly, 2-((2,4-difluorophenyl)amino)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (3.9 mg, white solid, yield: 3.9%) was obtained.

MS m/z (ESI): 458.3[M+H]+

$^1$H NMR (400 MHz, CDCl$_3$) δ 6.84-6.75 (m, 2H), 6.65-6.59 (m, 1H), 4.12 (dd, J$_1$=5.2 Hz, J$_2$=24.8 Hz, 2H), 3.61-3.27 (br, 1H), 2.80 (d, J=3.6 Hz, 1H), 2.01-1.77 (m, 10H), 1.76-1.56 (m, 3H), 1.53-1.46 (m, 1H), 1.28-1.19 (m, 10H), 1.00-0.93 (m, 2H), 0.73 (m, 3H), 0.50-0.44 (m, 1H).

Example 41 and Example 42

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(2H-pyrazolo[3,4-c]pyridin-2-yl)ethan-1-one 1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-pyrazolo[3,4-c]pyridin-1-yl)ethan-1-one

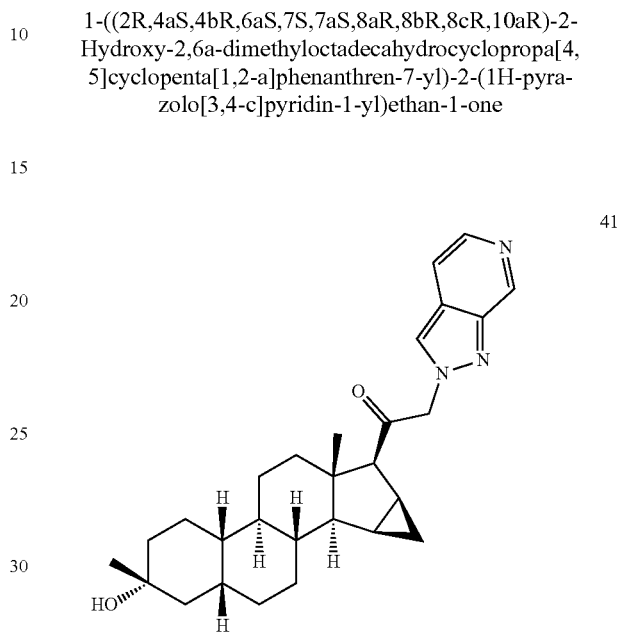

41

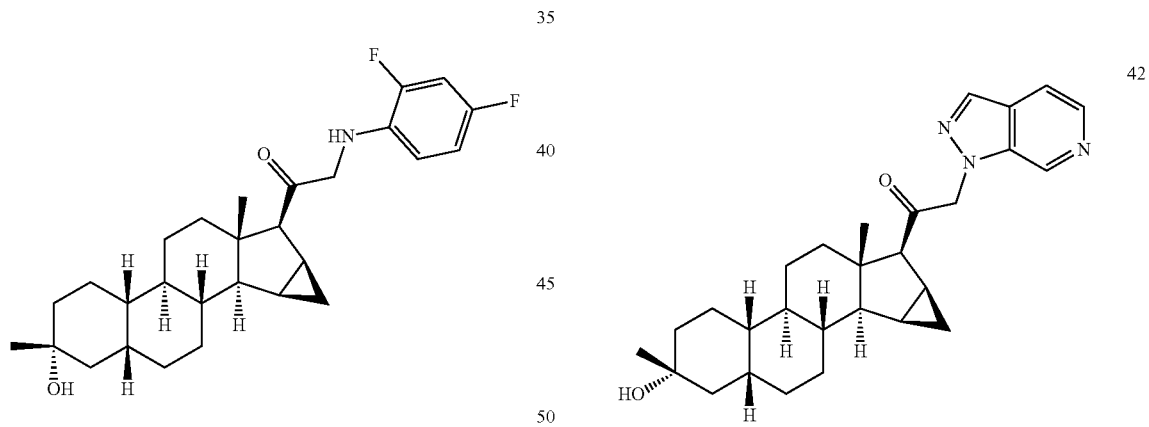

42

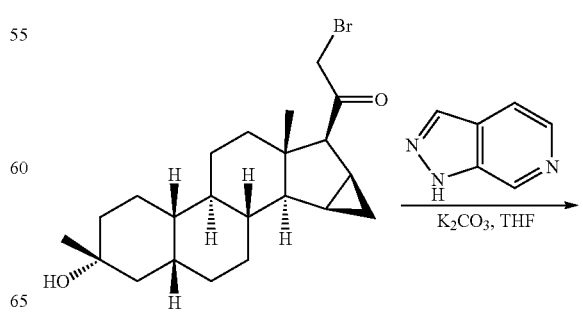

117

-continued

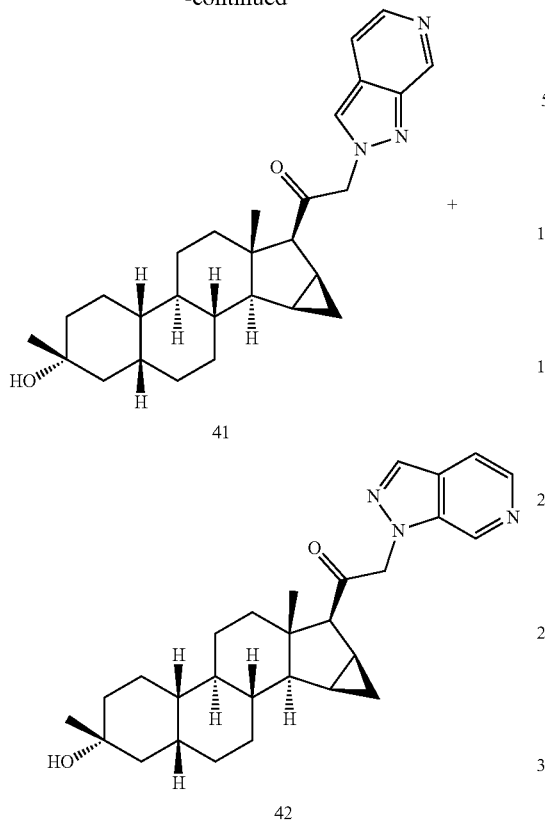

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 1H-pyrazolo[3,4-c]pyridine were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(2H-pyrazolo[3,4-c]pyridin-2-yl)ethan-1-one (41) (5.4 mg, yield: 6.2%) and 1-((2R, 4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-pyrazolo[3,4-c]pyridin-1-yl)ethan-1-one (42) (7.0 mg, yield: 8%) were obtained.

Example 41

MS m/z (ESI): 448.3 [M+H]⁺

¹H NMR (400 MHz, CDCl₃) δ 9.43 (s, 1H), 8.39 (s, 1H), 8.19 (d, J=6.4 Hz, 1H), 8.08 (d, J=6.4 Hz, 1H), 5.77-5.61 (m, 2H), 2.96 (s, 1H), 2.01-1.92 (m, 1H), 1.88-1.81 (m, 4H), 1.74-1.69 (m, 3H), 1.59-1.55 (m, 2H), 1.48-1.43 (m, 5H), 1.33-1.27 (m, 9H), 1.10-1.05 (m, 2H), 0.85 (s, 3H), 0.60-0.54 (m, 1H).

Example 42

MS m/z (ESI): 448.3 [M+H]⁺

¹H NMR (400 MHz, CDCl₃) δ 9.16 (s, 1H), 8.34 (d, J=5.8 Hz, 1H), 8.25 (s, 1H), 7.87 (d, J=5.2 Hz, 1H), 5.72-5.60 (m, 2H), 2.96 (d, J=3.9 Hz, 1H), 2.01-1.94 (m, 1H), 1.87-1.81 (m, 4H), 1.75-1.67 (m, 3H), 1.58-1.52 (m, 2H), 1.44-1.39 (m, 5H), 1.33-1.25 (m, 9H), 1.12-1.02 (m, 2H), 0.86 (s, 3H), 0.56-0.50 (m, 1H).

118

Example 46

2-(4-Fluoro-1H-pyrazol-1-yl)-1-((2R,4aS,4bR,6aS, 7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one

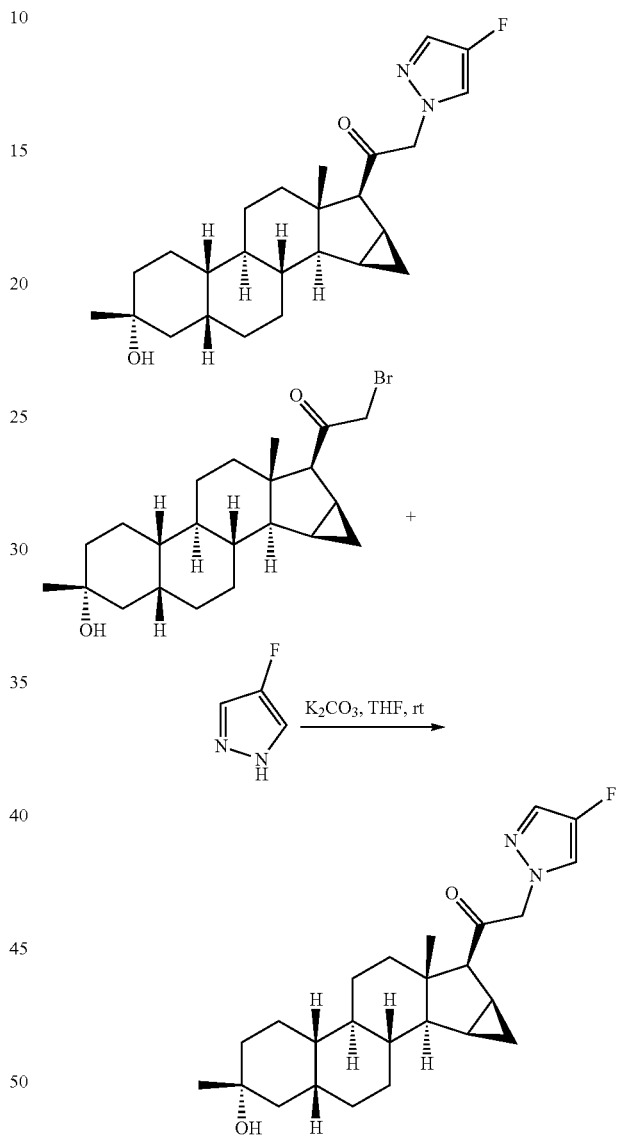

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 4-fluoropyrazole were used as the starting materials, accordingly, 2-(4-fluoro-1H-pyrazol-1-yl)-1-((2R,4aS,4bR,6aS,7S,7aS,8aR,8bR,8cR, 10aR)-2-hydroxy-2,6a-dimethyloctadecahydrocyclopropa[4,5]cyclopenta[1,2-a]phenanthren-7-yl)ethan-1-one (6.2 mg, white solid, yield: 7.7%) was obtained.

MS m/z (ESI): 415.2[M+H]⁺

¹H NMR (400 MHz, CDCl₃) δ 7.37 (d, J=4.0 Hz, 1H), 7.32 (d, J=4.0 Hz, 1H), 5.03 (d, J=3.6 Hz, 2H), 2.80 (d, J=3.6 Hz, 1H), 2.01-1.93 (m, 2H), 1.85-1.80 (m, 3H), 1.73-1.61

(m, 6H), 1.41-1.32 (m, 9H), 1.27 (s, 3H), 1.12-1.02 (m, 2H), 0.99-0.96 (m, 1H), 0.78 (s, 3H), 0.50-0.44 (m, 1H).

Example 51

Ethyl 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carboxylate

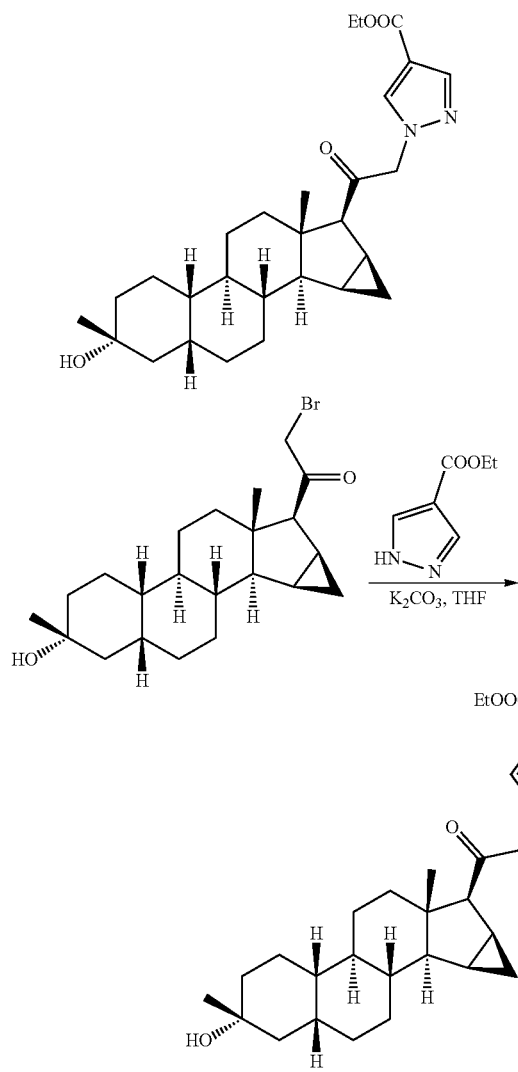

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and ethyl 1H-pyrazole-4-carboxylate were used as the starting materials, accordingly, ethyl 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carboxylate (29.6 mg, white solid, yield: 43%) was obtained.

MS m/z (ESI): 469.3 [M+H]$^+$ $^1$H NMR (400 MHz, CDCl$_3$) δ 7.95 (s, 2H), 5.32-4.99 (m, 2H), 4.36-4.24 (m, 2H), 2.83 (s, 1H), 1.99-1.92 (m, 1H), 1.87-1.79 (m, 3H), 1.72-1.52 (m, 6H), 1.49-1.16 (m, 17H), 1.14-0.96 (m, 2H), 0.83 (s, 3H), 0.53-0.44 (m, 1H).

Example 53, Example 54A and Example 54B 1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(5-methoxy-2H-benzo[d][1,2,3]triazol-2-yl)ethan-1-one (53)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(6-methoxy-1H-benzo[d][1,2,3]triazol-1-yl)ethan-1-one (54A)

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(5-methoxy-1H-benzo[d][1,2,3]triazol-1-yl)ethan-1-one (54B)

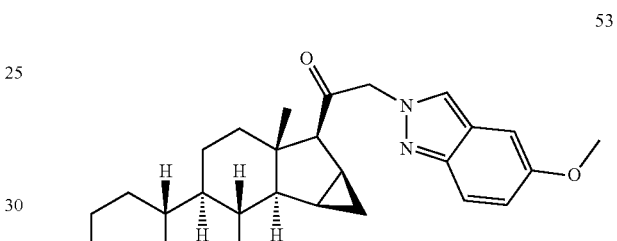

53

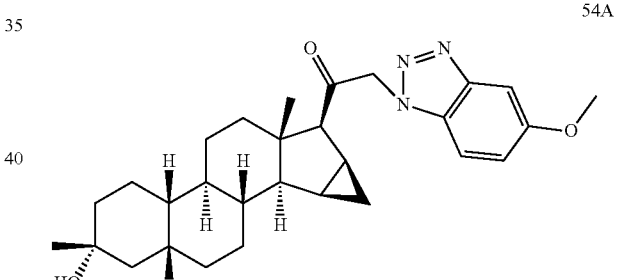

54A

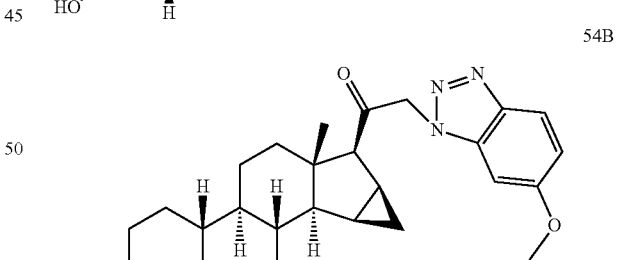

54B

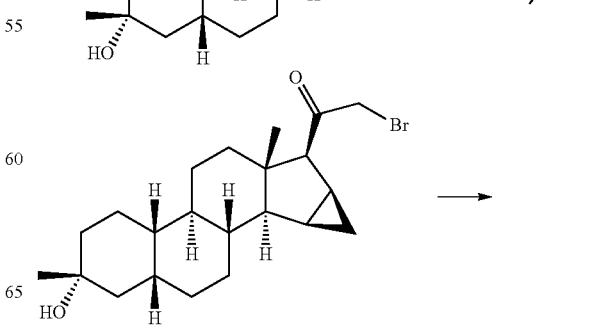

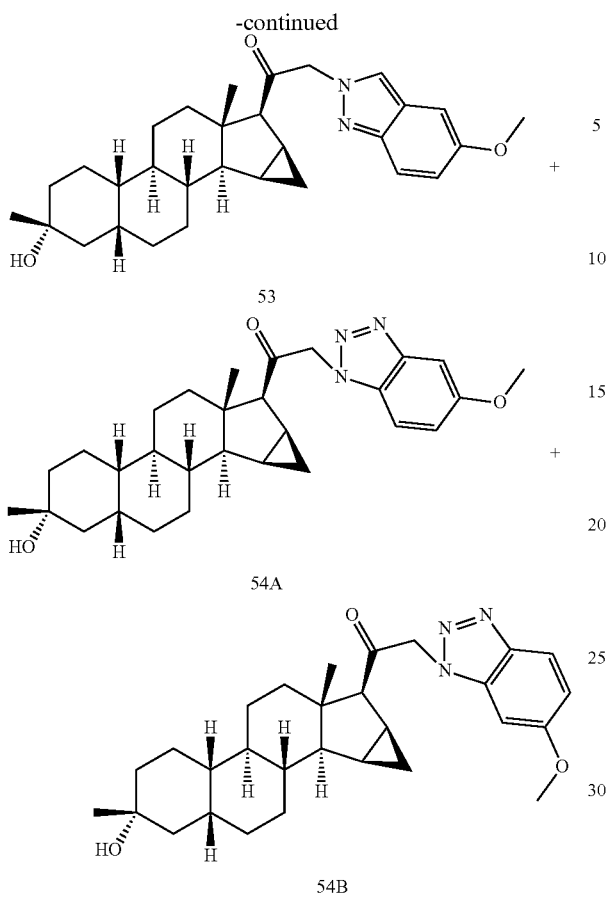

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 6-methoxy-1H-benzo[d][1,2,3]triazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(5-methoxy-2H-benzo[d][1,2,3]triazol-2-yl)ethan-1-one (11.8 mg, yield: 13.6%) and a mixture of Example 54A and Example 54B (approximately 1:1) (34 mg, yield: 39%) were obtained. The mixture was further separated by preparative chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(6-methoxy-1H-benzo[d][1,2,3]triazol-1-yl)ethan-1-one (54A) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(5-methoxy-1H-benzo[d][1,2,3]triazol-1-yl)ethan-1-one (54B).

Example 53

MS m/z (ESI): 478.3 [M+H]+

1H NMR (400 MHz, CDCl3) δ 7.74 (d, J=10.1 Hz, 1H), 7.14-7.03 (m, 2H), 5.73-5.59 (m, 2H), 3.88 (s, 3H), 2.88 (d, J=4.1 Hz, 1H), 2.01-1.93 (m, 1H), 1.86-1.78 (m, 4H), 1.74-1.63 (m, 3H), 1.55-1.51 (m, 1H), 1.46-1.25 (m, 15H), 1.15-1.00 (m, 2H), 0.88 (s, 3H), 0.53-0.45 (m, 1H).

Example 54A

MS m/z (ESI): 478.3 [M+H]+

Example 54B

MS m/z (ESI): 478.3 [M+H]+

Example 59

1-((3R,5R,8R,9R,10S,13S,14S,15R,17S)-3-Hydroxy-3,13,15-trimethylhexadecahydro-1H-cyclopenta[a]phenanthren-17-yl)-2-(4-(trifluoromethyl)-1H-pyrazol-1-yl)ethan-1-one

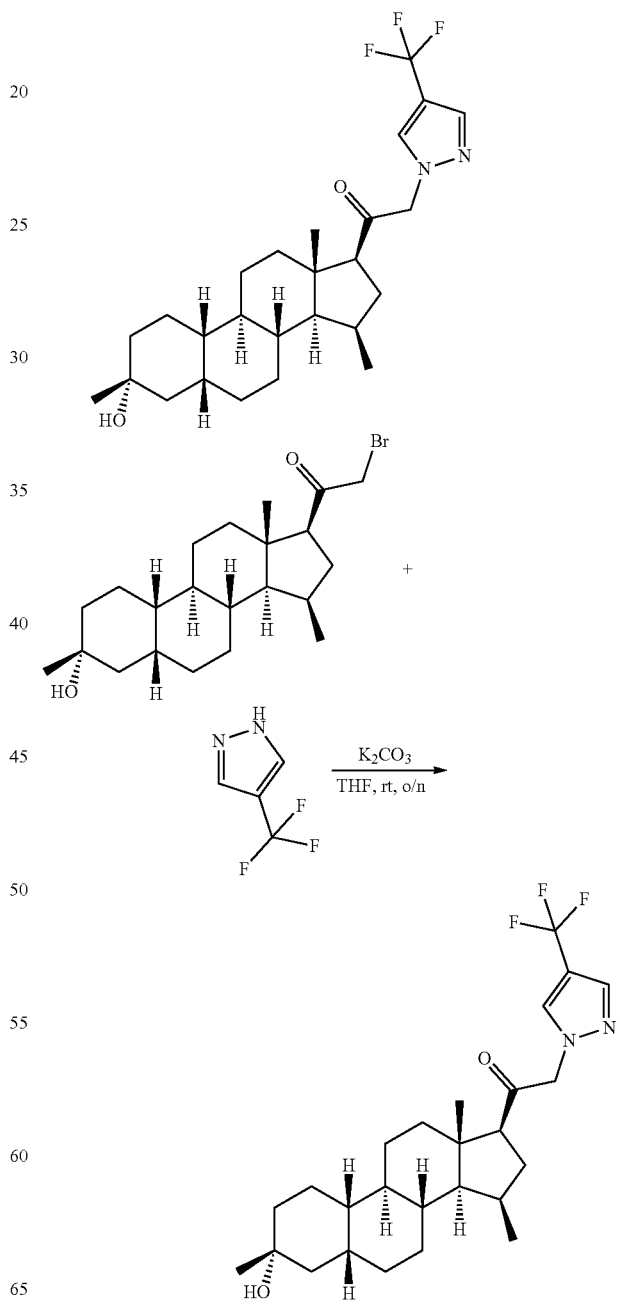

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 4-(trifluoromethyl)-1H-pyrazole (41 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((3R,5R,8R,9R,10S,13S,14S,15R,17S)-3-hydroxy-3,13,15-trimethylhexadecahydro-1H-cyclopenta[a]phenanthren-17-yl)-2-(4-(trifluoromethyl)-1H-pyrazol-1-yl)ethan-1-one (24.6 mg, yield: 26%).

$^1$H NMR (400 MHz, CDCl$_3$) δ 7.72 (s, 2H), 5.00 (d, J=16 Hz, 1H), 4.90 (d, J=16 Hz, 1H), 2.58-2.54 (m, 1H), 1.88-1.83 (m, 2H), 1.69-1.58 (m, 5H), 1.50-1.25 (m, 19H), 0.98 (d, J=8.0 Hz, 3H), 0.85 (s, 3H).

MS m/z (ESI): 467.3 [M+H]$^+$

Example 60

1-(2-((3R,5R,8R,9R,10S,13S,14S,15R,17S)-3-Hydroxy-3,13,15-trimethylhexadecahydro-1H-cyclopenta[a]phenanthren-17-yl)-2-oxoethyl)-1H-pyrazole-3-carbonitrile (60)

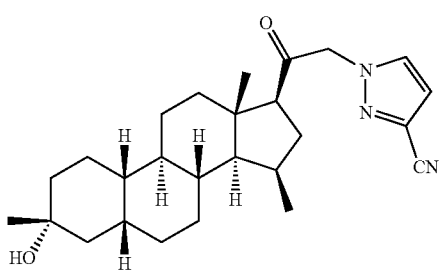

Step 1: Preparation of 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3-carbonitrile

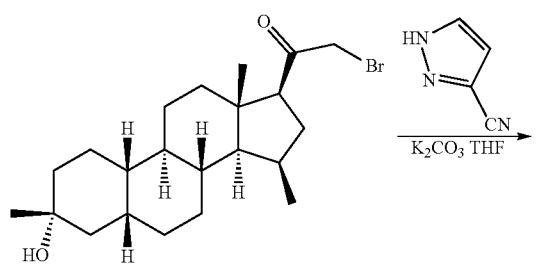

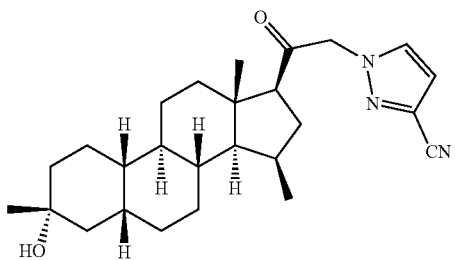

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3-carbonitrile (12.5 mg, yield: 20.2%) was obtained.

MS m/z (ESI): 424.1[M+H]$^+$.

$^1$H NMR (400 MHz, CDCl$_3$) δ 7.48 (d, J=2.4 Hz, 1H), 6.73 (d, J=2.4 Hz, 1H), 5.07-4.84 (m, 2H), 2.55 (t, J=8.1 Hz, 1H), 2.33-1.06 (m, 25H), 0.98 (d, J=7.0 Hz, 3H), 0.84 (s, 3H).

Example 61 and Example 132

1-((3R,5R,8R,9R,10S,13S,14S,15R,17S)-3-Hydroxy-3,13,15-trimethylhexadecahydro-1H-cyclopenta[a]phenanthren-17-yl)-2-(2H-1,2,3-triazol-2-yl)ethan-1-one (61)

1-((3R,5R,8R,9R,10S,13S,14S,15R,17S)-3-Hydroxy-3,13,15-trimethylhexadecahydro-1H-cyclopenta[a]phenanthren-17-yl)-2-(1H-1,2,3-triazol-1-yl)ethan-1-one (132)

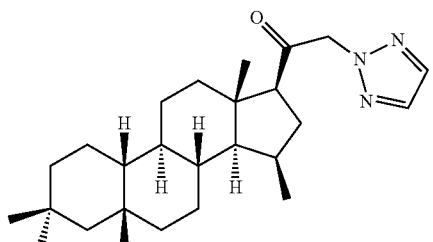

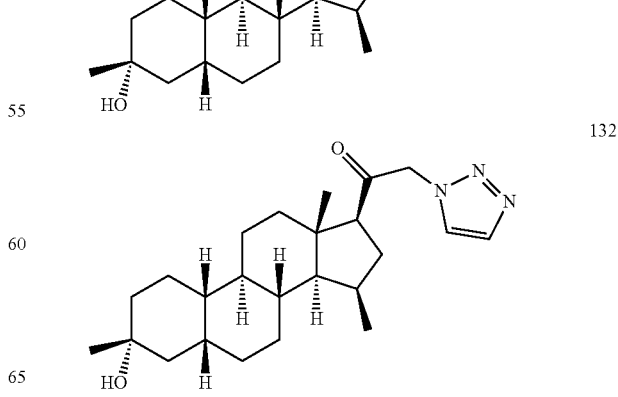

Step 1: Preparation of 1-((3R,5R,8R,9R,10S,13S,14S,15R,17S)-3-hydroxy-3,13,15-trimethylhexadecahydro-1H-cyclopenta[a]phenanthren-17-yl)-2-(2H-1,2,3-triazol-2-yl)ethan-1-one and 1-((3R,5R,8R,9R,10S,13S,14S,15R,17S)-3-hydroxy-3,13,15-trimethylhexadecahydro-1H-cyclopenta[a]phenanthren-17-yl)-2-(1H-1,2,3-triazol-1-yl)ethan-1-one

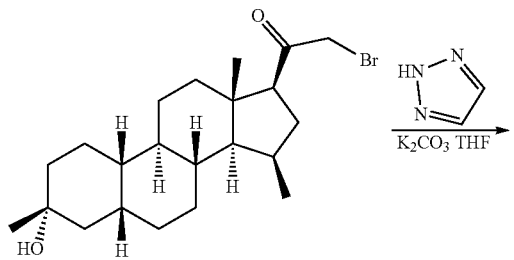

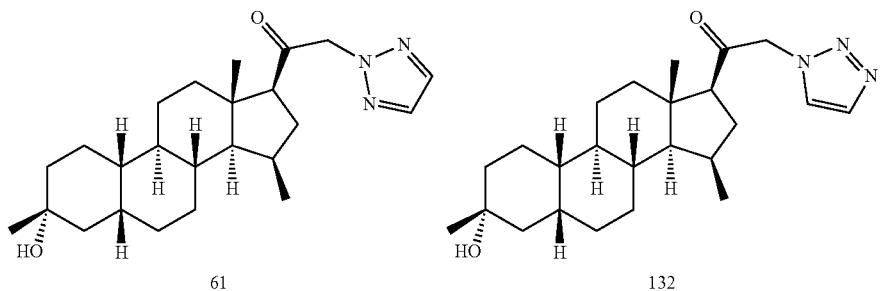

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(2H-1,2,3-triazol-2-yl)ethan-1-one (9.5 mg, yield: 16.3%) and 1-((3R,5R,8R,9R,10S,13S,14S,15R,17S)-3-hydroxy-3,13,15-trimethylhexadecahydro-1H-cyclopenta[a]phenanthren-17-yl)-2-(1H-1,2,3-triazol-1-yl)ethan-1-one (13 mg, yield: 22.3%) were obtained.

Example 61

MS m/z (ESI): 400.2[M+H]$^+$.
1H NMR (400 MHz, CDCl$_3$) δ 7.68 (s, 2H), 5.29-5.15 (m, 2H), 2.52 (t, J=8.0 Hz, 1H), 2.17-1.29 (m, 24H), 1.15-1.05 (m, 1H), 0.97 (d, J=7.0 Hz, 3H), 0.87 (s, 3H).

Example 132

MS m/z (ESI): 400.2[M+H]$^+$.
1H NMR (400 MHz, CDCl$_3$) δ 7.77 (s, 1H), 7.65 (s, 1H), 5.32-5.02 (m, 2H), 2.60 (t, J=9.1 Hz, 1H), 2.30-2.12 (m, 2H), 1.99-1.27 (m, 22H), 1.17-1.06 (m, 1H), 0.99 (d, J=6.9 Hz, 3H), 0.84 (s, 3H).

Example 62

1-((3R,5R,8R,9R,10S,13S,14S,15R,17S)-3-Hydroxy-3,13,15-trimethylhexadecahydro-1H-cyclopenta[a]phenanthren-17-yl)-2-(5-methyl-2H-tetrazol-2-yl)ethan-1-one (62)

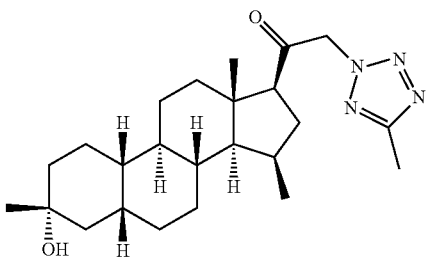

Step 1: Preparation of 1-((3R,5R,8R,9R,10S,13S,14S,15R,17S)-3-hydroxy-3,13,15-trimethylhexadecahydro-1H-cyclopenta[a]phenanthren-17-yl)-2-(5-methyl-2H-tetrazol-2-yl)ethan-1-one

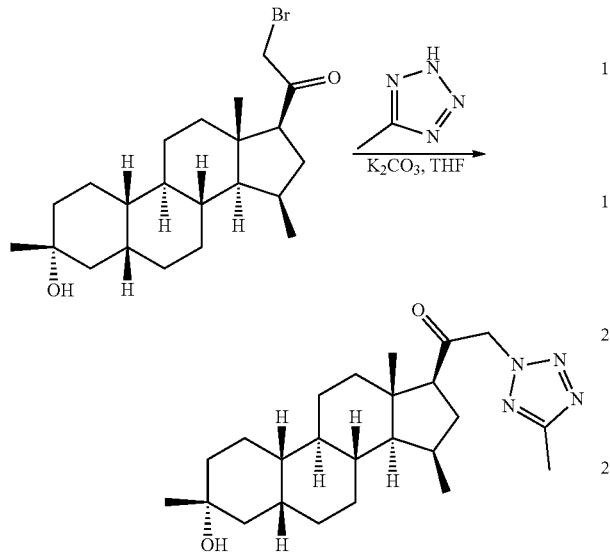

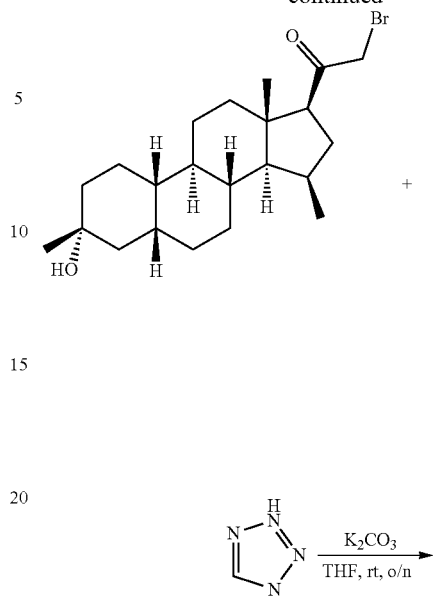

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(5-methyl-2H-tetrazol-2-yl)ethan-1-one (4.7 mg, yield: 7%) was obtained.

MS m/z (ESI): 415.3[M+H]$^+$ $^1$H NMR (400 MHz, CDCl$_3$) δ 5.36 (s, 2H), 2.57 (s, 3H), 2.27-2.11 (m, 2H), 2.00-198 (m, 1H), 1.87-1.83 (m, 5H), 1.77-1.57 (m, 6H), 1.52-1.30 (m, 12H), 1.11 (s, 2H), 0.98 (d, J=7.0 Hz, 3H), 0.88 (s, 3H).

Example 63

1-((3R,5R,8R,9R,10S,13S,14S,15R,17S)-3-Hydroxy-3,13,15-trimethylhexadecahydro-1H-cyclopenta[a]phenanthren-17-yl)-2-(2H-tetrazol-2-yl)ethan-1-one

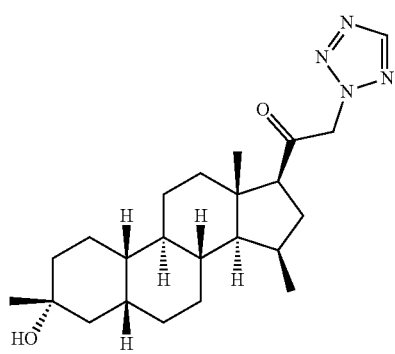

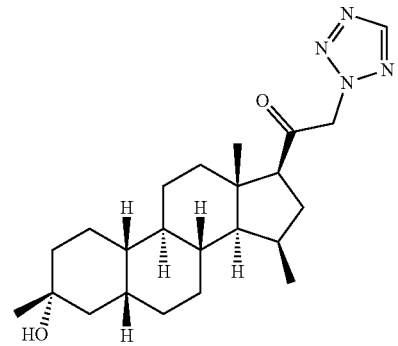

2-Bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one (82 mg, 0.2 mmol), 2H-tetrazole (21 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-((3R,5R,8R,9R,10S,13S,14S,15R,17S)-3-hydroxy-3,13,15-trimethylhexadecahydro-1H-cyclopenta[a]phenanthren-17-yl)-2-(2H-tetrazol-2-yl)ethan-1-one (15.7 mg, yield: 20%).

MS m/z (ESI): 401.3 [M+H]$^+$ $^1$H NMR (400 MHz, CDCl$_3$) δ 8.58 (s, 1H), 4.46 (s, 2H), 2.62-2.58 (m, 1H), 1.89-1.84 (m, 2H), 1.70-1.26 (m, 23H), 0.99 (d, J=8.0 Hz, 3H), 0.88 (s, 3H).

Example 64

2-(2,4-Difluorophenoxy)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (64)

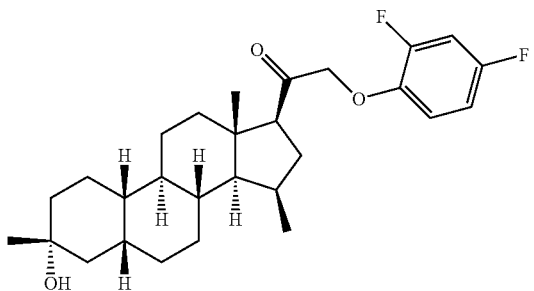

Step 1: Preparation of 2-(2,4-difluorophenoxy)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (64)

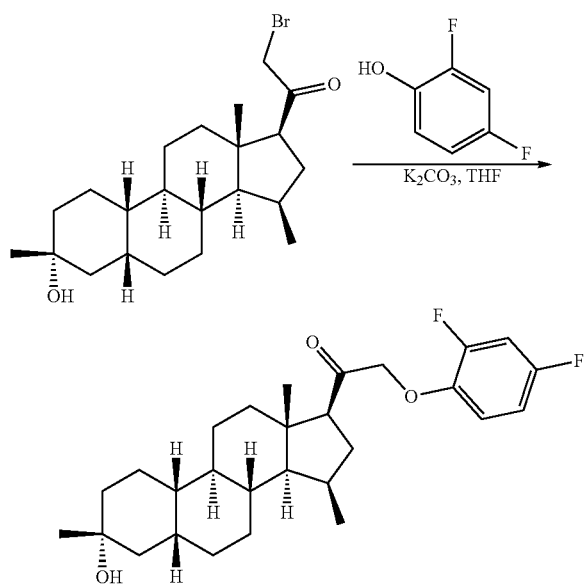

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 2-(2,4-difluorophenoxy)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (34 mg, yield: 45%) was obtained.

MS m/z (ESI): 461.3[M+H]$^+$ $^1$H NMR (400 MHz, CDCl$_3$) δ 6.91-6.82 (m, 2H), 6.77 (ddd, J=9.1, 5.3, 1.6 Hz, 1H), 4.56 (q, J=16.7 Hz, 2H), 2.74-2.68 (m, 1H), 2.27-2.14 (m, 1H), 2.13-1.99 (m, 1H), 1.95-1.74 (m, 4H), 1.74-1.61 (m, 3H), 1.57 (s, 3H), 1.52-1.35 (m, 4H), 1.36-1.18 (m, 6H), 1.21-1.00 (m, 3H), 0.98 (d, J=7.2 Hz, 3H), 0.82 (s, 3H).

Example 69

3-Cyclopropyl-1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-4-carbonitrile (69)

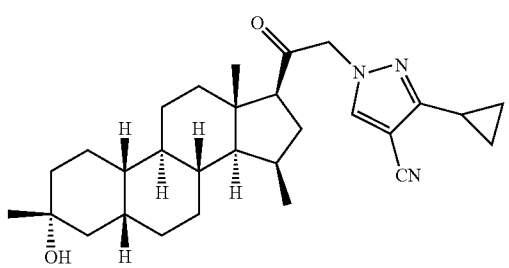

Step 1: Preparation of 3-cyclopropyl-1-(2-((3R,5R,8R,9R,10S,13S,14S,15R,17S)-3-hydroxy-3,13,15-trimethyl hexadecahydro-1H-cyclopenta[a]phenanthren-17-yl)-2-oxoethyl)-1H-pyrazole-4-carbonitrile (69)

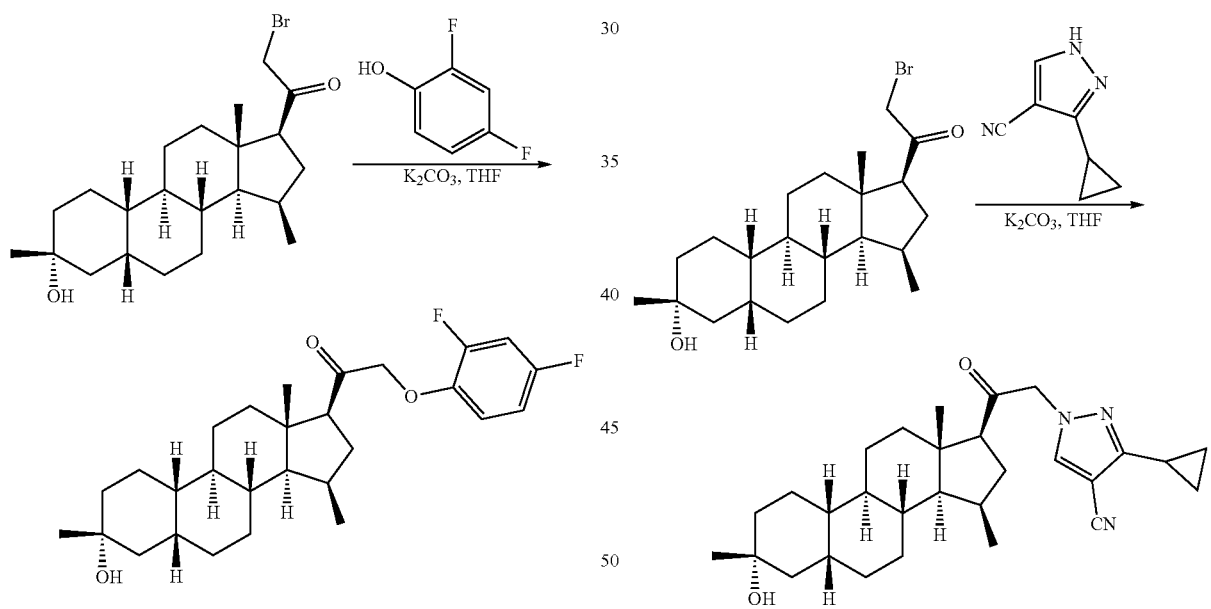

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 3-cyclopropyl-1-(2-((3R,5R,8R,9R,10S,13S,14S,15R,17S)-3-hydroxy-3,13,15-trimethyl hexadecahydro-1H-cyclopenta[a]phenanthren-17-yl)-2-oxoethyl)-1H-pyrazole-4-carbonitrile (30 mg, yield: 41%) was obtained.

MS m/z (ESI): 464.3[M+H]$^+$ $^1$H NMR (400 MHz, CDCl$_3$) δ 7.71 (s, 1H), 4.82 (q, J=17.9 Hz, 2H), 2.51-2.46 (m, 1H), 2.27-2.18 (m, 1H), 2.19-2.08 (m, 1H), 2.04-1.91 (m, 2H), 1.90-1.80 (m, 4H), 1.68-1.60 (m, 4H), 1.57 (s, 3H), 1.51-1.29 (m, 8H), 1.18-1.03 (m, 3H), 1.02-0.95 (m, 7H), 0.82 (s, 3H).

Example 71

1-(2-((3R,5R,8R,9R,10S,13S,14S,15S)-15-Cyclopropyl-3-hydroxy-3,13-dimethylhexadecahydro-1H-cyclopenta[a]phenanthren-17-yl)-2-oxoethyl)-1H-pyrazole-4-carbonitrile

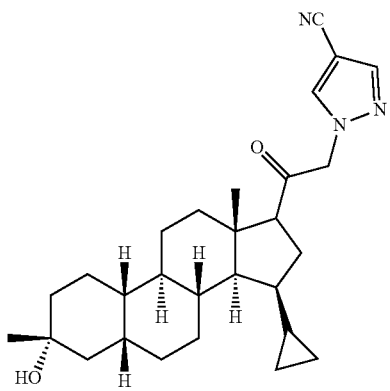

Step 1: (3R,5R,8R,9R,10S,13S,14S,15S)-15-Cyclopropyl-3-hydroxy-3,13-dimethylhexadecahydro-17H-cyclopenta[a]phenanthren-17-one

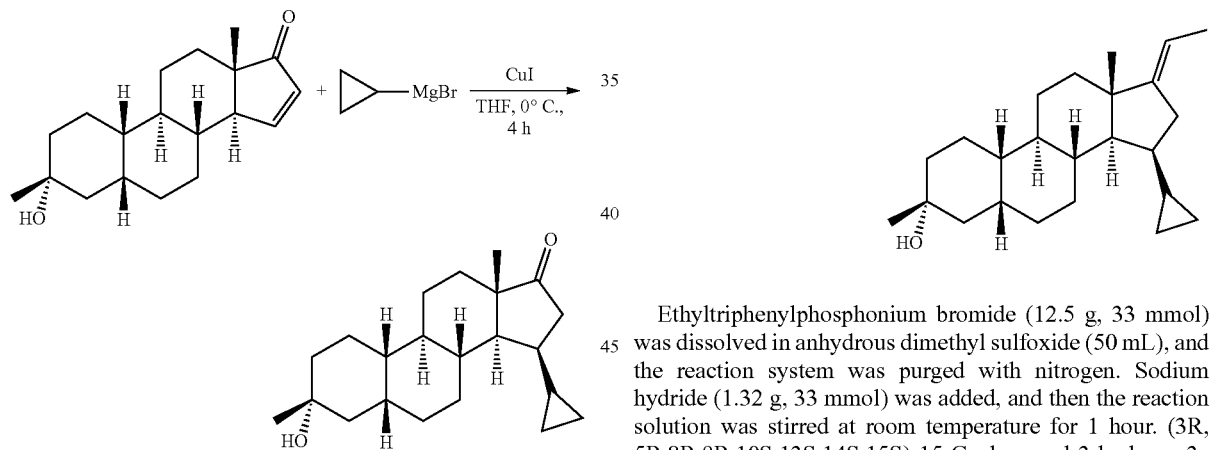

1.0 M cyclopropylmagnesium bromide (12.7 mL, 12.7 mmol) and 20 mL of anhydrous tetrahydrofuran were added to a dry 100 mL round bottom flask. The reaction system was purged with nitrogen, and cooled to 0° C. Cuprous iodide (1.97 g, 10.4 mmol) was added, and then the reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (1 g, 3.5 mmol) was dissolved in 10 ml of anhydrous tetrahydrofuran, and the resulting solution was slowly added dropwise to the reaction system. The reaction solution was stirred for 3 hours, and TLC showed that the reaction was completed. Saturated ammonium chloride solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: petroleum ether:ethyl acetate=2:1) to obtain (3R,5R,8R,9R,10S,13S,14S,15S)-15-cyclopropyl-3-hydroxy-3,13-dimethylhexadecahydro-17H-cyclopenta[a]phenanthren-17-one (1.11 g, 96%).

$^1$H NMR (400 MHz, CDCl$_3$) (2.45-2.30 (m, 2H), 1.85-1.76 (m, 9H), 1.59-1.52 (m, 5H), 1.59-1.27 (m, 12H), 1.11-0.98 (m, 1H), 0.67-0.64 (m, 1H), 0.47-0.43 (m, 1H), 0.22-0.18 (m, 1H), 0.09-0.07 (m, 1H).

Step 2: (3R,5R,8R,9R,10S,13S,14S,15S,E)-15-Cyclopropyl-17-ethylidene-3,13-dimethylhexadecahydro-1H-cyclopenta[a]phenanthren-3-ol

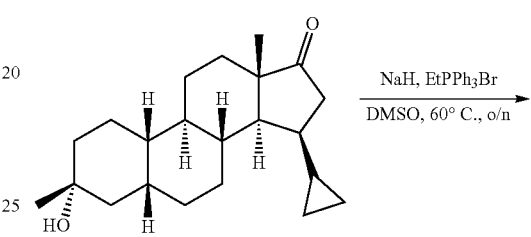

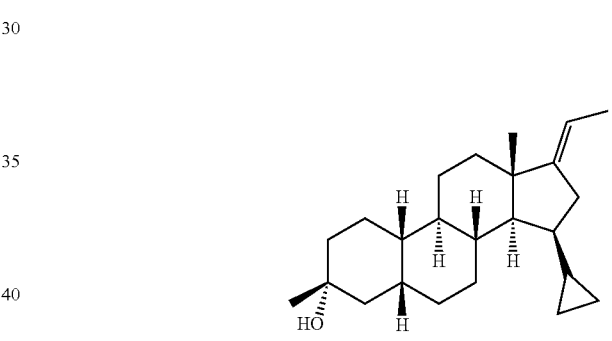

Ethyltriphenylphosphonium bromide (12.5 g, 33 mmol) was dissolved in anhydrous dimethyl sulfoxide (50 mL), and the reaction system was purged with nitrogen. Sodium hydride (1.32 g, 33 mmol) was added, and then the reaction solution was stirred at room temperature for 1 hour. (3R,5R,8R,9R,10S,13S,14S,15S)-15-Cyclopropyl-3-hydroxy-3,13-dimethylhexadecahydro-17H-cyclopenta[a]phenanthren-17-one (1.1 g, 3.3 mmol) was added, and then the reaction solution was stirred at 60° C. overnight. The reaction solution was cooled to room temperature. Water (200 mL) was added to the reaction solution to quench the reaction, and the aqueous phase was extracted with ethyl acetate (200 mL×2). The organic phases were combined, dried over anhydrous sodium sulfate, filtrated and concentrated. The resulting crude product was purified by column chromatography (petroleum ether/ethyl acetate: 50/1-3/1) to obtain (3R,5R,8R,9R,10S,13S,14S,15S,E)-15-cyclopropyl-17-ethylidene-3,13-dimethylhexadecahydro-1H-cyclopenta[a]phenanthren-3-ol (0.67 g, yield: 59%).

$^1$H NMR (400 MHz, CDCl$_3$) δ 5.15-5.09 (m, 1H), 2.45-2.38 (m, 1H), 2.38-2.18 (m, 2H), 1.90-1.07 (m, 28H), 0.86-0.78 (m, 1H), 0.56-0.50 (m, 1H), 0.38-0.32 (m, 1H), 0.12-0.02 (m, 2H).

Step 3: (3R,5R,8R,9R,10S,13S,14S,15S,17S)-15-Cyclopropyl-17-((R)-1-hydroxyethyl)-3,13-dimethylhexadecahydro-1H-cyclopenta[a]phenanthren-3-ol

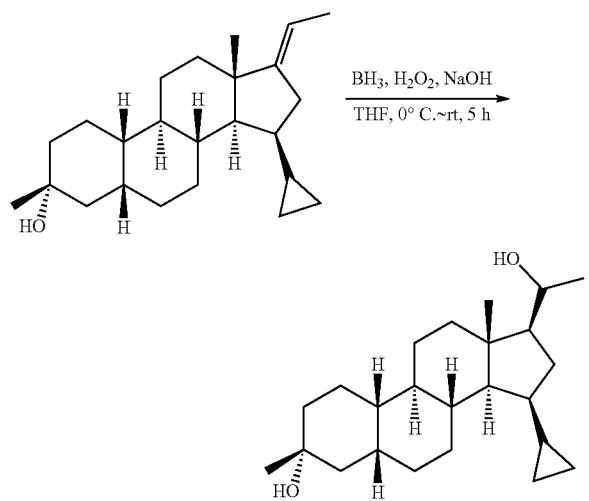

(3R,5R,8R,9R,10S,13S,14S,15S,E)-15-Cyclopropyl-17-ethylidene-3,13-dimethylhexadecahydro-1H-cyclopenta[a]phenanthren-3-ol (0.67 g, 1.96 mmol) was dissolved in anhydrous tetrahydrofuran (20 mL). The solution was cooled to 0° C., and then BH₃/THF (9.8 mL, 9.8 mmol) was added dropwise. The reaction solution was stirred at room temperature for 3 hours, and TLC showed that the reaction was completed. The reaction solution was cooled to 0° C., and then 3 M aqueous NaOH solution (10 mL) was slowly added, followed by the addition of 30% hydrogen peroxide (8 mL). The reaction solution was stirred at room temperature for 2 hours, and TLC showed that the reaction was completed. Ethyl acetate (50 mL) was added, and then the reaction solution was washed with saturated aqueous Na₂S₂O₃ solution (30 mL) and water (30 mL) successively. The organic phase was dried over anhydrous sodium sulfate, filtered and concentrated to obtain the crude product (0.71 g), which was used directly in the next step.

Step 4: 1-((3R,5R,8R,9R,10S,13S,14S,15S,17S)-15-Cyclopropyl-3-hydroxy-3,13-dimethylhexa decahydro-1H-cyclopenta[a]phenanthren-17-yl)ethan-1-one

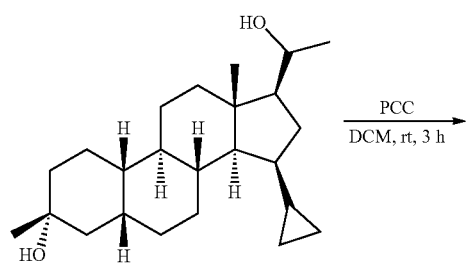

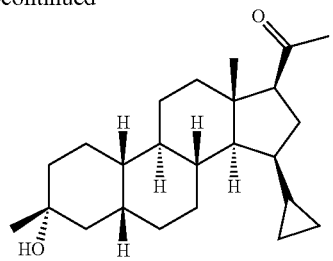

(3R,5R,8R,9R,10S,13S,14S,15S,17S)-15-Cyclopropyl-17-((R)-1-hydroxyethyl)-3,13-dimethylhexadecahydro-1H-cyclopenta[a]phenanthren-3-ol (0.71 g, crude) was dissolved in dichloromethane (20 mL). Pyridinium chlorochromate (1.27 g, 5.88 mmol) was added, and then the reaction solution was stirred at room temperature for 2 hours. The reaction solution was filtered, and the organic phase was concentrated. The resulting crude product was purified by column chromatography (petroleum ether/ethyl acetate: 1/1) to obtain 1-((3R,5R,8R,9R,10S,13S,14S,15S,17S)-15-cyclopropyl-3-hydroxy-3,13-dimethylhexa decahydro-1H-cyclopenta[a]phenanthren-17-yl)ethan-1-one (480 mg, yield of two steps: 68.3%).

¹H NMR (400 MHz, CDCl₃) δ 2.45-2.40 (m, 1H), 2.18-2.10 (m, 4H), 1.99-1.03 (m, 24H), 0.84-0.79 (m, 4H), 0.60-0.53 (m, 1H), 0.43-0.38 (m, 1H), 0.14-0.02 (m, 2H).

Step 5: 2-Bromo-1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one

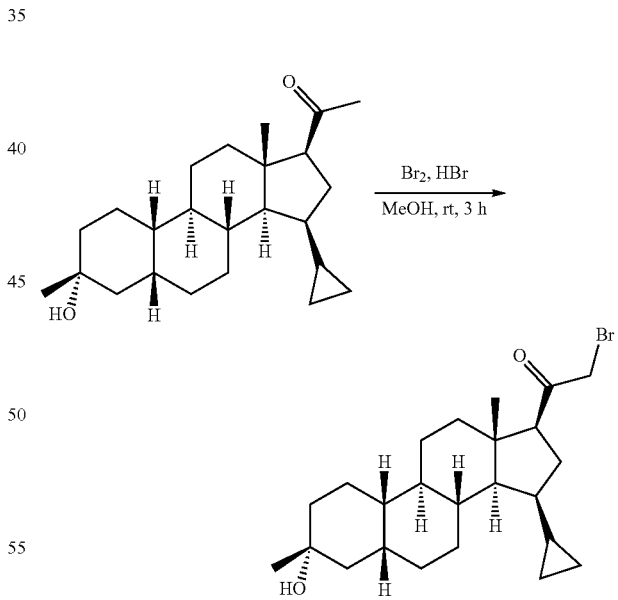

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)ethan-1-one (107 mg, 0.3 mmol) was dissolved in methanol (5 mL). A drop of hydrogen bromide was added to the solution, followed by the addition of liquid bromine (56 mg, 0.35 mmol), and then the reaction solution was stirred at room temperature for 1 hour. Water (20 mL) was added to the reaction solution, and the aqueous phase was extracted with ethyl acetate (20 mL×2). The organic phases were combined, dried over anhydrous sodium sulfate, filtrated and concentrated to obtain the crude product (120 mg, crude), which was used directly in the next step.

Step 6: 1-(2-((3R,5R,8R,9R,10S,13S,14S,15S)-15-Cyclopropyl-3-hydroxy-3,13-dimethylhexadecahydro-1H-cyclopenta[a]phenanthren-17-yl)-2-oxoethyl)-1H-pyrazole-4-carbonitrile

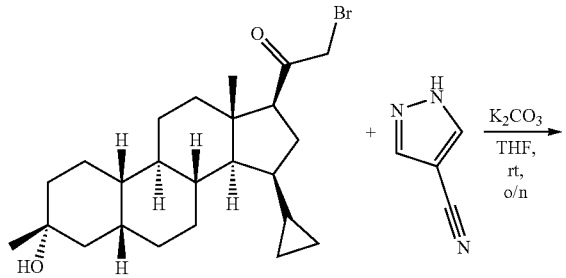

1-((3R,5R,8R,9R,10S,13S,14S,15S,17S)-15-Cyclopropyl-3-hydroxy-3,13-dimethylhexadecahydro-1H-cyclopenta[a]phenanthren-17-yl)ethan-1-one (60 mg, 0.14 mmol), 1H-pyrazole-4-carbonitrile (28 mg, 0.3 mmol) and potassium carbonate (54 mg, 0.3 mmol) were dissolved in anhydrous tetrahydrofuran (5 mL), and the resulting reaction solution was stirred at room temperature overnight. The reaction solution was filtrated, and the filtrate was concentrated. The resulting crude product was purified by high performance liquid chromatography to obtain 1-(2-((3R,5R,8R,9R,10S,13S,14S,15S)-15-cyclopropyl-3-hydroxy-3,13-dimethylhexadecahydro-1H-cyclopenta[a]phenanthren-17-yl)-2-oxoethyl)-1H-pyrazole-4-carbonitrile (31 mg, yield: 49%).

MS m/z (ESI): 450.3 [M+H]+

1H NMR (400 MHz, CDCl3) δ 7.86 (s, 1H), 7.81 (s, 1H), 5.02 (d, J=16.0 Hz, 1H), 4.92 (d, J=16.0 Hz, 1H), 2.51-2.47 (m, 1H), 2.09-1.71 (m, 9H), 1.48-1.10 (m, 16H), 0.90 (s, 3H), 0.83-0.79 (m, 1H), 0.62-0.58 (m, 1H), 0.45-0.40 (m, 1H), 0.14-0.11 (m, 1H), 0.05-0.02 (m, 1H).

Example 72

1-(2-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-oxoethyl)-1H-pyrazole-3-carbonitrile (72)

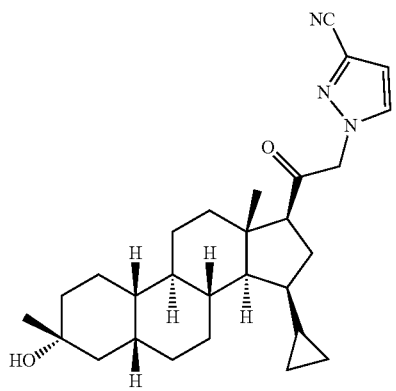

Step 1: Preparation of 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3-carbonitrile

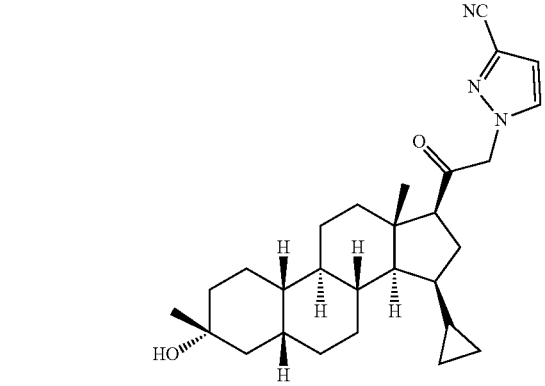

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)ethan-1-one was used as the starting material, accordingly, 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3-carbonitrile (20 mg, yield 20%) was obtained.

MS m/z (ESI): 432.2[M−H2O+H]+

¹H NMR (400 MHz, CDCl₃) δ 7.49 (d, J=2.4 Hz, 1H), 6.73 (d, J=2.4 Hz, 1H), 4.98 (dd, J=40.0, 17.8 Hz, 2H), 2.52-2.45 (m, 1H), 2.24-2.13 (m, 1H), 2.11-2.03 (m, 1H), 2.04-1.95 (m, 2H), 1.90-1.82 (m, 2H), 1.75-1.66 (m, 2H), 1.54-1.23 (m, 16H), 1.18-1.05 (m, 2H), 0.93-0.79 (m, 4H), 0.63-0.55 (m, 1H), 0.45-0.37 (m, 1H), 0.18-0.09 (m, 1H), 0.08-0.01 (m, 1H).

Example 73 and Example 145

1-((3R,5R,8R,9R,10S,13S,14S,15S,17S)-15-Cyclopropyl-3-hydroxy-3,13-dimethylhexa decahydro-1H-cyclopenta[a]phenanthren-17-yl)-2-(2H-1,2,3-triazol-2-yl)ethan-1-one (73)

1-((3R,5R,8R,9R,10S,13S,14S,15S,17S)-15-Cyclopropyl-3-hydroxy-3,13-dimethylhexa decahydro-1H-cyclopenta[a]phenanthren-17-yl)-2-(1H-1,2,3-triazol-1-yl)ethan-1-one (145)

Step 1: Preparation of 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(2H-1,2,3-triazol-2-yl)ethan-1-one and 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(1H-1,2,3-triazol-1-yl)ethan-1-one

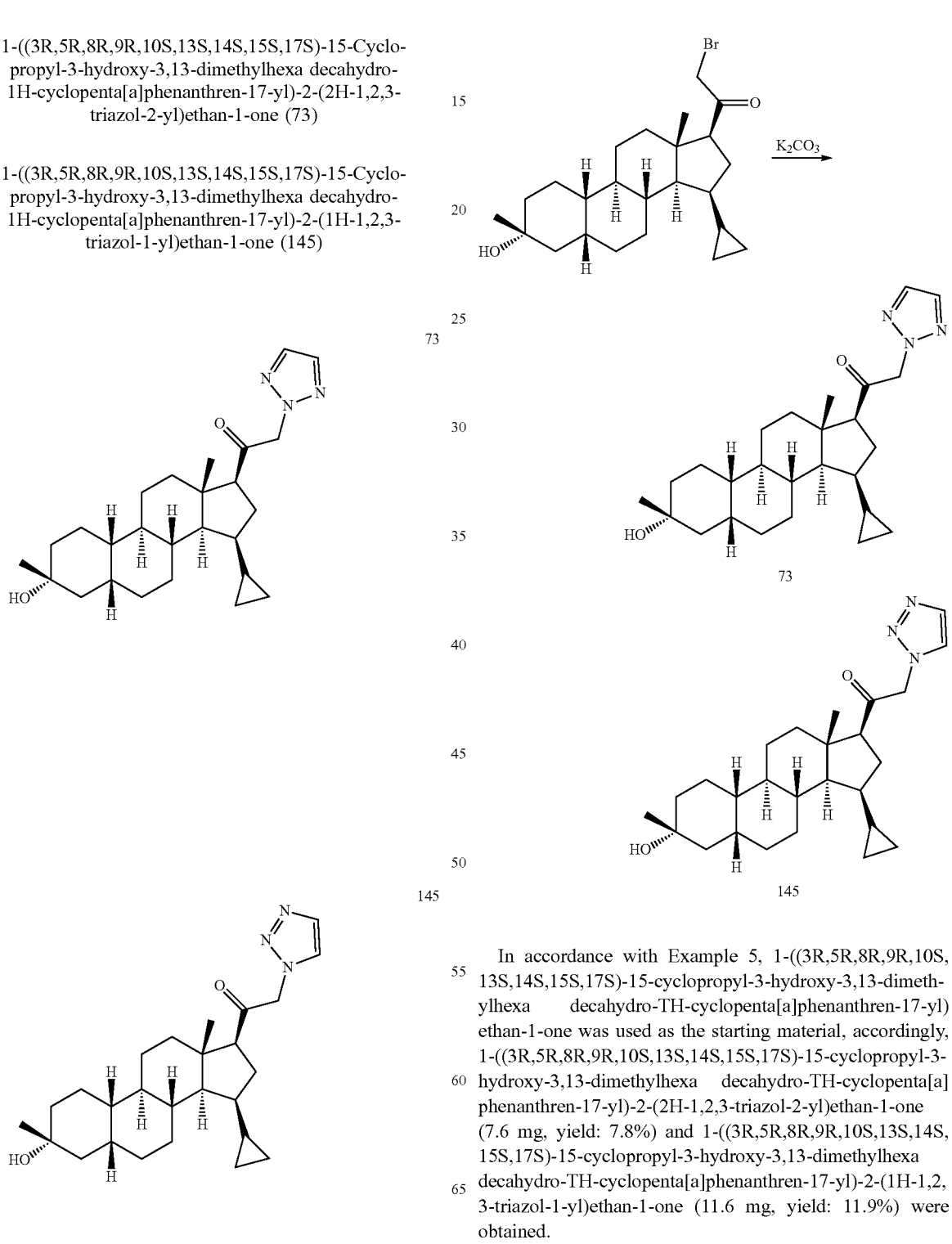

In accordance with Example 5, 1-((3R,5R,8R,9R,10S,13S,14S,15S,17S)-15-cyclopropyl-3-hydroxy-3,13-dimethylhexa decahydro-TH-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexa decahydro-TH-cyclopenta[a]phenanthren-17-yl)-2-(2H-1,2,3-triazol-2-yl)ethan-1-one (7.6 mg, yield: 7.8%) and 1-((3R,5R,8R,9R,10S,13S,14S,15S,17S)-15-cyclopropyl-3-hydroxy-3,13-dimethylhexa decahydro-TH-cyclopenta[a]phenanthren-17-yl)-2-(1H-1,2,3-triazol-1-yl)ethan-1-one (11.6 mg, yield: 11.9%) were obtained.

Example 73

MS m/z (ESI): 408.3[M–H$_2$O+H]$^+$ $^1$H NMR (400 MHz, CDCl$_3$) δ 7.68 (s, 2H), 5.24 (s, 2H), 2.49-2.42 (m, 1H), 2.23-2.14 (m, 1H), 2.10-1.94 (m, 3H), 1.91-1.81 (m, 3H), 1.75-1.66 (m, 2H), 1.48-1.24 (m, 15H), 1.17-1.04 (m, 2H), 0.94 (s, 3H), 0.86-0.76 (m, 1H), 0.63-0.54 (m, 1H), 0.45-0.38 (m, 1H), 0.14-0.01 (m, 2H).

Example 145

MS m/z (ESI): 426.3[M+H]$^+$ $^1$H NMR (400 MHz, CDCl$_3$) δ 7.78 (s, 1H), 7.67 (s, 1H), 5.22 (dd, J=47.1, 17.8 Hz, 2H), 2.59-2.50 (m, 1H), 2.25-2.15 (m, 1H), 2.14-1.98 (m, 2H), 1.96-1.79 (m, 3H), 1.76-1.58 (m, 6H), 1.56-1.25 (m, 12H), 1.22-1.04 (m, 2H), 0.91 (s, 3H), 0.87-0.77 (m, 1H), 0.62-0.55 (m, 1H), 0.47-0.36 (m, 1H), 0.18-0.02 (m, 2H).

Example 74

1-((3R,5R,8R,9R,10S,13S,14S,15S,17S)-15-Cyclopropyl-3-hydroxy-3,13-dimethylhexa decahydro-TH-cyclopenta[a]phenanthren-17-yl)-2-(5-methyl-2H-tetrazol-2-yl)ethan-1-one (74)

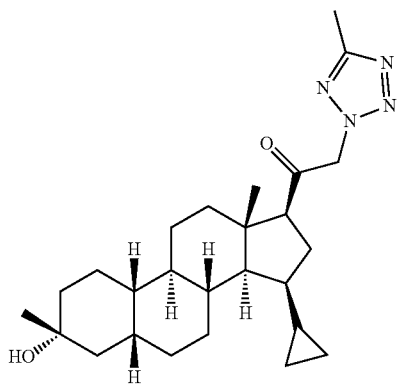

Step 1: Preparation of 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(5-methyl-2H-tetrazol-2-yl)ethan-1-one

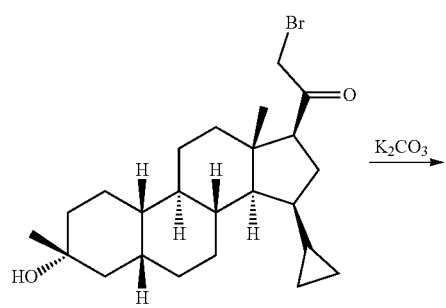

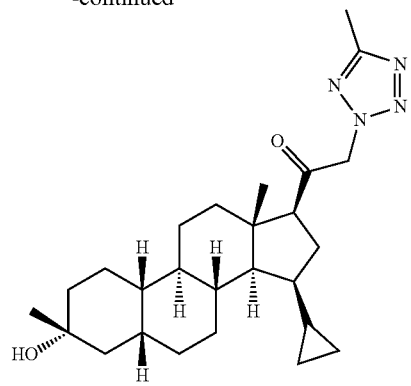

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(5-methyl-2H-tetrazol-2-yl)ethan-1-one (8.5 mg, yield: 9%) was obtained.

MS m/z (ESI): 441.3[M+H]$^+$ $^1$H NMR (400 MHz, CDCl$_3$) δ 5.36 (s, 2H), 2.57 (s, 3H), 2.54-2.47 (m, 1H), 2.25-2.15 (m, 1H), 2.13-1.95 (m, 3H), 1.92-1.79 (m, 3H), 1.77-1.66 (m, 2H), 1.50-1.24 (m, 15H), 1.18-1.05 (m, 2H), 0.94 (s, 3H), 0.87-0.78 (m, 1H), 0.63-0.55 (m, 1H), 0.45-0.37 (m, 1H), 0.17-0.02 (m, 2H).

Example 81

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-4-carbonitrile (81)

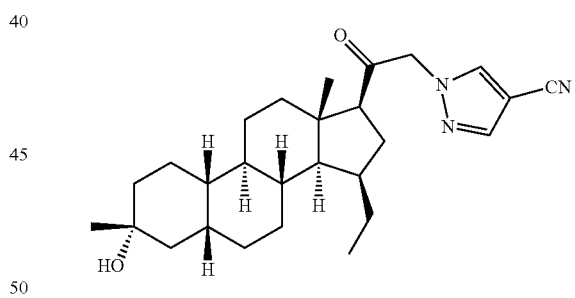

Step 1: (3R,5R,8R,9R,10S,13S,14S,15R)-15-Ethyl-3-hydroxy-3,13-dimethylhexadecahydro-17H-cyclopenta[a]phenanthren-17-one

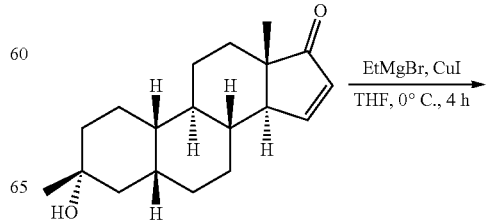

-continued

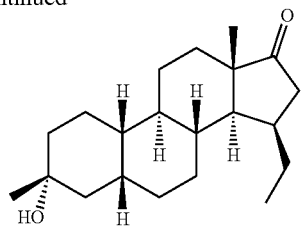

Tetrahydrofuran (15 mL) was added to a 100 mL three-neck flask, and ethyl magnesium bromide (10 mL, 1M, 10 mmol) was then added at 0° C. under a nitrogen atmosphere, followed by the addition of cuprous iodide (1.6 g, 8.4 mmol). The reaction solution was stirred at 0° C. for 1 hour. (3R,5R,8R,9R,10S,13S,14S)-3-Hydroxy-3,13-dimethyl-1,2,3,4,5,6,7,8,9,10,11,12,13,14-tetradecahydro-17H-cyclopenta[a]phenanthren-17-one (800 mg, 2.8 mmol) was dissolved in tetrahydrofuran (5 mL), and the resulting solution was slowly added dropwise to the reaction solution, which was then stirred at 0° C. for 4 hours. Saturated aqueous ammonium chloride solution was added to quench the reaction, and the reaction solution was extracted with ethyl acetate (20 mL). The organic phase was washed with saline (10 mL×3), dried over anhydrous sodium sulfate, filtrated and concentrated by rotary evaporation to dryness. The resulting crude product was purified by column chromatography (petroleum ether/ethyl acetate: 3/1) to obtain (3R,5R,8R,9R,10S,13S,14S,15R)-15-ethyl-3-hydroxy-3,13-dimethylhexadecahydro-17H-cyclopenta[a]phenanthren-17-one (750 mg, yield: 84.9%).

$^1$H NMR (400 MHz, CDCl$_3$) δ 2.37-2.30 (m, 1H), 2.15-2.02 (m, 2H), 1.91-1.31 (m, 17H), 1.27 (s, 3H), 1.24-1.03 (m, 4H), 0.98 (s, 3H), 0.90 (t, J=7.3 Hz, 3H).

Step 2: (3R,5R,8R,9R,10S,13S,14S,15R)-15-Ethyl-17-ethylidene-3,13-dimethylhexadecahydro-1H-cyclopenta[a]phenanthren-3-ol

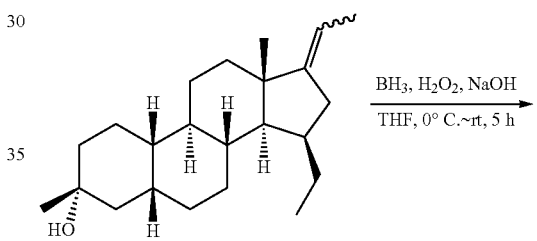

Dimethyl sulfoxide (20 mL) was added to a 100 mL three-neck flask, and ethyltriphenylphosphonium bromide (8.7 g, 23.5 mmol) was then added under a nitrogen atmosphere. Sodium hydride (60%) (940 mg, 23.5 mmol) was added in batches, and the reaction solution was stirred at room temperature for 1 hour. (3R,5R,8R,9R,10S,13S,14S,15R)-15-Ethyl-3-hydroxy-3,13-dimethylhexadecahydro-17H-cyclopenta[a]phenanthren-17-one (750 mg, 2.35 mmol) was dissolved in dimethyl sulfoxide (5 mL), and the resulting solution was slowly added dropwise to the reaction solution, which was then stirred under a nitrogen atmosphere at 80° C. for 5 hours. The reaction solution was cooled to room temperature. Saturated aqueous ammonium chloride solution was added to quench the reaction, and the reaction solution was extracted with ethyl acetate (50 mL). The organic phase was washed with saline (20 mL×3), dried over anhydrous sodium sulfate, filtrated and concentrated by rotary evaporation to dryness. The resulting crude product was purified by column chromatography (petroleum ether/ethyl acetate: 3/1) to obtain (3R,5R,8R,9R,10S,13S,14S,15R)-15-ethyl-17-ethylidene-3,13-dimethylhexadecahydro-1H-cyclopenta[a]phenanthren-3-ol (580 mg, yield: 71.7%).

$^1$H NMR (400 MHz, CDCl$_3$) δ 5.22-5.06 (m, 1H), 2.54-2.39 (m, 1H), 2.28-2.09 (m, 2H), 1.96-1.80 (m, 4H), 1.78-1.59 (m, 6H), 1.55-1.33 (m, 11H), 1.26 (s, 3H), 1.20-1.08 (m, 3H), 1.05 (s, 3H), 0.82 (t, J=7.3 Hz, 3H).

Step 3: (3R,5R,8R,9R,10S,13S,14S,15R,17R)-15-Ethyl-17-(1-hydroxyethyl)-3,13-dimethylhexadecahydro-1H-cyclopenta[a]phenanthren-3-ol

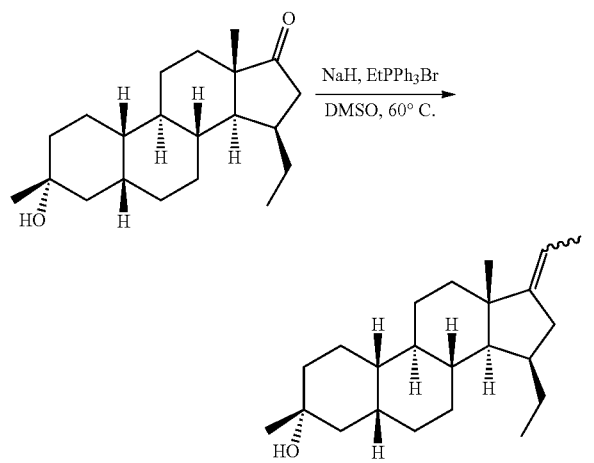

In accordance with Step 3 of Example 71, (3R,5R,8R,9R,10S,13S,14S,15R)-15-ethyl-17-ethylidene-3,13-dimethylhexadecahydro-1H-cyclopenta[a]phenanthren-3-ol was used as the starting material, accordingly, (3R,5R,8R,9R,10S,13S,14S,15R,17R)-15-ethyl-17-(1-hydroxyethyl)-3,13-dimethylhexa decahydro-1H-cyclopenta[a]phenanthren-3-ol (600 mg, yield: 98.1%) was obtained.

Step 4: 1-((3R,5R,8R,9R,10S,13S,14S,15R,17S)-15-Ethyl-3-hydroxy-3,13-dimethylhexadecahydro-1H-cyclopenta[a]phenanthren-17-yl)ethan-1-one

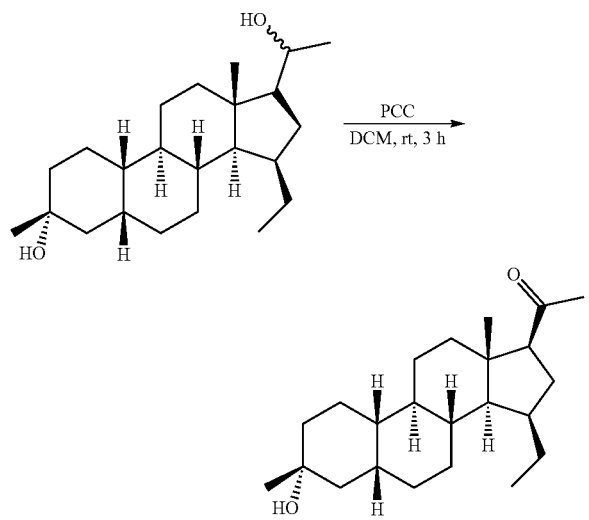

In accordance with Step 4 of Example 71, (3R,5R,8R,9R,10S,13S,14S,15R,17R)-15-ethyl-7-(1-hydroxyethyl)-3,13-dimethylhexa decahydro-1H-cyclopenta[a]phenanthren-3-ol was used as the starting material, accordingly, 1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one (500 mg, yield: 83.8%) was obtained.

1H NMR (400 MHz, CDCl$_3$) δ 2.51 (t, J=8.0 Hz, 1H), 2.12 (s, 3H), 2.00-1.30 (m, 20H), 1.28 (s, 3H), 1.25-1.00 (m, 4H), 0.84 (t, J=7.2 Hz, 3H), 0.73 (s, 3H).

Step 5: 2-Bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one

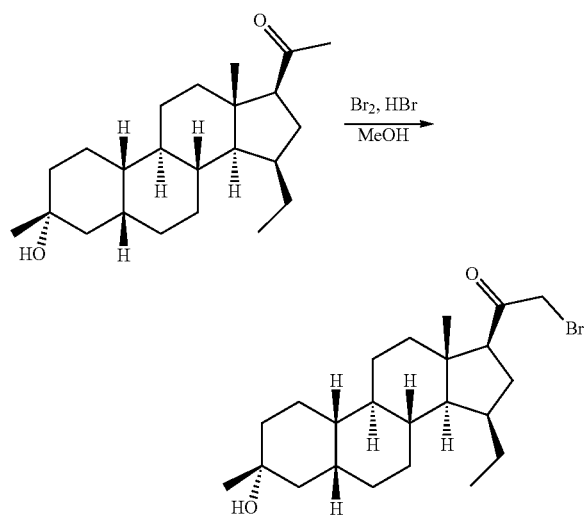

In accordance with Step 5 of Example 71, 1-((3R,5R,8R,9R,10S,13S,14S,15R,17S)-15-ethyl-3-hydroxy-3,13-dim- ethylhexadecahydro-1H-cyclopenta[a]phenanthren-17-yl)ethan-1-one was used as the starting materials, accordingly, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one (500 mg, yield: 81.4%) was obtained.

Step 6: 1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-4-carbonitrile

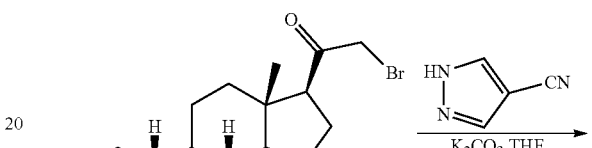

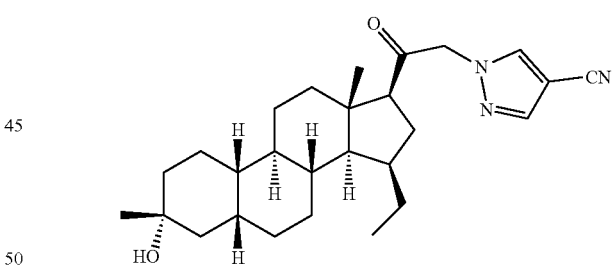

In accordance with Step 6 of Example 71, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-4-carbonitrile (24 mg, yield: 38.8%) was obtained.

MS m/z (ESI): 438.2[M+H]$^+$.

$^1$H NMR (400 MHz, CDCl$_3$) δ 7.86 (s, 1H), 7.81 (s, 1H), 5.08-4.78 (m, 2H), 2.58 (t, J=8.0 Hz, 1H), 2.07-1.29 (m, 20H), 1.28 (s, 3H), 1.27-1.06 (m, 4H), 0.85 (t, J=7.3 Hz, 3H), 0.79 (s, 3H).

Example 91

2-(4-Chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (91)

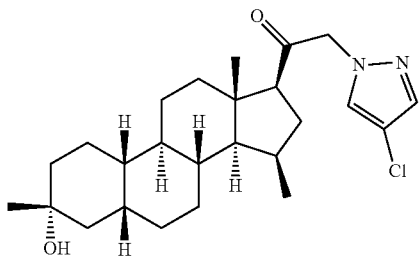

Step 1: Preparation of 2-(4-chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

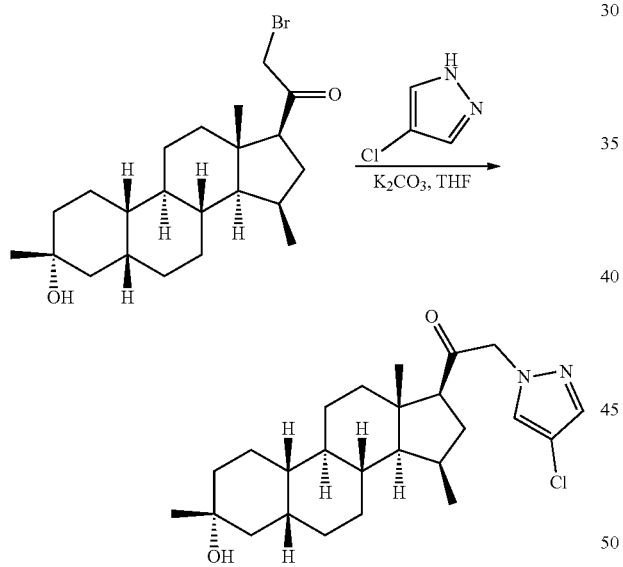

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 2-(4-chloro-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (10 mg, yield: 14%) was obtained.

MS m/z (ESI): 433.3[M+H]⁺

¹H NMR (400 MHz, CDCl₃) δ 7.45 (s, 1H), 7.41 (s, 1H), 4.86 (q, J=17.9 Hz, 2H), 2.61-2.44 (m, 1H), 2.30-2.07 (m, 2H), 2.02-1.91 (m, 1H), 1.86-1.80 (m, 4H), 1.76-1.57 (m, 4H), 1.51-1.38 (m, 6H), 1.37-1.20 (m, 6H), 1.20-1.03 (m, 2H), 0.98 (d, J=7.1 Hz, 3H), 0.83 (s, 3H).

Example 92 and Example 93

2-(5-Fluoro-2H-benzo[d][1,2,3]triazol-2-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (92)

2-(5-Fluoro-1H-benzo[d][1,2,3]triazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (93A) and 2-(6-Fluoro-1H-benzo[d][1,2,3]triazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (93B)

92

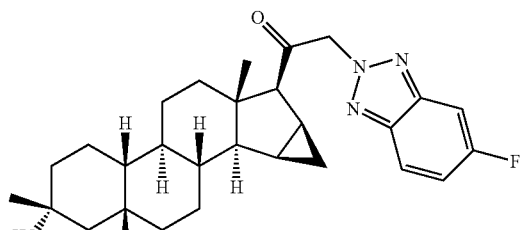

93A

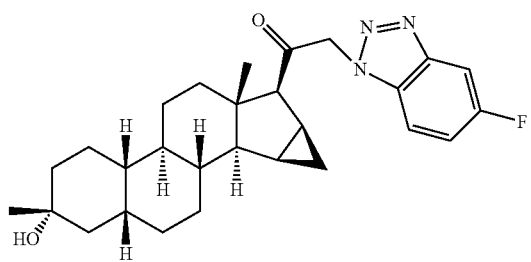

93B

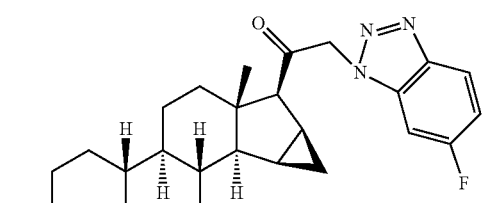

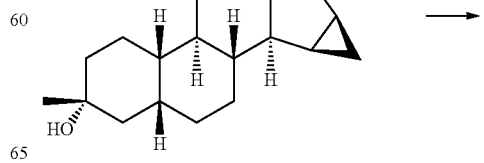

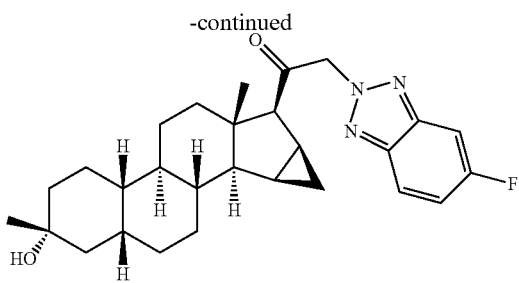

92

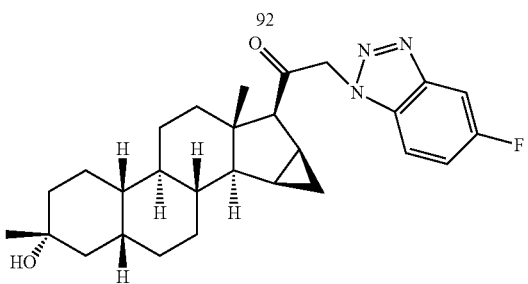

93A

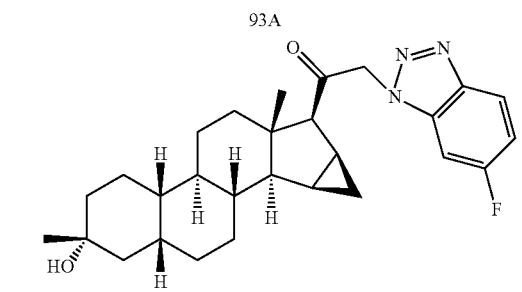

93B

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a] phenanthren-7-yl)ethan-1-one and 5-fluoro-2H-benzo[d][1, 2,3]triazole were used as the starting materials, accordingly, 2-(5-fluoro-2H-benzo[d][1,2,3]triazol-2-yl)-1-((2R,4aS, 4bR,6aS,7S,7aS,8aR,8bR,8cR,10aR)-2-hydroxy-2,6a-dimethyloctadecahydrocyclopropa[4,5]cyclopenta[1,2-a] phenanthren-7-yl)ethan-1-one (11.5 mg, white solid, yield: 12.7%) and a mixture of Example 93A and Example 93B (about 3:2) (21.6 mg, white solid, yield: 23.9%) were obtained.

The mixture was further separated by preparative chromatography to obtain 2-(5-fluoro-1H-benzo[d][1,2,3]triazol-1-yl)-1-((2R,4aS,4bR,6aS,7S,7aS,8aR,8bR,8cR, 10aR)-2-hydroxy-2,6a-dimethyloctadecahydrocyclopropa [4,5]cyclopenta[1,2-a]phenanthren-7-yl)ethan-1-one and 2-(6-fluoro-1H-benzo[d][1,2,3]triazol-1-yl)-1-((2R,4aS, 4bR,6aS,7S,7aS,8aR,8bR,8cR,10aR)-2-hydroxy-2,6a-dimethyloctadecahydrocyclopropa[4,5]cyclopenta[1,2-a] phenanthren-7-yl)ethan-1-one.

Example 92

MS m/z (ESI): 466.2[M+H]$^+$
$^1$H NMR (400 MHz, CDCl$_3$) δ 7.87 (dd, J$_1$=9.2 Hz, J$_2$=4.8 Hz, 1H), 7.47 (dd, J$_1$=9.2 Hz, J$_2$=2.0 Hz, 1H), 7.23-7.18 (m, 1H), 5.73 (dd, J$_1$=17.6 Hz, J$_2$=4.4 Hz, 2H), 2.90 (d, J=4.0 Hz, 1H), 1.99-1.96 (m, 1H), 1.85-1.81 (m, 4H), 1.74-1.63 (m, 3H), 1.57-1.38 (m, 10H), 1.30-1.11 (m, 6H), 1.14-1.01 (m, 2H), 0.88 (s, 3H), 0.53-0.48 (m, 1H).

Example 93A

MS m/z (ESI): 466.2[M+H]$^+$

Example 93B

MS m/z (ESI): 466.2[M+H]$^+$

Example 94

2-(2,4-Difluorophenoxy)-1-((2R,4aS,4bR,6aS,7S, 7aS,8aR,8bR,8cR,10aR)-2-hydroxy-2,6a-dimethyl-octadecahydrocyclopropa[4,5]cyclopenta[1,2-a] phenanthren-7-yl)ethan-1-one

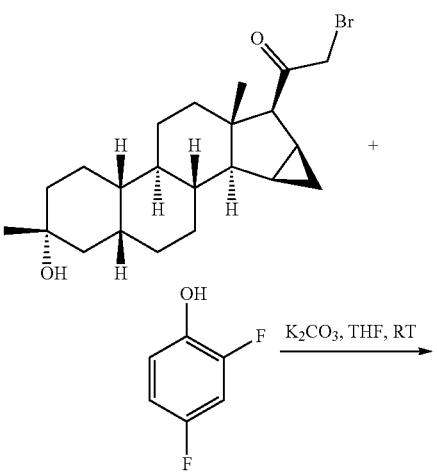

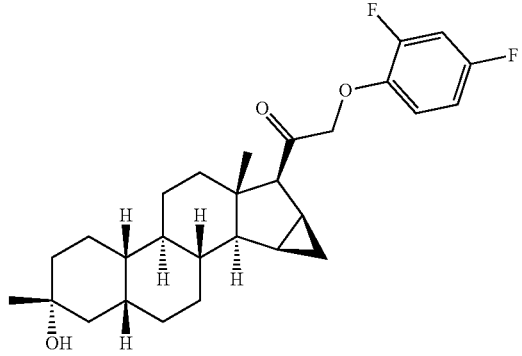

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a] phenanthren-7-yl)ethan-1-one and 2,4-difluorophenol were used as the starting materials, accordingly, 2-(2,4-difluorophenoxy)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (27.4 mg, white solid, yield: 38.6%) was obtained.

MS m/z (ESI): 441.2[M+H]$^+$
$^1$H NMR (400 MHz, CDCl$_3$) δ 6.93-6.80 (m, 2H), 6.79-6.74 (m, 1H), 4.77 (dd, J$_1$=16.8 Hz, J$_2$=3.6 Hz, 2H), 2.93 (d, J=3.2 Hz, 1H), 1.89-1.76 (m, 5H), 1.75-1.60 (m, 3H), 1.55-1.50 (m, 1H), 1.46-1.41 (m, 6H), 1.27-1.11 (m, 9H), 0.98-0.95 (m, 1H), 0.94-0.89 (m, 1H), 0.76 (s, 3H), 0.46-0.39 (m, 1H).

Example 95

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-methyl-1H-pyrazol-1-yl)ethan-1-one

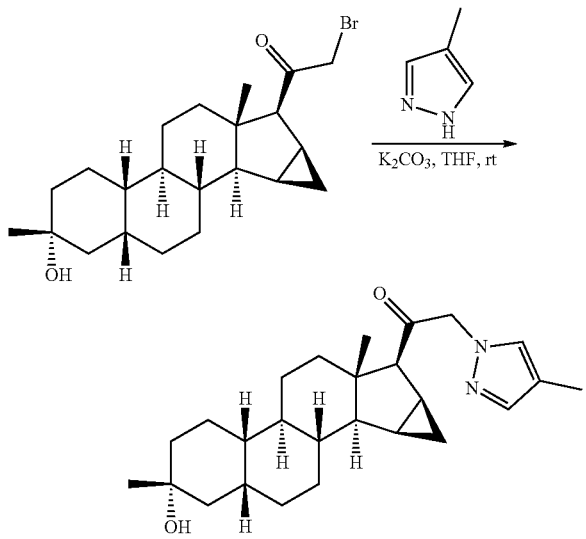

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 4-methylpyrazole were used as the starting materials, accordingly, 1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)-2-(4-methyl-1H-pyrazol-1-yl)ethan-1-one (12.6 mg, white solid, yield: 15.7%) was obtained.

MS m/z (ESI): 411.3[M+H]$^+$ $^1$H NMR (400 MHz, CDCl$_3$) δ 7.44 (s, 1H), 7.26 (s, 1H), 5.23 (m, 2H), 2.83 (d, J=4.4 Hz, 1H), 2.13 (s, 3H), 1.98-1.85 (m, 2H), 1.83-1.69 (m, 9H), 1.60-1.56 (m, 1H), 1.40-1.27 (m, 12H), 1.09-1.01 (m, 2H), 0.80 (s, 3H), 0.48-0.45 (in, 1H).

Example 96

2-((4-Fluorophenyl)amino)-1-((3R,5R,8R,9R,10S,13S,14S,15R,17S)-3-hydroxy-3,13,15-trimethyl-hexadecahydro-1H-cyclopenta[a]phenanthren-17-yl)ethan-1-one

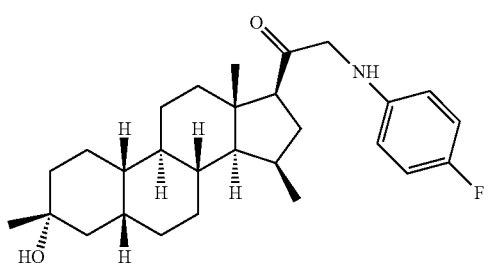

Step 1: Preparation of 2-((4-fluorophenyl)amino)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

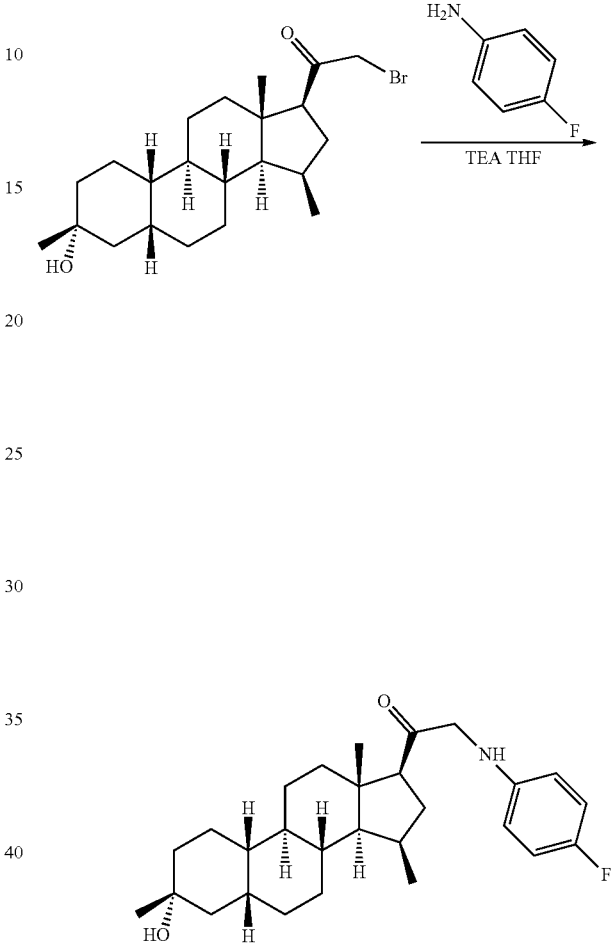

2-Bromo-1-((3R,5R,8R,10S,13S,14S,15R,17S)-3-hydroxy-3,13,15-trimethylhexadecahydro-1H-cyclopenta[a]phenanthren-17-yl)ethan-1-one (50 mg, 0.12 mmol) was dissolved in tetrahydrofuran (3 mL). 4-Fluoroaniline (42 mg, 0.2 mmol) and triethylamine (60 mg, 0.6 mmol) were added, and the reaction solution was stirred at room temperature for 12 hours. The reaction solution was concentrated, and the resulting residue was purified by high performance liquid chromatography to obtain 2-((4-fluorophenyl)amino)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (7 mg, white solid, yield: 13%).

MS m/z (ESI): 442.3[M+H]$^+$.

$^1$H NMR (400 MHz, CDCl$_3$) δ 6.95-6.86 (m, 2H), 6.59-6.53 (m, 2H), 3.95-3.85 (m, 2H), 2.55-2.47 (m, 1H), 2.25-2.15 (m, 2H), 1.90-1.80 (m, 5H), 1.75-1.25 (m, 18H), 1.00 (d, J=8.0 Hz, 3H), 0.81 (s, 3H).

Example 97

2-((4-Fluorophenyl)amino)-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one

Example 98

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(1H-imidazol-1-yl)ethan-1-one

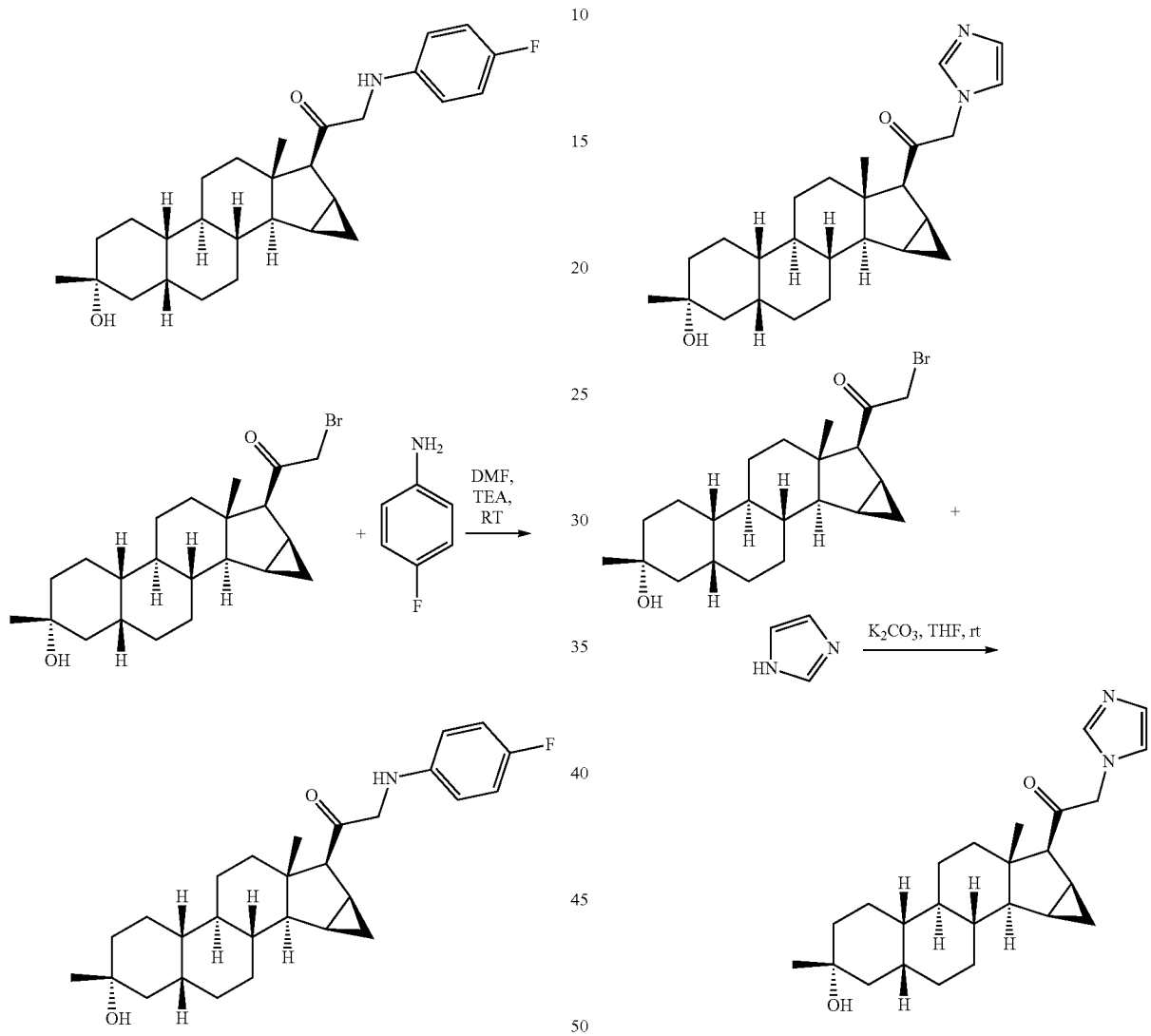

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and p-fluoroaniline were used as the starting materials, and N,N-dimethylformamide was used as the solvent, accordingly, 2-((4-fluorophenyl)amino)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (14.9 mg, yellow oil, yield: 26.7%) was obtained.

MS m/z (ESI): 440.2[M+H]$^+$ $^1$H NMR (400 MHz, CDCl$_3$) δ 7.00-6.95 (m, 2H), 6.91-6.83 (m, 2H), 4.19 (dd, J$_1$=20.0 Hz, J$_2$=2.8 Hz, 2H), 2.80 (d, J=4.0 Hz, 1H), 1.92-1.58 (m, 14H), 1.45-1.40 (m, 8H), 1.27 (s, 3H), 1.09-0.91 (m, 2H), 0.69 (s, 3H), 0.48-0.43 (m, 1H).

In accordance with Example 63, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and imidazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(1H-imidazol-1-yl)ethan-1-one (23.3 mg, white solid, yield: 34.4%) was obtained.

MS m/z (ESI): 397.2[M+H]$^+$ $^1$H NMR (400 MHz, CDCl$_3$) δ 7.48 (s, 1H), 7.12 (s, 1H), 6.88 (s, 1H), 4.98-4.87 (m, 2H), 2.82 (d, J=2.8 Hz, 1H), 1.94-1.91 (m, 1H), 1.85-1.81 (m, 4H), 1.70-1.53 (m, 10H), 1.41-1.28 (m, 9H), 1.13-0.95 (m, 2H), 0.78 (s, 3H), 0.52-0.46 (m, 1H).

Example 99 and Example 100

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4,5,6,7-tetrahydro-1H-indazol-1-yl)ethan-1-one 1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4,5,6,7-tetrahydro-2H-indazol-2-yl)ethan-1-one

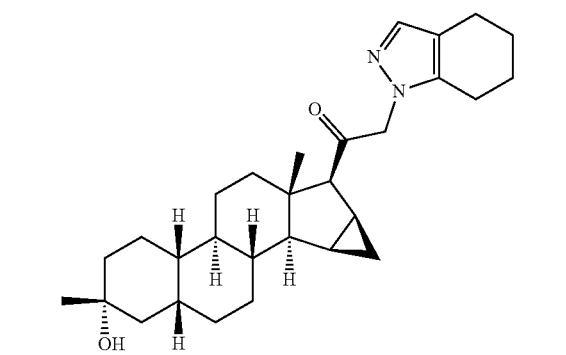

99

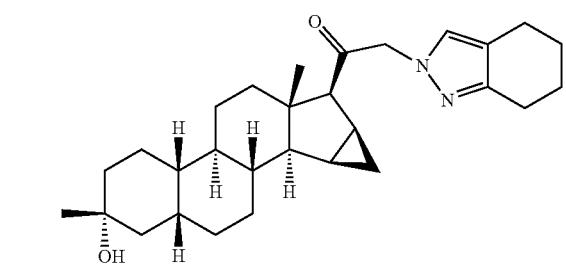

100

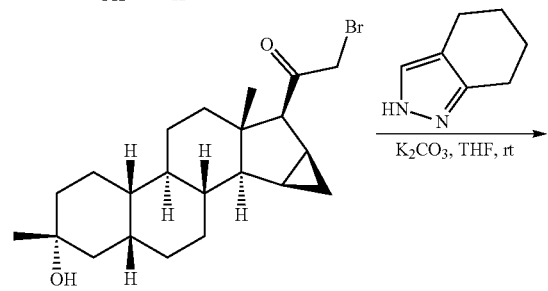

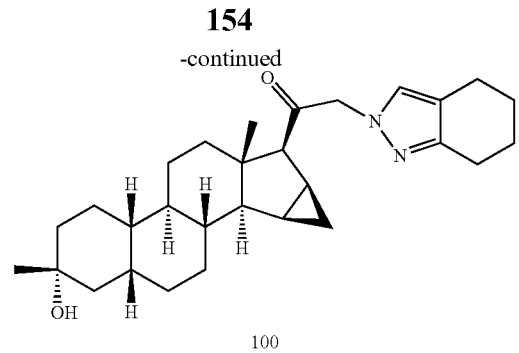

100

In accordance with Example 5, 2-bromo-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one and 4,5,6,7-tetrahydro-2H-indazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4,5,6,7-tetrahydro-1H-indazol-1-yl)ethan-1-one (99) (5.5 mg, white solid, yield: 6.8%) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4,5,6,7-tetrahydro-2H-indazol-2-yl)ethan-1-one (100) (3.1 mg, white solid, yield: 3.8%) were obtained.

Example 99

MS m/z (ESI): 415.3[M+H]$^+$
$^1$H NMR (400 MHz, CDCl$_3$) δ 7.12 (s, 1H), 5.14-5.05 (m, 2H), 2.80 (d, J=4.0 Hz, 1H), 2.69 (t, J=6.0 Hz, 2H), 2.56 (t, J=6.0 Hz, 2H), 1.97-1.93 (m, 1H), 1.85-1.61 (m, 12H), 1.55-1.52 (m, 2H), 1.43-1.21 (m, 13H), 1.11-0.94 (m, 2H), 0.79 (s, 3H), 0.48-0.42 (m, 1H).

Example 100

MS m/z (ESI): 415.3[M+H]$^+$
$^1$H NMR (400 MHz, CDCl$_3$) δ 7.50 (s, 1H), 5.74-5.35 (m, 2H), 2.89 (d, J=4.0 Hz, 1H), 2.58 (t, J=6.0 Hz, 2H), 2.48 (t, J=6.0 Hz, 2H), 1.96-1.91 (m, 1H), 1.80-1.72 (m, 8H), 1.40-1.22 (m, 19H), 1.12-0.99 (m, 2H), 0.82 (s, 3H), 0.51-0.45 (m, 1H).

Example 101

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(5-methyl-1H-tetrazol-1-yl)ethan-1-one

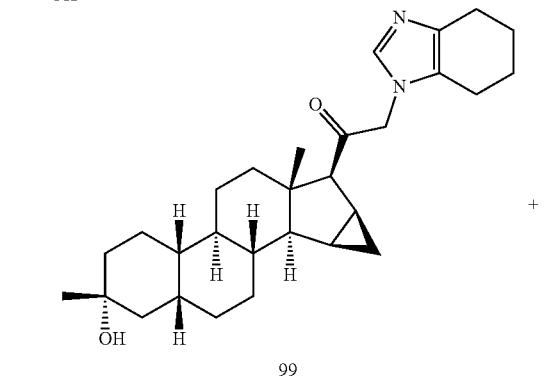

99

+

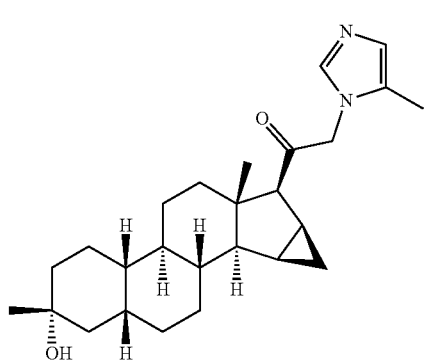

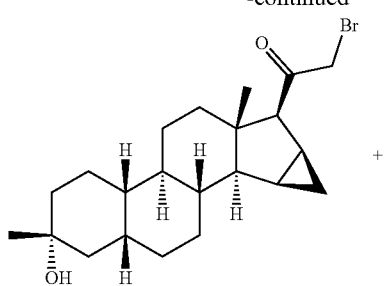

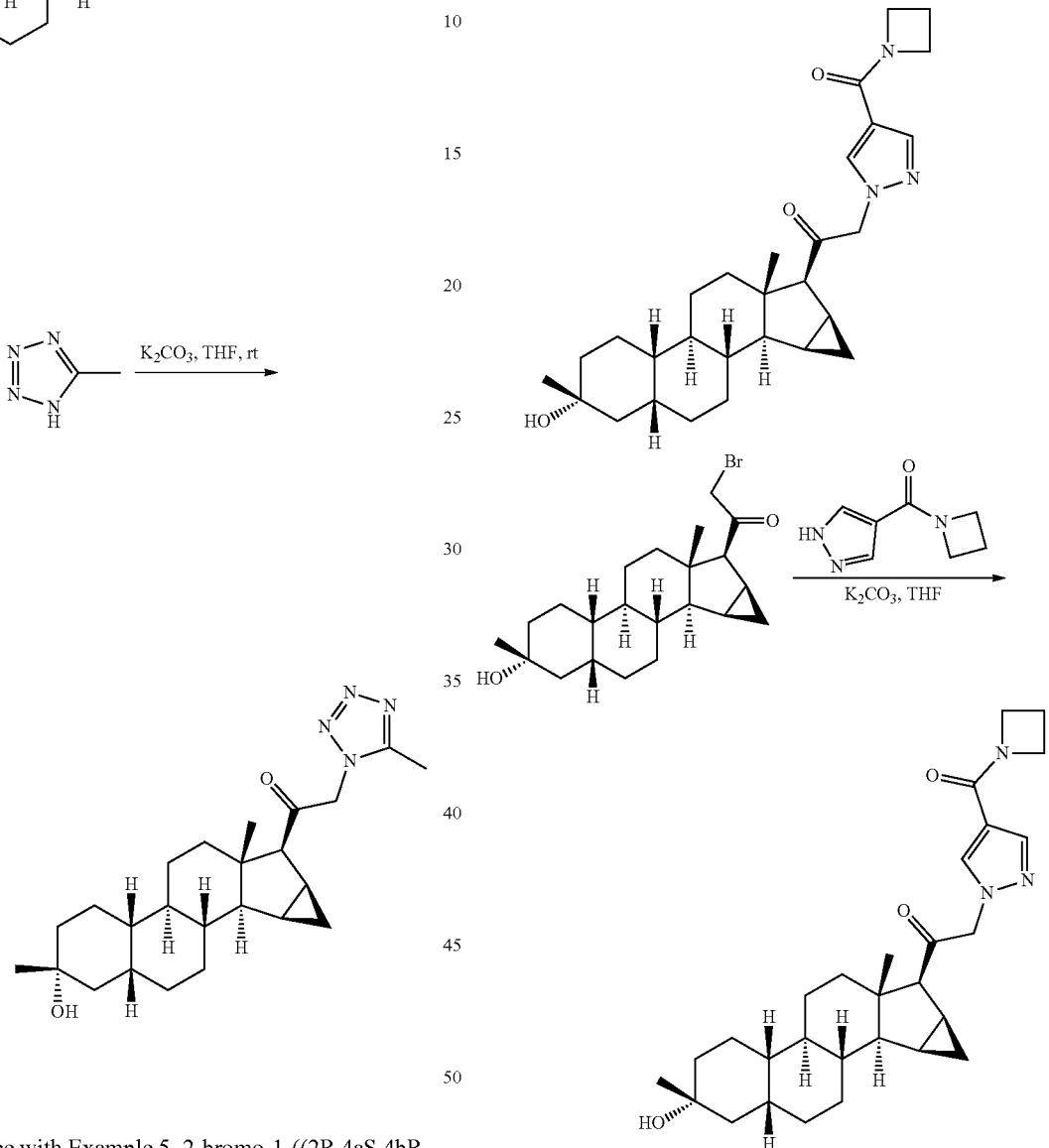

Example 102

2-(4-(Azetidine-1-carbonyl)-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 5-methyl-1H-4-tetrazole were used as the starting materials, accordingly, 1-((2R,4aS,4bR,6aS,7S,7aS,8aR,8bR,8cR,10aR)-2-hydroxy-2,6a-dim-ethyloctadecahydrocyclopropa[4,5]cyclopenta[1,2-a]phenanthren-7-yl)-2-(5-methyl-1H-tetrazol-1-yl)ethan-1-one (19 mg, white solid, yield: 23.5%) was obtained.

MS m/z (ESI): 413.2[M+H]$^+$ $^1$H NMR (400 MHz, CDCl$_3$) δ 5.58 (dd, J$_1$=17.6 Hz, J$_2$=7.6 Hz, 2H), 2.86 (d, J=4.0 Hz, 1H), 2.57 (s, 3H), 1.96-1.93 (m, 1H), 1.89-1.61 (m, 8H), 1.55-1.22 (m, 14H), 1.14-0.97 (m, 3H), 0.84 (s, 3H), 0.47-0.53 (m, 1H).

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and azetidin-1-yl(1H-pyrazol-4-yl)methanone were used as the starting materials, accordingly, 2-(4-(azetidine-1-carbonyl)-1H-pyrazol-1-yl)-1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)ethan-1-one (10.0 mg, yield: 14.3%) was obtained.

MS m/z (ESI): 480.3 [M+H]$^+$ $^1$H NMR (400 MHz, CDCl$_3$) δ 7.85-7.80 (m, 1H), 7.80-7.74 (m, 1H), 5.20-5.05 (m, 2H), 4.53-4.10 (m, 4H), 2.82 (d,

J=3.3 Hz, 1H), 2.44-2.31 (m, 2H), 1.98-1.90 (m, 1H), 1.86-1.79 (m, 3H), 1.74-1.64 (m, 3H), 1.57-1.53 (m, 2H), 1.44-1.24 (m, 15H), 1.13-0.97 (m, 2H), 0.79 (s, 3H), 0.51-0.44 (m, 1H).

Example 103

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-nitro-1H-pyrazol-1-yl)ethan-1-one

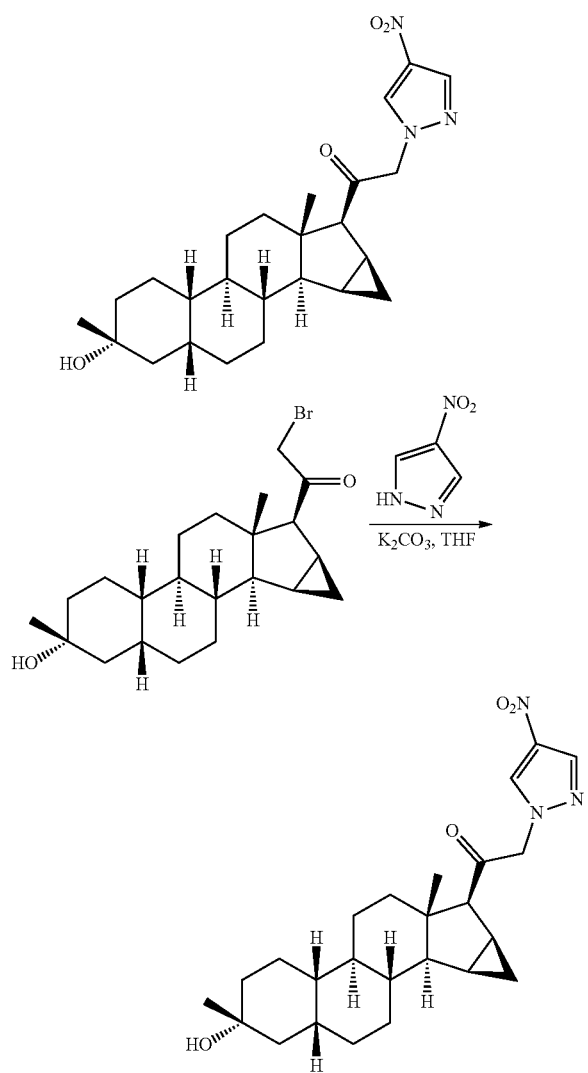

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one and 4-nitro-1H-pyrazole were used as the starting materials, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-nitro-1H-pyrazol-1-yl)ethan-1-one (32.5 mg, yield: 60%) was obtained.

MS m/z (ESI): 424.2 [M+H—H$_2$O]$^+$ $^1$H NMR (400 MHz, CDCl$_3$) δ 8.20 (s, 1H), 8.09 (s, 1H), 5.26-5.09 (m, 2H), 2.85 (s, 1H), 1.98-1.91 (m, 1H), 1.87-1.79 (m, 4H), 1.74-1.65 (m, 3H), 1.56-1.52 (m, 2H), 1.47-1.35 (m, 7H), 1.34-1.24 (m, 7H), 1.13-0.97 (m, 2H), 0.79 (s, 3H), 0.55-0.47 (m, 1H).

Example 104

(3R,5R,8R,9R,10S,13S,14S,16R,17S)-17-Acetyl-3-hydroxy-3,13-dimethylhexadecahydro-1H-cyclopenta[a]phenanthrene-16-carbonitrile (104)

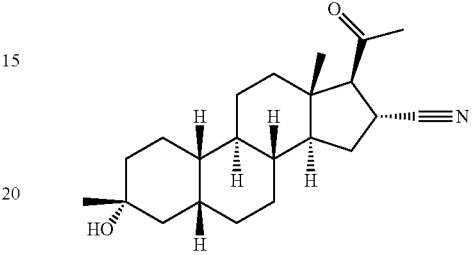

Step 1: Preparation of (3R,5R,8R,9R,10S,13S,14S,16R,17S)-17-acetyl-3-hydroxy-3,13-dimethylhexadecahydro-1H-cyclopenta[a]phenanthrene-16-carbonitrile

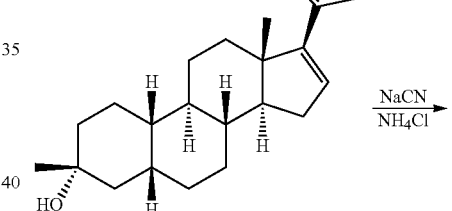

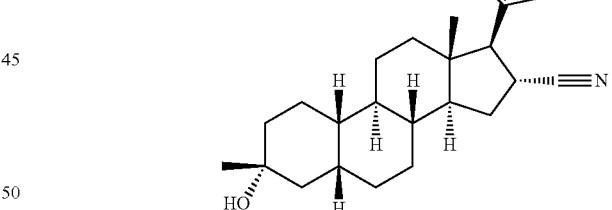

1-((3R,5R,8R,9R,10S,13S,14S)-3-Hydroxy-3,13-dimethyl-2,3,4,5,6,7,8,9,10,11,12,13,14,15-tetradecahydro-1H-cyclopenta[a]phenanthren-17-yl)ethan-1-one (270 mg, 0.853 mmol), ammonium chloride (250 mg, 4.69 mmol) and 18-crown-6 (23 mg, 0.853 mmol) were added to a mixed solution of dimethyl sulfoxide (7 mL) and water (2 mL) at 85° C., followed by the addition of a mixed solution of sodium cyanide (230 mg, 4.69 mmol), dimethyl sulfoxide (4 mL) and water (1 mL). The reaction solution was stirred at 85° C. for 16 hours. Water (30 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting residue was purified by column chromatography (petroleum ether/ethyl acetate=1:1) to obtain (3R,5R,8R,9R,10S,13S,14S,16R,17S)-17-acetyl-3-hydroxy-3,13-dimethylhexadecahydro-1H-cyclopenta[a]phenanthrene-16-carbonitrile as a white solid (250 mg, yield: 85%).

Example 105

1-(2-((3R,5R,8R,9R,10S,13S,14R,17S)-3-Hydroxy-3,13-dimethyl-15-(nitromethyl)hexa decahydro-1H-cyclopenta[a]phenanthren-17-yl)-2-oxoethyl)-1H-pyrazole-4-carbonitrile

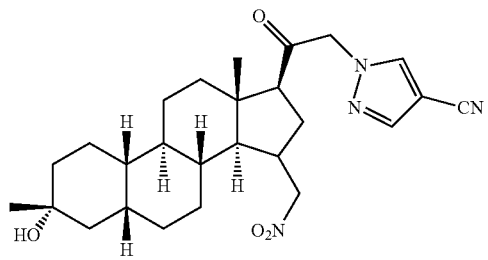

Example 105 was synthesized by the following specific scheme:

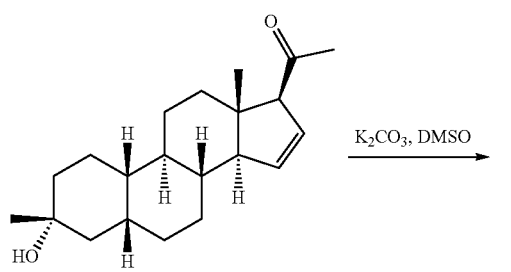

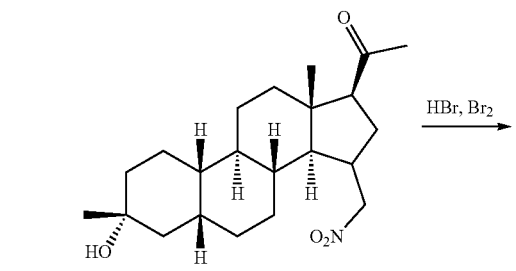

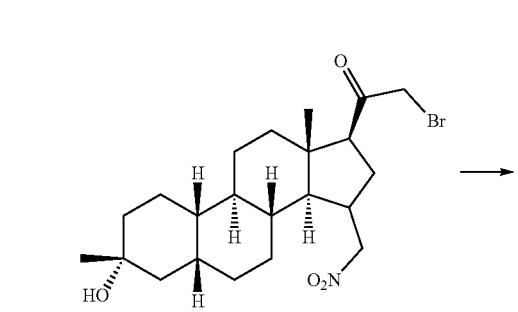

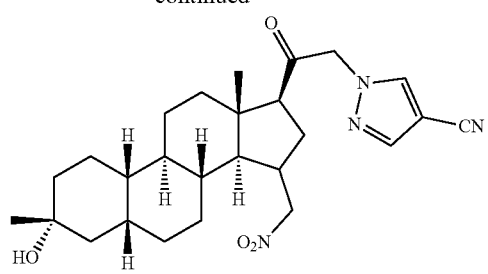

MS m/z (ESI): 469.3 [M+1]$^+$.

Example 121

3-Cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

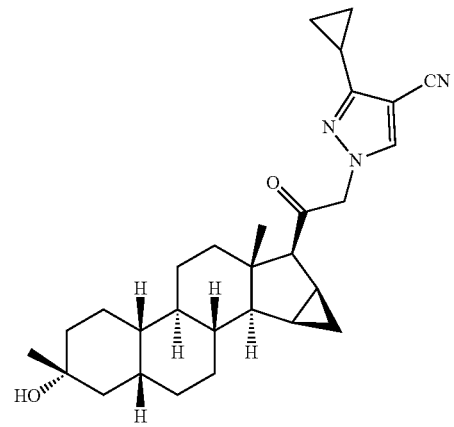

Step 1: Preparation of 3-cyclopropyl-1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)-1H-pyrazole-4-carbonitrile

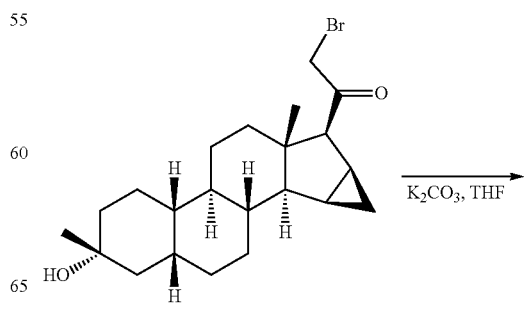

-continued

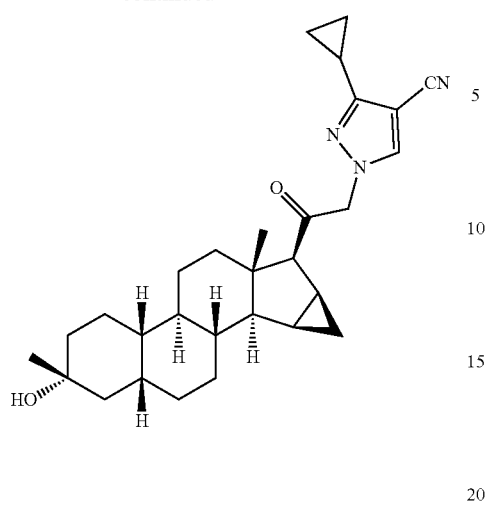

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 3-cyclopropyl-1-(2-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)-2-oxoethyl)-1H-pyrazole-4-carbonitrile (19.2 mg, yield: 21%) was obtained.

MS m/z (ESI): 462.3 [M+H]$^+$ $^1$H NMR (400 MHz, CDCl$_3$) δ 7.73 (s, 1H), 5.13-4.95 (m, 2H), 2.80 (d, J=2.2 Hz, 1H), 2.04-1.89 (m, 2H), 1.86-1.79 (m, 3H), 1.76-1.63 (m, 3H), 1.58-1.49 (m, 3H), 1.46-1.21 (m, 14H), 1.12-0.93 (m, 6H), 0.76 (s, 3H), 0.51-0.43 (m, 1H).

Example 122

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one (122)

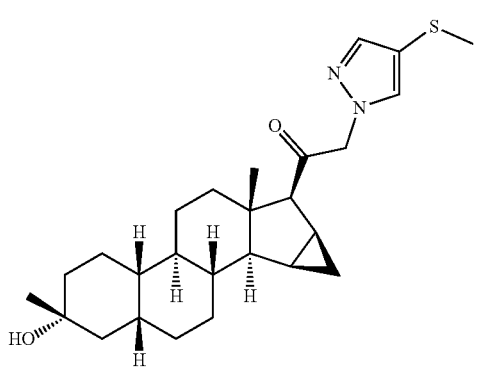

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one

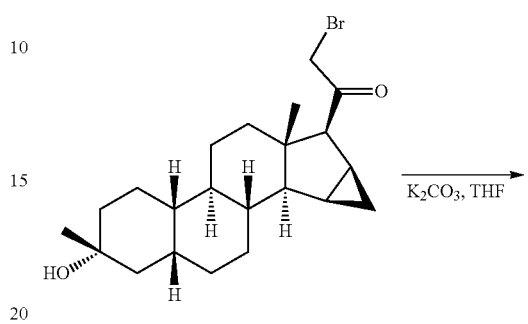

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one (8.7 mg, yield: 16%) was obtained.

MS m/z (ESI): 443.2 [M+H]$^+$ $^1$H NMR (400 MHz, CDCl$_3$) δ 7.54 (s, 1H), 7.45 (s, 1H), 5.17-5.00 (m, 2H), 2.81 (d, J=3.8 Hz, 1H), 2.35 (s, 3H), 1.99-1.91 (m, 1H), 1.88-1.76 (m, 4H), 1.73-1.63 (m, 3H), 1.55-1.50 (m, 1H), 1.43-1.18 (m, 15H), 1.12-0.97 (m, 2H), 0.79 (s, 3H), 0.50-0.41 (m, 1H).

Example 123 and Example 124

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one (123) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one (124)

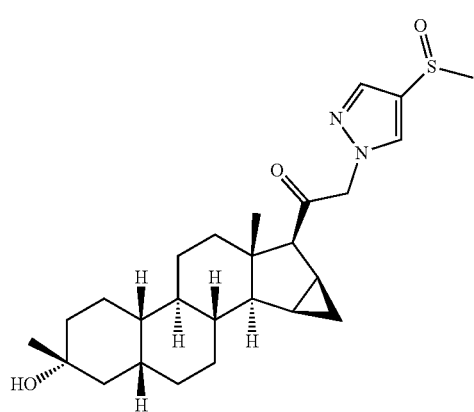

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one 1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(methylthio)-1H-pyrazol-1-yl)ethan-1-one (80 mg, 0.18 mmol) was dissolved in dichloromethane (10 mL), and the solution was cooled to −78° C. m-Chloroperoxybenzoic acid (55 mg, 0.27 mmol) was added, and the reaction solution was stirred for 1 hour.

Water (10 mL) was added, and then the reaction solution was washed with saturated aqueous sodium bicarbonate solution (10 mL). The organic phase was separated, dried over anhydrous sodium sulfate, filtrated and concentrated by rotary evaporation to dryness. The resulting crude product was purified by high performance liquid chromatography to obtain 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfinyl)-1H-pyrazol-1-yl)ethan-1-one (17.2 mg, yield: 20%) and 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(methylsulfonyl)-1H-pyrazol-1-yl)ethan-1-one (20.4 mg, yield: 25%).

Example 123

MS m/z (ESI): 441.3 [M−H$_2$O+H]$^+$ $^1$H NMR (400 MHz, CDCl$_3$) δ 7.85 (s, 1H), 7.83 (s, 1H), 5.30-5.09 (m, 2H), 2.91 (s, 3H), 2.85-2.82 (m, 1H), 1.98-1.90 (m, 1H), 1.87-1.78 (m, 3H), 1.75-1.50 (m, 8H), 1.47-1.21 (m, 12H), 1.13-0.96 (m, 2H), 0.79 (s, 3H), 0.54-0.45 (m, 1H).

Example 124

MS m/z (ESI): 457.2 [M−H$_2$O+H]$^+$ $^1$H NMR (400 MHz, CDCl$_3$) δ 7.94 (s, 1H), 7.87 (s, 1H), 5.26-5.10 (m, 2H), 3.14 (s, 3H), 2.85 (d, J=2.7 Hz, 1H), 1.98-1.91 (m, 1H), 1.87-1.79 (m, 3H), 1.76-1.64 (m, 3H), 1.59-1.52 (m, 1H), 1.50-1.18 (m, 16H), 1.15-0.96 (m, 2H), 0.79 (s, 3H), 0.55-0.46 (m, 1H).

Example 125

3-Fluoro-4-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethoxy)benzonitrile (125)

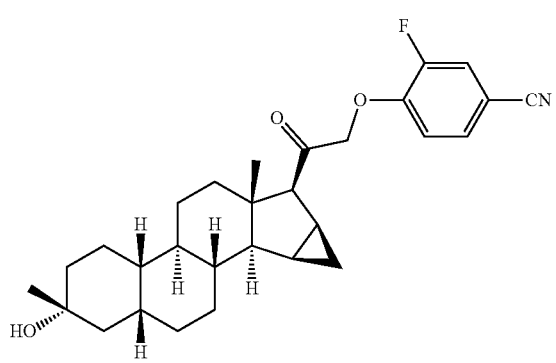

Step 1: Preparation of 3-fluoro-4-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethoxy)benzonitrile

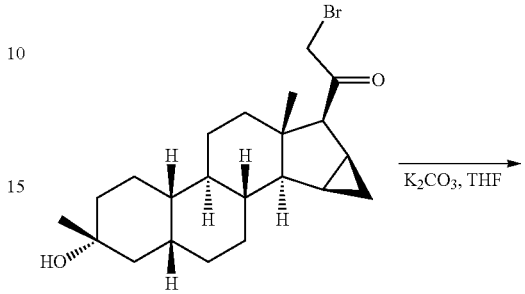

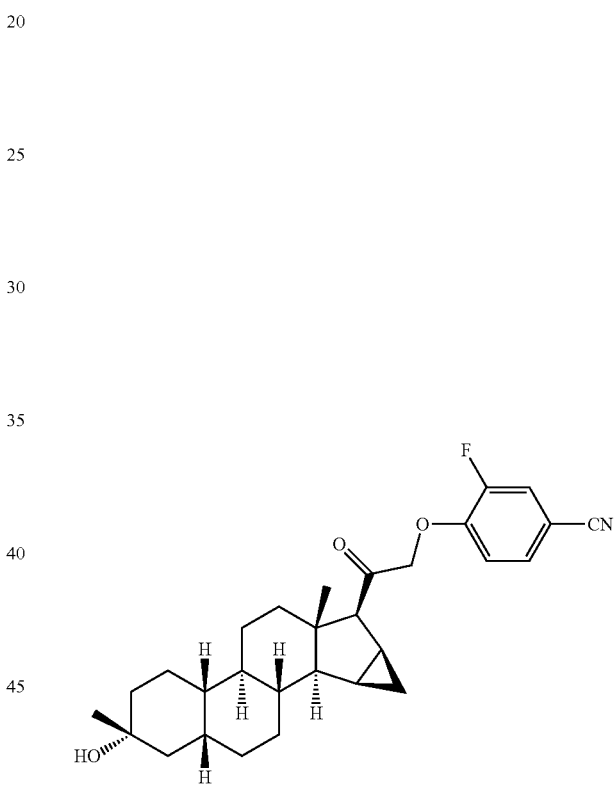

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 3-fluoro-4-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethoxy)benzonitrile (12.5 mg, yield: 18%) was obtained.

MS m/z (ESI): 448.2 [M−H$_2$O+H]$^+$ $^1$H NMR (400 MHz, CDCl$_3$) δ 7.43-7.33 (m, 2H), 6.91-6.84 (m, 1H), 4.91 (s, 2H), 2.96-2.88 (m, 1H), 1.90-1.76 (m, 4H), 1.75-1.62 (m, 3H), 1.55-1.26 (m, 17H), 1.12-1.04 (m, 1H), 0.98-0.92 (m, 1H), 0.78 (s, 3H), 0.50-0.41 (m, 1H).

Example 126

5-Fluoro-2-(2-((2R,4aS,4bR,6aS,7S,7aS,8aR,8bR, 8cR,10aR)-2-hydroxy-2,6a-dimethyloctadecahydro-cyclopropa[4,5]cyclopenta[1,2-a]phenanthren-7-yl)-2-oxoethoxy)benzonitrile (126)

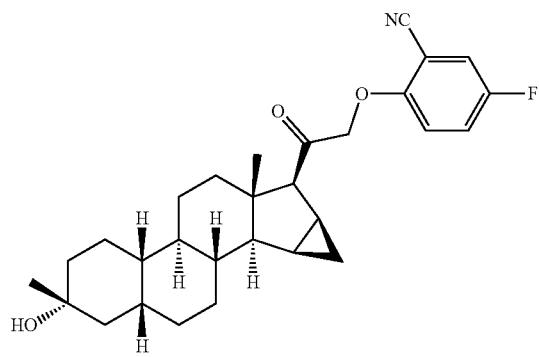

Step 1: Preparation of 5-fluoro-2-(2-((2R,4aS,4bR, 6aS,7S,7aS,8aR,8bR,8cR,10aR)-2-hydroxy-2,6a-dimethyloctadecahydrocyclopropa[4,5]cyclopenta[1, 2-a]phenanthren-7-yl)-2-oxoethoxy)benzonitrile

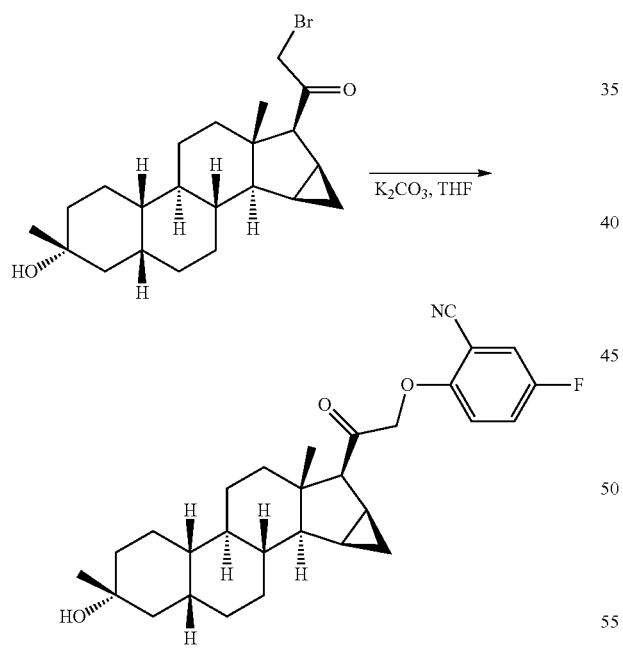

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a] phenanthren-7-yl)ethan-1-one was used as the starting material, accordingly, 5-fluoro-2-(2-((2R,4aS,4bR,6aS,7S, 7aS,8aR,8bR,8cR,10aR)-2-hydroxy-2,6a-dimethylocta-decahydrocyclopropa[4,5]cyclopenta[1,2-a]phenanthren-7-yl)-2-oxoethoxy)benzonitrile (11.4 mg, yield: 10%) was obtained.

MS m/z (ESI): 448.2 [M−H$_2$O+H]$^+$ $^1$H NMR (400 MHz, CDCl$_3$) δ 7.34-7.28 (m, 1H), 7.25-7.18 (m, 1H), 6.78-6.72 (m, 1H), 4.91-4.78 (m, 2H), 2.99 (d, J=3.3 Hz, 1H), 1.91-1.78 (m, 4H), 1.76-1.64 (m, 3H), 1.57-1.25 (m, 17H), 1.08-0.92 (m, 2H), 0.78 (s, 3H), 0.50-0.40 (m, 1H).

Example 127

1-(2-((2R,4aS,4bR,6aS,7S,7aS,8aR,8bR,8cR,10aR)-2-Hydroxy-2,6a-dimethyloctadecahydrocyclopropa [4,5]cyclopenta[1,2-a]phenanthren-7-yl)-2-oxo-ethyl)-1H-pyrazole-3,5-dicarbonitrile (127)

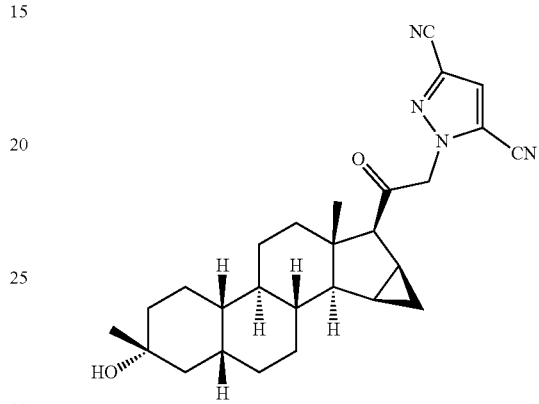

Step 1: Preparation of 1-(2-((2R,4aS,4bR,6aS,7S, 7aS,8aR,8bR,8cR,10aR)-2-hydroxy-2,6a-dimethyl-octadecahydrocyclopropa[4,5]cyclopenta[1,2-a] phenanthren-7-yl)-2-oxoethyl)-1H-pyrazole-3,5-dicarbonitrile

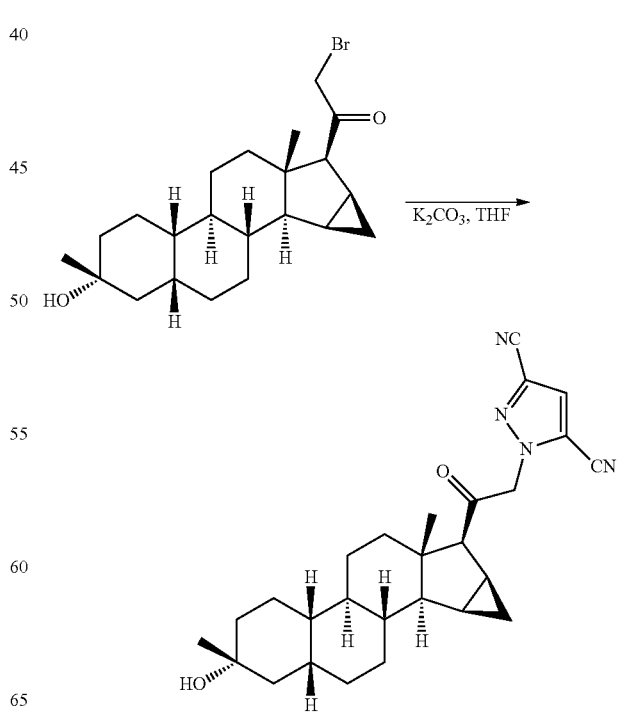

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxo-ethyl)-1H-pyrazole-3,5-dicarbonitrile (18.0 mg, yield: 31.8%) was obtained.

MS m/z (ESI): 429.2 [M–H$_2$O+H]$^+$ $^1$H NMR (400 MHz, CDCl$_3$) δ 7.21 (s, 1H), 5.38 (q, J=18.0 Hz, 2H), 2.87 (d, J=3.0 Hz, 1H), 1.97-1.91 (m, 1H), 1.88-1.75 (m, 4H), 1.76-1.64 (m, 3H), 1.58-1.51 (m, 1H), 1.48-1.26 (m, 15H), 1.15-0.99 (m, 2H), 0.83 (s, 3H), 0.58-0.48 (m, 1H).

Example 128

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one (128)

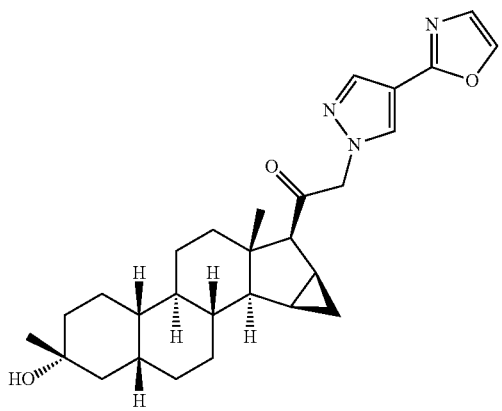

Step 1: Preparation of 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one

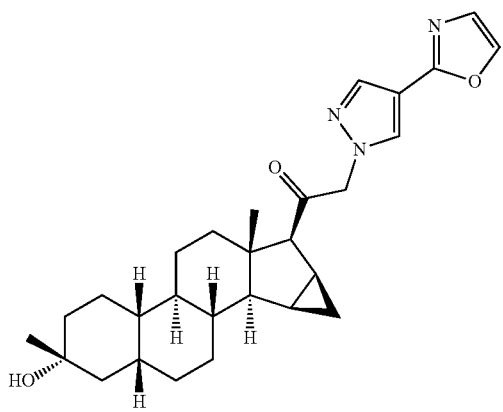

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-(4-(oxazol-2-yl)-1H-pyrazol-1-yl)ethan-1-one (16.0 mg, yield: 14%) was obtained.

MS m/z (ESI): 464.3 [M+H]$^+$ $^1$H NMR (400 MHz, CDCl$_3$) δ 7.89 (s, 1H), 7.79 (s, 1H), 7.73 (s, 1H), 7.13 (s, 1H), 5.27-5.13 (m, 2H), 2.85 (d, J=4.0 Hz, 1H), 2.01-1.93 (m, 1H), 1.87-1.65 (m, 11H), 1.58-1.50 (m, 1H), 1.44-1.22 (m, 11H), 1.14-0.98 (m, 2H), 0.81 (s, 3H), 0.53-0.44 (m, 1H).

Example 129

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-(pyridazin-4-yloxy)ethan-1-one (129)

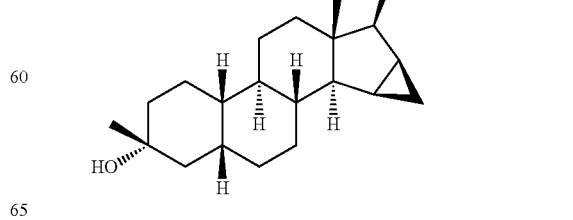

Step 1: Preparation of 1-((2R,4aS,4bR,6aS,7S,7aS, 8aR,8bR,8cR,10aR)-2-hydroxy-2,6a-dimethyloctadecahydrocyclopropa[4,5]cyclopenta[1,2-a]phenanthren-7-yl)-2-(pyridazin-4-yloxy)ethan-1-one

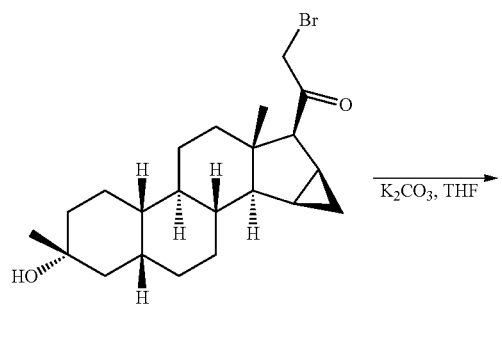

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR, 8cR,10aR)-2-hydroxy-2,6a-dimethyloctadecahydrocyclopropa[4,5]cyclopenta[1,2-a]phenanthren-7-yl)-2-(pyridazin-4-yloxy)ethan-1-one (16.0 mg, yield: 26%) was obtained.

MS m/z (ESI): 425.3 [M+H]$^+$ $^1$H NMR (400 MHz, CDCl$_3$) δ 7.88 (s, 1H), 7.61 (d, J=6.8 Hz, 1H), 6.53 (d, J=6.8 Hz, 1H), 5.17-4.85 (m, 2H), 2.83 (s, 1H), 1.99-1.90 (m, 1H), 1.88-1.78 (m, 3H), 1.76-1.54 (m, 10H), 1.46-1.25 (m, 10H), 1.14-0.95 (m, 2H), 0.79 (s, 3H), 0.55-0.46 (m, 1H).

Example 130

1-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-((2-(trifluoromethyl)pyrimidin-5-yl)oxy)ethan-1-one Step 1: Preparation of 1-((2R,4aS,4bR,6aS,7S,7aS, 8aR,8bR,8cR,10aR)-2-hydroxy-2,6a-dimethyloctadecahydrocyclopropa[4,5]cyclopenta[1,2-a]phenanthren-7-yl)-2-((2-(trifluoromethyl)pyrimidin-5-yl)oxy)ethan-1-one

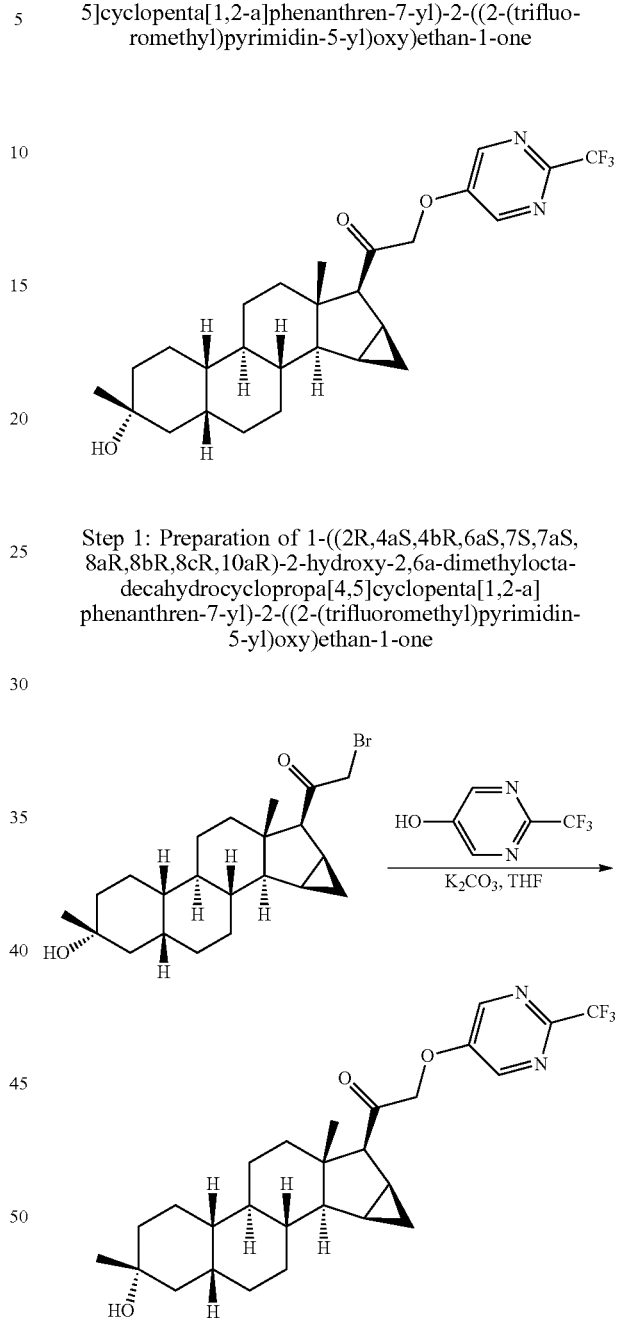

In accordance with Example 5, 2-bromo-1-((2R,4aS,4bR, 6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 1-((2R,4aS,4bR,6aS,7S,7aS,8aR,8bR, 8cR,10aR)-2-hydroxy-2,6a-dimethyloctadecahydrocyclopropa[4,5]cyclopenta[1,2-a]phenanthren-7-yl)-2-((2-(trifluoromethyl)pyrimidin-5-yl)oxy)ethan-1-one (23.0 mg, yield: 38.3%) was obtained.

MS m/z (ESI): 493.2[M+H]$^+$

1H NMR (400 MHz, CDCl$_3$) δ 8.45 (s, 2H), 5.01 (s, 2H), 2.86 (s, 1H), 1.89 (m, 1H), 1.83 (m, 4H), 1.75 (dm, 1H), 1.68

(m, 2H), 1.57 (m, 1H), 1.38 (m, 8H), 1.31 (m, 2H), 1.28 (s, 3H), 1.26-1.20 (m, 1H), 1.13-1.03 (m, 1H), 0.96 (m, 1H), 0.80 (s, 3H), 0.48 (m, 1H).

Example 131

1-((3R,5R,8R,9R,10S,13S,14S,15R,17S)-3-Hydroxy-3,13,15-trimethylhexadecahydro-1H-cyclopenta[a]phenanthren-17-yl)-2-(3-(trifluoromethyl)-1H-pyrazol-1-yl)ethan-1-one (131)

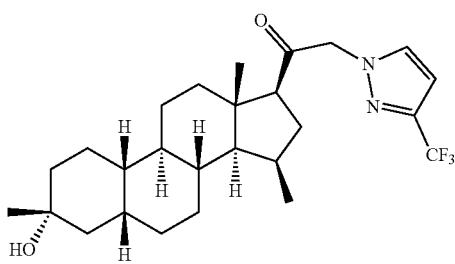

Step 1: 1-((3R,5R,8R,9R,10S,13S,14S,15R,17S)-3-Hydroxy-3,13,15-trimethylhexadecahydro-1H-cyclopenta[a]phenanthren-17-yl)-2-(3-(trifluoromethyl)-1H-pyrazol-1-yl)ethan-1-one

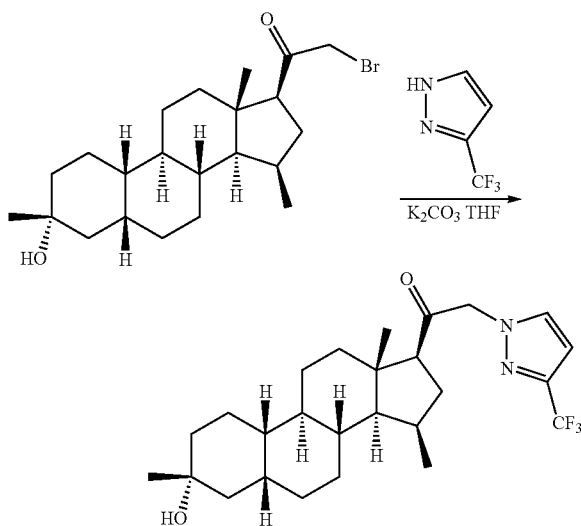

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-(3-(trifluoromethyl)-1H-pyrazol-1-yl)ethan-1-one (20.5 mg, yield: 30.1%) was obtained.

MS m/z (ESI): 467.2[M+H]$^+$.

$^1$H NMR (400 MHz, CDCl$_3$) δ 7.49-7.43 (m, 1H), 6.59 (d, J=2.4 Hz, 1H), 5.14-4.85 (m, 2H), 2.54 (t, J=8.1 Hz, 1H), 2.26-2.08 (m, 2H), 2.02-1.93 (m, 1H), 1.90-1.79 (m, 4H), 1.74-1.59 (m, 3H), 1.57-1.19 (m, 14H), 1.21-1.04 (m, 1H), 0.98 (d, J=7.0 Hz, 3H), 0.84 (s, 3H).

Example 133

2-(4-(Azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (133)

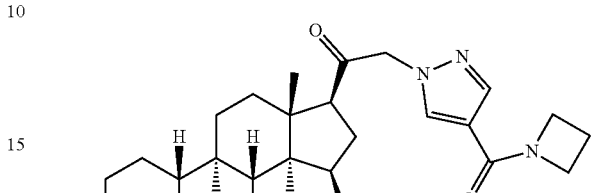

Step 1: Preparation of 2-(4-(azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one

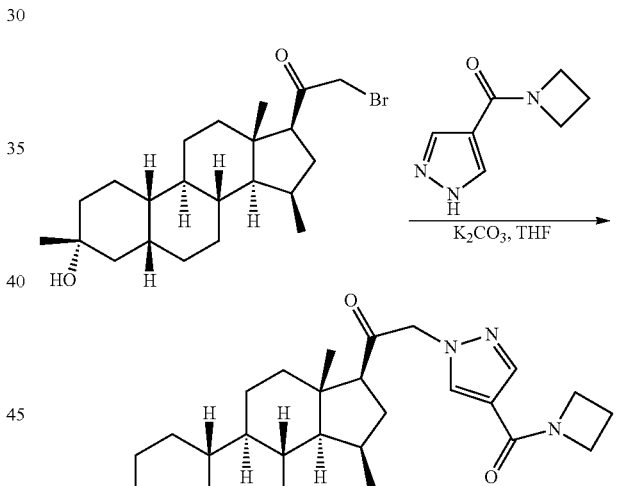

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 2-(4-(azetidine-1-carbonyl)-1H-pyrazol-1-yl)-1-((3R,5R,8R,9R,10S,13S,14S,15R,17S)-3-hydroxy-3,13,15-trimethylhexadecahydro-1H-cyclopenta[a]phenanthren-17-yl)ethan-1-one (12.0 mg, yield: 21%) was obtained.

MS m/z (ESI): 482.3[M+H]$^+$.

$^1$H NMR (400 MHz, CDCl$_3$) δ 7.78 (s, 2H), 5.00-4.77 (m, 2H), 4.38-4.25 (m, 4H), 2.54 (t, J=7.6 Hz, 1H), 2.43-2.32 (m, 2H), 2.26-2.08 (m, 2H), 1.98-1.96 (m, 1H), 1.88-1.83 (m, 3H), 1.69-1.62 (m, 5H), 1.48-1.42 (m, 4H), 1.38-1.26 (m, 9H), 1.16-1.07 (m, 2H), 0.98 (d, J=7.0 Hz, 3H), 0.84 (s, 3H).

Example 134

3-Chloro-1-(2-((3R,5R,8R,9R,10S,13S,14S,15R,17S)-3-hydroxy-3,13,15-trimethylhexa decahydro-1H-cyclopenta[a]phenanthren-17-yl)-2-oxoethyl)-1H-pyrazole-4-carbonitrile (134)

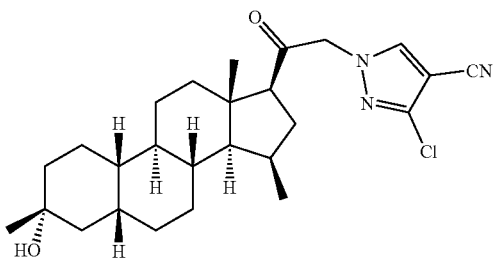

Step 1: Preparation of 3-chloro-1-(2-((3R,5R,8R,9R,10S,13S,14S,15R,17S)-3-hydroxy-3,13,15-trimethylhexa decahydro-1H-cyclopenta[a]phenanthren-17-yl)-2-oxoethyl)-1H-pyrazole-4-carbonitrile

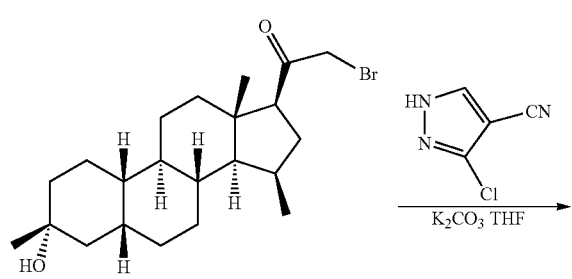

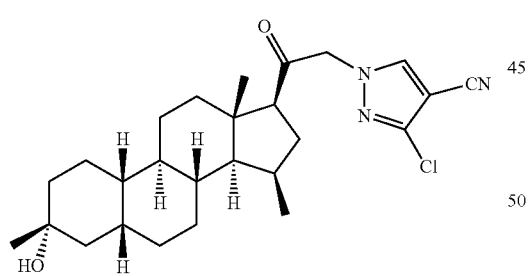

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, the product 3-chloro-1-(2-((3R,5R,8R,9R,10S,13S,14S,15R,17S)-3-hydroxy-3,13,15-trimethylhexa decahydro-1H-cyclopenta[a]phenanthren-17-yl)-2-oxoethyl)-1H-pyrazole-4-carbonitrile (37 mg, yield: 55.3%) was obtained.

MS m/z (ESI): 456.2[M–H]–.

$^1$H NMR (400 MHz, CDCl$_3$) δ 7.81 (s, 1H), 5.03-4.75 (m, 2H), 2.54 (t, J=8.0 Hz, 1H), 2.31-2.13 (m, 2H), 1.93-1.06 (m, 23H), 0.99 (d, J=7.1 Hz, 3H), 0.83 (s, 3H).

Example 135

1-(2-((3R,5R,8R,9R,10S,13S,14S,15R,17S)-3-Hydroxy-3,13,15-trimethylhexadecahydro-1H-cyclopenta[a]phenanthren-17-yl)-2-oxoethyl)-1H-pyrazole-3,5-dicarbonitrile (135)

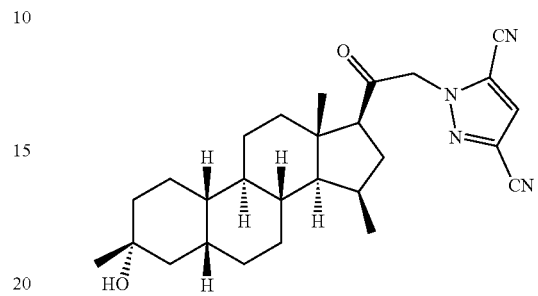

Step 1: Preparation of 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3,5-dicarbonitrile

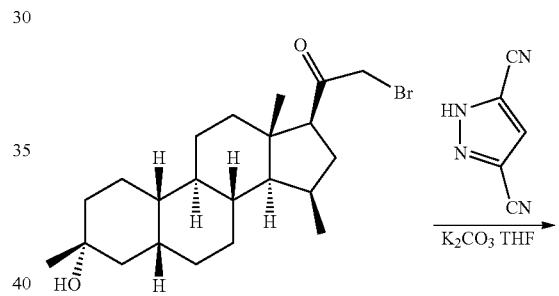

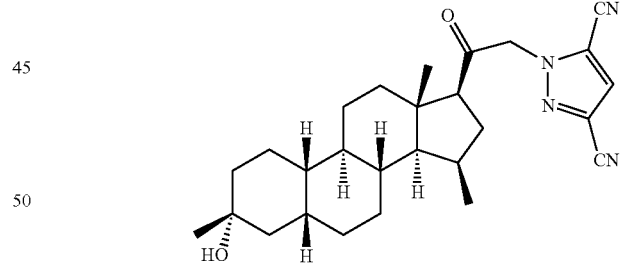

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)-1H-pyrazole-3,5-dicarbonitrile (18 mg, yield 27.5%) was obtained.

MS m/z (ESI): 447.2[M–H]–.

$^1$H NMR (400 MHz, CDCl$_3$) δ 7.20 (s, 1H), 5.23-5.07 (m, 2H), 2.68-2.52 (m, 1H), 2.28-1.36 (m, 21H), 1.28 (s, 3H), 1.18-1.08 (m, 1H), 1.00 (d, J=6.9 Hz, 3H), 0.88 (s, 3H).

Example 136

3-(2-((3R,5R,8R,9R,10S,13S,14S,15R,17S)-3-Hydroxy-3,13,15-trimethylhexadecahydro-1H-cyclopenta[a]phenanthren-17-yl)-2-oxoethyl)thiazolidine-2,4-dione (136)

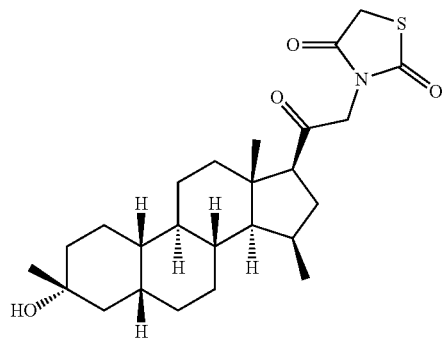

Step 1: Preparation of 3-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)thiazolidine-2,4-dione

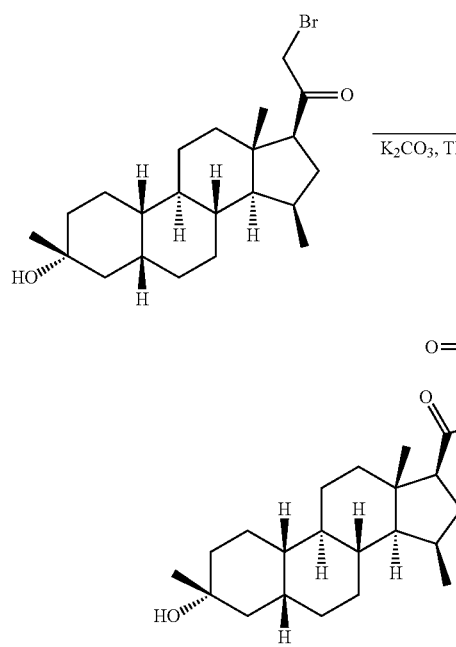

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 3-(2-((3R,5R,8R,9R,10S,13S,14S,15R,17S)-3-hydroxy-3,13,15-trimethylhexadecahydro-1H-cyclopenta[a]phenanthren-17-yl)-2-oxoethyl)thiazolidine-2,4-dione (24.0 mg, yield: 31.5%) was obtained.

MS m/z (ESI): 430.2 [M–H$_2$O+H]$^+$ $^1$H NMR (400 MHz, CDCl$_3$) δ 4.37 (s, 2H), 4.04-3.98 (m, 2H), 2.56-2.49 (m, 1H), 2.22-2.03 (m, 2H), 1.91-1.81 (m, 4H), 1.73-1.61 (m, 3H), 1.47-1.26 (m, 15H), 1.17-1.05 (m, 2H), 0.97 (d, J=7.1 Hz, 3H), 0.81 (s, 3H).

Example 137

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-3-carbonitrile (137)

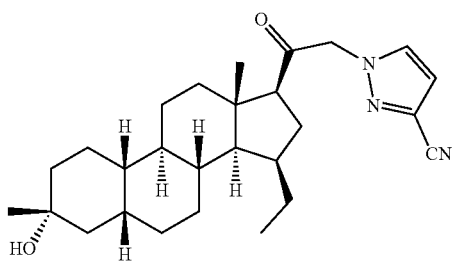

Step 1: Preparation of 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3-carbonitrile

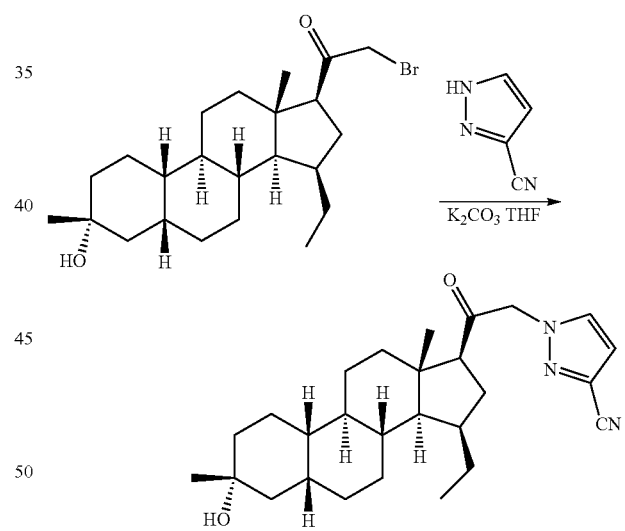

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3-carbonitrile (16 mg, yield: 25.9%) was obtained.

MS m/z (ESI): 438.2[M+H]$^+$.

$^1$H NMR (400 MHz, CDCl$_3$) δ 7.49 (d, J=2.5 Hz, 1H), 6.73 (d, J=2.4 Hz, 1H), 5.22-4.78 (m, 2H), 2.57 (t, J=8.0 Hz, 1H), 2.15-1.30 (m, 20H), 1.28 (s, 3H), 1.16-1.03 (m, 4H), 0.84 (t, J=7.3 Hz, 3H), 0.79 (s, 3H).

Example 138

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one (138)

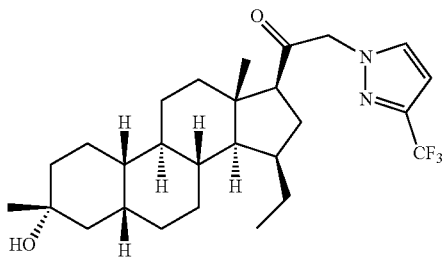

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one

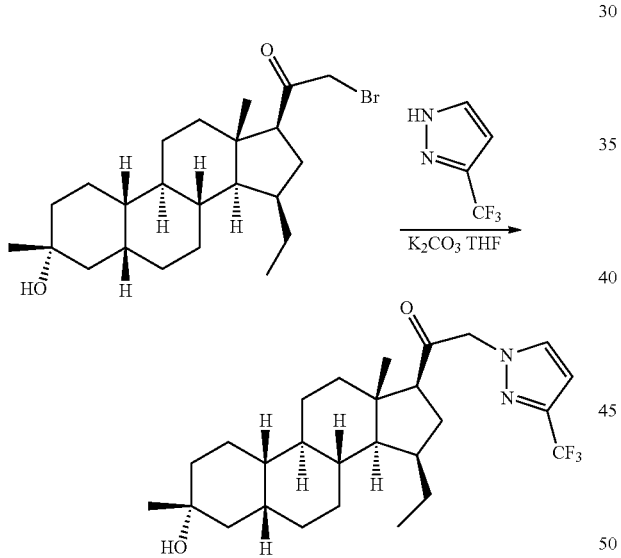

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(3-(trifluoromethyl)-1H-pyrazol-1-yl)ethan-1-one (23 mg, yield: 33.9%) was obtained.

MS m/z (ESI): 481.3[M+H]$^+$.

$^1$H NMR (400 MHz, CDCl$_3$) δ 7.47 (d, J=4.0 Hz, 1H), 6.59 (d, J=4.0 Hz 1H), 5.07-4.89 (m, 2H), 2.56 (t, J=9.3 Hz, 1H), 2.20-1.29 (m, 20H), 1.28 (s, 3H), 1.27-1.03 (m, 4H), 0.84 (t, J=7.3 Hz, 3H), 0.80 (s, 3H).

Example 139

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(5-methyl-2H-tetrazol-2-yl)ethan-1-one (139)

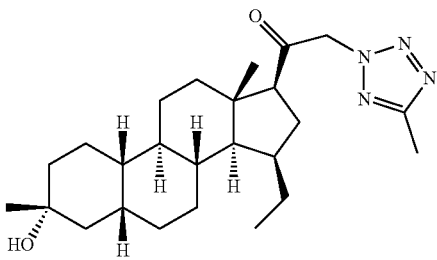

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(5-methyl-2H-tetrazol-2-yl)ethan-1-one

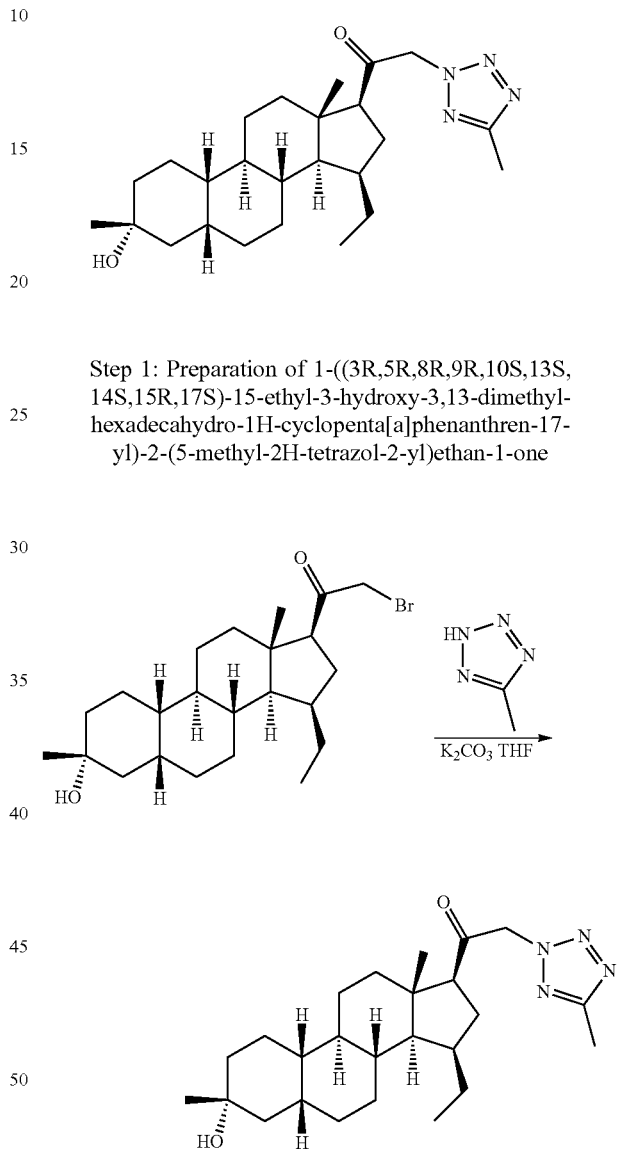

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(5-methyl-2H-tetrazol-2-yl)ethan-1-one (13.5 mg, yield: 22.3%) was obtained.

MS m/z (ESI): 429.3[M+H]$^+$.

$^1$H NMR (400 MHz, CDCl$_3$) δ 5.39-5.29 (m, 2H), 2.63-2.57 (m, 1H), 2.56 (s, 3H), 2.10-1.30 (m, 20H), 1.28 (s, 3H), 1.27-1.05 (m, 4H), 0.87-0.81 (m, 6H).

Example 140 and Example 141

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(1H-1,2,3-triazol-1-yl)ethan-1-one (140)

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(2H-1,2,3-triazol-2-yl)ethan-1-one (141)

140

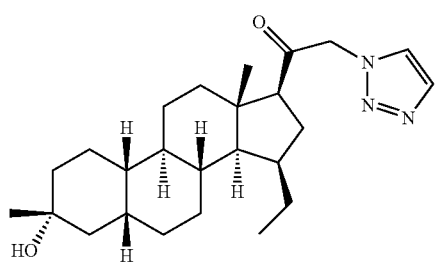

141

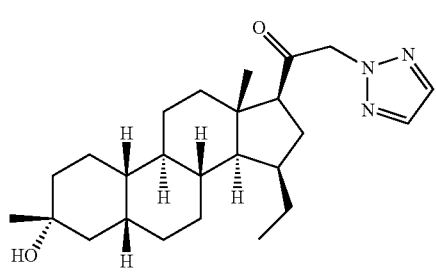

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(1H-1,2,3-triazol-1-yl)ethan-1-one and 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-1,2,3-triazol-2-yl)ethan-1-one

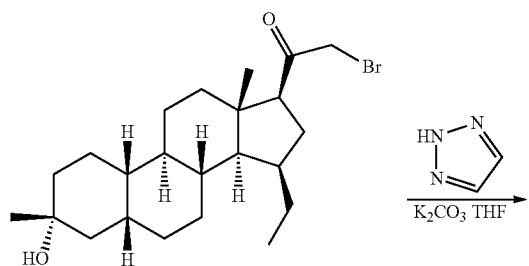

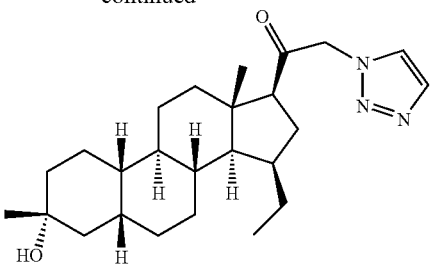

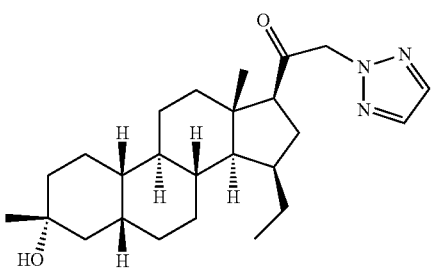

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the products 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(1H-1,2,3-triazol-1-yl)ethan-1-one (17 mg, yield: 29.1%) and 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-1,2,3-triazol-2-yl)ethan-1-one (9.2 mg, yield: 15.7%) were obtained.

Example 140

MS m/z (ESI): 414.3[M+H]$^+$.

$^1$H NMR (400 MHz, CDCl$_3$) δ 7.77 (s, 1H), 7.67 (s, 1H), 5.37-5.09 (m, 2H), 2.62 (t, J=9.2 Hz, 1H), 2.28-1.20 (m, 25H), 1.16-1.05 (m, 2H), 0.85 (t, J=7.3 Hz, 3H), 0.80 (s, 3H).

Example 141

MS m/z (ESI): 414.3[M+H]$^+$.

$^1$H NMR (400 MHz, CDCl$_3$) δ 7.68 (s, 2H), 5.28-5.20 (m, 2H), 2.54 (t, J=8.0 Hz, 1H), 1.99-1.23 (m, 25H), 1.13-1.06 (m, 2H), 0.88-0.78 (m, 6H).

183

Example 142

1-(2-((3R,5R,8R,9R,10S,13S,14S,15R,17S)-15-Ethyl-3-hydroxy-3,13-dimethylhexadecahydro-1H-cyclopenta[a]phenanthren-17-yl)-2-oxoethyl)-1H-pyrazole-3,5-dicarbonitrile (142)

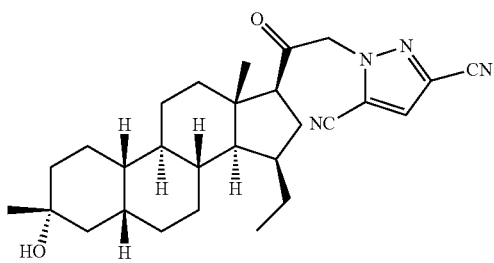

Step 1: Preparation of 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3,5-dicarbonitrile

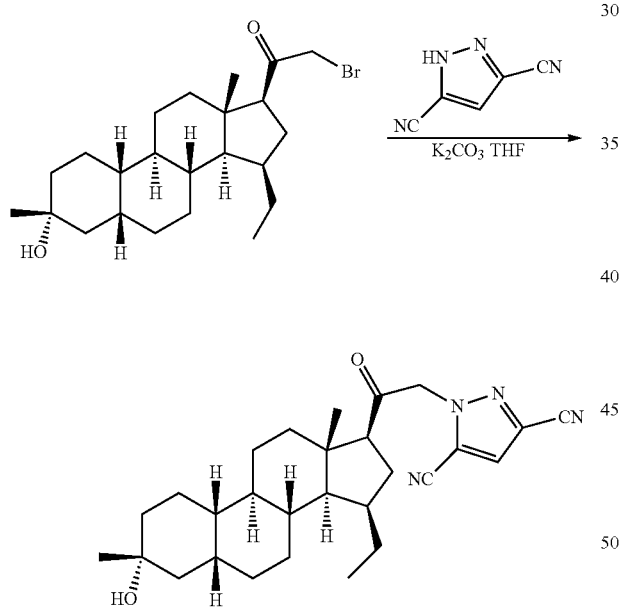

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-(2-((3R,5R,8R,9R,10S,13S,14S,15R,17S)-15-ethyl-3-hydroxy-3,13-dimethylhexadecahydro-1H-cyclopenta[a]phenanthren-17-yl)-2-oxoethyl)-1H-pyrazole-3,5-dicarbonitrile (5 mg, yield: 9.2%) was obtained.

MS m/z (ESI): 463.2[M+H]$^+$.

$^1$H NMR (400 MHz, CDCl$_3$) δ 7.21 (s, 1H), 5.29-5.02 (m, 2H), 2.61 (t, J=9.3 Hz, 1H), 2.24-1.34 (m, 19H), 1.28 (s, 3H), 1.26-1.02 (m, 5H), 0.92-0.76 (m, 6H).

184

Example 143

1-(2-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-oxoethyl)-1H-pyrazole-3,5-dicarbonitrile (143)

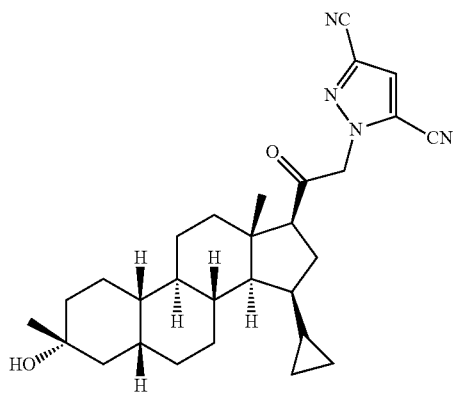

Step 1: Preparation of 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3,5-dicarbonitrile

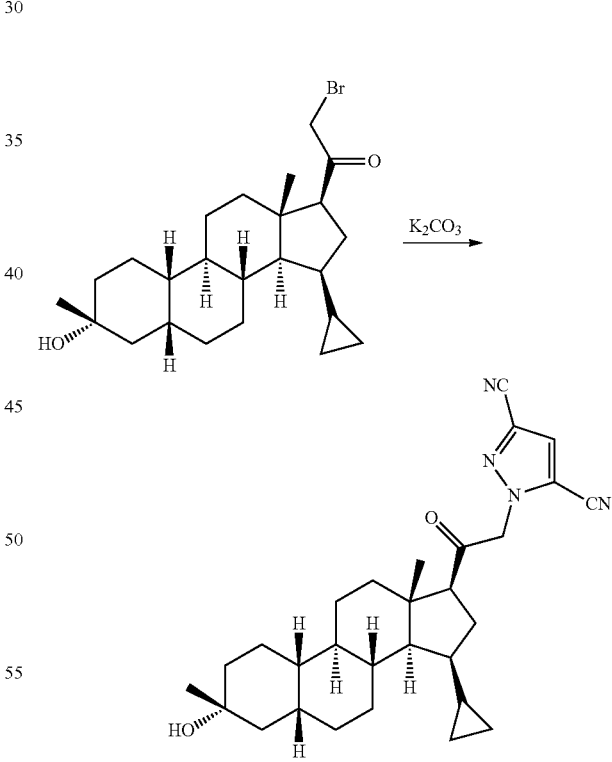

In accordance with Example 5, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-3,5-dicarbonitrile (19.6 mg, yield: 18%) was obtained.

MS m/z (ESI): 473.2[M–H]⁻

¹H NMR (400 MHz, CDCl₃) δ 7.20 (s, 1H), 5.24-5.09 (m, 2H), 2.58-2.50 (m, 1H), 2.26-2.07 (m, 2H), 2.06-1.95 (m, 2H), 1.90-1.80 (m, 2H), 1.78-1.66 (m, 2H), 1.58-1.22 (m, 16H), 1.19-1.06 (m, 2H), 0.94 (s, 3H), 0.87-0.78 (m, 1H), 0.64-0.56 (m, 1H), 0.45-0.39 (m, 1H), 0.18-0.02 (m, 2H).

Example 144

1-((3R,5R,8R,9R,10S,13S,14S,15S,17S)-15-Cyclopropyl-3-hydroxy-3,13-dimethylhexa decahydro-1H-cyclopenta[a]phenanthren-17-yl)-2-(3-(trifluoromethyl)-1H-pyrazol-1-yl)ethan-1-one (144)

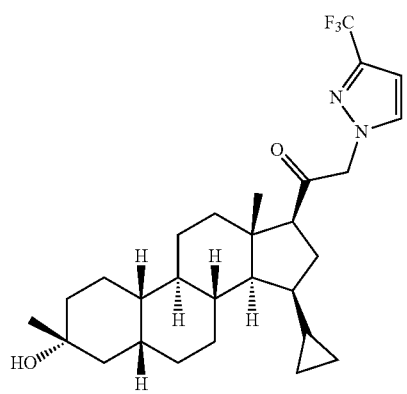

Step 1: Preparation of 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(3-(trifluoromethyl)-1H-pyrazol-1-yl)ethan-1-one

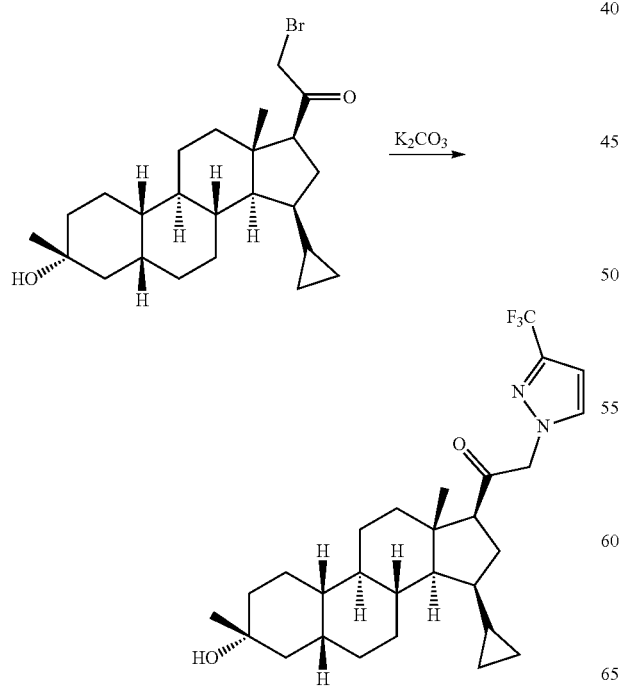

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)-2-(3-(trifluoromethyl)-1H-pyrazol-1-yl)ethan-1-one (18.0 mg, yield: 23%) was obtained.

MS m/z (ESI): 491.3[M–H]⁻

¹H NMR (400 MHz, CDCl₃) δ 7.47 (d, J=2.0 Hz, 1H), 6.59 (d, J=2.0 Hz, 1H), 5.08-4.90 (m, 2H), 2.53-2.42 (m, 1H), 2.24-1.94 (m, 4H), 1.91-1.79 (m, 3H), 1.78-1.66 (m, 2H), 1.52-1.22 (m, 15H), 1.18-1.02 (m, 2H), 0.91 (s, 3H), 0.88-0.76 (m, 1H), 0.65-0.54 (m, 1H), 0.48-0.36 (m, 1H), 0.18-0.00 (m, 2H).

Example 146

1-((3R,5R,8R,9R,10S,13S,14S,15S,17S)-15-Cyclopropyl-3-hydroxy-3,13-dimethylhexa decahydro-1H-cyclopenta[a]phenanthren-17-yl)-2-(2H-tetrazol-2-yl)ethan-1-one (146)

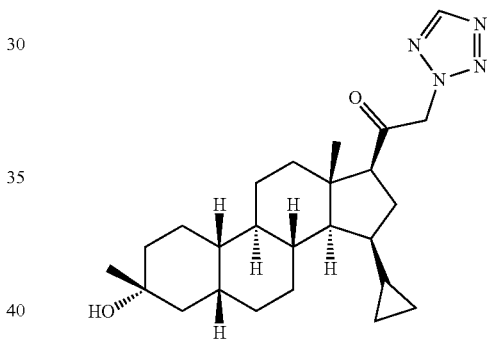

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-(2H-tetrazol-2-yl)ethan-1-one

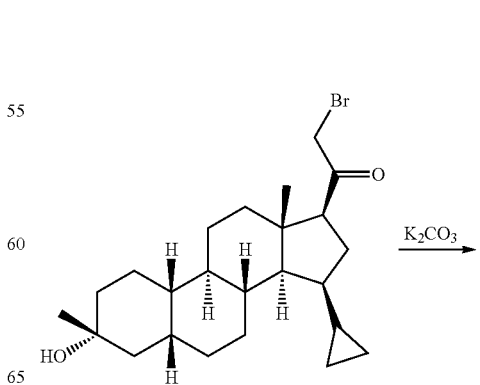

187
-continued

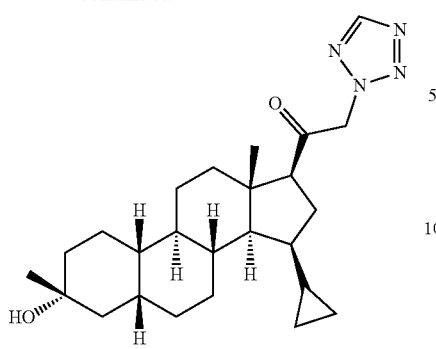

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl) ethan-1-one was used as the starting material, accordingly, 1-((3R,5R,8R,9R,10S,13S,14S,15S,17S)-15-cyclopropyl-3-hydroxy-3,13-dimethylhexa decahydro-1H-cyclopenta[a] phenanthren-17-yl)-2-(2H-tetrazol-2-yl)ethan-1-one (12.9 mg, yield: 13.2%) was obtained.

MS m/z (ESI): 409.3[M−H₂O+H]⁺

¹H NMR (400 MHz, CDCl₃) δ 8.57 (s, 1H), 5.46 (s, 2H), 2.58-2.47 (m, 1H), 2.24-1.94 (m, 4H), 1.93-1.80 (m, 3H), 1.77-1.66 (m, 2H), 1.50-1.21 (m, 15H), 1.18-1.06 (m, 2H), 0.95 (s, 3H), 0.87-0.78 (m, 1H), 0.64-0.55 (m, 1H), 0.46-0.38 (m, 1H), 0.17-0.01 (m, 2H).

Example 147

3-Chloro-1-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)-1H-pyrazole-4-carbonitrile (147)

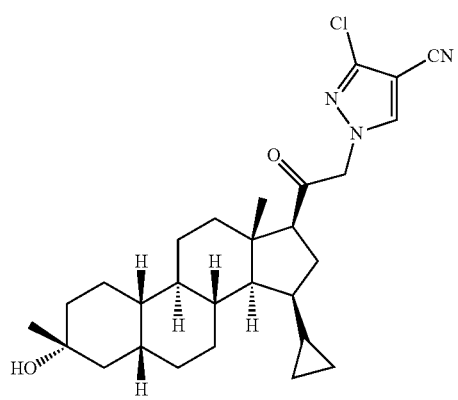

188

Step 1: Preparation of 3-chloro-1-(2-((3R,5R,8R, 9R,10S,13S,14S,15S,17S)-15-cyclopropyl-3-hydroxy-3,13-di methylhexadecahydro-1H-cyclopenta [a]phenanthren-17-yl)-2-oxoethyl)-1H-pyrazole-4-carbonitrile

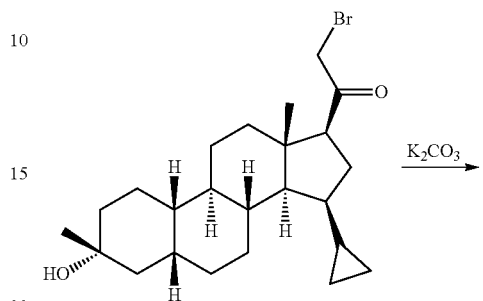

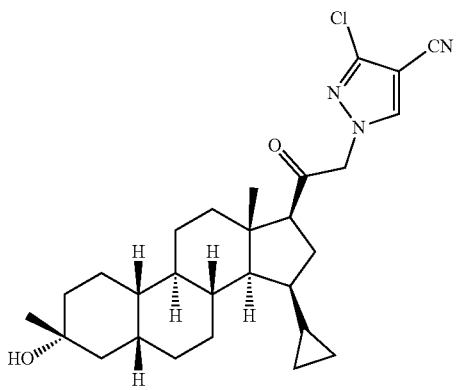

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl) ethan-1-one was used as the starting material, accordingly, 3-chloro-1-(2-((3R,5R,8R,9R,10S,13S,14S,15S,17S)-15-cyclopropyl-3-hydroxy-3,13-di methylhexadecahydro-1H-cyclopenta[a]phenanthren-17-yl)-2-oxoethyl)-1H-pyrazole-4-carbonitrile (13.5 mg, yield: 17.4%) was obtained.

MS m/z (ESI): 482.2[M−H]⁻

¹H NMR (400 MHz, CDCl₃) δ 7.82 (s, 1H), 5.01-4.76 (m, 2H), 2.55-2.41 (m, 1H), 2.22-1.94 (m, 4H), 1.91-1.77 (m, 3H), 1.76-1.66 (m, 2H), 1.56-1.24 (m, 15H), 1.18-1.04 (m, 2H), 0.90 (s, 3H), 0.87-0.75 (m, 1H), 0.64-0.53 (m, 1H), 0.46-0.38 (m, 1H), 0.17-0.02 (m, 2H).

Example 148

3-(2-((3R,5R,8R,9R,10S,13S,14S,15S,17S)-15-Cyclopropyl-3-hydroxy-3,13-dimethylhexadecahydro-1H-cyclopenta[a]phenanthren-17-yl)-2-oxoethyl)thiazolidine-2,4-dione (148)

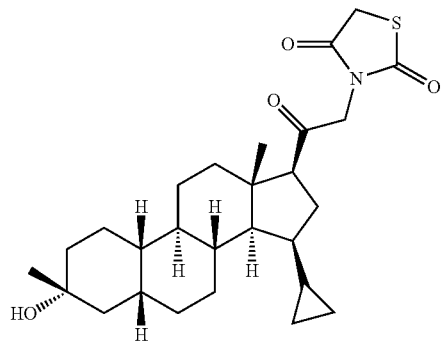

Step 1: Preparation of 3-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)thiazolidine-2,4-dione

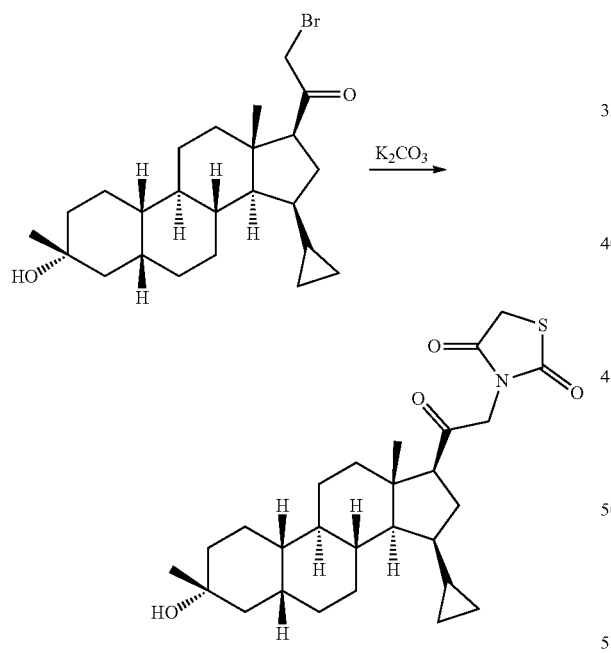

In accordance with Example 5, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)ethan-1-one was used as the starting material, accordingly, 3-(2-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-oxoethyl)thiazolidine-2,4-dione (10.0 mg, yield: 13%) was obtained.

MS m/z (ESI): 456.2[M−H₂O+H]⁺

¹H NMR (400 MHz, CDCl₃) δ 4.38 (s, 2H), 4.04 (s, 2H), 2.51-2.43 (m, 1H), 2.24-2.00 (m, 4H), 1.91-1.80 (m, 3H), 1.75-1.67 (m, 2H), 1.49-1.27 (m, 15H), 1.17-1.05 (m, 2H), 0.88 (s, 3H), 0.84-0.78 (m, 1H), 0.62-0.53 (m, 1H), 0.46-0.36 (m, 1H), 0.15-0.01 (m, 2H).

Example 149

1-((3R,5R,8R,9R,10S,13S,14S,15R,17S)-15-Ethyl-3-hydroxy-3,13-dimethylhexadecahydro-1H-cyclopenta[a]phenanthren-17-yl)-2-(2H-tetrazol-2-yl)ethan-1-one (149)

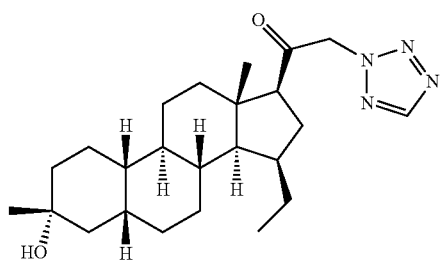

Step 1: Preparation of 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-tetrazol-2-yl)ethan-1-one

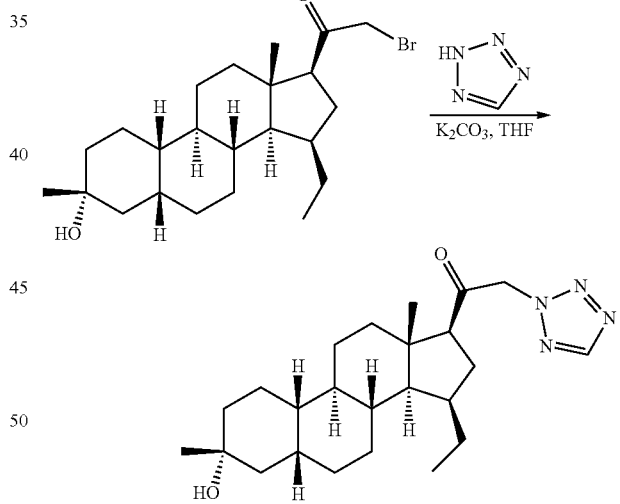

In accordance with Example 5, 2-bromo-1-((3R,5R,8R,9R,10S,13S,14S,15R,17S)-15-ethyl-3-hydroxy-3,13-dimethylhexadecahydro-1H-cyclopenta[a]phenanthren-17-yl)ethan-1-one was used as the starting material, accordingly, the product 1-((3R,5R,8R,9R,10S,13S,14S,15R,17S)-15-ethyl-3-hydroxy-3,13-dimethylhexadecahydro-1H-cyclopenta[a]phenanthren-17-yl)-2-(2H-tetrazol-2-yl)ethan-1-one (11 mg, white solid, yield: 18.8%) was obtained.

MS m/z (ESI): 397.2[M−H₂O+H]⁺

¹H NMR (400 MHz, CDCl₃) δ 8.57 (s, 1H), 5.50-5.41 (m, 2H), 2.62 (t, J=8.5 Hz, 1H), 2.29-1.30 (m, 20H), 1.28 (s, 3H), 1.27-1.05 (m, 4H), 0.85-0.82 (m, 6H).

Example 150

1-((3R,5R,8R,9R,10S,13S,14S,15R,17S)-3-Hydroxy-3,13,15-trimethylhexadecahydro-1H-cyclopenta[a]phenanthren-17-yl)-2-((2-(trifluoromethyl)pyrimidin-5-yl)oxy)ethan-1-one (150)

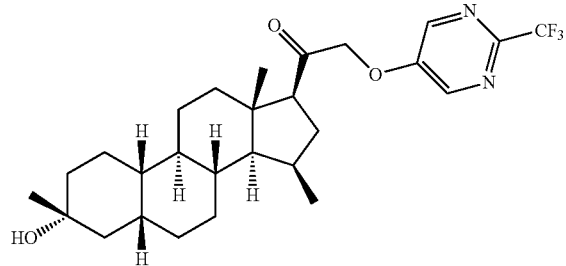

Step 1: Preparation of 1-((3R,5R,8R,9R,10S,13S,14S,15R,17S)-3-Hydroxy-3,13,15-trimethylhexadecahydro-1H-cyclopenta[a]phenanthren-17-yl)-2-((2-(trifluoromethyl)pyrimidin-5-yl)oxy)ethan-1-one

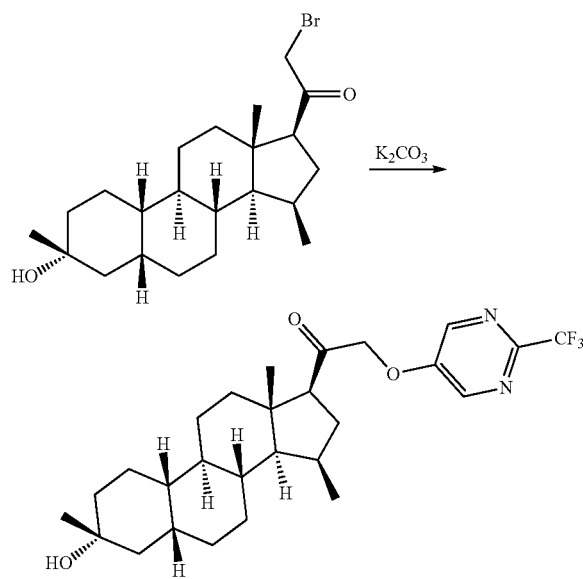

In accordance with Example 5, 2-bromo-1-((3R,5R,8R,9R,10S,13S,14S,15R,17S)-3-hydroxy-3,13,15-trimethylhexadecahydro-1H-cyclopenta[a]phenanthren-17-yl)ethan-1-one was used as the starting material, accordingly, 1-((3R,5R,8R,9R,10S,13S,14S,15R,17S)-3-hydroxy-3,13,15-trimethylhexadecahydro-1H-cyclopenta[a]phenanthren-17-yl)-2-((2-(trifluoromethyl)pyrimidin-5-yl)oxy)ethan-1-one (16.1 mg, yield: 19%) was obtained.

MS m/z (ESI): 477.3[M−H$_2$O+H]$^+$ $^1$H NMR (400 MHz, CDCl$_3$) δ 8.44 (s, 2H), 4.85-4.71 (m, 2H), 2.67-2.57 (m, 1H), 2.30-2.10 (m, 2H), 1.93-1.81 (m, 4H), 1.74-1.61 (m, 3H), 1.48-1.23 (m, 15H), 1.18-1.06 (m, 2H), 1.00 (d, J=7.1 Hz, 3H), 0.87 (s, 3H).

Example 151

1-((3R,5R,8R,9R,10S,13S,14S,15S,17S)-15-Cyclopropyl-3-hydroxy-3,13-dimethylhexa decahydro-1H-cyclopenta[a]phenanthren-17-yl)-2-((2-(trifluoromethyl)pyrimidin-5-yl)oxy)ethan-1-one (151)

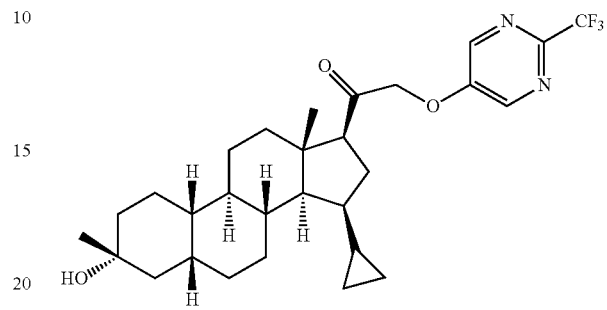

Step 1: Preparation of 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-((2-(trifluoromethyl)pyrimidin-5-yl)oxy)ethan-1-one

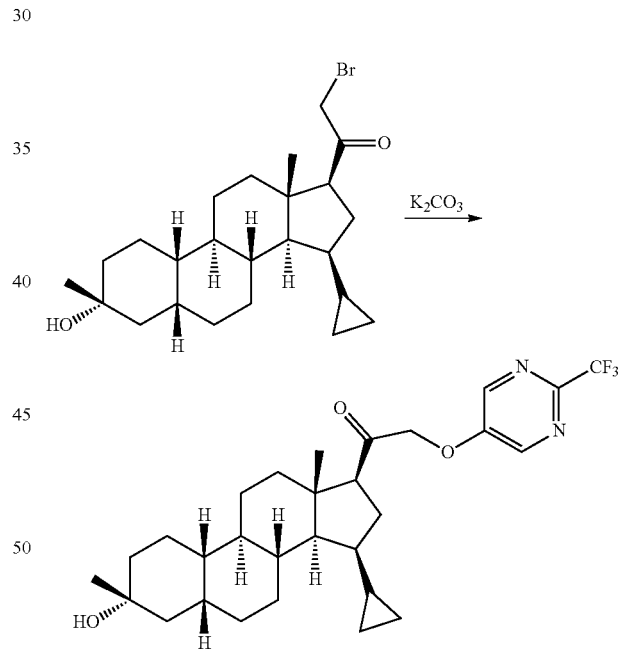

In accordance with Example 5, 1-((3R,5R,8R,9R,10S,13S,14S,15S,17S)-15-cyclopropyl-3-hydroxy-3,13-dimethylhexa decahydro-1H-cyclopenta[a]phenanthren-17-yl)ethan-1-one was used as the starting material, accordingly, 1-((3R,5R,8R,9R,10S,13S,14S,15S,17S)-15-cyclopropyl-3-hydroxy-3,13-dimethylhexadecahydro-1H-cyclopenta[a]phenanthren-17-yl)-2-((2-(trifluoromethyl)pyrimidin-5-yl)oxy)ethan-1-one (22.9 mg, yield: 27.6%) was obtained.

MS m/z (ESI): 503.3[M−H$_2$O+H]$^+$ $^1$H NMR (400 MHz, CDCl$_3$) δ 8.44 (s, 2H), 4.87-4.69 (m, 2H), 2.62-2.50 (m, 1H), 2.25-1.96 (m, 3H), 1.92-1.84 (m, 3H), 1.77-1.66 (m, 2H), 1.54-1.23 (m, 15H), 1.18-1.04 (m,

2H), 0.93 (s, 3H), 0.87-0.78 (m, 1H), 0.65-0.56 (m, 1H), 0.49-0.38 (m, 1H), 0.20-0.02 (m, 2H).

Example 152

3-(2-((2R,4aS,4bR,6aS,7S,7aS,8aR,8bR,8cR,10aR)-2-Hydroxy-2,6a-dimethyloctadecahydrocyclopropa[4,5]cyclopenta[1,2-a]phenanthren-7-yl)-2-oxoethyl)thiazolidine-2,4-dione (152)

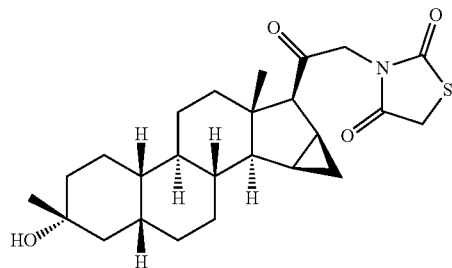

Step 1: Preparation of 3-(2-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)-2-oxoethyl)thiazolidine-2,4-dione

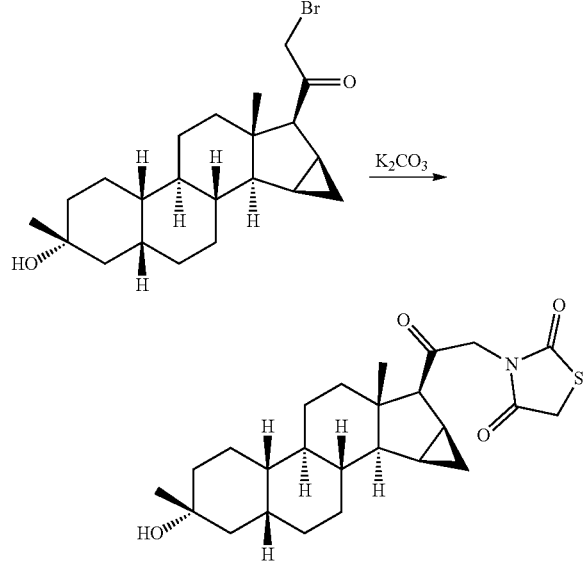

In accordance with Example 5, 2-bromo-1-((2R,4aS,4bR,6aS,7S,7aS,8aR,8bR,8cR,10aR)-2-hydroxy-2,6a-dimethyl-octadecahydrocyclopropa[4,5]cyclopenta[1,2-a]phenanthren-7-yl)ethan-1-one was used as the starting material, accordingly, 3-(2-((2R,4aS,4bR,6aS,7S,7aS,8aR,8bR,8cR,10aR)-2-hydroxy-2,6a-dimethyloctadecahydrocyclopropa[4,5]cyclopenta[1,2-a]phenanthren-7-yl)-2-oxoethyl)thiazolidine-2,4-dione (7.1 mg, yield: 9.3%) was obtained.

MS m/z (ESI): 446.2[M+H]+

$^1$H NMR (400 MHz, CDCl$_3$) δ 4.66-4.50 (m, 2H), 4.04 (s, 2H), 2.78 (d, J=4.0 Hz, 1H), 1.98-1.92 (m, 1H), 1.85-1.52 (m, 11H), 1.44-1.24 (m, 12H), 1.13-0.97 (m, 2H), 0.77 (s, 3H), 0.49-0.41 (m, 1H).

Example 157

1-((8S,9S,13S,14S,17S)-3-Hydroxy-13-methyl-7,8,9,11,12,13,14,15,16,17-decahydro-6H-cyclopenta[a]phenanthren-17-yl)ethan-1-one (157)

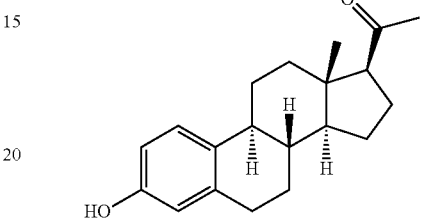

Step 1: Preparation of (8R,9S,13S,14S)-3-(benzyloxy)-13-methyl-6,7,8,9,11,12,13,14,15,16-decahydro-17H-cyclopenta[a]phenanthren-17-one

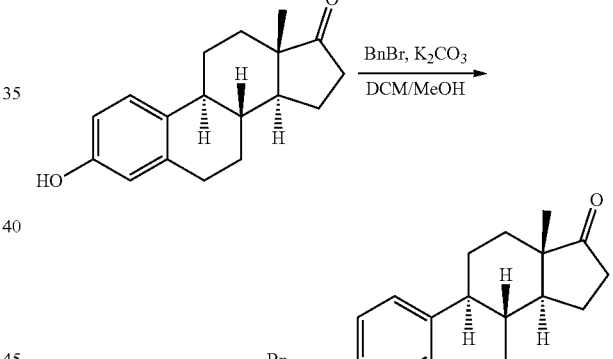

(8R,9S,13S,14S)-3-Hydroxy-13-methyl-6,7,8,9,11,12,13,14,15,16-decahydro-17H-cyclopenta[a]phenanthren-17-one (4.1 g, 15 mmol) and a solution of dichloromethane/methanol (1/1, 50 mL) were added to a 100 mL three-neck flask, followed by the addition of potassium carbonate (6.2 g, 45 mmol) and benzyl bromide (7.6 g, 45 mmol). The reaction solution was refluxed at 65° C. for 5 hours. The reaction solution was cooled, filtrated and washed with methanol. The reaction solution was concentrated, and the resulting residue was purified by column chromatography with petroleum ether/ethyl acetate (1/3) to obtain (8R,9S,13S,14S)-3-(benzyloxy)-13-methyl-6,7,8,9,11,12,13,14,15,16-decahydro-17H-cyclopenta[a]phenanthren-17-one (5 g, yield: 93%).

1H NMR (400 MHz, CDCl$_3$) δ 7.45-7.29 (m, 5H), 7.20 (d, J=8.5 Hz, 1H), 6.79 (dd, J=8.6, 2.7 Hz, 1H), 6.73 (d, J=2.6 Hz, 1H), 5.04 (s, 2H), 2.95-2.85 (m, 2H), 2.50 (dd, J=18.8, 8.5 Hz, 1H), 2.43-2.36 (m, 1H), 2.30-2.23 (m, 1H), 2.20-1.94 (m, 4H), 1.63-1.40 (m, 6H), 0.91 (s, 3H).

Step 2: Preparation of (8S,9S,13S,14S)-3-(benzyloxy)-17-ethylidene-13-methyl-7,8,9,11,12,13,14,15,16,17-decahydro-6H-cyclopenta[a]phenanthrene

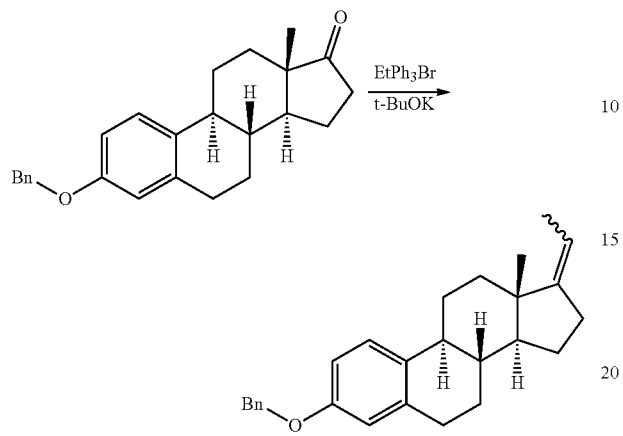

Potassium tert-butoxide (7.8 g, 70 mmol) was suspended in tetrahydrofuran (100 mL). Ethyltriphenylphosphonium bromide (26.3 g, 70 mmol) was slowly added at 0° C., and the reaction solution was stirred at 60° C. for 2 hours. (8R,9S,13S,14S)-3-(Benzyloxy)-13-methyl-6,7,8,9,11,12,13,14,15,16-decahydro-17H-cyclopenta[a]phenanthren-17-one (5 g, 14 mmol) was added to the above reaction solution. After reacting at 60° C. for 2 hours, the reaction solution was cooled to room temperature. Saturated aqueous ammonium chloride solution was added to quench the reaction, and the reaction solution was extracted with ethyl acetate. The organic phase was washed with saturated saline, dried, filtrated and concentrated. The resulting residue was purified by column chromatography with petroleum ether to obtain (8S,9S,13S,14S)-3-(benzyloxy)-17-ethylidene-13-methyl-7,8,9,11,12,13,14,15,16,17-decahydro-6H-cyclopenta[a]phenanthrene (5 g, yield: 96%).

Step 3: Preparation of 1-((8S,9S,13S,14S)-3-(benzyloxy)-13-methyl-7,8,9,11,12,13,14,15,16,17-decahydro-6H-cyclopenta[a]phenanthren-17-yl)ethan-1-ol

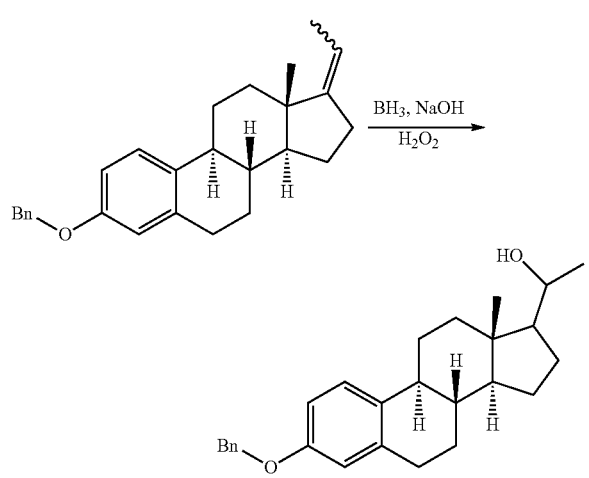

(8S,9S,13S,14S)-3-(Benzyloxy)-17-ethylidene-13-methyl-7,8,9,11,12,13,14,15,16,17-decahydro-6H-cyclopenta[a]phenanthrene (2.5 g, 6.9 mmol) was dissolved in anhydrous tetrahydrofuran (50 mL). A solution of borane in tetrahydrofuran (1 M, 20 mL) was added dropwise at room temperature, and the resulting reaction solution was stirred at room temperature for 1 hour. The reaction solution was cooled with ice water, and sodium hydroxide solution (10%, 15 mL) was slowly added dropwise to release a large amount of gas. Hydrogen peroxide (30%, 20 mL) was slowly added dropwise, and the reaction solution was stirred at room temperature for 2 hours. The reaction solution was extracted with ethyl acetate, washed with sodium thiosulfate solution and saturated saline, and dried to obtain the product (2.5 g), which was used directly in the next step.

Step 4: Preparation of 1-((8S,9S,13S,14S,17S)-3-(benzyloxy)-13-methyl-7,8,9,11,12,13,14,15,16,17-decahydro-6H-cyclopenta[a]phenanthren-17-yl)ethan-1-one

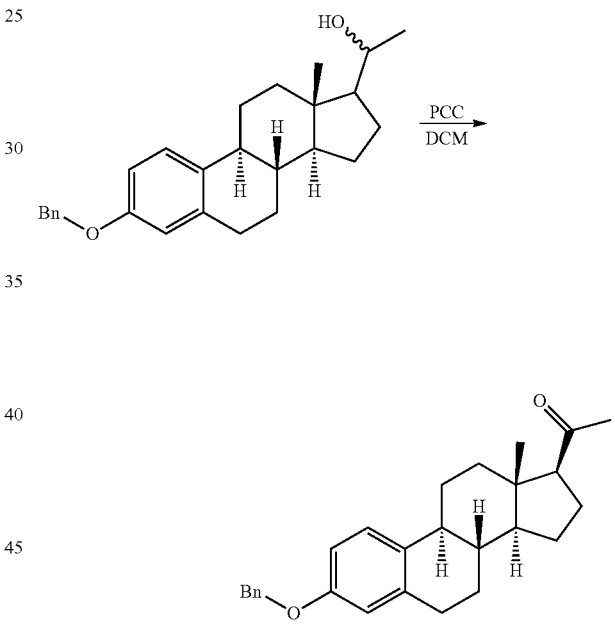

1-((8S,9S,13S,14S)-3-(Benzyloxy)-13-methyl-7,8,9,11,12,13,14,15,16,17-decahydro-6H-cyclopenta[a]phenanthren-17-yl)ethan-1-ol (2.5 g, 6.5 mmol) was dissolved in dichloromethane (30 mL). Pyridinium chlorochromate (2.06 g, 9.6 mmol) was added, and the reaction solution was stirred at room temperature for 12 hours. The reaction solution was filtrated and concentrated by rotary evaporation to dryness. The resulting residue was purified by column chromatography with petroleum ether/ethyl acetate (1/5) to obtain 1-((8S,9S,13S,14S,17S)-3-(benzyloxy)-13-methyl-7,8,9,11,12,13,14,15,16,17-decahydro-6H-cyclopenta[a]phenanthren-17-yl)ethan-1-one (1.6 g, yield: 65%). 1H NMR (400 MHz, CDCl$_3$) δ 7.44-7.28 (m, 5H), 7.20 (d, J=8.6 Hz, 1H), 6.78 (dd, J=8.5, 2.6 Hz, 1H), 6.72 (d, J=2.6 Hz, 1H), 5.03 (s, 2H), 2.90-2.80 (m, 2H), 2.61 (t, J=9.1 Hz, 1H), 2.40-2.17 (m, 4H), 2.15 (s, 3H), 1.96-1.27 (m, 9H), 0.65 (s, 3H).

Step 5: Preparation of 1-((8S,9S,13S,14S,17S)-3-hydroxy-13-methyl-7,8,9,11,12,13,14,15,16,17-decahydro-6H-cyclopenta[a]phenanthren-17-yl)ethan-1-one Step 1: Preparation of 1-((8S,9S,13S,14S,17S)-3-(benzyloxy)-2-bromo-13-methyl-7,8,9,11,12,13,14,15,16,17-decahydro-6H-cyclopenta[a]phenanthren-17-yl)-2-bromoethan-1-one

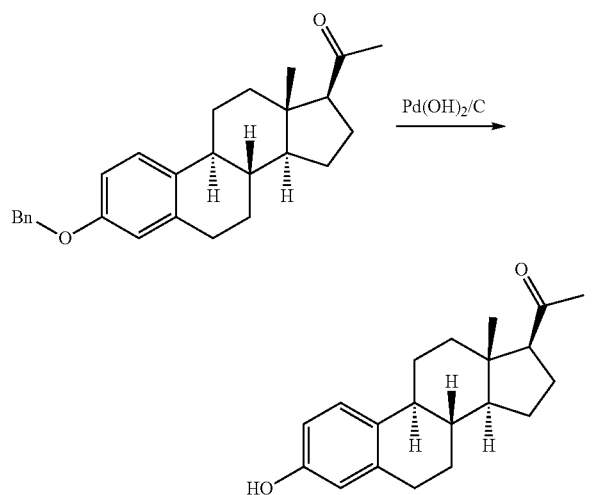

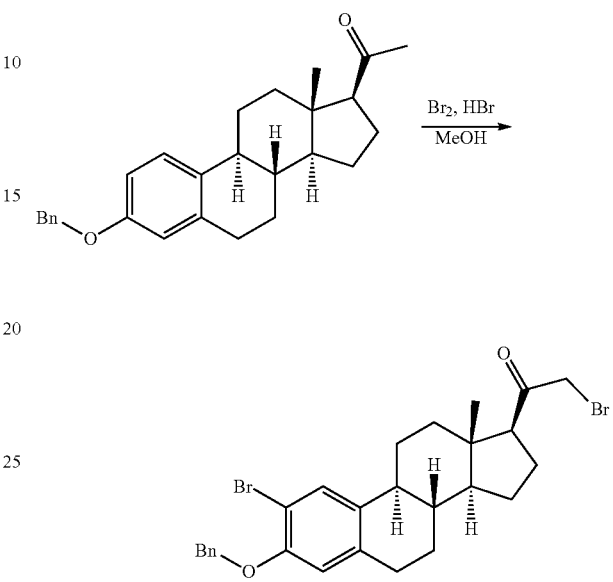

1-((8S,9S,13S,14S,17S)-3-(Benzyloxy)-13-methyl-7,8,9,11,12,13,14,15,16,17-deca hydro-6H-cyclopenta[a]phenanthren-17-yl)ethan-1-one (200 mg, 0.52 mmol) was dissolved in methanol/tetrahydrofuran (5 mL/5 mL). Palladium hydroxide on activated carbon (30 mg, 20%) was added, and the reaction solution was reacted under a hydrogen atmosphere at 45° C. for 12 hours to obtain the final product 1-((8S,9S,13S,14S,17S)-3-hydroxy-13-methyl-7,8,9,11,12,13,14,15,16,17-decahydro-6H-cyclopenta[a]phenanthren-17-yl)ethan-1-one (50 mg, yield: 32%).

MS m/z (ESI): 298.1 [M]+.

1H NMR (400 MHz, CDCl$_3$) δ 7.15 (d, J=8.4 Hz, 1H), 6.63 (dd, J=8.4, 2.6 Hz, 1H), 6.56 (d, J=2.6 Hz, 1H), 4.62 (s, 1H), 2.92-2.74 (m, 2H), 2.62 (t, J=9.1 Hz, 1H), 2.40-2.17 (m, 4H), 2.16 (s, 3H), 1.95-1.30 (m, 9H), 0.65 (s, 3H).

Example 158

1-((8S,9S,13S,14S,17S)-3-Hydroxy-13-methyl-7,8,9,11,12,13,14,15,16,17-decahydro-6H-cyclopenta[a]phenanthren-17-yl)-2-(1H-1,2,3-triazol-1-yl)ethan-1-one (158)

1-((8S,9S,13S,14S,17S)-3-(Benzyloxy)-13-methyl-7,8,9,11,12,13,14,15,16,17-deca hydro-6H-cyclopenta[a]phenanthren-17-yl)ethan-1-one (300 mg, 0.78 mmol) was dissolved in methanol (15 mL). Five drops of hydrogen bromide solution was added, followed by the dropwise addition of liquid bromine (255 mg, 1.6 mmol). After stirring at room temperature for 2 hours, the reaction solution was poured into ice water, and extracted with ethyl acetate. The organic phase was washed with saturated saline, dried over anhydrous sodium sulfate, and concentrated by rotary evaporation to dryness to obtain 300 mg of the product 1-((8S,9S,13S,14S,17S)-3-(benzyloxy)-2-bromo-13-methyl-7,8,9,11,12,13,14,15,16,17-decahydro-6H-cyclopenta[a]phenanthren-17-yl)-2-bromoethan-1-one, which was used directly in the next step.

Step 2: Preparation of 1-((8S,9S,13S,14S,17S)-3-(benzyloxy)-2-bromo-13-methyl-7,8,9,11,12,13,14,15,16,17-decahydro-6H-cyclopenta[a]phenanthren-17-yl)-2-(1H-1,2,3-triazol-1-yl)ethan-1-one

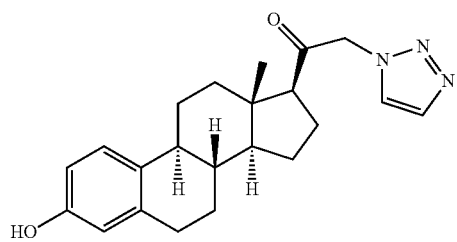

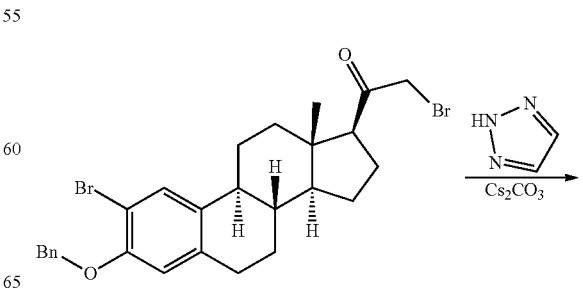

-continued

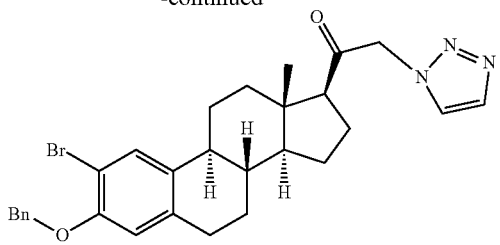

1-((8S,9S,13S,14S,17S)-3-(Benzyloxy)-2-bromo-13-methyl-7,8,9,11,12,13,14,15,16,17-decahydro-6H-cyclopenta[a]phenanthren-17-yl)-2-bromoethan-1-one (300 mg, 0.55 mmol) was dissolved in tetrahydrofuran (10 mL). Cesium carbonate (536 mg, 1.65 mmol) and 1,2,3-triazole (190 mg, 2.7 mmol) were added, and the reaction solution was reacted at 35° C. for 5 hours. The reaction solution was filtrated and concentrated. The resulting residue was purified by column chromatography with petroleum ether/ethyl acetate (1/1) to obtain 1-((8S,9S,13S,14S,17S)-3-(benzyloxy)-2-bromo-13-methyl-7,8,9,11,12,13,14,15,16,17-decahydro-6H-cyclopenta[a]phenanthren-17-yl)-2-(1H-1,2,3-triazol-1-yl)ethan-1-one (70 mg, yellow solid, yield: 20%).

MS m/z (ESI): 534.1/536.1 (50/50) [M+H]+.

Step 3: Preparation of 1-((8S,9S,13S,14S,17S)-3-hydroxy-13-methyl-7,8,9,11,12,13,14,15,16,17-decahydro-6H-cyclopenta[a]phenanthren-17-yl)-2-(1H-1,2,3-triazol-1-yl)ethan-1-one

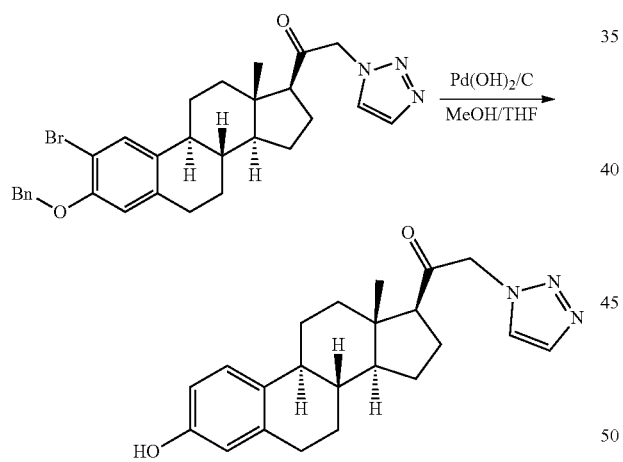

1-((8S,9S,13S,14S,17S)-3-(Benzyloxy)-2-bromo-13-methyl-7,8,9,11,12,13,14,15,16,17-decahydro-6H-cyclopenta[a]phenanthren-17-yl)-2-(1H-1,2,3-triazol-1-yl)ethan-1-one (70 mg, 0.13 mmol) was dissolved in methanol/tetrahydrofuran (5 mL/5 mL). Palladium hydroxide on activated carbon (30 mg, 20%) was added, and the reaction solution was reacted under a hydrogen atmosphere at 45° C. for 12 hours. The reaction solution was filtrated, and concentrated to obtain 1-((8S,9S,13S,14S,17S)-3-hydroxy-13-methyl-7,8,9,11,12,13,14,15,16,17-decahydro-6H-cyclopenta[a]phenanthren-17-yl)-2-(1H-1,2,3-triazol-1-yl)ethan-1-one (30 mg, white solid, yield: 62.6%).

MS m/z (ESI): 366.1 [M+H]+.

1H NMR (400 MHz, CDCl$_3$) δ 7.78 (s, 1H), 7.67 (s, 1H), 7.15 (d, J=8.0 Hz, 1H), 6.65 (dd, J=6.4, 2.4 Hz, 1H), 6.60-6.56 (m, 1H), 5.40-5.15 (m, 2H), 5.04 (s, 1H), 2.89-2.70 (m, 3H), 2.40-2.21 (m, 3H), 1.96-1.27 (m, 10H), 0.71 (s, 3H).

Example 159

((3R,5R,8R,9R,10S,13S,14S,17S)-3-Hydroxy-3,13-dimethylhexadecahydro-1H-cyclopenta[a]phenanthren-17-yl)dimethylphosphine oxide (159)

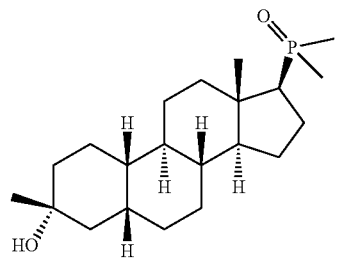

Step 1: Preparation of (3R,5R,8R,9R,10S,13S,14S)-3-((tert-butyldimethylsilyl)oxy)-3,13-dimethylhexadecahydro-17H-cyclopenta[a]phenanthren-17-one

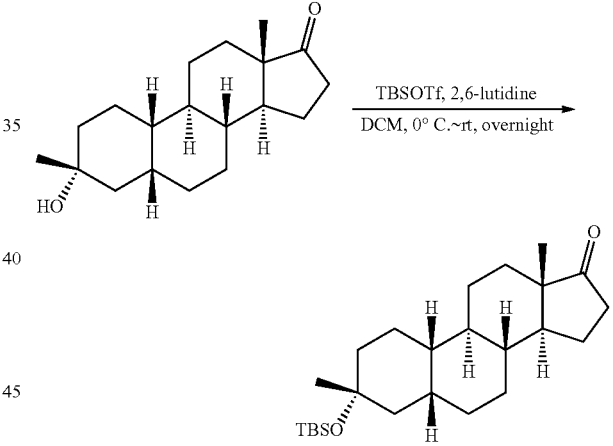

(3R,5R,8R,9R,10S,13S,14S)-3-Hydroxy-3,13-dimethylhexadecahydro-17H-cyclopenta[a]phenanthren-17-one (5 g, 17 mmol) (Shanghai Yinling Pharmaceutical Technology Co., Ltd.), 2,6-lutidine (4.5 g, 42.5 mmol) and anhydrous dichloromethane (80 mL) were successively added to a 100 mL round bottom flask. The reaction system was cooled to 0° C. in an ice water bath, and tert-butyldimethylsilyl trifluoromethanesulfonate (9 g, 34 mmol) was added dropwise. The reaction system was warmed up to room temperature and stirred overnight. TLC showed that the reaction was completed. The reaction solution was diluted with dichloromethane. The organic phase was washed with water and saturated saline, dried over anhydrous sodium sulfate, filtrated and concentrated by rotary evaporation to dryness. The resulting crude product was purified by column chromatography (petroleum ether:ethyl acetate=20:1) to obtain (3R,5R,8R,9R,10S,13S,14S)-3-((tert-butyldimethylsilyl)oxy)-3,13-dimethylhexadecahydro-17H-cyclopenta[a]phenanthren-17-one (6.2 g, yield: 90.1%).

$^1$H NMR (400 MHz, CDCl$_3$) (2.37 (dd, J=18.8, 8.0 Hz, 1H), 2.06-1.97 (m, 1H), 1.90-1.84 (m, 1H), 1.75-1.68 (m, 5H), 1.59-1.55 (m, 1H), 1.47-0.89 (m, 17H), 0.80 (s, 3H), 0.79 (s, 9H), 0.00 (m, 6H).

Step 2: Preparation of (3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl trifluoromethanesulfonate

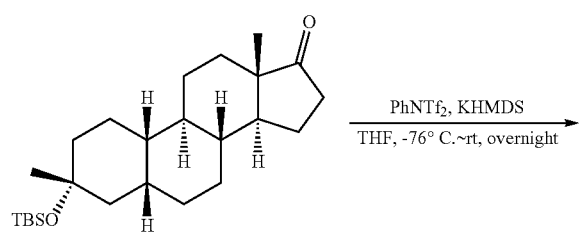

(3R,5R,8R,9R,10S,13S,14S)-3-((tert-butyldimethylsilyl)oxy)-3,13-dimethylhexadecahydro-17H-cyclopenta[a]phenanthren-17-one (1.2 g, 3 mmol) and 50 ml of anhydrous tetrahydrofuran were successively added to a 100 mL round bottom flask. The reaction system was cooled to −78° C., and a solution of potassium hexamethyldisilazide in tetrahydrofuran (3 mL, 3 mmol) was added dropwise to the reaction system. The reaction solution was stirred at −78° C. for 1 hour, and then N-phenylbis(trifluoromethanesulfonimide) (1.29 g, 3.6 mmol) dissolved in 5 ml of anhydrous tetrahydrofuran was added dropwise to the reaction system. After completion of the addition, the reaction solution was warmed naturally up to room temperature and stirred overnight. After completion of the reaction, saturated ammonium chloride solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: petroleum ether) to obtain (3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl trifluoromethanesulfonate (1.4 g, yield: 87%).

$^1$H NMR (400 MHz, CDCl$_3$) (5.56 (s, 1H), 2.27-2.18 (m, 1H), 2.00-1.93 (m, 1H), 1.80-1.61 (m, 7H), 1.49-1.23 (m, 15H), 0.97 (s, 3H), 0.86 (s, 9H), 0.08 (s, 6H).

Step 3: Preparation of ((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)dimethylphosphine oxide

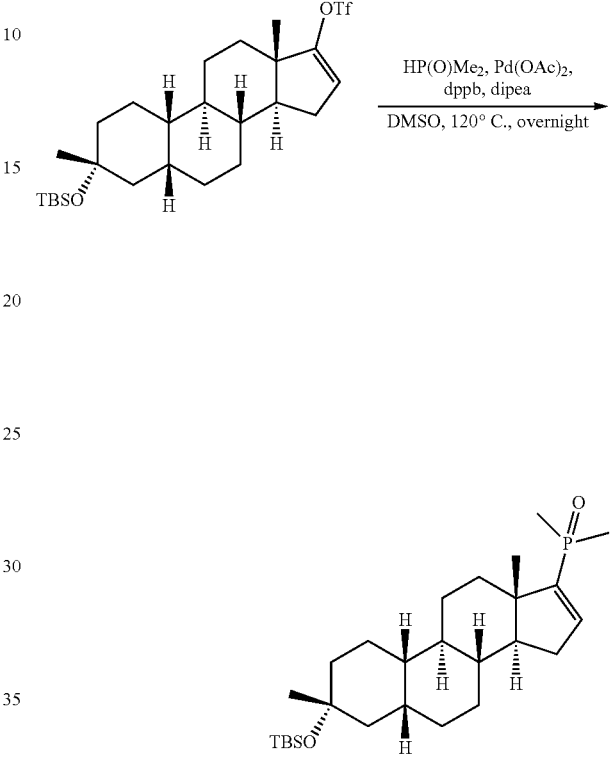

(3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl trifluoromethanesulfonate (840 mg, 1.57 mmol), dimethylphosphine oxide (146 mg, 1.89 mmol), palladium diacetate (35 mg, 0.16 mmol), 1,4-bis(diphenylphosphino)butane (69 mg, 0.16 mmol), N,N-diisopropylethylamine (1.6 g, 12.6 mmol) and 10 ml of anhydrous dimethyl sulfoxide were successively added to a 100 mL round bottom flask. The reaction system was purged with nitrogen, slowly warmed up to 120° C. and stirred overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)dimethylphosphine oxide (642 mg, yield: 88%).

$^1$H NMR (400 MHz, CDCl$_3$) δ 6.54 (dd, J=10.8, 1.6 Hz, 1H), 2.33-2.27 (m, 1H), 2.11-2.01 (m, 2H), 1.66-1.58 (m, 12H), 1.48-1.1.13 (m, 15H), 1.00 (s, 3H), 0.86 (s, 9H), 0.07 (s, 6H).

Step 4: Preparation of ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)dimethylphosphine oxide

Step 5: Preparation of ((3R,5R,8R,9R,10S,13S,14S,17S)-3-hydroxy-3,13-dimethylhexadecahydro-1H-cyclopenta[a]phenanthren-17-yl)dimethylphosphine oxide

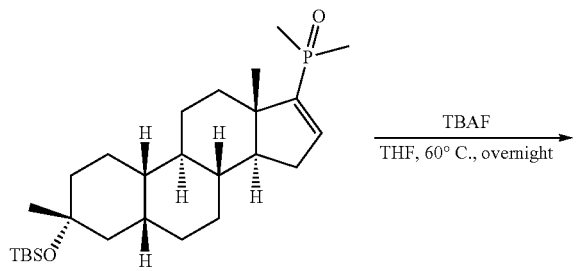

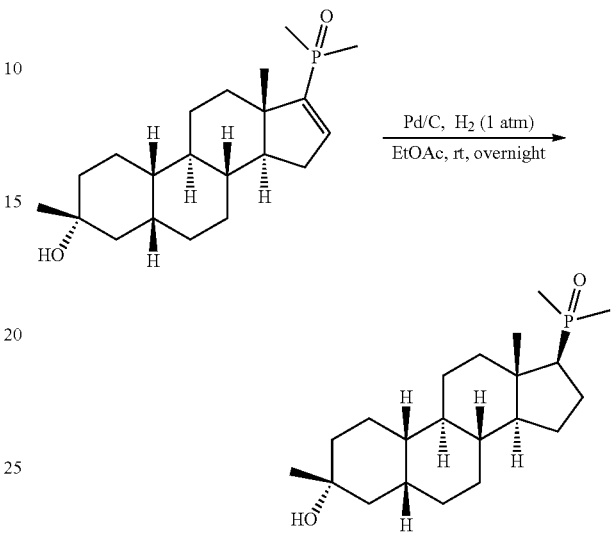

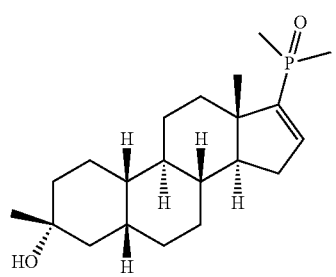

((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)dimethylphosphine oxide (642 mg, 1.38 mmol) was dissolved in 5 mL of anhydrous tetrahydrofuran in a 100 mL round bottom flask, and a 1.0 M solution of tetrabutylammonium fluoride in tetrahydrofuran (5 mL) was added to the reaction system. The reaction solution was stirred at 60° C. overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)dimethylphosphine oxide (170 mg, yield: 35%).

$^1$H NMR (400 MHz, CDCl$_3$) δ 6.57-6.54 (m, 1H), 2.45 (br, 1H), 2.35-2.28 (m, 1H), 2.12-2.00 (m, 2H), 1.87-1.70 (m, 4H), 1.67-1.14 (m, 23H), 1.00 (s, 3H).

((3R,5R,8R,9R,10S,13S,14S)-3-Hydroxy-3,13-dimethyl-2,3,4,5,6,7,8,9,10,11,12,13,14,15-tetradecahydro-1H-cyclopenta[a]phenanthren-17-yl)dimethylphosphine oxide (100 mg, 0.29 mmol), palladium on carbon (100 mg, 10%) and 10 mL of ethyl acetate were added to a 100 mL round bottom flask. The reaction system was purged with hydrogen three times, and reacted at 1 atmosphere overnight. After completion of the reaction, the reaction solution was filtrated through celite to remove excess palladium on carbon, and the filtrate was concentrated by rotary evaporation to dryness. The resulting crude product was purified by high performance liquid chromatography to obtain ((3R,5R,8R,9R,10S,13S,14S,17S)-3-hydroxy-3,13-dimethylhexadecahydro-1H-cyclopenta[a]phenanthren-17-yl)dimethylphosphine oxide (39.5 mg, yield: 39%).

MS m/z (ESI): 353.3 [M+H]$^+$.

$^1$H NMR (400 MHz, CDCl$_3$) (2.13-1.62 (m, 22H), 1.35-1.27 (m, 8H), 1.16-1.06 (m, 4H), 0.99 (s, 3H).

Example 160

((3R,5R,8R,9R,10S,13S,14S,17S)-3-Hydroxy-3,13-dimethylhexadecahydro-1H-cyclopenta[a]phenanthren-17-yl)diphenylphosphine oxide (160)

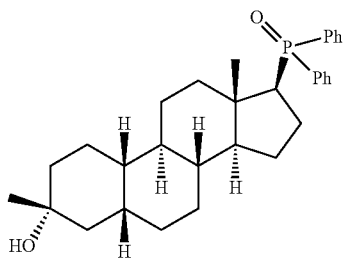

Step 1: Preparation of ((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)diphenylphosphine oxide

Step 2: Preparation of ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)diphenylphosphine oxide

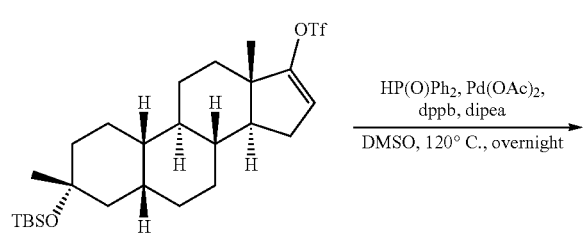

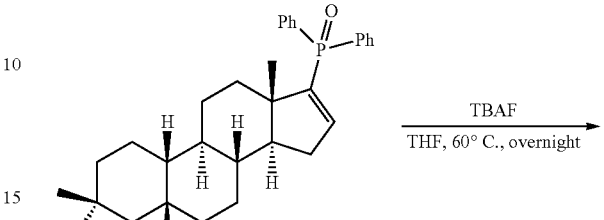

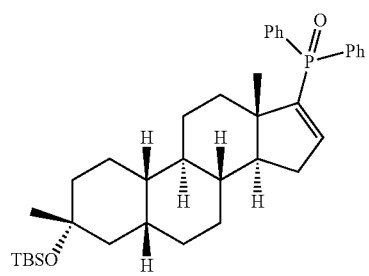

(3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl trifluoromethanesulfonate (350 mg, 0.65 mmol), diphenylphosphine oxide (158 mg, 0.78 mmol), palladium diacetate (35 mg, 0.16 mmol), 1,4-bis(diphenylphosphino)butane (69 mg, 0.16 mmol), N,N-diisopropylethylamine (660 mg, 5.2 mmol) and 10 ml of anhydrous dimethyl sulfoxide were successively added to a 100 mL round bottom flask. The reaction system was purged with nitrogen, slowly warmed up to 120° C. and stirred overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)diphenylphosphine oxide (290 mg, 76%).

$^1$H NMR (400 MHz, CDCl$_3$) (7.85-7.80 (m, 2H), 7.67-7.62 (m, 2H), 7.59-7.40 (m, 6H), 6.01-5.98 (m, 1H), 2.31-2.25 (m, 1H), 2.09-2.02 (m, 2H), 1.89-1.10 (m, 21H), 1.07 (s, 3H), 0.86 (s, 9H), 0.07 (s, 6H).

((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)diphenylphosphine oxide (270 mg, 0.46 mmol) was dissolved in 5 mL of anhydrous tetrahydrofuran in a 100 mL round bottom flask, and a 1.0 M solution of tetrabutylammonium fluoride in tetrahydrofuran (5 mL) was added to the reaction system. The reaction solution was stirred at 60° C. overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)diphenylphosphine oxide (120 mg, yield: 55%).

$^1$H NMR (400 MHz, CDCl$_3$) (6.57-6.54 (m, 1H), 2.45 (br, 1H), 2.35-2.28 (m, 1H), 2.12-2.00 (m, 2H), 1.87-1.70 (m, 4H), 1.67-1.14 (m, 26H), 1.00 (s, 3H).

Step 3: Preparation of ((3R,5R,8R,9R,10S,13S,14S,17S)-3-hydroxy-3,13-dimethylhexadecahydro-1H-cyclopenta[a]phenanthren-17-yl)diphenylphosphine oxide

Step 1: Preparation of (8R,10R,13S,14S)-10,13-dimethyl-17-oxo-2,7,8,9,10,11,12,13,14,15,16,17-dodecahydro-1H-cyclopenta[a]phenanthren-3-yl acetate

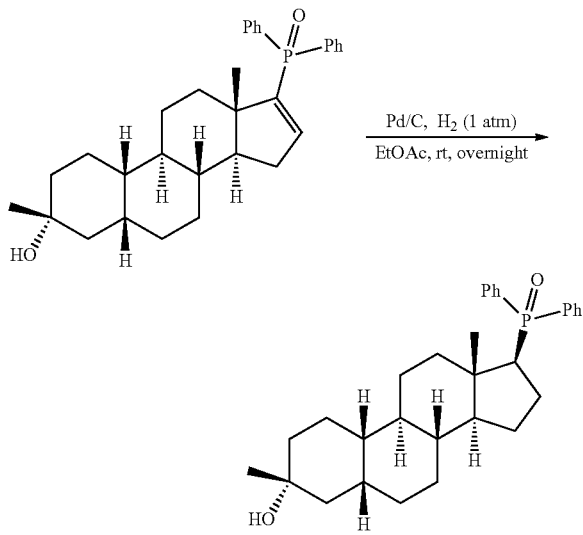

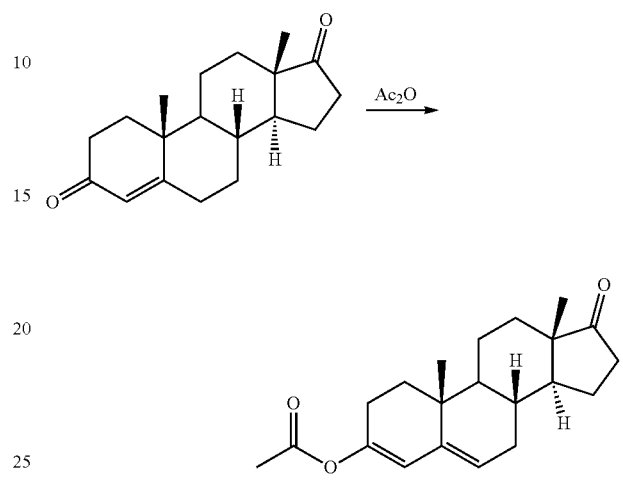

((3R,5R,8R,9R,10S,13S,14S)-3-Hydroxy-3,13-dimethyl-2,3,4,5,6,7,8,9,10,11,12,13,14,15-tetradecahydro-1H-cyclopenta[a]phenanthren-17-yl)diphenylphosphine oxide (120 mg, 0.25 mmol), palladium on carbon (120 mg, 10%) and 10 mL of ethyl acetate were added to a 100 mL round bottom flask. The reaction system was purged with hydrogen three times, and reacted at 1 atmosphere overnight. After completion of the reaction, the reaction solution was filtrated through celite to remove excess palladium on carbon, and the filtrate was concentrated by rotary evaporation to dryness. The resulting crude product was purified by high performance liquid chromatography to obtain ((3R,5R,8R,9R,10S,13S,14S,17S)-3-hydroxy-3,13-dimethylhexadecahydro-1H-cyclopenta[a]phenanthren-17-yl)diphenylphosphine oxide (40 mg, yield: 33%).

MS m/z (ESI): 477.3 [M+H]$^+$.

$^1$H NMR (400 MHz, CDCl$_3$) (7.91-7.83 (m, 4H), 7.54-7.44 (m, 6H), 2.37-2.15 (m, 2H), 2.11-2.09 (m, 1H), 2.07-1.95 (m, 6H), 1.84-1.04 (m, 22H). $^{31}$P NMR (162 MHz, CDCl$_3$) δ 30.00.

Example 161

1-((3R,6R,8S,10S,13S,14S,17S)-3-Hydroxy-3,13-dimethylhexadecahydro-6,10-(epoxymethano)cyclopenta[a]phenanthren-17-yl)ethan-1-one (161)

(8R,10R,13S,14S)-10,13-Dimethyl-1,6,7,8,9,10,11,12,13,14,15,16-dodecahydro-3H-cyclopenta[a]phenanthrene-3,17(2H)-dione (19.0 g, 66.43 mmol) was dissolved in ethyl acetate (500 mL), and acetic anhydride (100 mL) and perchloric acid (0.5 mL) were added. The reaction solution was stirred at room temperature for 1 hour, and TLC showed that the reaction was completed. Saturated sodium carbonate solution (300 mL) was added to the reaction solution. The organic phase was washed with saturated sodium carbonate solution (300 mL*2) and saturated saline (300 mL), dried over anhydrous sodium sulfate and concentrated. The resulting residue was purified by silica gel column chromatography (ethyl acetate:petroleum ether=0-40%) to obtain (8R,10R,13S,14S)-10,13-dimethyl-17-oxo-2,7,8,9,10,11,12,13,14,15,16,17-dodecahydro-1H-cyclopenta[a]phenanthren-3-yl acetate (13.0 g, yield: 59.7%).

1H NMR (400 MHz, CDCl$_3$) δ: 5.71 (s, 1H), 5.42 (t, J=2.4 Hz, 1H), 2.51-2.43 (m, 2H), 2.34-2.27 (m, 1H), 2.18-2.04 (m, 5H), 2.00-1.69 (m, 6H), 1.62-1.27 (m, 5H), 1.13-1.06 (m, 1H), 1.03 (s, 3H), 0.92 (s, 3H).

Step 2: Preparation of (8R,10R,13S,14S)-6-hydroxy-10,13-dimethyl-1,6,7,8,9,10,11,12,13,14,15,16-dodecahydro-3H-cyclopenta[a]phenanthrene-3,17(2H)-dione

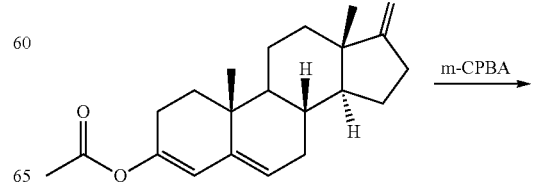

-continued

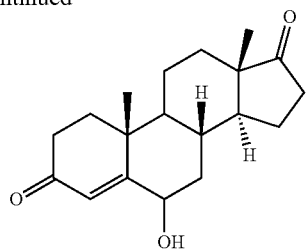

(8R,10R,13S,14S)-10,13-Dimethyl-17-oxo-2,7,8,9,10,11,12,13,14,15,16,17-dodecahydro-1H-cyclopenta[a]phenanthren-3-yl acetate (5.0 g, 15.24 mmol) was dissolved in ethanol (180 mL), and m-chloroperoxybenzoic acid (5.0 g, 24.71 mmol) was added. The reaction solution was stirred at room temperature for 3 hours, and LC/MS showed that the reaction was completed. Saturated sodium carbonate solution (200 mL) was added, and then the reaction solution was extracted with ethyl acetate (300 mL). The organic phase was washed with saturated sodium carbonate solution (200 mL*2) and saturated saline (200 mL), dried over anhydrous sodium sulfate and concentrated to obtain (8R,10R,13S,14S)-6-hydroxy-10,13-dimethyl-1,6,7,8,9,10,11,12,13,14,15,16-dodecahydro-3H-cyclopenta[a]phenanthrene-3,17(2H)-dione (3.5 g, yield: 76.0%).

MS m/z (ESI): 303.0 [M+H]$^+$.

Step 3: Preparation of (8R,10R,13S,14S)-6-hydroxy-10,13-dimethyltetradecahydro-3H-cyclopenta[a]phenanthrene-3,17(2H)-dione

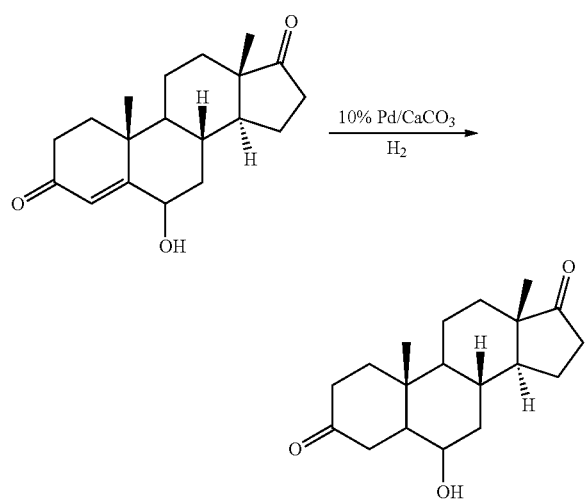

(8R,10R,13S,14S)-6-Hydroxy-10,13-dimethyl-1,6,7,8,9,10,11,12,13,14,15,16-dodecahydro-3H-cyclopenta[a]phenanthrene-3,17(2H)-dione (8.0 g, 26.5 mmol) was dissolved in pyridine (50 mL), and 10% Pd Lindlar's catalyst (2.0 g) was added to the above solution. The reaction system was equipped with a hydrogen balloon and purged with hydrogen three times, and stirred at room temperature for 16 hours. The reaction solution was filtrated, and the filter cake was washed with ethyl acetate (30 mL). The filtrate was diluted with ethyl acetate (200 mL), and washed with 1N hydrochloric acid (100 mL*2). The organic phase was washed with saturated saline (100 mL), dried over anhydrous sodium sulfate and concentrated. The resulting residue was purified by silica gel column chromatography (ethyl acetate:petroleum ether=1:1) to obtain (8R,10R,13S,14S)-6-hydroxy-10,13-dimethyltetradecahydro-3H-cyclopenta[a]phenanthrene-3,17(2H)-dione (2.0 g, yield: 25.0%).

1H NMR (400 MHz, DMSO-d6) δ: 4.60 (s, 1H), 3.51 (m, 1H), 2.45-2.31 (m, 3H), 2.06-1.82 (m, 7H), 1.69-1.51 (m, 5H), 1.48-1.23 (m, 5H), 1.14 (s, 3H), 0.82 (s, 3H).

Step 4: Preparation of (6R,8R,10S,13S,14S)-13-methyltetradecahydro-6,10-(epoxymethano)cyclopenta[a]phenanthrene-3,17-dione

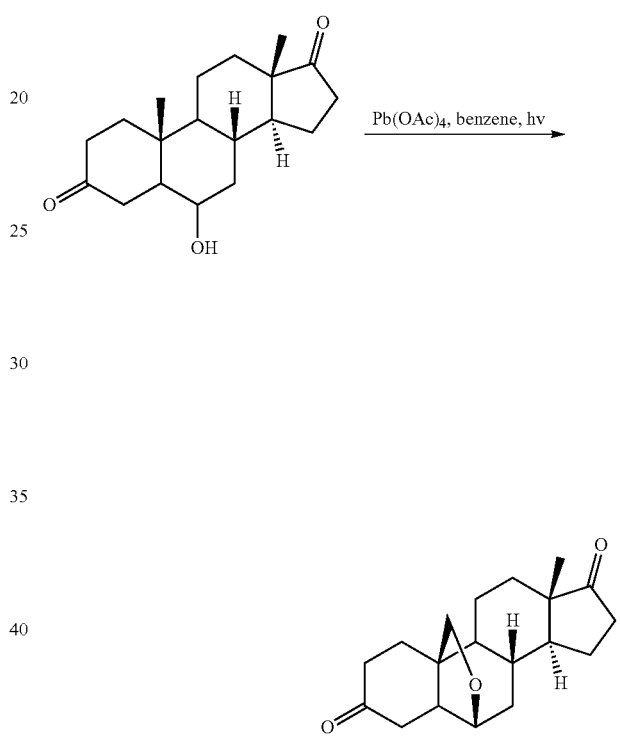

(8R,10R,13S,14S)-6-Hydroxy-10,13-dimethyltetradecahydro-3H-cyclopenta[a]phenanthrene-3,17(2H)-dione (1.0 g, 3.29 mmol) was dissolved in benzene (50 mL)/pyridine (0.8 mL), and lead tetraacetate (7.3 g, 16.5 mmol) was added to the above solution. The reaction solution was stirred under an incandescent lamp (500W) for 2 hours, and the reaction was then stopped. Ethyl acetate (100 mL) was added to the reaction solution to precipitate a large amount of solid, and the reaction solution was then filtrated. The filtrate was washed with 1N hydrochloric acid (50 mL*2). The organic phase was washed with saturated saline (50 mL), dried over anhydrous sodium sulfate and concentrated. The resulting residue was purified by silica gel column chromatography (ethyl acetate:petroleum ether=1:2) to obtain (6R,8R,10S,13S,14S)-13-methyltetradecahydro-6,10-(epoxymethano)cyclopenta[a]phenanthrene-3,17-dione (600 mg, yield: 60.0%).

1H NMR (400 MHz, CDCl$_3$) δ: 4.25-4.22 (m, 1H), 4.06 (d, J=8.4 Hz, 1H), 3.39 (d, J=8.4 Hz, 1H), 2.63-2.44 (m, 3H), 2.35-2.06 (m, 5H), 1.98-1.80 (m, 4H), 1.72-1.24 (m, 8H), 0.96 (s, 3H).

Step 5: Preparation of (3R,6R,8R,10S,13S,14S)-3-hydroxy-3,13-dimethyltetradecahydro-6,10-(epoxymethano)cyclopenta[a]phenanthren-17(1H)-one

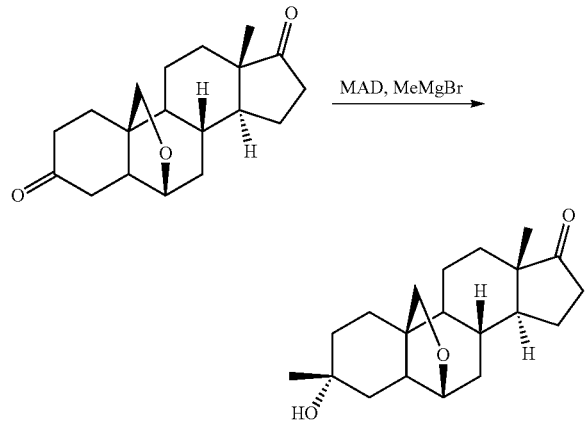

2,6-Di-tert-butyl-p-methylphenol (3.5 g, 15.9 mmol) and toluene (35 mL) were added to a three-neck flask. 2M trimethylaluminum (4 mL, 8 mmol) was added dropwise at 0-10° C. under a nitrogen atmosphere. After completion of the addition, the reaction solution was stirred at room temperature for 1 hour. The reaction solution was cooled to −78° C. in a dry ice/acetone bath, and (6R,8R,10S,13S,14S)-13-methyltetradecahydro-6,10-(epoxymethano)cyclopenta[a]phenanthrene-3,17-dione (0.8 g, 2.65 mmol) dissolved in toluene (30 mL) was added dropwise, and then the reaction solution was reacted at −78° C. for 1 hour. 3M methylmagnesium bromide (2.3 mL, 6.9 mmol) was added, and then the reaction solution was reacted at −78° C. for 1 hour. Saturated ammonium chloride solution (50 mL) was added, and then the reaction solution was extracted with ethyl acetate (120 mL). The organic phase was washed with saturated saline (50 mL), dried over anhydrous sodium sulfate and concentrated. The resulting residue was purified by silica gel column chromatography (ethyl acetate:petroleum ether=1:1) to obtain (3R,6R,8R,10S,13S,14S)-3-hydroxy-3,13-dimethyltetradecahydro-6,10-(epoxymethano)cyclopenta[a]phenanthren-17(1H)-one (400 mg, yield: 47.5%).

1H NMR (400 MHz, CDCl$_3$) δ: 4.15-4.12 (m, 1H), 3.96 (d, J=8.0 Hz, 1H), 3.32 (d, J=8.0 Hz, 1H), 2.48-2.41 (m, 1H), 2.13-2.03 (m, 1H), 1.92-1.79 (m, 5H), 1.75-1.63 (m, 3H), 1.60-1.43 (m, 6H), 1.38-1.10 (m, 7H), 0.92 (s, 3H).

Step 6: Preparation of (3R,6R,8S,10S,13S,14S)-17-ethylidene-3,13-dimethylhexadecahydro-6,10-(epoxymethano)cyclopenta[a]phenanthren-3-ol

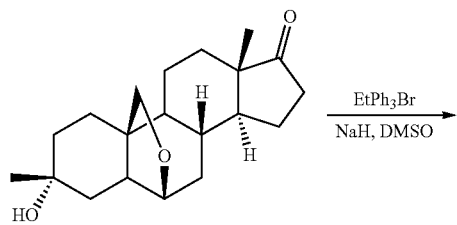

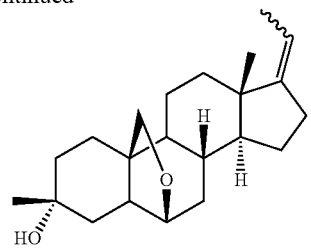

Ethyltriphenylphosphonium bromide (11.65 g, 31.4 mmol) was dissolved in dimethyl sulfoxide (25 mL). 60% sodium hydrogen (1.26 g, 31.4 mmol) was added, and then the reaction solution was stirred at room temperature under a nitrogen atmosphere for 1 hour. (3R,6R,8R,10S,13S,14S)-3-Hydroxy-3,13-dimethyltetradecahydro-6,10-(epoxymethano)cyclopenta[a]phenanthren-17(1H)-one (0.5 g, 1.57 mmol) dissolved in dimethyl sulfoxide (5 mL) was added, and then the reaction solution was heated to 60° C. and reacted for 16 hours. Saturated ammonium chloride solution (50 mL) was added, and then the reaction solution was extracted with ethyl acetate (60 mL). The organic phase was washed with saturated sodium carbonate solution (50 mL*2) and saturated saline (50 mL) successively, dried over anhydrous sodium sulfate and concentrated. The resulting residue was purified by silica gel column chromatography (ethyl acetate:petroleum ether=1:3) to obtain (3R,6R,8S,10S,13S,14S)-17-ethylidene-3,13-dimethylhexadecahydro-6,10-(epoxymethano)cyclopenta[a]phenanthren-3-ol (350 mg, yield 67.6%).

1H NMR (400 MHz, CDCl$_3$) δ: 5.12-5.09 (m, 1H), 4.15-4.12 (m, 1H), 3.96 (d, J=8.0 Hz, 1H), 3.26 (d, J=8.0 Hz, 1H), 2.39-2.13 (m, 3H), 1.91-1.85 (m, 3H), 1.70-1.50 (m, 12H), 1.30-1.07 (m, 8H), 0.91 (s, 3H).

Step 7: Preparation of (3R,6R,8S,10S,13S,14S,17S)-17-((S)-1-hydroxyethyl)-3,13-dimethylhexadecahydro-6,10-(epoxymethano)cyclopenta[a]phenanthren-3-ol

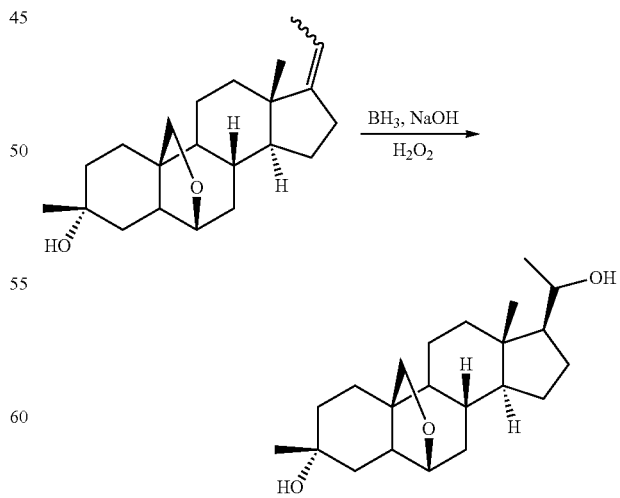

(3R,6R,8S,10S,13S,14S)-17-Ethylidene-3,13-dimethylhexadecahydro-6,10-(epoxymethano)cyclopenta[a]phenanthren-3-ol (250 mg, 0.76 mmol) was dissolved in tetrahydrofuran (8 mL), and the solution was cooled to 0° C. A solution of borane in tetrahydrofuran (1 M, 15 mL, 15 mmol) was added, and the reaction solution was stirred at room temperature for 3 hours. The reaction solution was cooled to 0° C., and sodium hydroxide (3M, 10 mL) was added dropwise. After completion of the dropwise addition, hydrogen peroxide (30%, 8 mL) was added, and the reaction solution was stirred at room temperature for 1 hour. The reaction solution was diluted with ethyl acetate (60 mL), and washed with saturated sodium thiosulfate solution (30 mL). The organic phase was washed with saturated saline (50 mL), dried over anhydrous sodium sulfate, and concentrated to obtain (3R,6R,8S,10S,13S,14S,17S)-17-((S)-1-hydroxyethyl)-3,13-dimethylhexadecahydro-6,10-(epoxymethano)cyclopenta[a]phenanthren-3-ol (260 mg, yield: 100%), which was used directly in the next step without further purification.

Step 8: Preparation of 1-((3R,6R,8S,10S,13S,14S,17S)-3-hydroxy-3,13-dimethylhexadecahydro-6,10-(epoxymethano)cyclopenta[a]phenanthren-17-yl)ethan-1-one

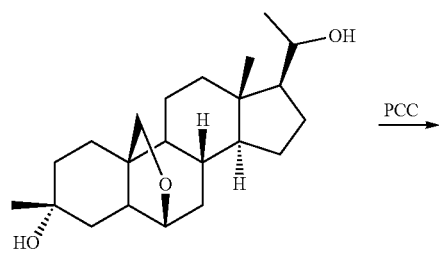

(3R,6R,8S,10S,13S,14S,17S)-17-((S)-1-hydroxyethyl)-3,13-dimethylhexadecahydro-6,10-(epoxymethano)cyclopenta[a]phenanthren-3-ol (260 mg, 0.75 mmol) was dissolved in dichloromethane (10 mL), and the solution was cooled to 0° C. PCC (322 mg, 1.5 mmol) was added, and then the reaction solution was stirred at room temperature for 3 hours. TLC showed that the reaction was completed. The reaction solution was filtrated, and the filter cake was washed with ethyl acetate (20 mL). The filtrate was diluted with ethyl acetate (30 mL), and washed with saturated sodium thiosulfate solution (30 mL). The organic phase was washed with saturated saline (50 mL), dried over anhydrous sodium sulfate and concentrated. The resulting residue was purified by silica gel column chromatography (ethyl acetate:petroleum ether=1:2) to obtain 1-((3R,6R,8S,10S,13S,14S,17S)-3-hydroxy-3,13-dimethylhexadecahydro-6,10-(epoxymethano)cyclopenta[a]phenanthren-17-yl)ethan-1-one (150 mg, yield: 57.8%).

1H NMR (400 MHz, CDCl$_3$) δ: 4.14-4.12 (m, 1H), 3.94 (d, J=7.6 Hz, 1H), 3.27 (d, J=7.6 Hz, 1H), 2.53 (t, J=8.8 Hz, 1H), 2.18-2.04 (m, 5H), 1.91-1.86 (m, 3H), 1.70-1.49 (m, 10H), 1.34-1.49 (m, 8H), 0.66 (s, 3H).

Example 162

1-(2-((3R,6R,8S,10S,13S,14S,17S)-3-Hydroxy-3,13-dimethylhexadecahydro-6,10-(epoxymethano)cyclopenta[a]phenanthren-17-yl)-2-oxoethyl)-1H-pyrazole-4-carbonitrile (162)

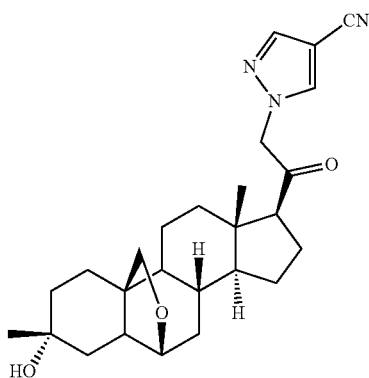

Step 1: Preparation of 2-bromo-1-((3R,6R,8S,10S,13S,14S,17S)-3-hydroxy-3,13-dimethylhexadecahydro-6,10-(epoxymethano)cyclopenta[a]phenanthren-17-yl)ethan-1-one

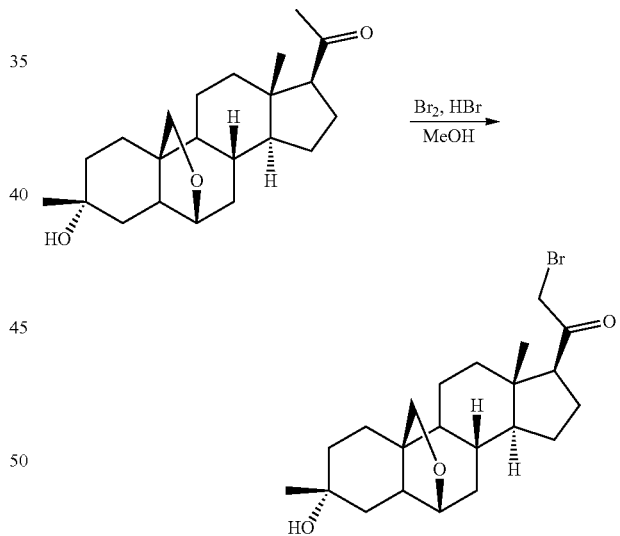

1-((3R,6R,8S,10S,13S,14S,17S)-3-Hydroxy-3,13-dimethylhexadecahydro-6,10-(epoxymethano)cyclopenta[a]phenanthren-17-yl)ethan-1-one (135 mg, 0.39 mmol) was dissolved in methanol (6 mL). A drop of hydrogen bromide was added, followed by the addition of 5 drops of liquid bromine under stirring at room temperature, and then the reaction solution was stirred at room temperature for 1 hour. TLC showed that the reaction was completed. Saturated sodium bicarbonate solution (30 mL) was added, and then the reaction solution was extracted with ethyl acetate (50 mL). The organic phase was washed with saturated saline (50 mL), dried over anhydrous sodium sulfate, and concentrated to obtain 2-bromo-1-((3R,6R,8S,10S,13S,14S,17S)-

3-hydroxy-3,13-dimethylhexadecahydro-6,10-(epoxymethano)cyclopenta[a]phenanthren-17-yl)ethan-1-one (160 mg, yield: 96.5%), which was used directly in the next step without further purification.

Step 2: Preparation of 1-(2-((3R,6R,8S,10S,13S, 14S,17S)-3-hydroxy-3,13-dimethylhexadecahydro-6, 10-(epoxymethano)cyclopenta[a]phenanthren-17-yl)-2-oxoethyl)-1H-pyrazole-4-carbonitrile

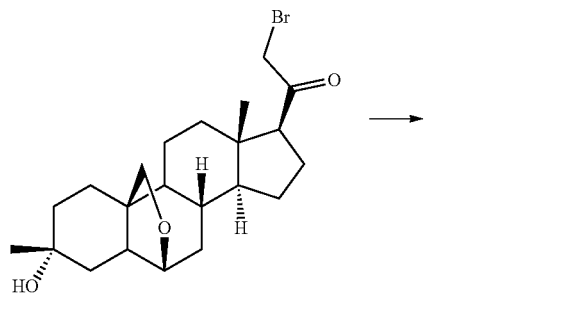

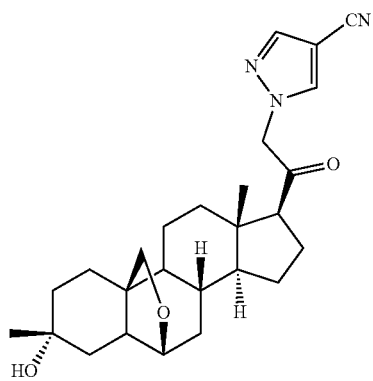

2-Bromo-1-((3R,6R,8S,10S,13S,14S,17S)-3-hydroxy-3, 13-dimethylhexadecahydro-6,10-(epoxymethano)cyclopenta[a]phenanthren-17-yl)ethan-1-one (85 mg, 0.2 mmol) and 4-cyanopyrazole (92 mg, 1.0 mmol) were dissolved in tetrahydrofuran (5 mL), and potassium carbonate (138 mg, 1.0 mmol) was added. The reaction solution was stirred at room temperature for 16 hours, and TLC and LCMS showed that the reaction was completed. The reaction solution was filtrated and concentrated. The resulting residue was purified by flash preparative chromatography to obtain 1-(2-((3R, 6R,8S,10S,13S,14S,17S)-3-hydroxy-3,13-dimethylhexadecahydro-6,10-(epoxymethano)cyclopenta[a]phenanthren-17-yl)-2-oxoethyl)-1H-pyrazole-4-carbonitrile (29.7 mg, yield: 34.0%).

MS m/z (ESI): 438.3 [M+H]+.

1H NMR (400 MHz, CDCl$_3$) δ: 7.87 (s, 1H), 7.81 (s, 1H), 5.01-4.87 (m, 2H), 4.15-4.12 (m, 1H), 3.93 (d, J=8.4 Hz, 1H), 3.28 (d, J=8.4 Hz, 1H), 2.60 (t, J=6.8 Hz, 1H), 2.22-2.08 (m, 2H), 1.91-1.49 (m, 13H), 1.39-1.24 (m, 6H), 1.19-1.13 (m, 2H), 0.72 (s, 3H).

Example 163

1-(2-((3R,6R,8S,10S,13S,14S,17S)-3-Hydroxy-3,13-dimethylhexadecahydro-6,10-(epoxymethano)cyclopenta[a]phenanthren-17-yl)-2-oxoethyl)-1H-pyrazole-3-carbonitrile (163)

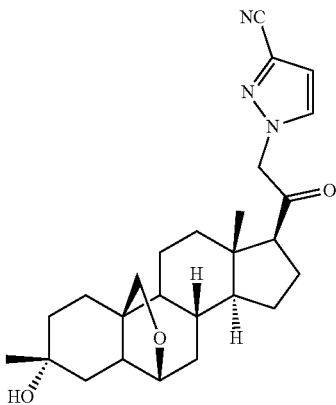

Preparation of 1-(2-((3R,6R,8S,10S,13S,14S,17S)-3-Hydroxy-3,13-dimethylhexadecahydro-6,10-(epoxymethano)cyclopenta[a]phenanthren-17-yl)-2-oxoethyl)-1H-pyrazole-3-carbonitrile

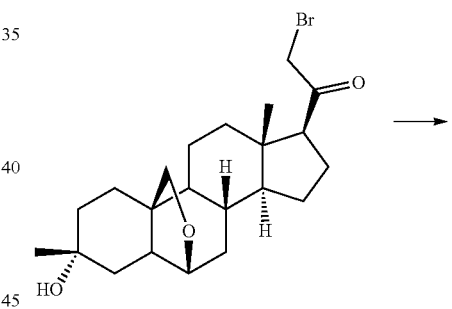

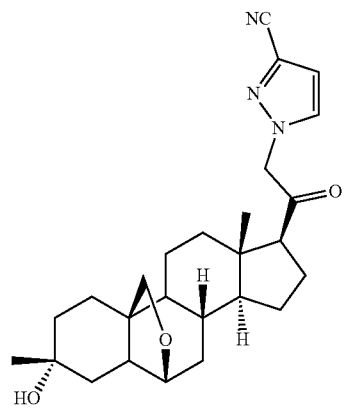

2-Bromo-1-((3R,6R,8S,10S,13S,14S,17S)-3-hydroxy-3, 13-dimethylhexadecahydro-6,10-(epoxymethano)cyclopenta[a]phenanthren-17-yl)ethan-1-one (80 mg, 0.19 mmol) and 3-cyanopyrazole (88 mg, 0.95 mmol) were dissolved in tetrahydrofuran (5 mL), and potassium carbonate (130 mg, 0.95 mmol) was added. The reaction solution was stirred at room temperature for 16 hours, and TLC and LCMS showed that the reaction was completed. The reaction solution was filtrated and concentrated. The resulting residue was purified by flash preparative chromatography to obtain 1-(2-((3R,6R,8S,10S,13S,14S,17S)-3-Hydroxy-3,13-dimethylhexadecahydro-6,10-(epoxymethano)cyclopenta[a]phenanthren-17-yl)-2-oxoethyl)-1H-pyrazole-3-carbonitrile (36.5 mg, yield: 44.4%).

MS m/z (ESI): 438.3 [M+H]$^+$.

1H NMR (400 MHz, CDCl$_3$) δ: 7.49 (d, J=2.0 Hz, 1H), 7.76 (d, J=2.0 Hz, 1H), 5.10-4.90 (m, 2H), 4.15-4.12 (m, 1H), 3.94 (d, J=8.0 Hz, 1H), 3.28 (d, J=8.0 Hz, 1H), 2.60 (t, J=8.8 Hz, 1H), 2.21-2.09 (m, 2H), 1.91-1.50 (m, 13H), 1.39-1.24 (m, 6H), 1.19-1.13 (m, 2H), 0.72 (s, 3H).

Example 164

1-((3R,6R,8S,10S,13S,14S,17S)-3-Hydroxy-3,13-dimethylhexadecahydro-6,10-(epoxymethano)cyclopenta[a]phenanthren-17-yl)-2-(4-(trifluoromethyl)-1H-pyrazol-1-yl)ethan-1-one (164)

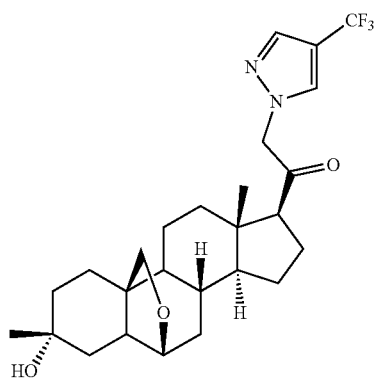

Preparation of 1-((3R,6R,8S,10S,13S,14S,17S)-3-hydroxy-3,13-dimethylhexadecahydro-6,10-(epoxymethano)cyclopenta[a]phenanthren-17-yl)-2-(4-(trifluoromethyl)-1H-pyrazol-1-yl)ethan-1-one

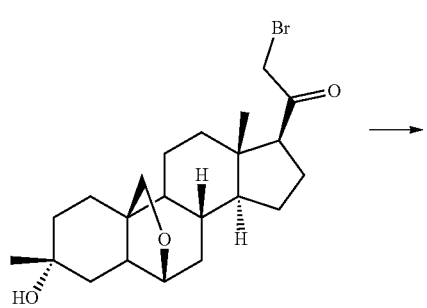

-continued

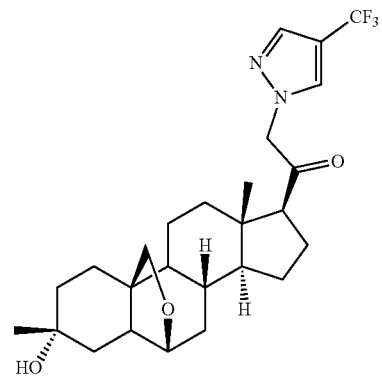

2-Bromo-1-((3R,6R,8S,10S,13S,14S,17S)-3-hydroxy-3,13-dimethylhexadecahydro-6,10-(epoxymethano)cyclopenta[a]phenanthren-17-yl)ethan-1-one (80 mg, 0.19 mmol) and 4-trifluoromethylpyrazole (128 mg, 0.95 mmol) were dissolved in tetrahydrofuran (5 mL), and potassium carbonate (130 mg, 0.95 mmol) was added. The reaction solution was stirred at room temperature for 16 hours, and TLC and LCMS showed that the reaction was completed. The reaction solution was filtrated and concentrated. The resulting residue was purified by flash preparative chromatography to obtain 1-((3R,6R,8S,10S,13S,14S,17S)-3-hydroxy-3,13-dimethylhexadecahydro-6,10-(epoxymethano)cyclopenta[a]phenanthren-17-yl)-2-(4-(trifluoromethyl)-1H-pyrazol-1-yl)ethan-1-one (29.5 mg, yield: 32.7%).

MS m/z (ESI): 481.2 [M+H]$^+$.

1H NMR (400 MHz, CDCl$_3$) δ: 7.72 (s, 2H), 5.01-4.87 (m, 2H), 4.15-4.12 (m, 1H), 3.94 (d, J=8.0 Hz, 1H), 3.28 (d, J=8.0 Hz, 1H), 2.60 (t, J=8.8 Hz, 1H), 2.22-2.09 (m, 2H), 1.91-1.49 (m, 13H), 1.39-1.24 (m, 6H), 1.19-1.13 (m, 2H), 0.73 (s, 3H).

Example 165

1-(2-((1S,4aS,4bR,6aR,8R,10aS,10bR,12aS)-8-Hydroxy-8,12a-dimethyloctadecahydrochrysen-1-yl)-2-oxoethyl)-1H-pyrazole-4-carbonitrile (165)

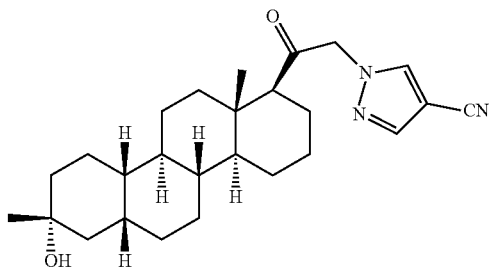

Step 1: Preparation of (3R,5R,8R,9R,10S,13S,14S)-3,13-dimethyl-17-oxohexadecahydro-1H-cyclopenta[a]phenanthren-3-yl acetate Step 2: Preparation of ethyl 2-((3R,5R,8R,9R,10S,13S,14S)-3-acetoxy-17-hydroxy-3,13-dimethylhexadecahydro-1H-cyclopenta[a]phenanthren-17-yl)-2-diazoacetate

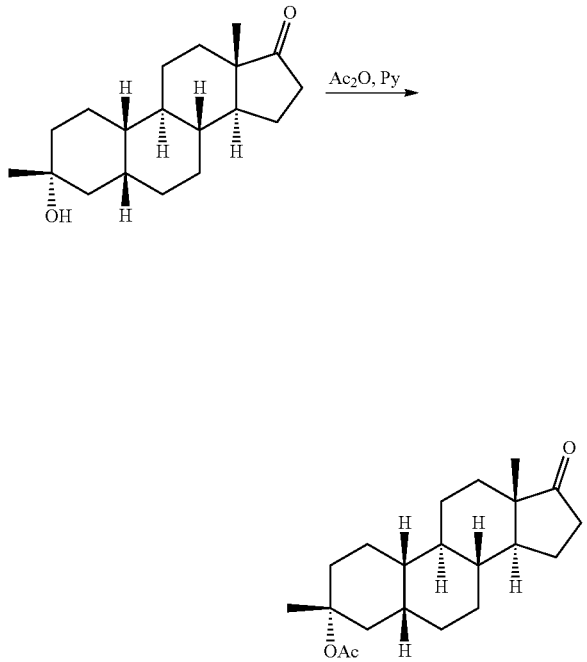

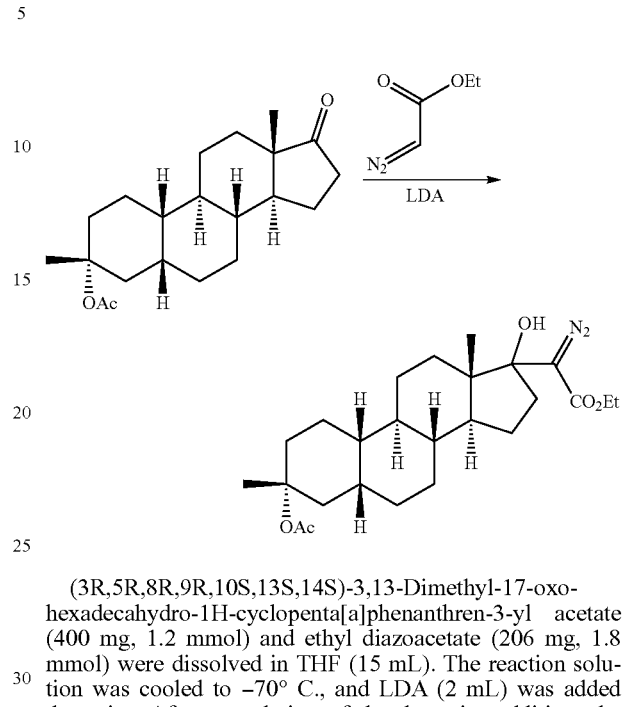

(3R,5R,8R,9R,10S,13S,14S)-3-Hydroxy-3,13-dimethyl-hexadecahydro-17H-cyclopenta[a]phenanthren-17-one (580 mg, 2.0 mmol) was dissolved in acetic anhydride (15 mL). Pyridine (158 mg, 2.0 mmol) was added, and the reaction solution was reacted under a $N_2$ atmosphere at 80° C. overnight. The reaction solution was concentrated under reduced pressure to remove acetic anhydride. $H_2O$ (20 mL) was added to the resulting residue, and then the mixture was extracted with EA (15 mL×3). The EA phases were combined, washed successively with $H_2O$ (20 mL) and saturated saline (20 mL), dried over anhydrous $Na_2SO_4$, and concentrated under reduced pressure. The resulting residue was purified by column chromatography to obtain (3R,5R,8R,9R,10S,13S,14S)-3,13-dimethyl-17-oxohexadecahydro-1H-cyclopenta[a]phenanthren-3-yl acetate (560 mg, yield: 84%).

$^1$H NMR (400 MHz, CDCl$_3$) δ 2.44 (dd, J=19.2, 8.1 Hz, 1H), 2.24-2.06 (m, 1H), 1.97 (s, 3H), 1.96-1.76 (m, 8H), 1.71-1.57 (m, 3H), 1.55 (s, 3H), 1.55-0.99 (m, 10H), 0.87 (s, 3H).

(3R,5R,8R,9R,10S,13S,14S)-3,13-Dimethyl-17-oxo-hexadecahydro-1H-cyclopenta[a]phenanthren-3-yl acetate (400 mg, 1.2 mmol) and ethyl diazoacetate (206 mg, 1.8 mmol) were dissolved in THF (15 mL). The reaction solution was cooled to −70° C., and LDA (2 mL) was added dropwise. After completion of the dropwise addition, the reaction solution was reacted at the same temperature for 1 hour. A solution of AcOH (400 mg) in ether (20 mL) was added, and the reaction solution was warmed up to room temperature, and $H_2O$ (50 mL) was added. The reaction solution was extracted with ether (25 mL×2). The ether phases were combined, washed successively with $H_2O$ (50 mL), saturated NaHCO$_3$ solution (30 mL) and saturated saline (30 mL), dried over anhydrous Na$_2$SO$_4$, and concentrated under reduced pressure to dryness. The resulting residue was purified by column chromatography to obtain ethyl 2-((3R,5R,8R,9R,10S,13S,14S)-3-acetoxy-17-hydroxy-3,13-dimethylhexadecahydro-1H-cyclopenta[a]phenanthren-17-yl)-2-diazoacetate (500 mg, yield: 93%).

$^1$H NMR (400 MHz, CDCl$_3$) δ 4.70 (bs, 1H), 4.36-4.17 (m, 2H), 2.24-2.11 (m, 1H), 2.00 (s, 3H), 1.96-1.87 (m, 2H), 1.85-1.83 (m, 4H), 1.74-1.58 (m, 4H), 1.55 (s, 3H), 1.52-1.35 (m, 2H), 1.32 (t, J=7.1 Hz, 3H), 1.29-1.17 (m, 4H), 1.17-0.94 (m, 5H), 0.92 (s, 3H), 0.91-0.81 (m, 1H).

Step 3: Preparation of ethyl (4aS,4bR,6aR,8R,10aS,10bR,12aS)-8-acetoxy-8,12a-dimethyl-1-oxooctadecahydrochrysene-2-carboxylate

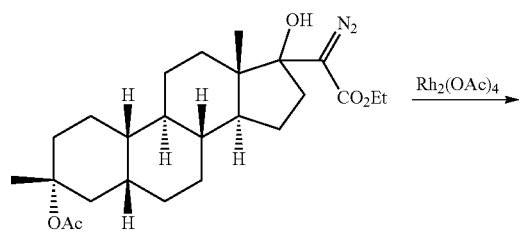

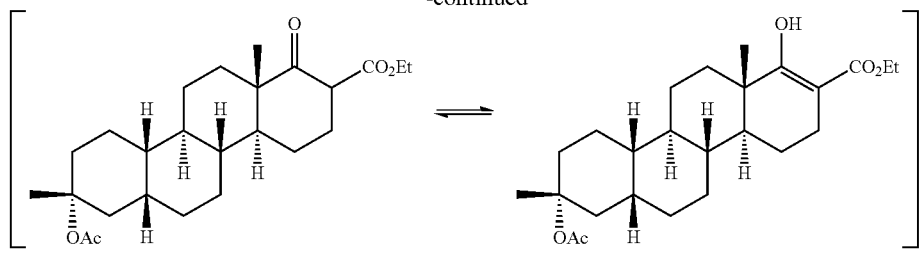

Ethyl 2-((3R,5R,8R,9R,10S,13S,14S)-3-acetoxy-17-hydroxy-3,13-dimethylhexadecahydro-1H-cyclopenta[a]phenanthren-17-yl)-2-diazoacetate (500 mg, 1.1 mmol) was dissolved in ethylene glycol dimethyl ether (10 mL). Rhodium acetate dimer (5.0 mg) was added, and the reaction solution was reacted under a $N_2$ atmosphere at room temperature for 0.5 hour. The reaction solution was filtrated to remove the insoluble matter, and the filtrate was concentrated under reduced pressure. The resulting residue was purified by column chromatography to obtain ethyl (4aS, 4bR,6aR,8R,10aS,10bR,12aS)-8-acetoxy-8,12a-dimethyl-1-oxooctadecahydrochrysene-2-carboxylate (436 mg, yield: 93%).

$^1$H NMR (400 MHz, CDCl$_3$) δ 12.35 (s, 0.82H), 4.13 (q, J=7.1 Hz, 2H), 3.63 (dd, J=13.5, 6.0 Hz, 0.15H), 2.27 (dd, J=16.2, 6.1 Hz, 1H), 2.14-1.96 (m, 2H), 1.89 (s, 3H), 1.88-1.65 (m, 7H), 1.58 (dd, J=20.4, 10.4 Hz, 3H), 1.48 (s, 3H), 1.36-1.13 (m, 8H), 1.11-1.04 (m, 2H), 1.03 (s, 3H), 0.99-0.88 (m, 3H).

Step 4: Preparation of (4aS,4bR,6aR,8R,10aS,10bR,12aS)-8-hydroxy-8,12a-dimethylhexadecahydrochrysen-1(2H)-one

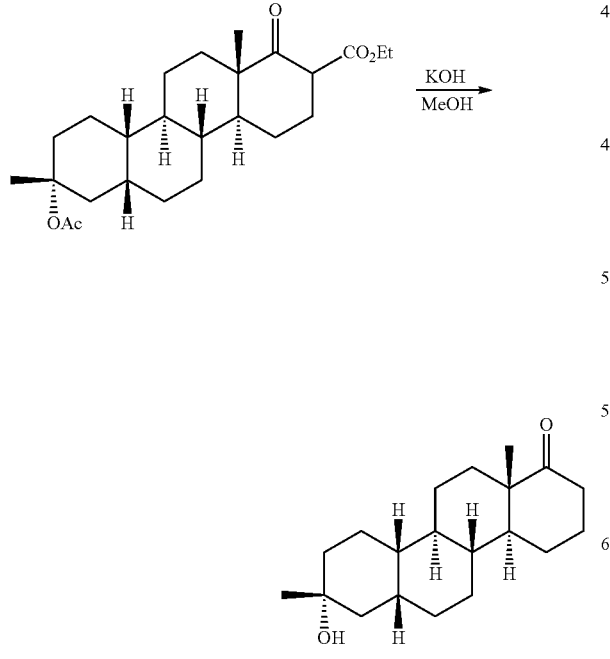

KOH (4.0 g) was dissolved in methanol (60 mL). Ethyl (4aS,4bR,6aR,8R,10aS,10bR,12aS)-8-acetoxy-8,12a-dimethyl-1-oxooctadecahydrochrysene-2-carboxylate (400 mg) was added, and then the reaction solution was heated to reflux under a $N_2$ atmosphere for 1 hour. The reaction solution was cooled to room temperature, and poured into ice water (150 mL). After stirring for 20 minutes, the reaction solution was filtrated. The filter cake was washed with a small amount of water and acetone, and dried to obtain (4aS,4bR,6aR,8R,10aS,10bR,12aS)-8-hydroxy-8,12a-dimethylhexadecahydrochrysen-1 (2H)-one (320 mg).

$^1$H NMR (400 MHz, CDCl$_3$) δ 2.61 (td, J=14.0, 6.8 Hz, 1H), 2.25-2.15 (m, 1H), 2.11-2.00 (m, 1H), 1.87 (dd, J=9.8, 7.7 Hz, 2H), 1.84-1.70 (m, 5H), 1.67-1.57 (m, 3H), 1.56-1.47 (m, 2H), 1.45-1.27 (m, 7H), 1.26 (s, 3H), 1.20-1.10 (m, 1H), 1.08 (s, 3H), 1.07-0.91 (m, 2H).

Step 5: Preparation of (2R,4aS,4bR,6aS,10aS,10bR,12aR)-7-ethylidene-2,6a-dimethyloctadecahydrochrysen-2-ol

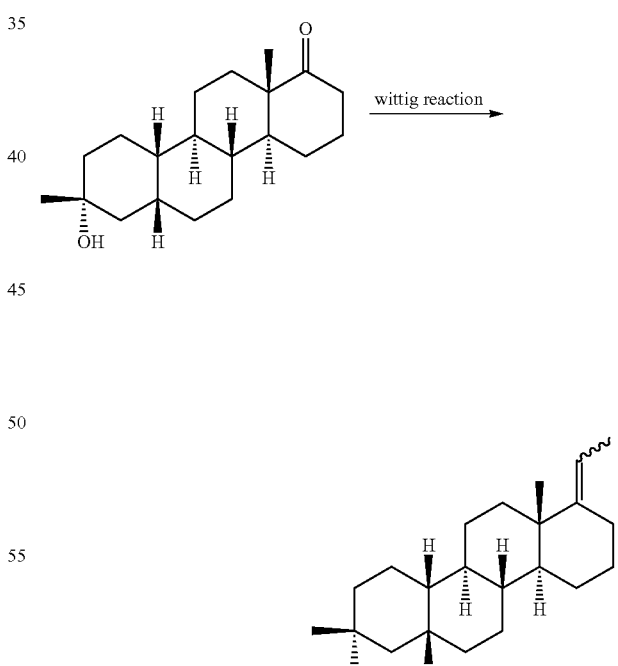

In accordance with Step 4 of Example 1, (4aS,4bR,6aR,8R,10aS,10bR,12aS)-8-hydroxy-8,12a-dimethylhexadecahydrochrysen-1(2H)-one was used as the starting material, accordingly, (2R,4aS,4bR,6aS,10aS,10bR,12aR)-7-ethylidene-2,6a-dimethyloctadecahydrochrysen-2-ol (288 mg) was obtained.

Step 6: Preparation of (2R,4aS,4bR,6aS,7S,10aS, 10bR,12aR)-7-(1-hydroxyethyl)-2,6a-dimethyloctadecahydro chrysen-2-ol

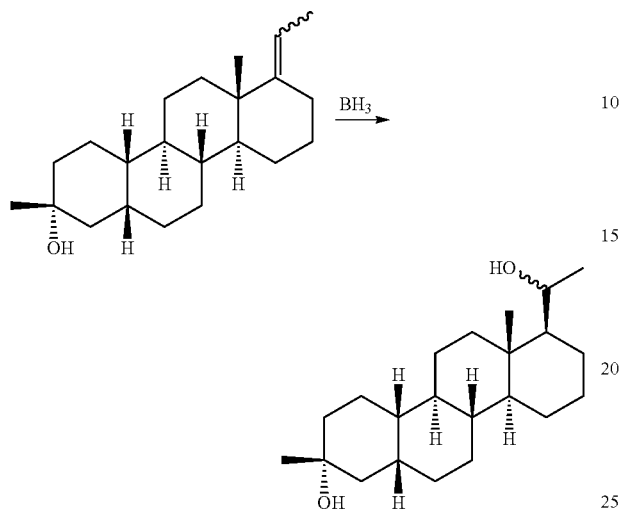

In accordance with Step 5 of Example 1, (2R,4aS,4bR, 6aS,10aS,10bR,12aR)-7-ethylidene-2,6a-dimethyloctadecahydrochrysen-2-ol was used as the starting material, accordingly, (2R,4aS,4bR,6aS,7S,10aS,10bR,12aR)-7-(1-hydroxyethyl)-2,6a-dimethyloctadecahydro chrysen-2-ol (150 mg, containing a small amount of impurities) was obtained, which was used directly in the next step without purification.

Step 7: Preparation of 1-((1S,4aS,4bR,6aR,8R,10aS, 10bR,12aS)-8-hydroxy-8,12a-dimethyloctadecahydrochrysen-1-yl)ethan-1-one

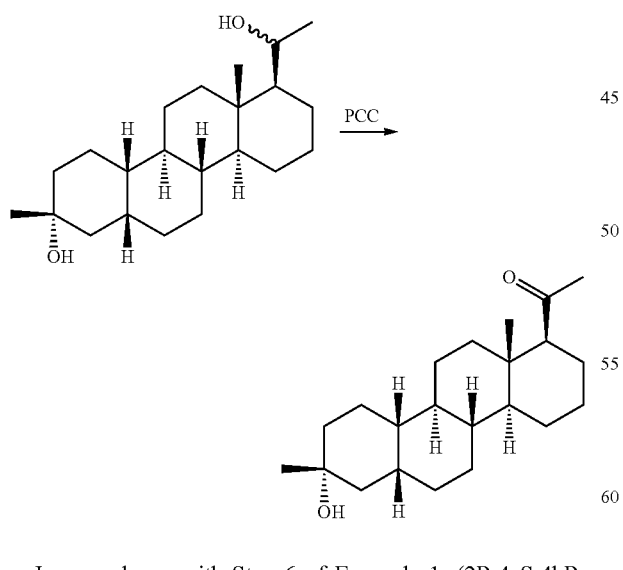

In accordance with Step 6 of Example 1, (2R,4aS,4bR, 6aS,7S,10aS,10bR,12aR)-7-(1-hydroxyethyl)-2,6a-dimethyloctadecahydro chrysen-2-ol was used as the starting material, accordingly, 1-((1S,4aS,4bR,6aR,8R,10aS,10bR,12aS)-8-hydroxy-8,12a-dimethyloctadecahydrochrysen-1-yl) ethan-1-one (80 mg, containing a small amount of impurities) was obtained, which was used directly in the next step without purification.

Step 8: Preparation of 2-bromo-1-((1S,4aS,4bR, 6aR,8R,10aS,10bR,12aS)-8-hydroxy-8,12a-dimethyloctadecahydrochrysen-1-yl)ethan-1-one

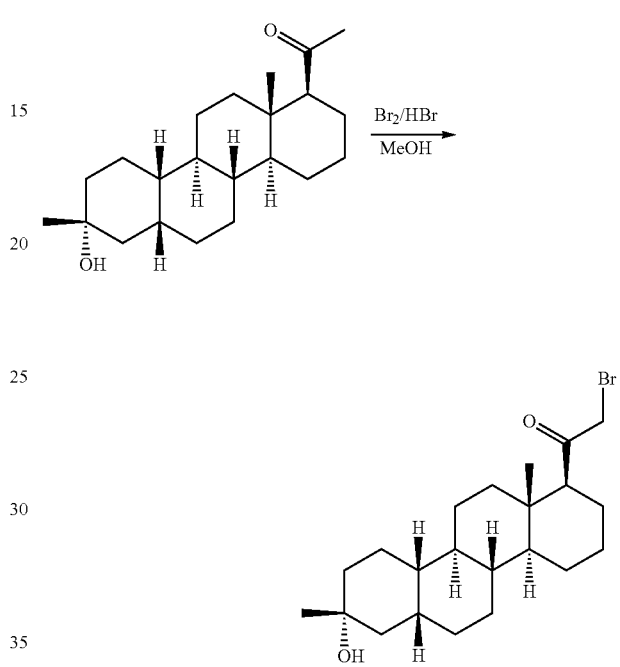

In accordance with Step 1 of Example 2, 1-((1S,4aS,4bR, 6aR,8R,10aS,10bR,12aS)-8-hydroxy-8,12a-dimethyloctadecahydrochrysen-1-yl)ethan-1-one was used as the starting material, accordingly, 2-bromo-1-((1S,4aS,4bR,6aR,8R, 10aS,10bR,12aS)-8-hydroxy-8,12a-dimethyloctadecahydrochrysen-1-yl)ethan-1-one (50 mg, containing a small amount of impurities) was obtained, which was used directly in the next step without purification.

Step 9: Preparation of 1-(2-((1S,4aS,4bR,6aR,8R, 10aS,10bR,12aS)-8-hydroxy-8,12a-dimethyloctadecahydrochrysen-1-yl)-2-oxoethyl)-1H-pyrazole-4-carbonitrile

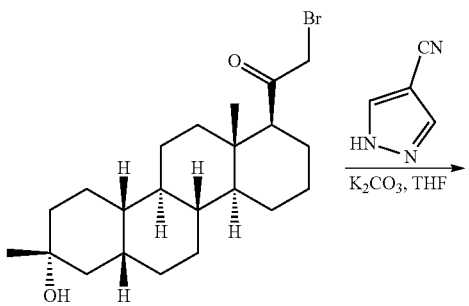

225
-continued

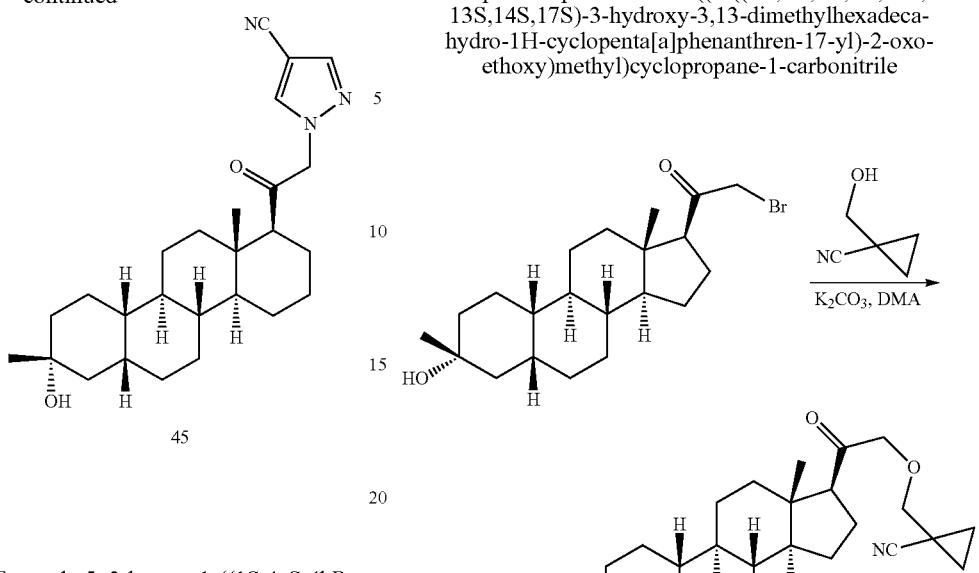

In accordance with Example 5, 2-bromo-1-((1S,4aS,4bR,6aR,8R,10aS,10bR,12aS)-8-hydroxy-8,12a-dimethyloctadecahydrochrysen-1-yl)ethan-1-one was used as the starting material, accordingly, 1-(2-((1S,4aS,4bR,6aR,8R,10aS,10bR,12aS)-8-hydroxy-8,12a-dimethyloctadecahydrochrysen-1-yl)-2-oxoethyl)-1H-pyrazole-4-carbonitrile (5.5 mg) was obtained.

$^1$H NMR (400 MHz, CDCl$_3$) δ 7.87 (s, 1H), 7.83 (s, 1H), 5.06-4.88 (m, 2H), 2.47 (d, J=4.9 Hz, 1H), 1.90-1.81 (m, 2H), 1.78-1.67 (m, 5H), 1.58-1.50 (m, 6H), 1.41-1.34 (m, 4H), 1.29-1.24 (m, 9H), 0.99 (s, 3H), 0.96-0.83 (m, 3H).

Example 166

1-((2-((3R,5R,8R,9R,10S,13S,14S,17S)-3-Hydroxy-3,13-dimethylhexadecahydro-1H-cyclopenta[a]phenanthren-17-yl)-2-oxoethoxy)methyl)cyclopropane-1-carbonitrile (166)

226

Step 1: Preparation of 1-((2-((3R,5R,8R,9R,10S,13S,14S,17S)-3-hydroxy-3,13-dimethylhexadecahydro-1H-cyclopenta[a]phenanthren-17-yl)-2-oxoethoxy)methyl)cyclopropane-1-carbonitrile 2-Bromo-1-((3R,5R,8R,9R,10S,13S,14S,17S)-3-hydroxy-3,13-dimethylhexadecahydro-1H-cyclopenta[a]phenanthren-17-yl)ethan-1-one (80 mg, 0.2 mmol), 1-(hydroxymethyl)cyclopropane-1-carbonitrile (29 mg, 0.3 mmol) and potassium carbonate (138 mg, 1.0 mmol) were dissolved in N,N-dimethylacetamide (3 mL), and the resulting reaction solution was stirred at 70° C. overnight. Water (20 mL) was added to the reaction solution, and the water phase was extracted with ethyl acetate (20 mL×2). The organic phases were combined, dried over anhydrous sodium sulfate, filtrated and concentrated. The resulting crude product was purified by column chromatography (petroleum ether/ethyl acetate: 50/1-3/1) to obtain 1-((2-((3R,5R,8R,9R,10S,13S,14S,17S)-3-hydroxy-3,13-dimethylhexadecahydro-1H-cyclopenta[a]phenanthren-17-yl)-2-oxoethoxy)methyl)cyclopropane-1-carbonitrile (10 mg, yield: 12%).

1H NMR (400 MHz, CDCl$_3$) δ 4.21-4.09 (m, 2H), 3.53 (s, 2H), 2.61-2.54 (m, 1H), 2.21-2.12 (m, 1H), 1.90-1.78 (m, 4H), 1.75-1.61 (m, 4H), 1.49-1.40 (m, 5H), 1.34-1.26 (m, 13H), 1.10-1.04 (m, 4H), 0.63 (s, 3H).

Example 167

1-((((3R,5R,8R,9R,10S,13S,14S,17S)-3-Hydroxy-3,13-dimethylhexadecahydro-1H-cyclopenta[a]phenanthren-17-yl)thio)methyl)-1H-pyrazole-4-carbonitrile

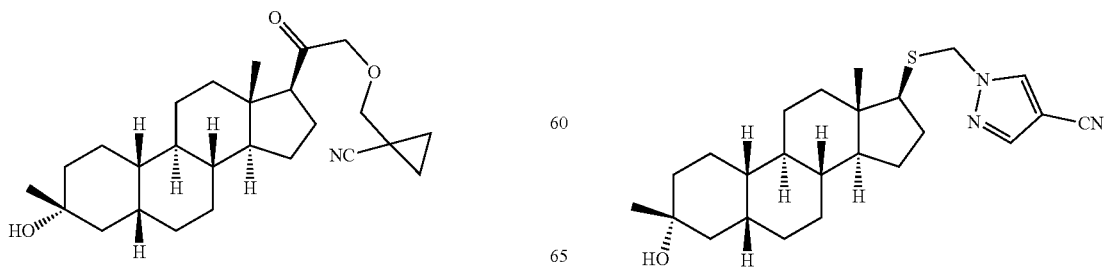

Step 1: Preparation of (3R,5R,8R,9R,10S,13S,14S)-3-((tert-butyldimethylsilyl)oxy)-3,13-dimethylhexadecahydro-17H-cyclopenta[a]phenanthrene-17-thione

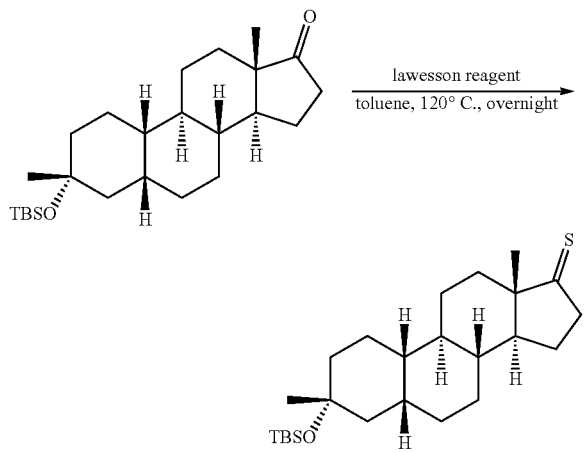

(3R,5R,8R,9R,10S,13S,14S)-3-((tert-butyldimethylsilyl)oxy)-3,13-dimethylhexadecahydro-17H-cyclopenta[a]phenanthren-17-thione (1.2 g, 3 mmol), 2,4-bis(p-methoxyphenyl)-1,3-dithiadiphosphetane-2,4-sulfide (971 mg, 2.4 mmol) and 20 mL anhydrous toluene were successively added to a dry 100 mL round bottom flask. The reaction system was purged with argon, heated to reflux and stirred overnight. After completion of the reaction, the reaction solution was filtrated through neutral alumina, and the filtrate was concentrated by rotary evaporation to dryness. The resulting crude product was purified by column chromatography (eluent: petroleum ether/ethyl acetate=50/1) to obtain (3R,5R,8R,9R,10S,13S,14S)-3-((tert-butyldimethylsilyl)oxy)-3,13-dimethylhexadecahydro-17H-cyclopenta[a]phenanthrene-17-thione (860 mg, 68%).

$^1$H NMR (400 MHz, CDCl$_3$) (2.90 (dd, J=8.4, 21.6 Hz, 1H), 2.63-2.55 (m, 1H), 1.97-1.93 (m, 2H), 1.73-1.17 (m, 22H), 0.84 (s, 3H), 0.79 (s, 9H), 0.07 (s, 6H).

Step 2: Preparation of (3R,5R,8R,9R,10S,13S,14S)-3-((tert-butyldimethylsilyl)oxy)-3,13-dimethylhexadecahydro-17H-cyclopenta[a]phenanthrene-17-thiol

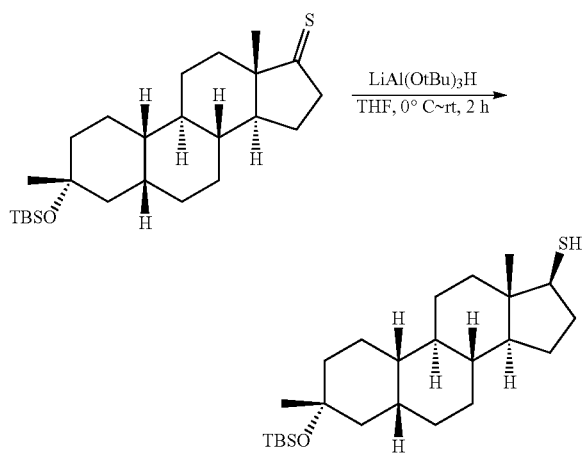

(3R,5R,8R,9R,10S,13S,14S)-3-((tert-butyldimethylsilyl)oxy)-3,13-dimethylhexadecahydro-17H-cyclopenta[a]phenanthrene-17-thione (860 mg, 2 mmol) and 30 ml of anhydrous tetrahydrofuran were added to a dry 100 mL round bottom flask. The reaction system was cooled to 0° C., and 1.0 M tri-tert-butoxy lithium aluminum hydride (6 mL, 6 mmol) was added dropwise. The reaction solution was stirred at 0° C. for 2 hours, and stirred at room temperature for 1 hour. TLC showed that the reaction was completed. Saturated sodium bicarbonate solution was added to carefully quench the reaction, and the reaction solution was extracted with dichloromethane. The organic phases were combined, washed with water and saturated saline, dried over anhydrous sodium sulfate, filtrated, and concentrated by rotary evaporation to dryness to obtain the crude product, which was used directly in the next step without purification.

$^1$H NMR (400 MHz, CDCl$_3$) (2.60-2.58 (m, 1H), 2.10-2.07 (m, 1H), 1.72-0.98 (m, 25H), 0.79 (s, 9H), 0.64 (s, 3H), 0.04 (s, 6H).

Step 3: Preparation of 1-(hydroxymethyl)-1H-pyrazole-4-carbonitrile

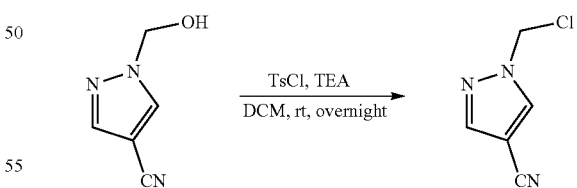

1H-Pyrazole-4-carbonitrile (930 mg, 10 mmol), 30% aqueous formaldehyde solution (8 g, 100 mmol) and 10 mL of methanol were added to a 100 mL round bottom flask. The reaction system was stirred at room temperature overnight. The reaction solution was concentrated by rotary evaporation to dryness to obtain 1-(hydroxymethyl)-1H-pyrazole-4-carbonitrile (900 mg, 73%).

$^1$H NMR (400 MHz, CDCl$_3$) (8.05 (s, 1H), 7.87 (s, 1H), 4.96-4.80 (m, 2H).

Step 4: Preparation of 1-(chloromethyl)-1H-pyrazole-4-carbonitrile 1-(Hydroxymethyl)-1H-pyrazole-4-carbonitrile (900 mg, 7.3 mmol), triethylamine (1.5 g, 14.6 mmol) and 20 ml of dichloromethane were added to a 100 mL round bottom flask. P-Toluenesulfonyl chloride (2.1 g, 11 mmol) was added in batches under stirring, and the reaction system was stirred at room temperature overnight. Water was added to quench the reaction, and the reaction solution was extracted with dichloromethane. The organic phase was washed with water and saturated saline, dried over anhydrous sodium sulfate, filtrated and concentrated by rotary evaporation to dryness. The resulting crude product was purified by column chromatography (eluent: petroleum ether/ethyl acetate=10/1) to obtain 1-(chloromethyl)-1H-pyrazole-4-carbonitrile (790 mg, 76.7%).

¹H NMR (400 MHz, CDCl₃) δ 8.08 (s, 1H), 7.89 (s, 1H), 5.87 (s, 2H).

Step 5: Preparation of 1-(((3R,5R,8R,9R,10S,13S,14S,17S)-3-((tert-butyldimethylsilyl)oxy)-3,13-dimethylhexadecahydro-1H-cyclopenta[a]phenanthren-17-yl)thio)methyl)-1H-pyrazole-4-carbonitrile

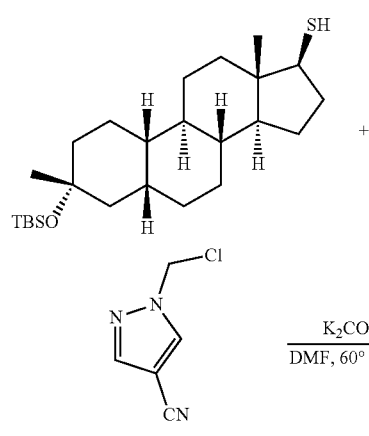

+

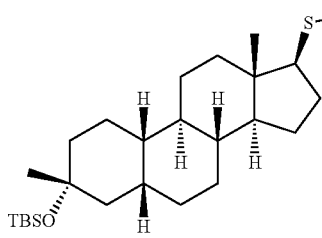

K₂CO₃, NaI
————————→
DMF, 60° C., overnight

Step 6: 1-((((3R,5R,8R,9R,10S,13S,14S,17S)-3-Hydroxy-3,13-dimethylhexadecahydro-1H-cyclopenta[a]phenanthren-17-yl)thio)methyl)-1H-pyrazole-4-carbonitrile

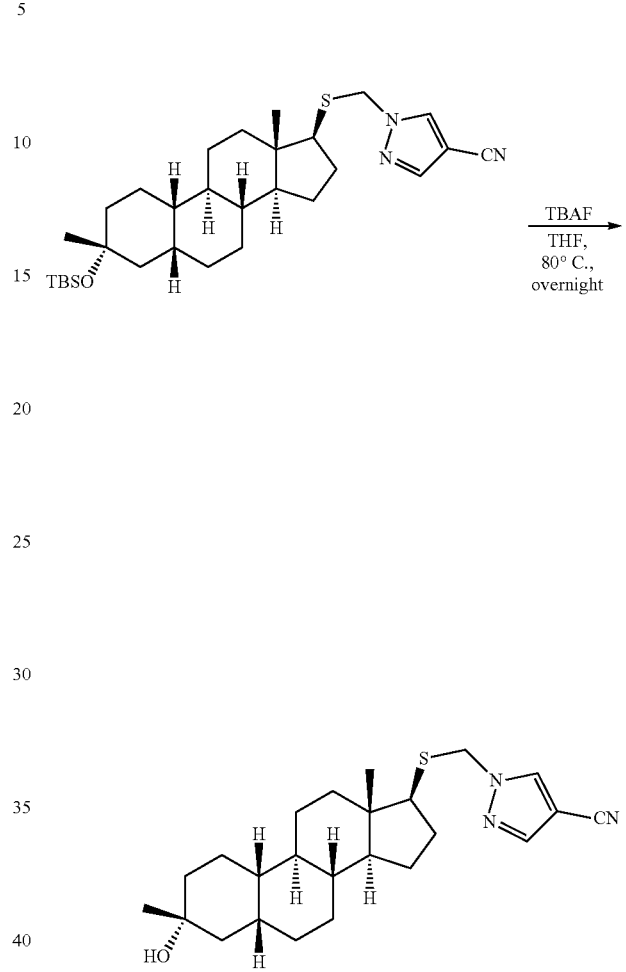

(3R,5R,8R,9R,10S,13S,14S)-3-((tert-butyldimethylsilyl)oxy)-3,13-dimethylhexadecahydro-17H-cyclopenta[a]phenanthrene-17-thiol (210 mg, 0.5 mmol), 1-(chloromethyl)-1H-pyrazole-4-carbonitrile (72 mg, 0.6 mmol), potassium carbonate (136 mg, 1 mmol), sodium iodide (10 mg, catalytic amount) and 5 ml of anhydrous N,N-dimethylformamide were added to a dry 100 mL round bottom flask. The reaction system was heated to 60° C. and stirred overnight. The reaction solution was cooled to room temperature. Water was added to quench the reaction, and the reaction solution was extracted with dichloromethane. The organic phase was washed with water and saturated saline, dried over anhydrous sodium sulfate, filtrated and concentrated by rotary evaporation to dryness. The resulting crude product was purified by column chromatography (petroleum ether/ethyl acetate=10/1) to obtain 1-((((3R,5R,8R,9R,10S,13S,14S,17S)-3-((tert-butyldimethylsilyl)oxy)-3,13-dimethylhexadecahydro-1H-cyclopenta[a]phenanthren-17-yl)thio)methyl)-1H-pyrazole-4-carbonitrile (170 mg, yield: 64.5%).

¹H NMR (400 MHz, CDCl₃) (8.10 (s, 1H), 7.79 (s, 1H), 5.18 (dd, J=14.4, 19.2 Hz, 2H), 2.62 (t, J=7.2 Hz, 1H), 2.05-1.98 (m, 2H), 1.90-0.90 (m, 24H), 0.86 (s, 9H), 0.72 (s, 3H), 0.07 (s, 6H).

1-((((3R,5R,8R,9R,10S,13S,14S,17S)-3-((tert-butyldimethylsilyl)oxy)-3,13-dimethylhexadecahydro-1H-cyclopenta[a]phenanthren-17-yl)thio)methyl)-1H-pyrazole-4-carbonitrile (170 mg, 0.32 mmol) was dissolved in 5 mL of anhydrous tetrahydrofuran in a 100 mL round bottom flask, and a 1.0 M solution of tetrabutylammonium fluoride in tetrahydrofuran (5 mL) was added to the reaction system. The reaction solution was stirred at 60° C. overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: petroleum ether/ethyl acetate=1/1) to obtain 1-((((3R,5R,8R,9R,10S,13S,14S,17S)-3-Hydroxy-3,13-dimethylhexadecahydro-1H-cyclopenta[a]phenanthren-17-yl)thio)methyl)-1H-pyrazole-4-carbonitrile (100 mg, 75%).

¹H NMR (400 MHz, CDCl₃) δ 8.09 (s, 1H), 7.79 (s, 1H), 5.28-5.02 (m, 2H), 2.58 (t, J=9.4 Hz, 1H), 2.12-1.93 (m, 1H), 1.89-0.94 (m, 26H), 0.72 (s, 3H).

Example 168 and Example 169

1-(((S)-((3R,5R,8R,9R,10S,13S,14S,17S)-3-Hydroxy-3,13-dimethylhexadecahydro-1H-cyclopenta[a]phenanthren-17-yl)sulfinyl)methyl)-1H-pyrazole-4-carbonitrile (168)

1-(((R)-((3R,5R,8R,9R,10S,13S,14S,17S)-3-Hydroxy-3,13-dimethylhexadecahydro-1H-cyclopenta[a]phenanthren-17-yl)sulfinyl)methyl)-1H-pyrazole-4-carbonitrile (169)

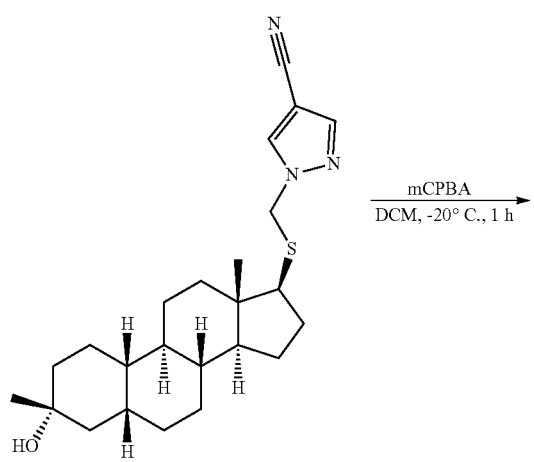

1-((((3R,5R,8R,9R,10S,13S,14S,17S)-3-Hydroxy-3,13-dimethylhexadecahydro-1H-cyclopenta[a]phenanthren-17-yl)thio)methyl)-1H-pyrazole-4-carbonitrile (25 mg, 0.06 mmol) was dissolved in 5 mL of anhydrous dichloromethane in a 100 mL round bottom flask. M-chloroperoxybenzoic acid (15 mg, 0.073 mmol) was added at −20° C., and the reaction solution was stirred at this temperature for 1 hour. After completion of the reaction, saturated sodium bicarbonate solution was added to quench the reaction, and the reaction solution was extracted with ethyl acetate. The organic phase was washed with water and saturated saline, dried over anhydrous sodium sulfate, filtrated and by rotary evaporation concentrated to dryness. The resulting crude product was purified by high performance liquid chromatography to obtain 1-(((S)-((3R,5R,8R,9R,10S,13S,14S,17S)-3-hydroxy-3,13-dimethylhexadecahydro-1H-cyclopenta[a]phenanthren-17-yl)sulfinyl)methyl)-1H-pyrazole-4-carbonitrile (7.5 mg, 29%) and 1-(((R)-((3R,5R,8R,9R,10S,13S,14S,17S)-3-hydroxy-3,13-dimethylhexadecahydro-1H-cyclopenta[a]phenanthren-17-yl)sulfinyl)methyl)-1H-pyrazole-4-carbonitrile (6.5 mg, yield: 25%).

Example 168

MS m/z (ESI): 430.3 [M+H]$^+$
$^1$H NMR (400 MHz, CDCl$_3$) δ 8.06 (s, 1H), 7.90 (s, 1H), 5.21 (d, J=12.0 Hz, 1H), 5.03 (d, J=12.0 Hz, 1H), 2.54 (t, J=9.2 Hz, 1H), 2.12-1.93 (m, 2H), 1.85-1.02 (m, 25H), 0.89 (s, 3H).

Example 169

MS m/z (ESI): 430.3 [M+H]$^+$
$^1$H NMR (400 MHz, CDCl$_3$) δ 8.10 (s, 1H), 7.91 (s, 1H), 5.18 (d, J=13.6 Hz, 1H), 5.03 (d, J=13.6 Hz, 1H), 2.32 (t, J=8.8 Hz, 1H), 2.05-1.94 (m, 2H), 1.85-1.12 (m, 25H), 1.05 (s, 3H).

Example 170

1-((((3R,5R,8R,9R,10S,13S,14S,17S)-3-Hydroxy-3,13-dimethylhexadecahydro-1H-cyclopenta[a]phenanthren-17-yl)sulfonyl)methyl)-1H-pyrazole-4-carbonitrile (170)

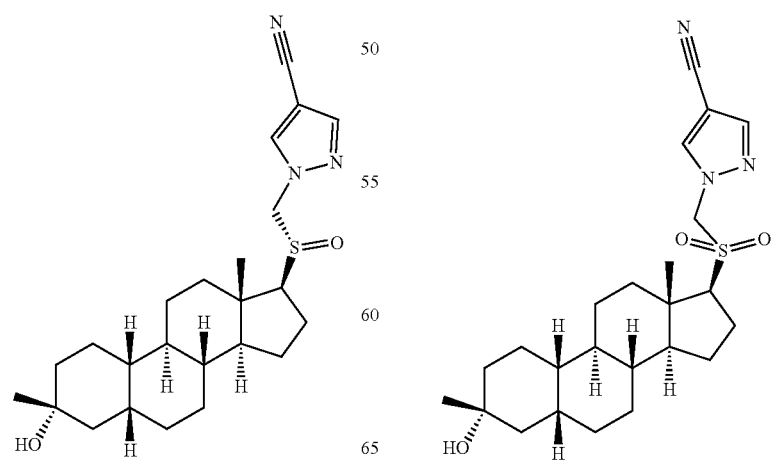

Step 1: Preparation of 1-((((3R,5R,8R,9R,10S,13S, 14S,17S)-3-hydroxy-3,13-dimethylhexadecahydro-1H-cyclopenta[a]phenanthren-17-yl)sulfonyl)methyl)-1H-pyrazole-4-carbonitrile

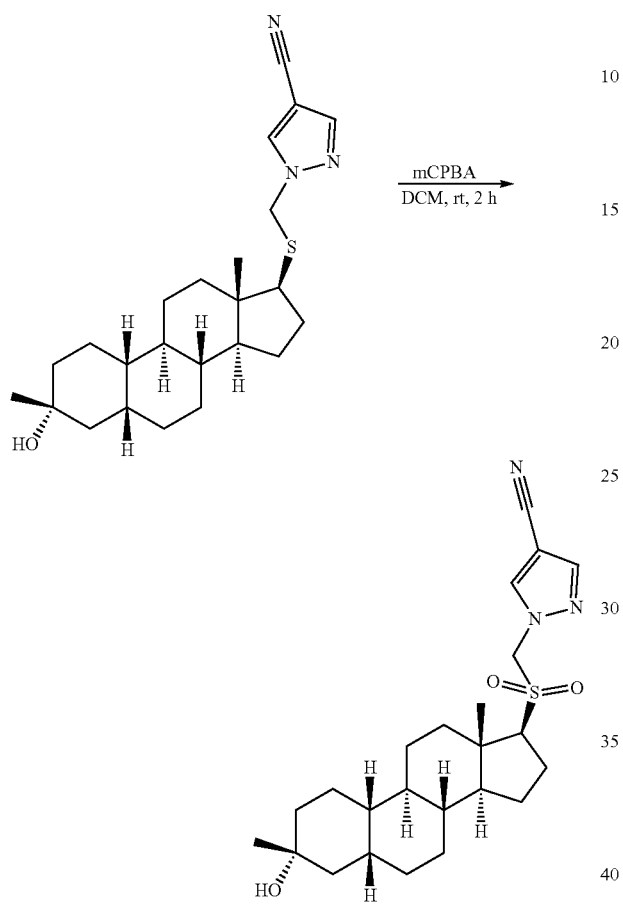

1-((((3R,5R,8R,9R,10S,13S,14S,17S)-3-Hydroxy-3,13-dimethylhexadecahydro-1H-cyclopenta[a]phenanthren-17-yl)thio)methyl)-1H-pyrazole-4-carbonitrile (25 mg, 0.06 mmol) was dissolved in 5 mL of anhydrous dichloromethane in a 100 mL round bottom flask. M-chloroperoxybenzoic acid (30 mg, 0.15 mmol) was added at 0° C., and the reaction solution was stirred at room temperature for 2 hours. After completion of the reaction, saturated sodium bicarbonate solution was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by preparative high performance liquid chromatography to obtain 1-((((3R,5R,8R,9R,10S,13S,14S,17S)-3-hydroxy-3,13-dimethylhexadecahydro-1H-cyclopenta[a]phenanthren-17-yl)sulfonyl)methyl)-1H-pyrazole-4-carbonitrile (9.1 mg, 34%).

MS m/z (ESI): 446.3 [M+H]$^+$ $^1$H NMR (400 MHz, CDCl$_3$) δ 8.13 (s, 1H), 7.89 (s, 1H), 5.24 (d, J=14.8 Hz, 1H), 5.02 (d, J=14.8 Hz, 1H), 2.88 (t, J=9.2 Hz, 1H), 2.24-2.18 (m, 1H), 2.11-1.92 (m, 3H), 1.84-1.00 (s, 26H).

Example 171

((3R,5R,8R,9R,10S,13S,14S,17S)-3-Hydroxy-3,13-dimethylhexadecahydro-1H-cyclopenta[a]phenanthren-17-yl)methylphenylphosphine oxide (171)

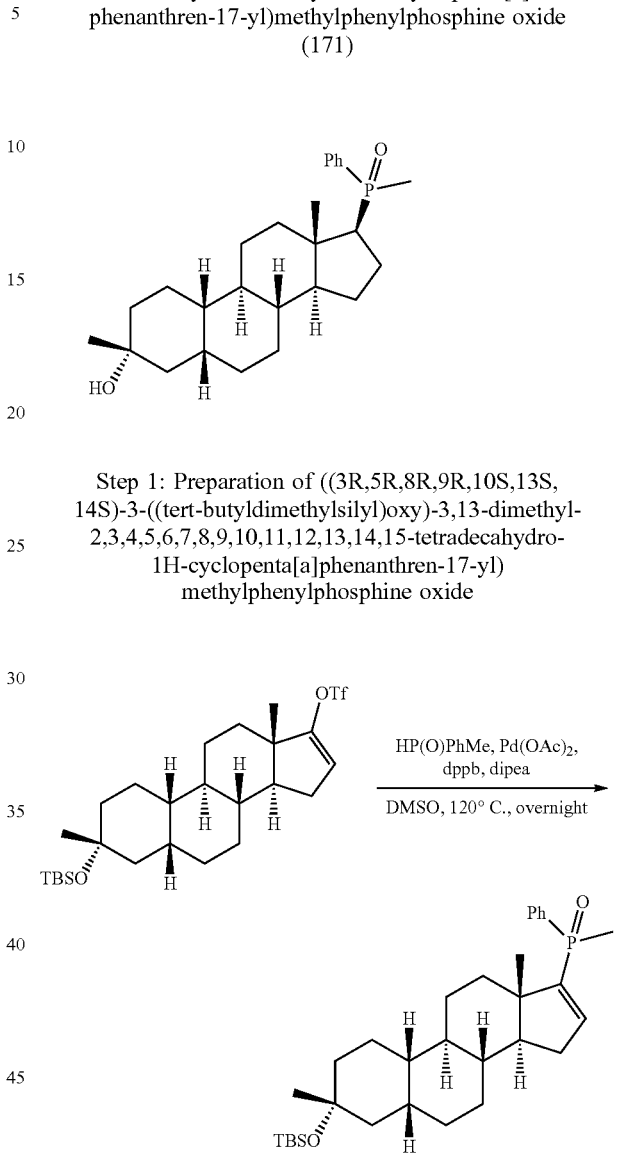

Step 1: Preparation of ((3R,5R,8R,9R,10S,13S, 14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)methylphenylphosphine oxide (3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl trifluoromethanesulfonate (230 mg, 0.43 mmol), methylphenylphosphine oxide (92 mg, 0.64 mmol), palladium diacetate (10 mg, 0.04 mmol), 1,4-bis(diphenylphosphino)butane (18 mg, 0.04 mmol), N,N-diisopropylethylamine (443 mg, 3.4 mmol) and 10 mL anhydrous dimethyl sulfoxide were successively added to a 100 mL round bottom flask. The reaction system was purged with nitrogen, slowly warmed up to 120° C. and stirred overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)methylphenylphosphine oxide (170 mg, 75%).

$^1$H NMR (400 MHz, CDCl$_3$) δ 7.77-7.72 (m, 2H), 7.55-7.48 (m, 3H), 6.53-6.50 (m, 1H), 2.44-1.16 (m, 27H), 1.00 (s, 3H), 0.86 (s, 9H), 0.05 (s, 6H).

Step 2: Preparation of ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)methylphenylphosphine oxide

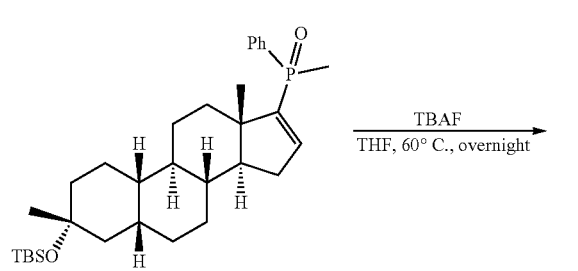

((3R,5R,8R,9R,10S,13S,14S)-3-((tert-butyldimethylsilyl)oxy)-3,13-dimethyl-2,3,4,5,6,7,8,9,10,11,12,13,14,15-tetradecahydro-1H-cyclopenta[a]phenanthren-17-yl)methyl phenylphosphine oxide (170 mg, 0.32 mmol) was dissolved in 5 mL of anhydrous tetrahydrofuran in a 100 mL round bottom flask, and a 1.0 M solution of tetrabutylammonium fluoride in tetrahydrofuran (5 mL) was added to the reaction system. The reaction solution was stirred at 60° C. overnight. After completion of the reaction, the reaction system was cooled to room temperature. Water was added to quench the reaction, and the reaction solution was extracted with ethyl acetate. The organic phase was washed with water and saturated saline, dried over anhydrous sodium sulfate, filtrated and concentrated by rotary evaporation to dryness. The resulting crude product was purified by column chromatography (eluent: dichloromethane/methanol=10/1) to obtain ((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)methylphenylphosphine oxide (50 mg, 38%).

Step 3: Preparation of ((3R,5R,8R,9R,10S,13S,14S,17S)-3-Hydroxy-3,13-dimethylhexadecahydro-1H-cyclopenta[a]phenanthren-17-yl)methylphenylphosphine oxide ((3R,5R,8R,9R,10S,13S,14S)-3-Hydroxy-3,13-dimethyl-2,3,4,5,6,7,8,9,10,11,12,13,14,15-tetradecahydro-1H-cyclopenta[a]phenanthren-17-yl)methylphenylphosphine oxide (50 mg, 0.12 mmol), palladium on carbon (50 mg, 10%) and 10 mL of ethyl acetate were added to a 100 mL round bottom flask. The reaction system was purged with hydrogen three times, and reacted at 1 atmosphere overnight. After completion of the reaction, the reaction solution was filtrated through celite to remove excess palladium on carbon, and the filtrate was concentrated by rotary evaporation to dryness. The resulting crude product was purified by high performance liquid chromatography to obtain ((3R,5R,8R,9R,10S,13S,14S,17S)-3-hydroxy-3,13-dimethylhexadecahydro-1H-cyclopenta[a]phenanthren-17-yl)methylphenylphosphine oxide (10 mg, 20%).

MS m/z (ESI): 415.3 [M+H]$^+$.

$^1$H NMR (400 MHz, CDCl$_3$) δ 7.79-7.74 (m, 2H), 7.55-7.50 (m, 3H), 2.41-2.34 (m, 1H), 2.03-1.60 (m, 12H), 1.55-0.73 (m, 21H).

Example 172

1-((3R,5R,8R,9R,10S,13S,14S)-13-Methyl-3-(methylamino)hexadecahydro-1H-cyclopenta[a]phenanthren-17-yl)ethan-1-one hydrochloride

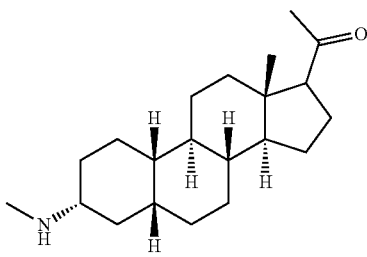

Step 1: Preparation of (3S,5R,8R,9R,10S,13S,14S)-3-hydroxy-13-methylhexadecahydro-17H-cyclopenta[a]phenanthren-17-one

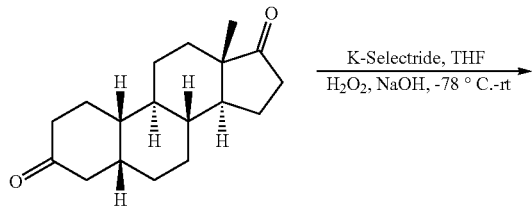

(5R,8R,9R,10S,13S,14S)-13-Methyltetradecahydro-3H-cyclopenta[a]phenanthrene-3,17(2H)-dione (5.90 g, 21.50 mmol) was dissolved in anhydrous tetrahydrofuran (150 mL) at −78° C. The reaction system was purged with nitrogen, and potassium triisobutylborohydride (1.0 M in THF, 32.25 mL, 32.25 mmol) was added dropwise to the reaction system. The reaction solution was reacted at −78° C. for 3 hours. Aqueous sodium hydroxide solution (10 wt %, 56.6 mL) and hydrogen peroxide (82.6 mL) were successively added dropwise, and then the reaction solution was stirred at room temperature for half an hour. Saturated sodium thiosulfate (100 mL) was added, and then the reaction solution was stirred at room temperature for 10 minutes. The reaction solution was extracted with ethyl acetate (100 mL×3). The organic phases were combined, dried over anhydrous sodium sulfate, filtrated and concentrated by rotary evaporation to dryness. The resulting crude product was purified by flash column chromatography (petroleum ether:ethyl acetate: 4:1) to obtain (3S,5R,8R,9R,10S,13S,14S)-3-hydroxy-13-methylhexadecahydro-17H-cyclopenta[a]phenanthren-17-one (5.0 g, white solid, yield: 84%).

Step 2: Preparation of (3S,5R,8R,9R,10S,13S,14S)-17-ethylidene-13-methylhexadecahydro-1H-cyclopenta[a]phenanthren-3-ol

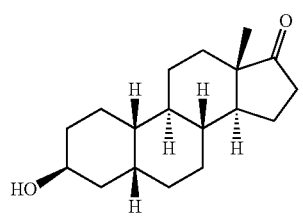

Sodium hydride (1.45 g, 36.18 mmol, 60% in mineral oil) was added in batches to a solution of ethyltriphenylphosphonium bromide (13.44 g, 36.18 mmol) in dimethyl sulfoxide (100 mL) under a nitrogen atmosphere. The reaction solution was stirred at room temperature for 1 hour, and a solution of (3S,5R,8R,9R,10S,13S,14S)-3-hydroxy-13-methylhexadecahydro-17H-cyclopenta[a]phenanthren-17-one (2.0 g, 7.24 mmol) in dimethyl sulfoxide (40 mL) was added dropwise. The reaction solution was heated to 60° C. overnight under a nitrogen atmosphere. The reaction solution was cooled to room temperature. Saturated saline (200 mL) was added, and then the reaction solution was extracted with dichloromethane (50 mL×3). The organic phases were combined, dried over anhydrous sodium sulfate, filtrated and concentrated by rotary evaporation to dryness. The resulting crude product was purified by flash column chromatography (petroleum ether:ethyl acetate: 10:1) to obtain (3S,5R,8R,9R,10S,13S,14S)-17-ethylidene-13-methylhexadecahydro-1H-cyclopenta[a]phenanthren-3-ol (1.60 g, white solid, yield: 76.7%).
$^1$H NMR (400 MHz, CDCl$_3$) δ 5.14-5.08 (m, 1H), 4.13-4.11 (m, 1H), 2.40-2.33 (m, 1H), 2.28-2.11 (m, 3H), 1.91-1.83 (m, 1H), 1.74-1.58 (m, 8H), 1.47-1.38 (m, 5H), 1.38-1.34 (m, 2H), 1.29-1.07 (m, 7H), 0.88 (s, 3H).

Step 3: Preparation of (3S,5R,8R,9R,10S,13S,14S)-17-ethylidene-13-methylhexadecahydro-1H-cyclopenta[a]phenanthren-3-yl methanesulfonate

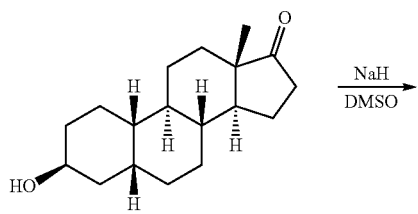

(3S,5R,8R,9R,10S,13S,14S)-17-Ethylidene-13-methylhexadecahydro-1H-cyclopenta[a]phenanthren-3-ol (0.40 g, 1.39 mmol) was dissolved in dichloromethane (20 mL) at room temperature. Pyridine (0.33 g, 4.16 mmol) and methanesulfonyl chloride (0.32 g, 2.77 mmol) were successively added dropwise, and then the reaction solution was reacted at room temperature overnight. After completion of the reaction, the reaction solution was diluted with dichloromethane (40 mL), and washed with saturated saline (10 mL×3). The organic phase was dried over anhydrous sodium sulfate, filtrated and concentrated by rotary evaporation to dryness. The resulting crude product was purified by flash column chromatography (petroleum ether:ethyl acetate: 10:1) to obtain (3S,5R,8R,9R,10S,13S,14S)-17-ethylidene-13-methylhexadecahydro-1H-cyclopenta[a]phenanthren-3-yl methanesulfonate (0.30 g, white solid, yield: 59%).

Step 4: Preparation of (3R,5R,8R,9R,10S,13S,14S)-17-ethylidene-N,13-dimethylhexadecahydro-1H-cyclopenta[a]phenanthren-3-amine

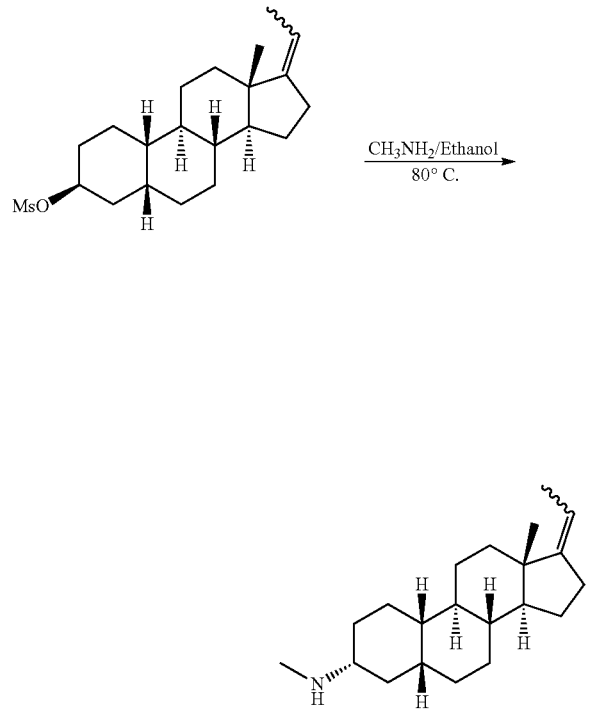

(3S,5R,8R,9R,10S,13S,14S)-17-Ethylidene-13-methylhexadecahydro-1H-cyclopenta[a]phenanthren-3-yl methanesulfonate (0.20 g, 0.55 mmol) was added to a microwave reaction tube (10 mL) at room temperature, and methylamine alcohol solution (3 mL) was added dropwise to the reaction system. The microwave reaction tube was sealed, and heated to 80° C. overnight. The reaction solution was cooled to room temperature and concentrated by rotary evaporation to dryness. The resulting residue was dissolved in ethyl acetate (20 mL). The organic phases were washed with saturated saline (20 mL×3), combined, dried over anhydrous sodium sulfate, filtrated and concentrated by rotary evaporation to dryness. The resulting crude product was purified by flash column chromatography (dichloromethane:methanol:triethylamine: 300:10:3) to obtain (3R, 5R,8R,9R,10S,13S,14S)-17-ethylidene-N,13-dimethylhexadecahydro-1H-cyclopenta[a]phenanthren-3-amine (70 mg, colorless oil, yield: 42.4%).

MS m/z (ESI): 302.5 [M+H]⁺.

Step 5: Preparation of 1-((3R,5R,8R,9R,10S,13S,14S)-13-methyl-3-(methylamino)hexadecahydro-1H-cyclopenta[a]phenanthren-17-yl)ethan-1-ol

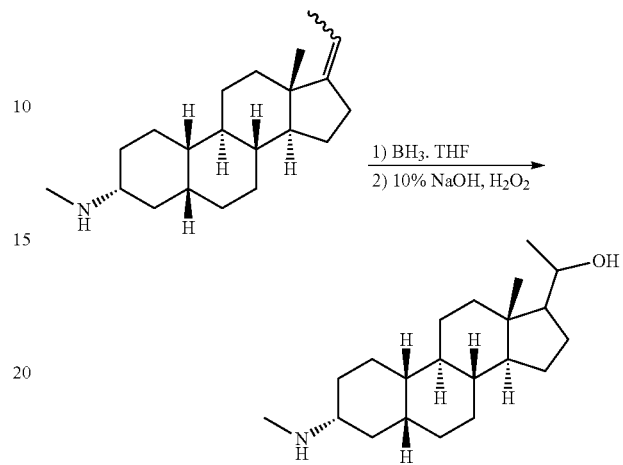

(3R,5R,8R,9R,10S,13S,14S)-17-Ethylidene-N,13-dimethylhexadecahydro-1H-cyclopenta[a]phenanthren-3-amine (0.07 g, 0.23 mmol) was dissolved in anhydrous tetrahydrofuran (3 mL) in an ice bath, and then a solution of borane in tetrahydrofuran (1.0 M in THF, 2.32 mL, 2.32 mmol) was added dropwise. The reaction solution was reacted for 3 hours. Sodium hydroxide solution (3N, 1 mL) and hydrogen peroxide (0.3 mL) were successively added dropwise, and then the reaction solution was stirred at room temperature for half an hour. The reaction solution was diluted with ethyl acetate (20 mL), and washed with saturated saline (10 mL×3). The organic phase was dried over anhydrous sodium sulfate, filtrated and concentrated by rotary evaporation to dryness to obtain the crude product 1-((3R,5R,8R,9R,10S, 13S,14S)-13-methyl-3-(methylamino)hexadecahydro-1H-cyclopenta[a]phenanthren-17-yl)ethan-1-ol (40 mg, colorless oil, crude product).

MS m/z (ESI): 320.5 [M+H]⁺.

Step 6: Preparation of 1-((3R,5R,8R,9R,10S,13S, 14S)-13-methyl-3-(methylamino)hexadecahydro-1H-cyclopenta[a]phenanthren-17-yl)ethan-1-one

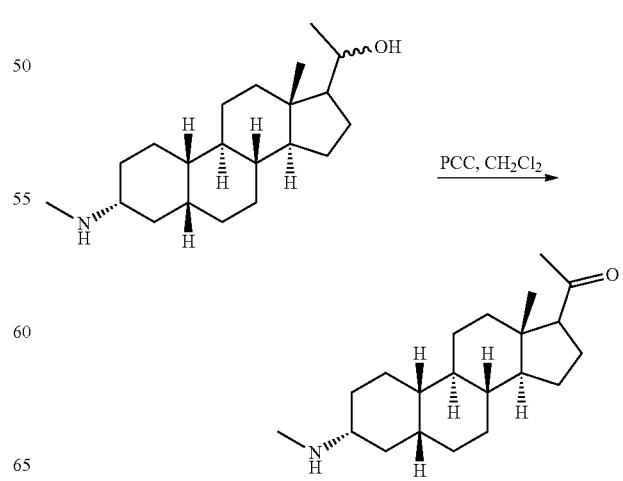

1-((3R,5R,8R,9R,10S,13S,14S)-13-Methyl-3-(methylamino)hexadecahydro-1H-cyclopenta[a]phenanthren-17-yl)ethan-1-ol (40 mg, 0.125 mmol) was dissolved in dichloromethane (5 mL) at room temperature. Pyridinium chlorochromate (54 mg, 0.25 mmol) was added, and then the reaction solution was reacted at room temperature for 3 hours. The reaction solution was diluted with dichloromethane (20 mL), and washed with saturated sodium thiosulfate (10 mL×3). The organic phase was dried over anhydrous sodium sulfate, filtrated and concentrated by rotary evaporation to dryness. The resulting crude product was purified by column chromatography (dichloromethane:methanol: 30:1) to obtain 1-((3R,5R,8R,9R,10S,13S,14S)-13-methyl-3-(methylamino)hexadecahydro-1H-cyclopenta[a]phenanthren-17-yl)ethan-1-one (15 mg, white solid, yield: 37.7%).

MS m/z (ESI): 318.5 [M+H]$^+$ $^1$H NMR (400 MHz, CDCl$_3$) δ 3.61-3.55 (m, 1H), 2.55-2.50 (m, 1H), 2.47 (s, 3H), 2.11 (s, 3H), 2.01-1.92 (m, 3H), 1.78-1.56 (m, 8H), 1.43-1.01 (m, 13H), 0.61 (s, 3H).

Example 173

1-((3R,8R,9R,10S,13S,14S,16R,17S)-16-Fluoro-3-hydroxy-3,13-dimethylhexadecahydro-1H-cyclopenta[a]phenanthren-17-yl)ethan-1-one (173)

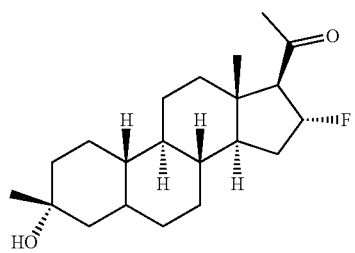

Step 1: Preparation of (3R,5R,8R,9R,10S,13S,14S,16R)-16-fluoro-3-hydroxy-3,13-dimethylhexadecahydro-17H-cyclopenta[a]phenanthren-17-one

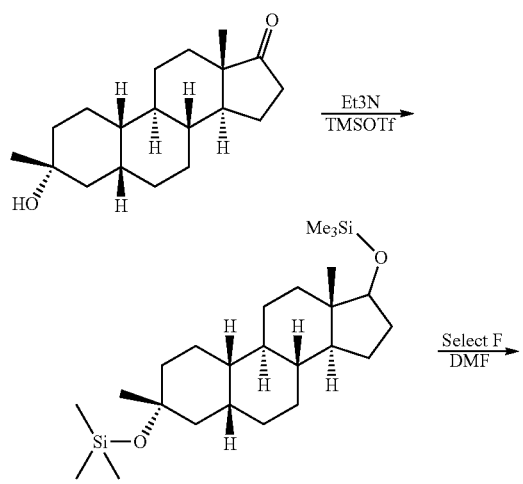

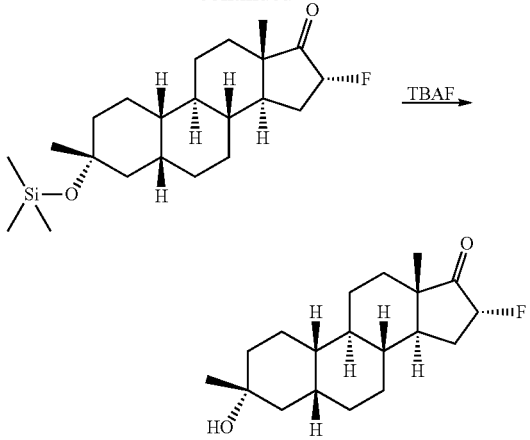

Trimethylsilyl triflate (5.6 mL, 31.0 mmol) was added dropwise to a solution of (3R,5R,8R,9R,10S,13S,14S)-3-hydroxy-3,13-dimethylhexadecahydro-17H-cyclopenta[a]phenanthren-17-one (3 g, 10.3 mmol) and triethylamine (36.0 mL, 258.2 mmol) in toluene (45 mL), and the resulting reaction solution was heated to reflux for 2 hours. The reaction solution was cooled, washed with saturated sodium bicarbonate, and extracted with n-hexane. The organic phase was concentrated to dryness to obtain the crude product (((3R,5R,8R,9R,10S,13S,14S)-3,13-dimethyl-2,3,4,5,6,7,8,9,10,11,12,13,14,15-tetradecahydro-1H-cyclopenta[a]phenanthrene-3,17-diyl)bis(oxy))bis(trimethylsilane). A selective fluorine reagent (4.0 g, 11.4 mmol) was added to a solution of (((3R,5R,8R,9R,10S,13S,14S)-3,13-dimethyl-2,3,4,5,6,7,8,9,10,11,12,13,14,15-tetradecahydro-1H-cyclopenta[a]phenanthrene-3,17-diyl)bis(oxy))bis(trimethylsilane) in N,N-dimethylformamide (25 mL), and the resulting reaction solution was stirred at room temperature for 2 hours to obtain (3R,5R,8R,9R,10S,13S,14S,16R)-16-fluoro-3,13-dimethyl-3-((trimethylsilyl)oxy)hexadecahydro-17H-cyclopenta[a]phenanthren-17-one. A solution of tetrabutylammonium fluoride in tetrahydrofuran (11.4 mL, 1 M) was added, and the resulting reaction solution was stirred at room temperature overnight. The reaction solution was extracted with ethyl acetate, and washed with saturated saline three times. The organic phase was concentrated to dryness, and the resulting crude product was purified by column chromatography (petroleum ether:ethyl acetate=6:4) to obtain (3R,5R,8R,9R,10S,13S,14S,16R)-16-fluoro-3-hydroxy-3,13-dimethylhexadecahydro-17H-cyclopenta[a]phenanthren-17-one (2.0 g, yield: 50.9%).

$^1$H NMR (400 MHz, CDCl$_3$) δ 5.09 (dd, J=50.6, 7.5 Hz, 1H), 2.18-1.58 (m, 10H), 1.54-1.01 (m, 14H), 0.92 (s, 3H).
$^{19}$F NMR (376 MHz, CDCl$_3$) δ −192.59.

Step 2: Preparation of (3R,5R,8R,9R,10S,13S,14S,16R)-17-ethylidene-16-fluoro-3,13-dimethylhexadecahydro-1H-cyclopenta[a]phenanthren-3-ol

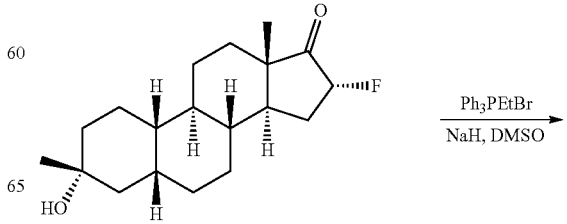

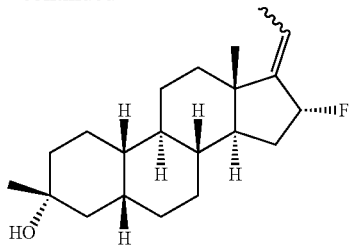

Sodium hydride (123 mg, 3.08 mmol, 60% w/w) was added to a solution of ethyltriphenylphosphonium bromide (1.2 g, 3.24 mmol) in dimethyl sulfoxide (20 mL) in batches under a nitrogen atmosphere, and the resulting reaction solution was stirred at room temperature for 1 hour. (3R,5R,8R,9R,10S,13S,14S,16R)-16-Fluoro-3-hydroxy-3,13-dimethylhexadecahydro-17H-cyclopenta[a]phenanthren-17-one (200 mg, 0.65 mmol) was added, and the reaction solution was heated to 70° C. under a nitrogen atmosphere overnight. The reaction solution was cooled, and saturated saline was added. 1 N hydrochloric acid was added to adjust pH to 6, and the reaction solution was extracted with ethyl acetate. The organic phase was washed with saturated saline, and concentrated to dryness to obtain a crude product. The crude product was purified by column chromatography (petroleum ether:ethyl acetate=7:3) to obtain (3R,5R,8R,9R,10S,13S,14S,16R)-17-ethylidene-16-fluoro-3,13-dimethyl-hexadecahydro-1H-cyclopenta[a]phenanthren-3-ol (80 mg, yield: 38.5%).

$^1$H NMR (400 MHz, CDCl$_3$) δ 5.71-5.59 (m, 1H), 5.12 (dt, J=57.2, 7.0 Hz, 1H), 2.27-2.11 (m, 2H), 1.92-1.24 (m, 21H), 1.22-1.09 (m, 4H), 1.06 (s, 3H).

$^{19}$F NMR (376 MHz, CDCl$_3$) δ -153.69.

Step 3: Preparation of (3R,8R,9R,10S,13S,14S,16R,17S)-16-fluoro-17-(1-hydroxyethyl)-3,13-dimethyl-hexadecahydro-1H-cyclopenta[a]phenanthren-3-ol

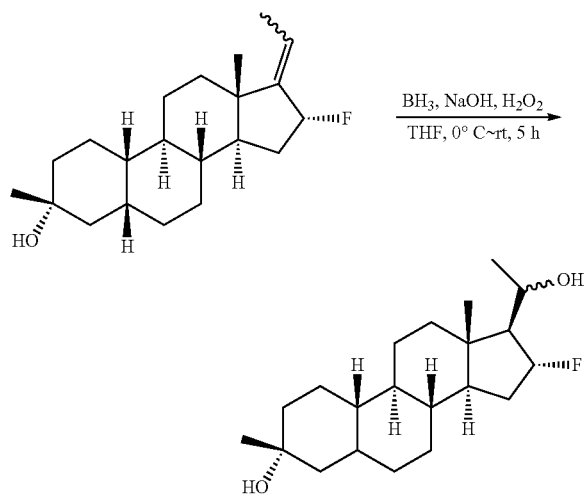

(3R,5R,8R,9R,10S,13S,14S,16R)-17-Ethylidene-16-fluoro-3,13-dimethylhexadecahydro-1H-cyclopenta[a]phenanthren-3-ol (80 mg, 0.25 mmol) was dissolved in anhydrous tetrahydrofuran (50 mL). A solution of borane in tetrahydrofuran (1 M, 2.5 mL) was added dropwise at room temperature, and the resulting reaction solution was stirred at room temperature for 1 hour. The reaction solution was cooled with ice water, and sodium hydroxide solution (3 M, 1 mL) was slowly added dropwise to release a large amount of gas. Hydrogen peroxide (25%, 0.58 mL) was slowly added dropwise, and the reaction solution was stirred at room temperature for 2 hours. The reaction solution was extracted with ethyl acetate, washed with sodium thiosulfate solution and saturated saline, and dried to obtain (3R,8R,9R,10S,13S,14S,16R,17S)-16-fluoro-17-(1-hydroxyethyl)-3,13-dimethylhexadecahydro-1H-cyclopenta[a]phenanthren-3-ol (80 mg), which was used directly in the next step.

$^1$H NMR (400 MHz, CDCl$_3$) δ 5.47-5.16 (m, 1H), 4.22-4.05 (m, 1H), 2.42-2.17 (m, 1H), 1.94-0.93 (m, 27H), 0.87 (s, 3H).

$^{19}$F NMR (376 MHz, CDCl$_3$) δ -178.27.

Step 4: Preparation of 1-((3R,8R,9R,10S,13S,14S,16R,17S)-16-fluoro-3-hydroxy-3,13-dimethylhexa-decahydro-1H-cyclopenta[a]phenanthren-17-yl)ethan-1-one

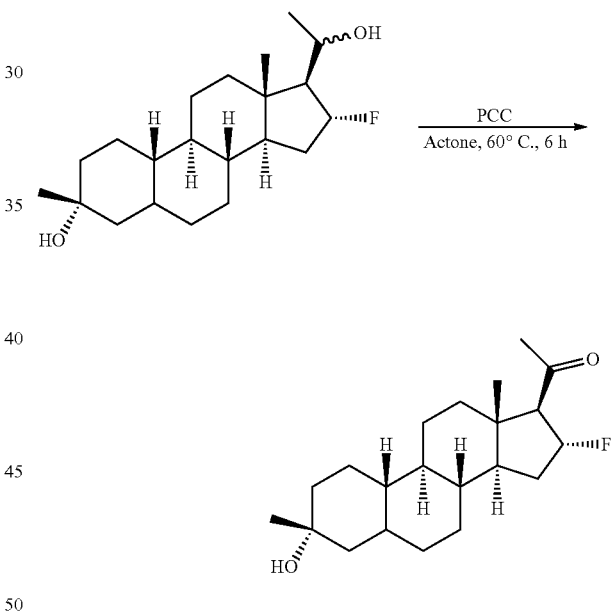

Pyridinium chlorochromate (102 mg, 0.47 mmol) was added to a solution of (3R,8R,9R,10S,13S,14S,16R,17S)-16-fluoro-17-(1-hydroxyethyl)-3,13-dimethylhexadeca-hydro-1H-cyclopenta[a]phenanthren-3-ol (80 mg) in acetone (2 mL), and the resulting reaction solution was reacted at 60° C. for 6 hours. The reaction solution was concentrated to dryness, and the resulting residue was purified by column chromatography (petroleum ether:ethyl acetate=5:2) to obtain 1-((3R,8R,9R,10S,13S,14S,16R,17S)-16-fluoro-3-hydroxy-3,13-dimethylhexadecahydro-1H-cyclopenta[a]phenanthren-17-yl)ethan-1-one (22 mg, yield: 25%).

$^1$H NMR (400 MHz, CDCl$_3$) δ 5.64-5.35 (m, 1H), 2.44-2.09 (m, 6H), 1.97-1.75 (m, 4H), 1.74-1.00 (m, 20H), 0.98-0.68 (m, 2H).

$^{19}$F NMR (376 MHz, CDCl$_3$) δ -168.20.

Example 174

1-((2aR,4R,6aS,6bR,8aS,8bS,9aS,10aS,10bR)-4-Hydroxy-4,8a-dimethylhexadecahydrocyclopropa[3,4]cyclopenta[1,2-a]phenanthren-8b(2H)-yl)ethan-1-one (174)

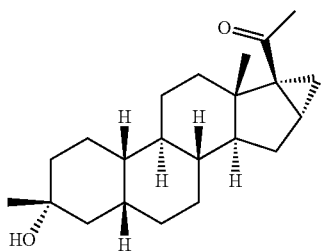

Step 1: Preparation of 1-((3R,5R,8R,9R,10S,13S,14S,17R)-17-bromo-3-hydroxy-3,13-dimethylhexadecahydro-1H-cyclopenta[a]phenanthren-17-yl)ethan-1-one

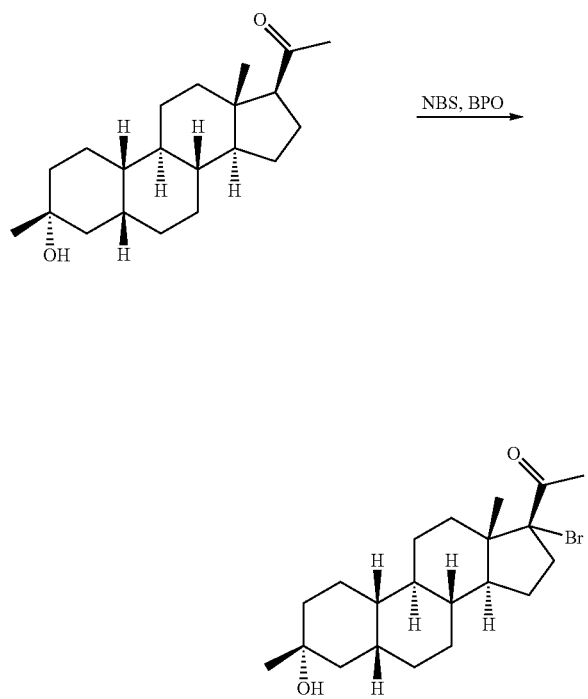

1-((3R,5R,8R,9R,10S,13S,14S,17S)-3-Hydroxy-3,13-dimethylhexadecahydro-1H-cyclopenta[a]phenanthren-17-yl)ethan-1-one (600 mg, 1.872 mmol) was dissolved in carbon tetrachloride (10 mL). N-Bromosuccinimide (666 mg, 3.744 mmol) and benzoyl peroxide (48 mg, 0.187 mmol) were added, and then the reaction solution was stirred at 80° C. for 2 hours. The reaction solution was cooled to room temperature. Water (30 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure, and the resulting residue was purified by column chromatography (petroleum ether/ethyl acetate=8/1) to obtain 1-((3R,5R,8R,9R,10S,13S,14S,17R)-17-bromo-3-hydroxy-3,13-dimethylhexadecahydro-1H-cyclopenta[a]phenanthren-17-yl)ethan-1-one (light yellow solid, 400 mg, yield: 54%).

$^1$H NMR (400 MHz, CDCl$_3$) δ 3.09-3.01 (m, 1H), 2.38 (s, 3H), 2.32-2.20 (m, 1H), 2.10-1.98 (m, 1H), 1.97-1.72 (m, 7H), 1.71-1.58 (m, 1H), 1.57-0.94 (m, 15H), 0.89-0.81 (m, 1H), 0.76 (s, 3H).

Step 2: Preparation of 1-((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)ethan-1-one

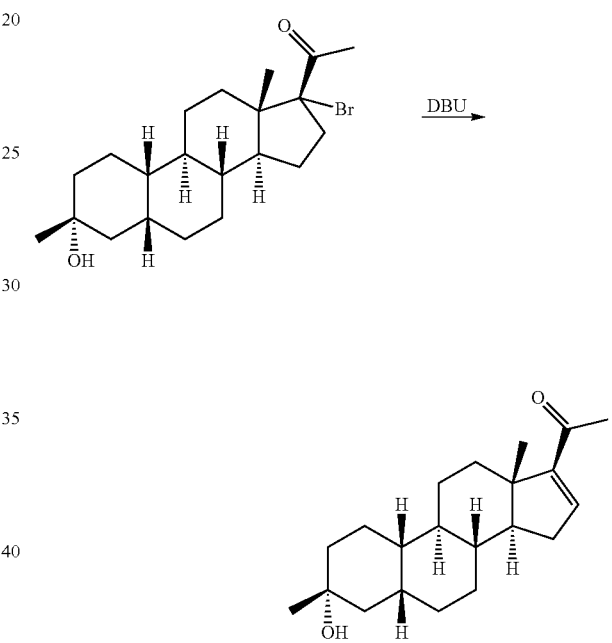

1-((3R,5R,8R,9R,10S,13S,14S,17R)-17-Bromo-3-hydroxy-3,13-dimethylhexadecahydro-1H-cyclopenta[a]phenanthren-17-yl)ethan-1-one (400 mg, 1 mmol) was dissolved in anhydrous toluene (10 mL). 1,8-Diazabicycloundec-7-ene (913 mg, 6 mmol) was added, and then the reaction solution was stirred at 110° C. for 16 hours. The reaction solution was cooled to room temperature. Water (20 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure, and the resulting residue was purified by column chromatography (petroleum ether/ethyl acetate=4/1) to obtain 1-((3R,5R,8R,9R,10S,13S,14S)-3-hydroxy-3,13-dimethyl-2,3,4,5,6,7,8,9,10,11,12,13,14,15-tetradecahydro-1H-cyclopenta[a]phenanthren-17-yl)ethan-1-one (colorless oil, 160 mg, yield: 51%).

$^1$H NMR (400 MHz, CDCl$_3$) δ 6.69 (dd, J=3.1, 1.7 Hz, 1H), 2.41-2.28 (m, 2H), 2.25 (s, 3H), 2.07-1.93 (m, 1H), 1.89-1.76 (m, 3H), 1.71-1.69 (m, 4H), 1.53-1.41 (m, 5H), 1.37-1.29 (m, 4H), 1.27 (s, 3H), 1.24-1.07 (m, 3H), 0.89 (s, 3H).

Step 3: Preparation of 1-((2aR,4R,6aS,6bR,8aS,8bS, 9aS,10aS,10bR)-4-hydroxy-4,8a-dimethylhexadeca-hydrocyclopropa[3,4]cyclopenta[1,2-a]phenanthren-8b(2H)-yl)ethan-1-one

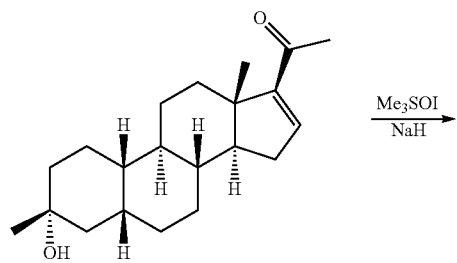

Sodium hydride (45 mg, 1.136 mmol, 60%) was suspended in dimethyl sulfoxide (2 mL). Trimethyl sulfoxide (100 mg, 0.451 mmol) was added, and then the reaction solution was stirred at room temperature for 1 hour. A mixed solution of 1-((3R,5R,8R,9R,10S,13S,14S)-3-hydroxy-3,13-dimethyl-2,3,4,5,6,7,8,9,10,11,12,13,14,15-tetradeca-hydro-1H-cyclopenta[a]phenanthren-17-yl)ethan-1-one (90 mg, 0.284 mmol) and tetrahydrofuran (2 mL) was added, and then the reaction solution was stirred at room temperature for 16 hours. Water (15 mL) was added, and then the reaction solution was extracted with ethyl acetate (10 mL×3). The organic phases were combined, washed with saturated saline (15 mL), dried over anhydrous sodium sulfate and filtrated. The filtrate was concentrated under reduced pressure, and the resulting residue was purified by column chromatography (petroleum ether/ethyl acetate=4/1) to obtain 1-((2aR,4R,6aS,6bR,8aS,8bS,9aS,10aS,10bR)-4-hydroxy-4,8a-dimethylhexadecahydrocyclopropa[3,4]cy-clopenta[1,2-a]phenanthren-8b(2H)-yl)ethan-1-one (colorless oil, 40 mg, yield: 43%).

¹H NMR (400 MHz, CDCl₃) δ 2.26-2.18 (m, 1H), 1.95 (s, 3H), 1.92-1.85 (m, 1H), 1.81 (m, 2H), 1.72-1.53 (m, 5H), 1.46-1.29 (m, 7H), 1.29-1.17 (m, 7H), 1.16-1.00 (m, 3H), 0.94 (s, 3H), 0.91-0.78 (m, 2H).

Example 175

1-(2-((2aR,4R,6aS,6bR,8aS,8bS,9aS,10aS,10bR)-4-Hydroxy-4,8a-dimethylhexadecahydrocyclopropa[3,4]cyclopenta[1,2-a]phenanthren-8b(2H)-yl)-2-oxo-ethyl)-1H-pyrazole-4-carbonitrile (175)

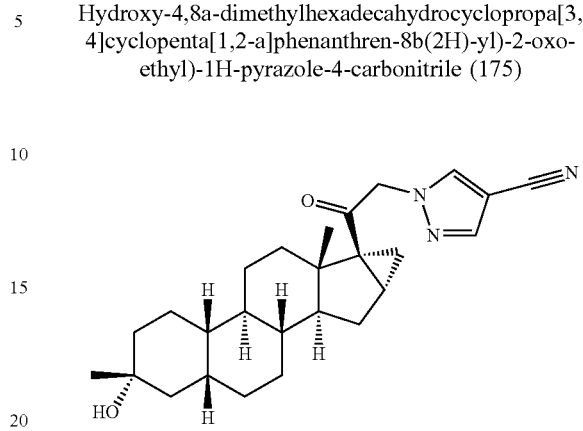

Step 1: Preparation of 2-bromo-1-((2aR,4R,6aS,6bR,8aS,8bS,9aS,10aS,10bR)-4-hydroxy-4,8a-dim-ethylhexadecahydrocyclopropa[3,4]cyclopenta[1,2-a]phenanthren-8b(2H)-yl)ethan-1-one

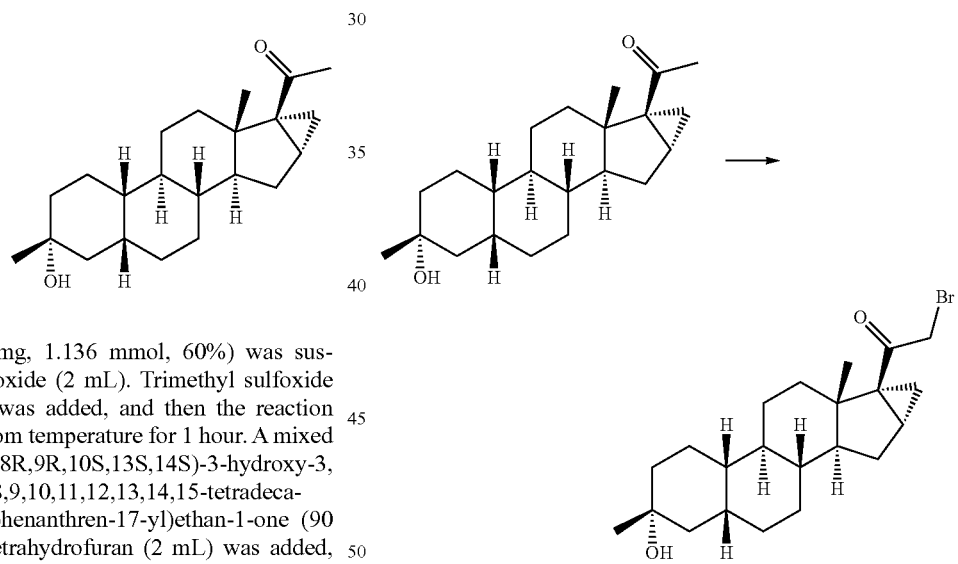

1-((2aR,4R,6aS,6bR,8aS,8bS,9aS,10aS,10bR)-4-Hydroxy-4,8a-dimethylhexadecahydrocyclopropa[3,4]cyclopenta[1,2-a]phenanthren-8b(2H)-yl)ethan-1-one (40 mg, 0.121 mmol) was dissolved in methanol (2 mL). A drop of hydrogen bromide and two drops of liquid bromine were added, and then the reaction solution was stirred at room temperature for 1.5 hours. Water (15 mL) was added, and then the reaction solution was extracted with ethyl acetate (10 mL×3). The organic phases were combined, washed with saturated saline (15 mL), dried over anhydrous sodium sulfate and filtrated. The filtrate was concentrated under reduced pressure to obtain 2-bromo-1-((2aR,4R,6aS,6bR, 8aS,8bS,9aS,10aS,10bR)-4-hydroxy-4,8a-dimethylhexa-decahydrocyclopropa[3,4]cyclopenta[1,2-a]phenanthren-8b(2H)-yl)ethan-1-one (50 mg, crude product).

Step 2: Preparation of 1-(2-((2aR,4R,6aS,6bR,8aS, 8bS,9aS,10aS,10bR)-4-hydroxy-4,8a-dimethylhexa- decahydrocyclopropa[3,4]cyclopenta[1,2-a] phenanthren-8b(2H)-yl)-2-oxoethyl)-1H-pyrazole-4- carbonitrile

Example 176

1-((2aR,4R,6aS,6bR,8aS,8bS,9aS,10aS,10bR)-4- Hydroxy-4,8a-dimethylhexadecahydrocyclopropa[3, 4]cyclopenta[1,2-a]phenanthren-8b(2H)-yl)-2-(4- (trifluoromethyl)-1H-pyrazol-1-yl)ethan-1-one (176)

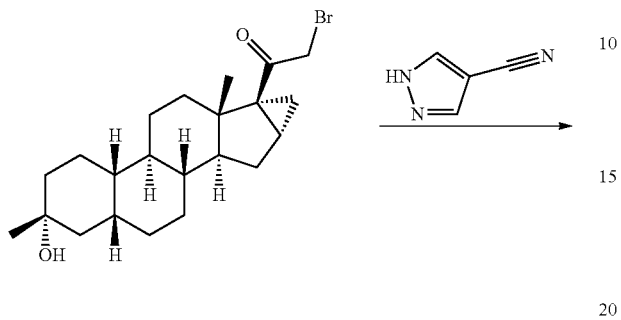

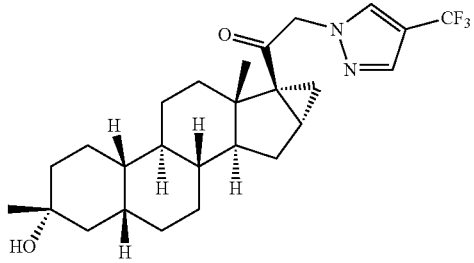

Step 1: Preparation of 1-((2aR,4R,6aS,6bR,8aS,8bS, 9aS,10aS,10bR)-4-hydroxy-4,8a-dimethylhexadeca- hydrocyclopropa[3,4]cyclopenta[1,2-a]phenanthren- 8b(2H)-yl)-2-(4-(trifluoromethyl)-1H-pyrazol-1-yl) ethan-1-one

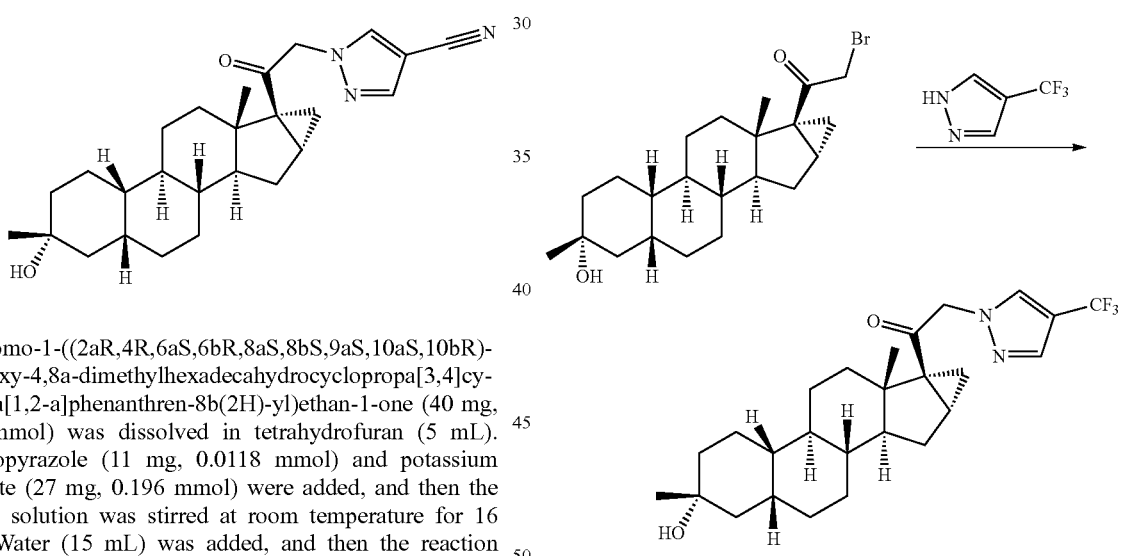

2-Bromo-1-((2aR,4R,6aS,6bR,8aS,8bS,9aS,10aS,10bR)- 4-hydroxy-4,8a-dimethylhexadecahydrocyclopropa[3,4]cy- clopenta[1,2-a]phenanthren-8b(2H)-yl)ethan-1-one (40 mg, 0.098 mmol) was dissolved in tetrahydrofuran (5 mL). 4-Cyanopyrazole (11 mg, 0.0118 mmol) and potassium carbonate (27 mg, 0.196 mmol) were added, and then the reaction solution was stirred at room temperature for 16 hours. Water (15 mL) was added, and then the reaction solution was extracted with ethyl acetate (10 mL×2). The organic phases were combined, washed with saturated saline (20 mL), dried over anhydrous sodium sulfate and filtrated. The filtrate was concentrated under reduced pressure, and the resulting crude product was purified by high perfor- mance liquid chromatography to obtain 1-(2-((2aR,4R,6aS, 6bR,8aS,8bS,9aS,10aS,10bR)-4-hydroxy-4,8a-dimethyl- hexadecahydrocyclopropa[3,4]cyclopenta[1,2-a] phenanthren-8b(2H)-yl)-2-oxoethyl)-1H-pyrazole-4- carbonitrile (18 mg, yield: 44%).

MS m/z (ESI): 422.2[M+H]+.

$^1$H NMR (400 MHz, CDCl$_3$) δ 7.76 (s, 1H), 7.74 (s, 1H), 5.11 (d, J=18.0 Hz, 1H), 4.91 (d, J=18.0 Hz, 1H), 3.61-3.49 (m, 1H), 2.96 (d, J=8.7 Hz, 1H), 2.17-2.05 (m, 2H), 1.90- 1.70 (m, 5H), 1.68-1.5 (m, 7H), 1.45-1.35 (m, 5H), 1.34- 1.01 (m, 7H), 0.65 (s, 3H).

2-Bromo-1-((2aR,4R,6aS,6bR,8aS,8bS,9aS,10aS,10bR)- 4-hydroxy-4,8a-dimethylhexadecahydrocyclopropa[3,4]cy- clopenta[1,2-a]phenanthren-8b(2H)-yl)ethan-1-one (40 mg, 0.098 mmol) was dissolved in tetrahydrofuran (5 mL). 3-Cyanopyrazole (11 mg, 0.0118 mmol) and potassium carbonate (27 mg, 0.196 mmol) were added, and then the reaction solution was stirred at room temperature for 16 hours. Water (15 mL) was added, and then the reaction solution was extracted with ethyl acetate (10 mL×2). The organic phases were combined, washed with saturated saline (20 mL), dried over anhydrous sodium sulfate and filtrated. The filtrate was concentrated under reduced pressure, and the resulting crude product was purified by high perfor- mance liquid chromatography to obtain 1-((2aR,4R,6aS, 6bR,8aS,8bS,9aS,10aS,10bR)-4-hydroxy-4,8a-dimethyl- hexadecahydrocyclopropa[3,4]cyclopenta[1,2-a]

phenanthren-8b(2H)-yl)-2-(4-(trifluoromethyl)-1H-pyrazol-1-yl)ethan-1-one (18 mg, yield: 44%).

MS m/z (ESI): 465.2[M+H]$^+$ $^1$H NMR (400 MHz, CDCl$_3$) δ 7.74 (s, 1H), 7.70 (s, 1H), 4.90 (d, J=17.3 Hz, 1H), 4.71 (d, J=17.3 Hz, 1H), 2.18 (m, 1H), 2.10-2.03 (m, 1H), 1.81 (m, 3H), 1.76-1.58 (m, 4H), 1.57-1.32 (m, 10H), 1.26 (s, 3H), 1.19-1.00 (m, 4H), 0.98 (s, 3H), 0.92 (m, 2H).

Example 177

1-(2-((2aR,4R,6aS,6bR,8aS,8bS,9aR,10aS,10bR)-4-Hydroxy-4,8a-dimethylhexadecahydro-8bH-naphtho[2',1':4,5]indeno[1,2-b]oxiren-8b-yl)-2-oxoethyl)-1H-pyrazole-4-carbo nitrile (177)

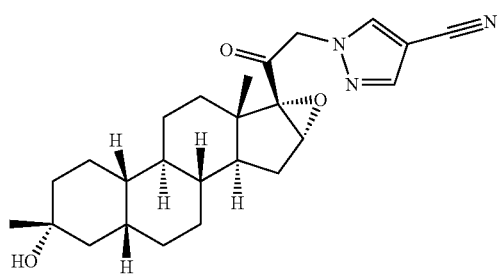

Step 1: Preparation of 1-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)ethan-1-one

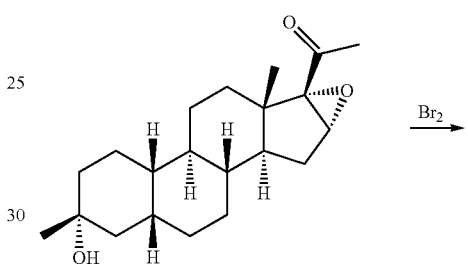

1-((3R,5R,8R,9R,10S,13,14S)-3-Hydroxy-3,13-dimethyl-2,3,4,5,6,7,8,9,10,11,12,13,14,15-tetradecahydro-1H-cyclopenta[a]phenanthren-17-yl)ethan-1-one (80 mg, 0.242 mmol) was dissolved in methanol (5 mL) and water (1 mL). Hydrogen peroxide (1.3 mL) and sodium hydroxide (30 mg, 0.75 mmol) were added, and then the reaction solution was stirred at 0° C. for 16 hours. Water (15 mL) was added, and then the reaction solution was extracted with ethyl acetate (15 mL×3). The organic phases were combined, washed with saturated saline (20 mL), dried over anhydrous sodium sulfate and filtrated. The filtrate was concentrated under reduced pressure, and the resulting residue was purified by column chromatography (petroleum ether/ethyl acetate=4/1) to obtain 1-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)ethan-1-one (60 mg, yield: 75%).

$^1$H NMR (400 MHz, CDCl$_3$) δ 3.66 (s, 1H), 2.03 (s, 3H), 1.94 (m, 1H), 1.87-1.75 (m, 3H), 1.74-1.61 (m, 3H), 1.47 (m, 2H), 1.43-1.37 (m, 4H), 1.35-1.30 (m, 3H), 1.25 (s, 6H), 1.17-1.07 (m, 3H), 1.03 (s, 3H).

Step 2: Preparation of 2-bromo-1-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)ethan-1-one

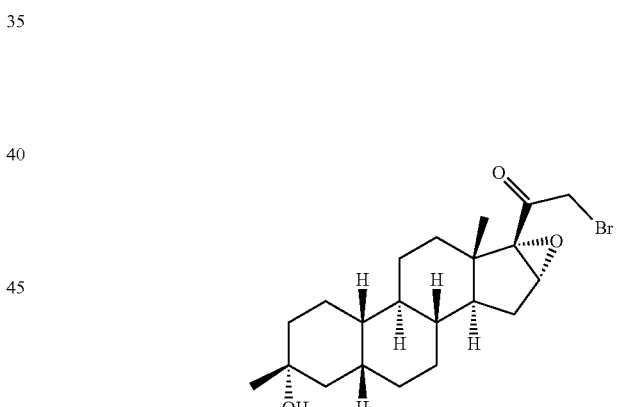

1-((2aR,4R,6aS,6bR,8aS,8bS,9aR,10aS,10bR)-4-Hydroxy-4,8a-dimethylhexadecahydro-8bH-naphtho[2',1':4,5]indeno[1,2-b]oxiren-8b-yl)ethan-1-one (50 mg, 0.15 mmol) was dissolved in methanol (3 mL). A drop of hydrogen bromide and two drops of liquid bromine were added, and then the reaction solution was stirred at room temperature for 8 hours. Water (10 mL) was added, and then the reaction solution was extracted with ethyl acetate (10 mL×3). The organic phases were combined, washed with saturated saline (15 mL), dried over anhydrous sodium sulfate and filtrated. The filtrate was concentrated under reduced pressure to obtain 2-bromo-1-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)ethan-1-one (60 mg, crude product).

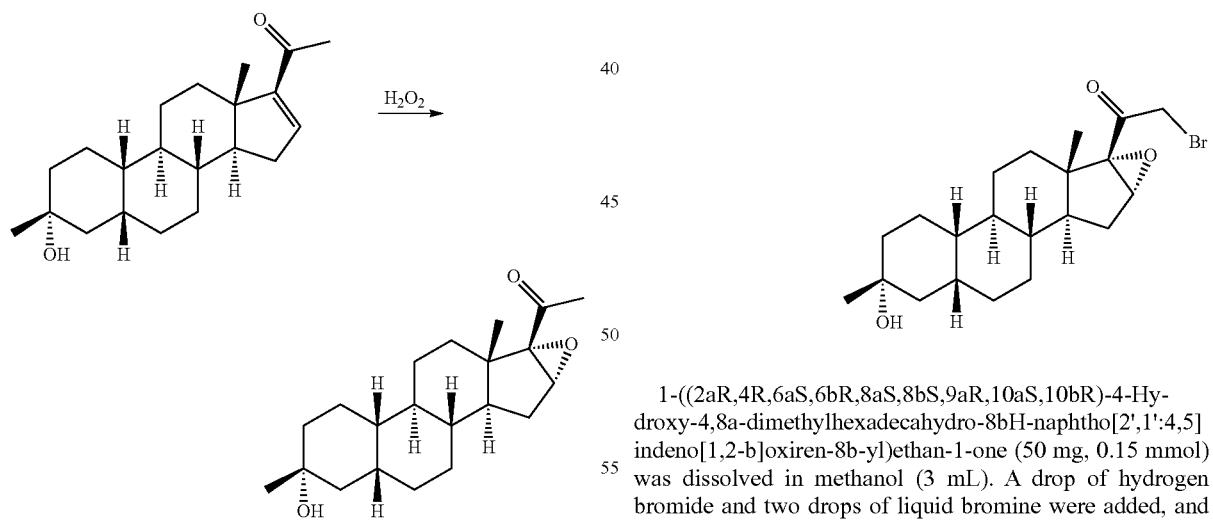

253

Step 3: Preparation of 1-(2-((2aR,4R,6aS,6bR,8aS, 8bS,9aR,10aS,10bR)-4-hydroxy-4,8a-dimethylhexa-decahydro-8bH-naphtho[2',1':4,5]indeno[1,2-b]ox-iren-8b-yl)-2-oxoethyl)-1H-pyrazole-4-carbonitrile

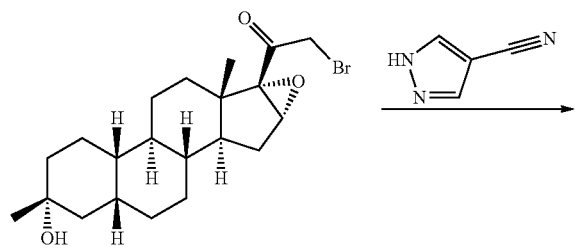

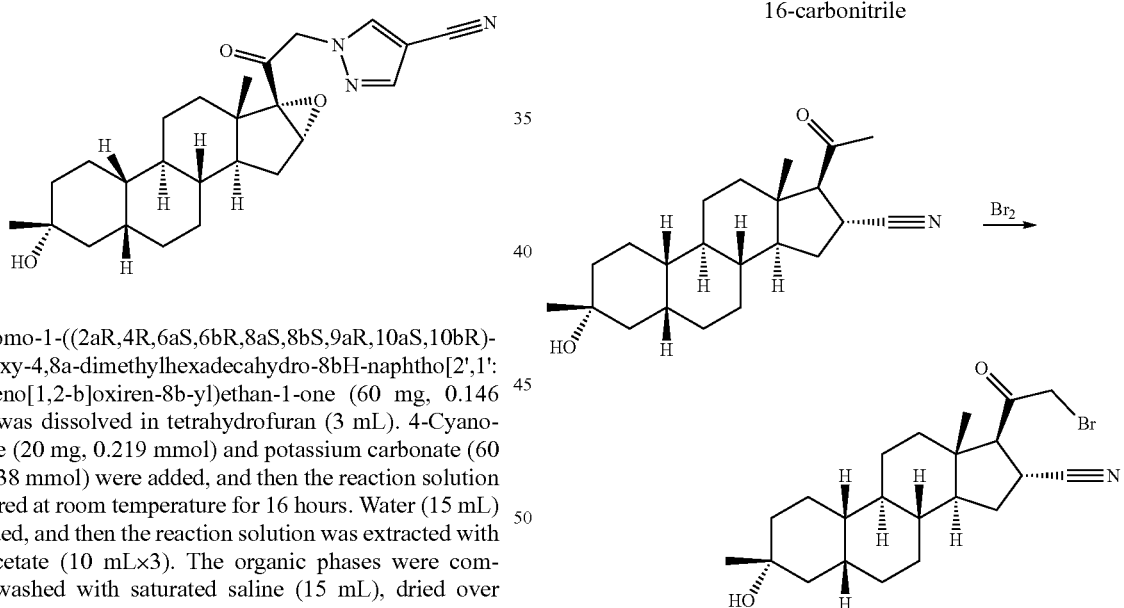

2-Bromo-1-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)ethan-1-one (60 mg, 0.146 mmol) was dissolved in tetrahydrofuran (3 mL). 4-Cyano-pyrazole (20 mg, 0.219 mmol) and potassium carbonate (60 mg, 0.438 mmol) were added, and then the reaction solution was stirred at room temperature for 16 hours. Water (15 mL) was added, and then the reaction solution was extracted with ethyl acetate (10 mL×3). The organic phases were combined, washed with saturated saline (15 mL), dried over anhydrous sodium sulfate and filtrated. The filtrate was concentrated under reduced pressure, and the resulting crude product was purified by high performance liquid chromatography to obtain 1-(2-((2aR,4R,6aS,6bR,8aS,8bS,9aR,10aS,10bR)-4-hydroxy-4,8a-dimethylhexadecahydro-8bH-naphtho[2',1':4,5]indeno[1,2-b]oxiren-8b-yl)-2-oxoethyl)-1H-pyrazole-4-carbonitrile (18 mg, yield: 29%).

MS m/z (ESI): 424.2[M+H]$^+$ $^1$H NMR (400 MHz, CDCl$_3$) δ 7.84 (s, 1H), 7.82 (s, 1H), 5.07 (d, J=18.3 Hz, 1H), 4.87 (d, J=18.3 Hz, 1H), 3.85 (s, 1H), 2.03 (dd, J=13.1, 5.6 Hz, 1H), 1.94-1.91 (m, 1H), 1.84-1.78 (m, 3H), 1.76-1.64 (m, 3H), 1.52-1.28 (m, 10H), 1.26 (s, 4H), 1.19-1.09 (m, 3H), 1.07 (s, 3H).

254

Example 178

(3R,5R,8R,9R,10S,13S,14S,16R,17S)-3-Hydroxy-3,13-dimethyl-17-(2-(4-(trifluoromethyl)-1H-pyrazol-1-yl)acetyl)hexadecahydro-1H-cyclopenta[a]phenanthrene-16-carbonitrile (178)

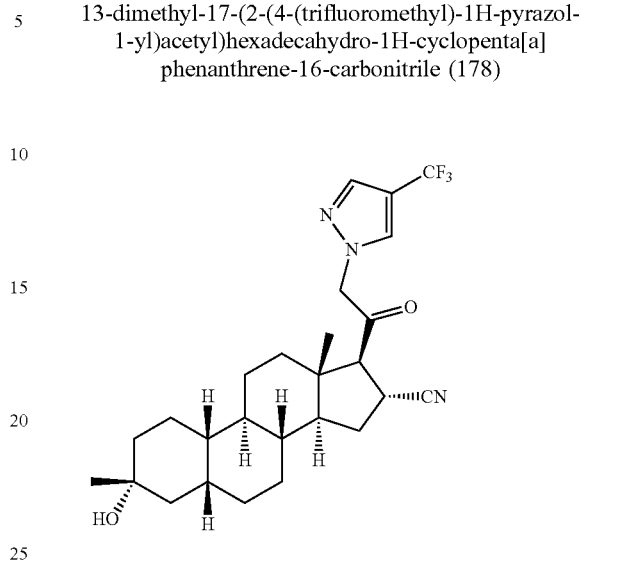

Step 1: Preparation of (3R,5R,8R,9R,10S,13S,14S, 16R,17S)-17-(2-bromoacetyl)-3-hydroxy-3,13-dimethylhexadecahydro-1H-cyclopenta[a]phenanthrene-16-carbonitrile (3R,5R,8R,9R,10S,13S,14S,16R,17S)-17-Acetyl-3-hydroxy-3,13-dimethylhexadecahydro-1H-cyclopenta[a]phenanthrene-16-carbonitrile (120 mg, 0.349 mmol) was dissolved in methanol (3 mL). Liquid bromine (83 mg, 0.524 mmol) and a drop of hydrogen bromide were added, and then the reaction solution was stirred at room temperature for 5 hours. Water (30 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness to obtain (3R,5R,8R,9R,10S,13S,14S,16R,17S)-17-

(2-bromoacetyl)-3-hydroxy-3,13-dimethylhexadecahydro-1H-cyclopenta[a]phenanthrene-16-carbonitrile (140 mg, crude product).

Step 2: Preparation of (3R,5R,8R,9R,10S,13S,14S,16R,17S)-3-hydroxy-3,13-dimethyl-17-(2-(4-(trifluoromethyl)-1H-pyrazol-1-yl)acetyl)hexadecahydro-1H-cyclopenta[a]phenanthrene-16-carbonitrile

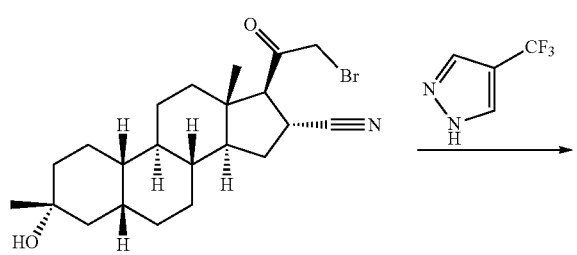

A mixture of (3R,5R,8R,9R,10S,13S,14S,16R,17S)-17-(2-bromoacetyl)-3-hydroxy-3,13-dimethylhexadecahydro-1H-cyclopenta[a]phenanthrene-16-carbonitrile (100 mg, 0.23 mmol), 4-(trifluoromethyl)-1H-pyrazole (63 mg, 0.46 mmol), potassium carbonate (95 mg, 0.69 mmol) and tetrahydrofuran (5 mL) was stirred at room temperature for 16 hours. Water (20 mL) was added, and then the reaction solution was extracted with ethyl acetate (20 mL×3). The organic phases were combined, washed with saturated saline (30 mL), dried over anhydrous sodium sulfate and filtrated. The filtrate was concentrated under reduced pressure to dryness, and the resulting crude product was purified by high performance liquid chromatography to obtain (3R,5R,8R,9R,10S,13S,14S,16R,17S)-3-hydroxy-3,13-dimethyl-17-(2-(4-(trifluoromethyl)-1H-pyrazol-1-yl)acetyl)hexadecahydro-1H-cyclopenta[a]phenanthrene-16-carbonitrile (25 mg, yield: 23%).

MS m/z (ESI): 478.2[M+H]$^+$.

$^1$H NMR (400 MHz, CDCl$_3$) δ 7.76 (s, 1H), 7.74 (s, 1H), 5.01 (dd, J=77.6, 18.0 Hz, 2H), 3.65-3.36 (m, 1H), 2.96 (d, J=8.7 Hz, 1H), 2.18-2.04 (m, 2H), 1.89-1.71 (m, 5H), 1.69-1.60 (m, 5H), 1.46-1.39 (m, 5H), 1.32-1.25 (m, 5H), 1.24-1.03 (m, 3H), 0.65 (s, 3H).

Example 179

2-(1-Hydroxy-4-aminoadamantane)-1-((3R,5R,8R,9R,10S,13S,14S,17S)-3-hydroxy-3,13-dimethyl-hexadecahydro-1H-cyclopenta[a]phenanthren-17-yl)ethan-1-one (179)

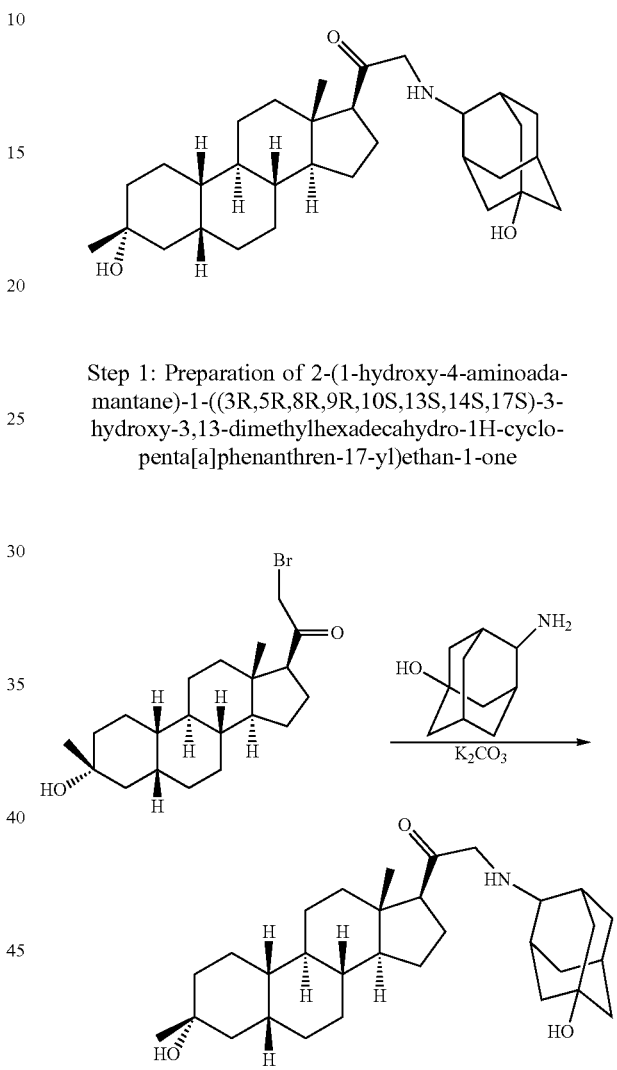

Step 1: Preparation of 2-(1-hydroxy-4-aminoadamantane)-1-((3R,5R,8R,9R,10S,13S,14S,17S)-3-hydroxy-3,13-dimethylhexadecahydro-1H-cyclopenta[a]phenanthren-17-yl)ethan-1-one

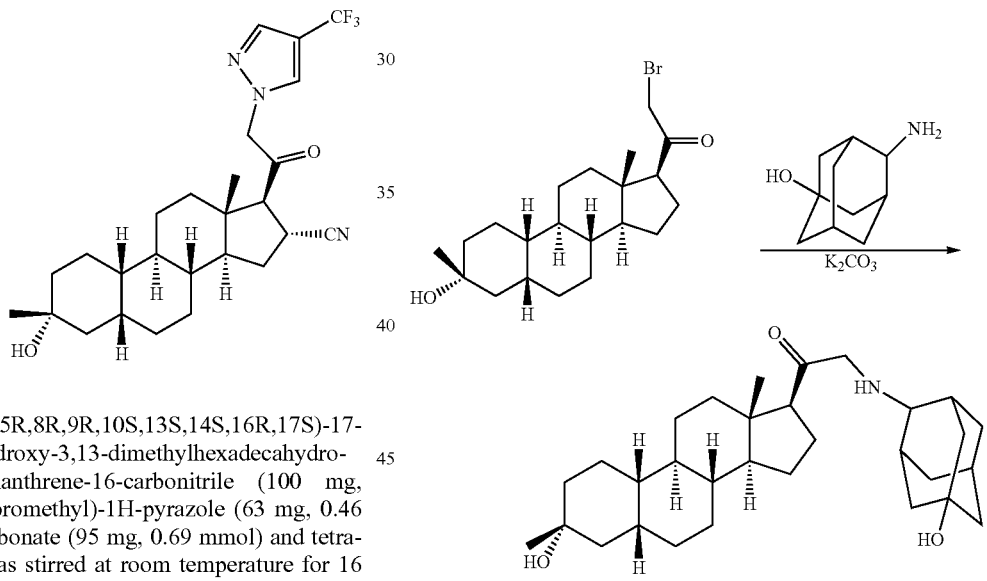

In accordance with Example 5, 2-bromo-1-((3R,5R,8R,10S,13S,14S,17S)-3-hydroxy-3,13-dimethylhexadecahydro-1H-cyclopenta[a]phenanthren-17-yl)ethan-1-one was used as the starting material, accordingly, 2-(1-hydroxy-4-aminoadamantane)-1-((3R,5R,8R,9R,10S,13S,14S,17S)-3-hydroxy-3,13-dimethylhexadecahydro-1H-cyclopenta[a]phenanthren-17-yl)ethan-1-one (7.5 mg, yield: 10.2%) was obtained.

$^1$H NMR (400 MHz, CDCl$_3$) δ 3.55 (d, J=2.8 Hz, 2H), 2.72 (s, 1H), 2.50 (t, J=8.9 Hz, 1H), 2.29-0.93 (m, 40H), 0.64 (s, 3H).

Biological Assay and Evaluation

The present invention is further described below in combination with the following test examples, which are not intended to limit the scope of the present invention.

I. GABA$_A$ Receptor Binding Ability Test of the Compound of the Present Invention 1.1 Experimental objective: The objective of this test example is to measure the ability of the compounds to allosterically inhibit the binding of the ion channel blocker (tert-butylbicyclophosphorothionate (TBPS)) to the GABA-A receptor.

Experimental Instruments:

| Instruments/Consumables | Supplier | Model |
|---|---|---|
| Vortex mixer | IKA | MS3 basic |
| Electric thermostat incubator | Shanghai Yiheng Instrument Co., Ltd. | DHP-9032 |
| TopCount | PerkinElmer | NTX |
| Universal Harvester | Perkin Elmer | UNIFILTER-96 |
| High-speed floor-standing centrifuge | Thermo | LYNX 4000 |
| Glass tissue homogenizer | Nanjing Luanyu Glass Instrument Co., Ltd. | 50 ml |
| Sprague-Dawley Rat | Pharmaron | |
| Protease inhibitor | roche | 11836170001 |
| 1.1 ml deep 96-well plate, round bottom | Axygen | P-DW-11-C |
| ULTIMA GOLD | Perkin Elmer | 77-16061 |
| UNIFILTER-96 GF/B filter plate | Perkin Elmer | 6005177 |
| Polyethylenimine (PEI), branched | Sigma | 408727 |

1.2 Experimental Procedures 1.2.1 Extraction of Cerebral Cortex Cell Membrane:

1. The cerebral cortex of male Sprague-Dawley rat was isolated.
2. A pre-chilled 0.32 M sucrose solution (one tablet of protease inhibitor was added per 100 ml) was added to the cerebral cortex (the volume of sucrose solution was 10 times the volume of the cerebral cortex). The mixture was crushed with a 50 mL glass tissue homogenizer in batches and mixed well.
3. The mixture was centrifuged at 1500 g, 4° C. for 10 minutes, and the supernatant was collected.
4. The mixture was centrifuged at 20000 g, 4° C. for 30 minutes, and the supernatant was discarded.
5. The precipitate was resuspended with the pre-chilled phosphate buffer saline (PBS) (one tablet of protease inhibitor was added per 100 ml). An average of 4 ml of PBS was added per rat, and the mixture was mixed well by a glass tissue homogenizer.
6. The mixture was centrifuged at 10000 g, 4° C. for 10 minutes, and the supernatant was discarded.
7. Steps 5 and 6 were repeated three times.
8. Finally, the precipitate was resuspended with 4 volumes of PBS. The resulting solution was dispensed, frozen in liquid nitrogen, and stored at −80° C.
9. The protein concentration was measured by the bicinchoninic acid (BCA) method.

1.2.2 $^{35}$S-TBPS Binding Assay 1. 230 μL of PBS was added to each well of a well plate with 1.1 ml volume.
2. 60 μL of the cerebral cortex cell membrane (5 μg/μL) solution was added to each well, and the mixture was mixed well.
3. The test compound (3 μL per well) was added, and the plate was incubated at 25° C. for 5 minutes. The DMSO concentration was 1%. The initial compound concentration was 1 μM, and a 3-fold dilution in gradient was carried out to obtain a total of 8 gradients and 2 replicates. 1% DMSO was used as a negative control, and 10 μM P026-2 was used as a positive control.
4. GABA was added at a final concentration of 5 μM, and incubated at 25° C. for 5 minutes. 1 mM GABA solution was formulated, and 1.5 μL of the solution was added to each well.
5. $^{35}$S-TBPS was added at a final concentration of 2 nM. The concentration of isotope mother solution was 9.7 μM. After dilution with PBS for 100 times, 6 μL of the diluted isotope solution was added to each well.
6. The plate was incubated at 4° C. for 20 hours.
7. The FilterMate GF/C plate was pre-treated with 0.5% PEI, and incubated at 4° C. for 1 hour.
8. The FilterMate GF/C plate was washed with Universal Harvester twice, 50 ml PBS each time.
9. The reaction solution was transferred to the GF/C plate, and each well was washed 4 times with 900 μL of PBS.
10. The washed GF/C plate was placed at 55° C. and dried for 10 minutes.
11. 40 μL of scintillation solution was added to each well, and the CPM value was read with TopCount.

1.2.3 Experimental Data Processing Method:

In the experiment, the CPM (counts per minute) value was read with TopCount. According to the readings of the High control (DMSO) and the Low control (10 sM of the positive compound) experimental groups, the 00 inhibition was calculated based on the following formula:

% Inhibition=100×(CPM$_{High\ control}$−CPM$_{Sample}$)/(CPM$_{High\ control}$−CPM$_{Low\ control}$)

The IC$_{50}$ of the compound was calculated according to the following 4-parameter nonlinear logic formula:

$Y$=Bottom+(Top−Bottom)/(1+10^((Log IC50−$X$)*Hill Slope)), wherein:

X represents the log of compound concentration,
Y represents the 0 Inhibition.

The effect of the compound of the present invention on the TBPS binding activity was determined by the above test, and the measured IC$_{50}$ values are shown in Table 1.

TABLE 1

IC$_{50}$ of the compounds of the present invention on inhibiting the TBPS binding activity

| Example No. | $^{35}$S-TBPS bindng test (nM) |
|---|---|
| 1 | 15.0 |
| 2 | 24.3 |
| 3 | 14.9 |
| 5 | 13.5 |
| 6 | 3.1 |
| 7 | 14.7 |
| 8 | 42 |
| 9 | 21.3 |
| 13 | 4.6 |
| 18 | 6.4 |
| 33 | 18.3 |
| 34 | 28.1 |
| 37A | 15.4 |
| 37B | 15.4 |
| 41 | 22.7 |
| 42 | 38.3 |
| 46 | 28.7 |
| 51 | 5.0 |
| 52 | 65 |
| 53 | 12.3 |
| 54A | 11.8 |
| 54B | 11.8 |
| 59 | 6.2 |
| 60 | 8.2 |
| 62 | 5.4 |
| 63 | 6.1 |
| 64 | 8.6 |

TABLE 1-continued

IC$_{50}$ of the compounds of the present invention on inhibiting the TBPS binding activity

| Example No. | $^{35}$S-TBPS bindng test (nM) |
|---|---|
| 69 | 7.6 |
| 71 | 7.5 |
| 91 | 9.6 |
| 92 | 10.8 |
| 93A | 3.0 |
| 93B | 3.0 |
| 94 | 10.2 |
| 95 | 34.1 |
| 97 | 30.2 |
| 98 | 37.8 |
| 101 | 11.4 |
| 102 | 65 |
| 103 | 10.2 |
| 121 | 18.3 |
| 122 | 46.0 |
| 125 | 30.7 |
| 126 | 4.9 |
| 127 | 6.1 |
| 128 | 15.8 |
| 130 | 4.2 |
| 131 | 8.0 |
| 132 | 24.6 |
| 133 | 17.8 |
| 134 | 6.7 |
| 135 | 4.3 |
| 136 | 26.5 |
| 137 | 16.2 |
| 138 | 25.2 |
| 139 | 27.0 |
| 140 | 33.1 |
| 141 | 23.9 |
| 142 | 16.2 |
| 143 | 28.5 |
| 144 | 18.6 |
| 145 | 16.9 |
| 146 | 21.4 |
| 147 | 24.4 |
| 149 | 25.6 |
| 150 | 8.8 |
| 151 | 26.2 |
| 166 | 38.4 |

Conclusion: The compounds of the examples of the present invention have a significant inhibitory effect on the TBPS binding activity.

II. Pharmacokinetic Assay in Balb/c Mice

1. Test Objective:

Balb/c mice were used as test animals. The pharmacokinetic behavior in mice (plasma and brain tissue) of the compounds of Examples 2, 3, 5, 6, 9, 13, 59, 60, 61, 63, 71-74, 81, 103, 130, 134, 135, 137, 138, 140, 141, 143, 145 and 146 orally administered at a dose of 5 mg/kg was studied.

2. Test Protocol 2.1 Test Compounds:

Compounds of Examples 59, 60, 61, 63, 71-74, 81, 103, 130, 134, 135, 137, 138, 140, 141, 143, 145 and 146 of the present invention, prepared by the applicant.

2.2 Test Animals:

Male Balb/c mice were purchased from Shanghai Jiesijie Laboratory Animal Co., LTD, with Certificate No.: SCXK (Shanghai) 2013-0006 N0.311620400001794.

2.3 Administration:

Each group had 24 male Balb/c mice. After an overnight fast, Balb/c mice were administered p.o. with the test compound at an administration dose of 5 mg/kg and an administration volume of 10 mL/kg.

2.4 Sample Collection:

0.2 ml of blood was taken from the heart before administration and at 0, 0.5, 1, 2, 4, 6, 8 and 24 hours after administration. The samples were stored in EDTA-K2 tubes, and centrifuged for 6 minutes at 4° C., 6000 rpm to separate the plasma. The plasma samples were stored at −80° C. The mice were sacrificed with $CO_2$, and the whole brain tissue was taken out, weighed, placed in a 2 mL centrifuge tube and stored at −80° C.

2.5 Sample Processing:

1) 160 µL of acetonitrile was added to 40 µL of the plasma sample for precipitation, and then the mixture was centrifuged for 5-20 minutes at 3500×g.

2) 90 µL of acetonitrile containing the internal standard (100 ng/mL) was added to 30 µL of the plasma and brain homogenate samples for precipitation, and then the mixture was centrifuged for 8 minutes at 13000 rpm.

3) 70 µL of the treated supernatant was taken and added to 70 µL of water, and mixed by vortex for 10 minutes. 20 µL of the mixture was taken to analyze the concentration of the test compound by LC/MS/MS. LC/MS/MS analysis instrument: AB Sciex API 4000 Qtrap.

2.6 Liquid Chromatography Analysis

Liquid chromatography condition: Shimadzu LC-20AD pump.

Chromatographic column: Agilent ZORBAX™ XDB-C18 (50×2.1 mm, 3.5 µm) (note: Aglient ZORBAX™ is a kind of column used in the reverse HPLC);

Mobile phase: Eluent A was 0.10% formic acid in water, and Eluent B was acetonitrile.

Flow rate: 0.4 mL/min

Elution time: 0-4.0 minutes, the eluent is as follows:

| Time/minute | Eluent A | Eluent B |
|---|---|---|
| 0.01 | 90% | 10% |
| 0.5 | 90% | 10% |
| 0.8 | 5% | 95% |
| 2.4 | 5% | 95% |
| 2.5 | 90% | 10% |
| 4.0 | Stop | |

3. Test Results and Analysis

The main parameters of pharmacokinetics were calculated by WinNonlin 6.1. The results of pharmacokinetic test in mice are shown in Table 2 below:

TABLE 2

Results of pharmacokinetic test in mice

Pharmacokinetic test (5 mg/kg)

| Example No. | Peak time $t_{max}$ (ng/mL) | Plasma concentration $C_{max}$ (ng/mL) | Area under curve $AUC_{0-t}$ (ng/mL × h) | Area under curve $AUC_{0-\infty}$ (ng/mL × h) | Half-life $t_{1/2}$(h) | Mean residence time MRT(h) |
|---|---|---|---|---|---|---|
| 2 plasma | 0.5 | 1099.3 | 1360.5 | 1374.2 | 0.54 | 1.21 |
| 2 brain tissue | 0.5 | 636.7 | 839.7 | 913.0 | 2.84 | 2.39 |

TABLE 2-continued

Results of pharmacokinetic test in mice

Pharmacokinetic test (5 mg/kg)

| Example No. | Peak time $t_{max}$ (ng/mL) | Plasma concentration $C_{max}$ (ng/mL) | Area under curve $AUC_{0-t}$ (ng/mL × h) | Area under curve $AUC_{0-\infty}$ (ng/mL × h) | Half-life $t_{1/2}$(h) | Mean residence time MRT(h) |
|---|---|---|---|---|---|---|
| 3 plasma | 0.5 | 673.3 | 569.7 | 573.8 | 0.50 | 1.01 |
| 3 brain tissue | 0.5 | 690.3 | 718.9 | 721.8 | 0.50 | 1.10 |
| 5 plasma | 0.5 | 461.0 | 1241.5 | 1254.2 | 5.12 | 4.80 |
| 5 brain tissue | 0.5 | 1406.3 | 2303.0 | 3067.4 | 4.72 | 5.53 |
| 6 plasma | 0.5 | 219.0 | 409.0 | 483.8 | 3.19 | 4.03 |
| 6 brain tissue | 0.5 | 464.0 | 917.2 | 964.3 | 1.90 | 2.40 |
| 9 plasma | 0.5 | 663.7 | 774.9 | 778.0 | 0.9 | 1.1 |
| 9 brain tissue | 0.5 | 605.3 | 677.0 | 679.9 | 0.5 | 0.9 |
| 13 plasma | 1.0 | 1210 | 5057.2 | 5065.8 | 2.5 | 3.6 |
| 13 brain tissue | 1.0 | 1060.0 | 4731.4 | 4744.7 | 2.5 | 3.9 |
| 59 plasma | 0.5 | 553.7 | 1305.0 | 1316.9 | 2.99 | 4.15 |
| 59 brain tissue | 1.0 | 678.0 | 2642.7 | 2680.6 | 3.18 | 4.81 |
| 60 plasma | 0.5 | 719.7 | 1704.9 | 1772.1 | 1.64 | 1.43 |
| 60 brain tissue | 1.0 | 998.0 | 2403.0 | 2498.4 | 2.37 | 2.35 |
| 61 plasma | 0.5 | 524.7 | 588.5 | 604.6 | 3.27 | 1.48 |
| 61 brain tissue | 0.5 | 710.7 | 657.1 | 676.0 | 3.95 | 1.41 |
| 63 plasma | 0.5 | 335.3 | 599 | 604.3 | 2.58 | 2.42 |
| 63 brain tissue | 0.5 | 486 | 602.6 | 617.9 | 0.72 | 1.21 |
| 71 plasma | 1.0 | 508.3 | 1577.3 | 1758.8 | 2.04 | 3.50 |
| 71 brain tissue | 1.0 | 382.7 | 1127.8 | 1275.4 | 2.00 | 3.66 |
| 72 plasma | 0.5 | 1146.3 | 2967.0 | 2972.0 | 2.79 | 3.71 |
| 72 brain tissue | 0.5 | 723.7 | 2051.0 | 2237.3 | 2.12 | 3.17 |
| 73 plasma | 0.5 | 1303.3 | 2430.5 | 2482.0 | 1.40 | 2.06 |
| 73 brain tissue | 0.5 | 635.7 | 1098.1 | 1117.6 | 1.31 | 1.91 |
| 74 plasma | 0.5 | 2136.7 | 7156.4 | 8601.3 | 3.06 | 4.59 |
| 74 brain tissue | 1.0 | 1523.3 | 5846.2 | 6511.2 | 2.28 | 3.82 |
| 81 plasma | 1.0 | 1146.7 | 4643.8 | 5922.3 | 2.64 | 4.96 |
| 81 brain tissue | 1.0 | 296.2 | 1439.7 | 2234.7 | 5.59 | 7.97 |
| 103 plasma | 1.0 | 386 | 1034.8 | 1060.9 | 1.19 | 2.12 |
| 103 brain tissue | 1.0 | 626.3 | 1676.2 | 1706.2 | 1.12 | 2.07 |
| 130 plasma | 0.5 | 307.3 | 1391.8 | 1560 | 2.21 | 3.83 |
| 130 brain tissue | 0.5 | 563.2 | 2308.8 | 2625.8 | 2.49 | 3.88 |
| 134 plasma | 0.5 | 1750.0 | 4627.3 | 5132.2 | 1.78 | 3.31 |
| 134 brain tissue | 1.0 | 892.0 | 3205.7 | 3501.3 | 1.59 | 3.22 |
| 135 plasma | 2.0 | 640.3 | 4103.8 | 4110.3 | 2.06 | 4.38 |
| 135 brain tissue | 2.0 | 724.0 | 3736.7 | 4450.7 | 2.82 | 4.71 |
| 137 plasma | 1.0 | 762.7 | 2785.0 | 3792.4 | 3.85 | 5.88 |
| 137 brain tissue | 1.0 | 613.0 | 2126.5 | 3162.6 | 6.02 | 7.58 |
| 138 plasma | 0.5 | 432.0 | 661.7 | 729.8 | 1.66 | 2.83 |
| 138 brain tissue | 0.5 | 314.0 | 772.7 | 934.8 | 1.47 | 2.38 |
| 140 plasma | 0.5 | 2483.3 | 5982.0 | 6106.9 | 1.19 | 2.22 |
| 140 brain tissue | 0.5 | 1738.0 | 4327.1 | 4539.1 | 1.21 | 2.10 |
| 141 plasma | 0.5 | 1633.3 | 3545.3 | 3634.6 | 1.35 | 2.55 |
| 141 brain tissue | 0.5 | 1048.0 | 2153.2 | 2251.2 | 1.68 | 2.68 |
| 143 plasma | 0.5 | 1650.0 | 6287.8 | 6492.4 | 1.70 | 3.08 |
| 143 brain tissue | 2.0 | 812.0 | 8818.0 | 9215.1 | 3.95 | 7.81 |

TABLE 2-continued

Results of pharmacokinetic test in mice

| Example No. | Pharmacokinetic test (5 mg/kg) | | | | | |
|---|---|---|---|---|---|---|
| | Peak time $t_{max}$ (ng/mL) | Plasma concentration $C_{max}$ (ng/mL) | Area under curve $AUC_{0-t}$ (ng/mL × h) | Area under curve $AUC_{0-\infty}$ (ng/mL × h) | Half-life $t_{1/2}$(h) | Mean residence time MRT(h) |
| 145 plasma | 1.0 | 2986.7 | 13411.8 | 13415.2 | 1.75 | 3.47 |
| 145 brain tissue | 1.0 | 1480.0 | 4821.6 | 5273.3 | 2.09 | 3.40 |
| 146 plasma | 1.0 | 2086.7 | 7785.5 | 8000.6 | 1.45 | 2.97 |
| 146 brain tissue | 1.0 | 1966.0 | 8677.8 | 12488.1 | 4.66 | 6.73 |

It can be seen from the results of the pharmacokinetic test of mice in the table that the compounds of the examples of the present invention showed good metabolic properties, and both the exposure amount AUC and the maximum blood drug concentration $C_{max}$ performed well.

III. In Vivo Pharmacodynamic Test in the Forced Swimming Model in Mice 3.1 Experimental Objective The antidepressant effect of the compound was evaluated by the forced swimming model in mice.

3.2 Main Instruments and Reagents of the Experiment 3.2.1 Instruments

Forced swimming device (JLBehv-FSC-4, Shanghai Jiliang Software Technology Co., Ltd.).

3.2.2 Reagents

Sodium carboxymethyl cellulose (CMC-Na, SLBV9664, Sigma)

Tween 80 (BCBV8843, Sigma)

3.2.3 Test Compounds

Compounds of Example 2, Example 3, Example 5, Example 6, Example 9, Example 13, Examples 59-63, Examples 71-74, Example 103, Example 135, Example 137, Example 145 and Example 146 of the present invention, prepared by the applicant.

3.3 Experimental Procedures 3.3.1 Adaptation:

Male ICR mice (25-35 g) were adapted in the test environment for 3 days before the forced swimming test.

According to the test design, the mice were randomly grouped on the day before the test according to body weight, with 12 mice in each group. Before the test, the compounds of each example were administered intragastrically according to the Tmax thereof in the brain in mice pharmacokinetic test as follows:

1) Model group (0.5% CMC-Na-1% Tween 80 solution, p.o., 10 mL/kg);
2) Compounds of Example 2, Example 3, Example 5, Example 6, Example 9, Examples 59-63, Examples 71-73, Example 103, Example 135, Example 137, Example 145 and Example 146 (10 mg/kg, p.o., 10 mL/kg); Example 13 and Example 74 (5 mg/kg, p.o., 5 mL/kg).

When being administered, the compounds of each example were suspended in 0.5% CMC-Na+1% Tween 80 solution to the desired concentration.

3.3.2 Forced Swimming Test:

0.5-1 hour after administration, ICR mice were placed in a forced swimming device (transparent glass drum (water depth 18 cm, water temperature 25-26° C.), one mouse per tank) and forced to swim for 6 minutes. The forced swimming device recorded the floating time of the ICR mice during the entire 6 minutes, and the data of the latter four minutes were used for data analysis. The mice were taken out immediately after the swimming test, wiped dry and put back in their original cages.

Note: The criterion for determining the immobility time is that the mouse stops struggling in water and floats, and there are only slight limb movements to keep the head floating on the water.

3.4 Data Analysis

Floating time percentage=100*floating time/240 s.

3.5 Test Data:

| Example No. | Dose (mpk) | Mean (immobility, s) | Mean (immobility, %) |
|---|---|---|---|
| Vehicle | / | 163.70 | 68.22 |
| Example 2 | 10 | 130.22 | 54.26 |
| Example 3 | 10 | 68.39 | 28.50 |
| Example 5 | 10 | 143.81 | 59.93 |
| Example 13 | 5 | 138.22 | 57.60 |
| Example 60 | 10 | 84.90 | 35.30 |
| Example 61 | 10 | 85.8 | 35.75 |
| Example 71 | 10 | 134.21 | 55.92 |
| Example 72 | 10 | 85.77 | 35.74 |
| Example 73 | 10 | 70.96 | 29.57 |
| Example 74 | 5 | 91.21 | 38.00 |
| Example 137 | 10 | 88.61 | 36.92 |
| Example 145 | 5 | 73.72 | 30.72 |
| Example 146 | 5 | 80.5 | 33.54 |

3.6 Test Results

It can be seen from the above results that the compounds of the examples of the present application can significantly shorten the cumulative immobility time of the forced-swimming mice, and have a significant antidepressant effect.

The immobility time during the latter four minutes of the compounds of Example 3, Example 60, Example 61, Example 72, Example 73, Example 137 and Example 146 was significantly different compared with that of the model group.

IV. In Vivo Pharmacodynamic Test in the PTZ-Induced Epilepsy Model in Mice 4.1 Test Objective The PTZ-induced epilepsy model in CD-1 mice was established, and the antiepileptic effect of the compounds of Example 3, Example 60, Example 61 and Example 74 was evaluated using this model.

4.2 Test Method 4.2.1 Test Animals 50 male CD-1 mice were purchased from Beijing Vital River Laboratory Animal Technology Co. Ltd. The test animals were adapted at the animal room in the third building of Shanghai ChemPartner Co., Ltd for 7 days before the test. The average body weight of the animals on the test day was 32.2±0.2 grams. Feeding environment: 5 animals/cage, room temperature 23±2° C., 12/12 hours of light and dark cycle, free acess to food and water.

The mice were randomly grouped for the test on the test day.

4.2.2 Test Compounds

Compounds of Example 3, Example 60, Example 61 and Example 74 (prepared by the applicant). The test compounds were stored in a refrigerator at 4° C.

TABLE 3

Test reagent information

| Name | Article number | Batch number | Property | Supplier | Total weight | Purity | Store condition |
|---|---|---|---|---|---|---|---|
| pentylene-tetrazol (PTZ) | P6500 | SLBD3876V | White crystal | Sigma | 25 g | 100% | −20° C. refrigeration |
| Sodium carboxy-methyl cellulose | 9004-32-4 | LAB0R36 | White solid | Beijing J&K Scientific Co., Ltd. | 100 G | 800 cps | Room temperature/ dry/in the dark |
| Tween-80 | 9005-65-6 | P1279207 | Transparent liquid | GENERAL-REAGENT® | 500 mL | 100% | Room temperature/ dry |
| Hydroxy-propyl β-cyclodextrin | 19184C | OP1901A | White powder | Seebio Biotech | 500 g | ≥98% | 2-8° C. refrigeration |
| 0.9% sodium chloride injection | H37022749 | H18010314 | Transparent liquid | Shandong Hualu Pharmaceutical Co., Ltd. | 500 mL | 100% | Room temperature/ dry |

4.2.1 Test Equipments 1 ml sterile disposable syringe with needle (purchased from Zhejiang Kangdelai Medical Devices Co., Ltd.)

Pipette: Eppendorf Research Plus (100-1000 L)

Vortex mixer: Kylin-Bell Vortex 5

Ultrasonic instrument: JL-360 ultrasonic cleaner

Balance: METTLER TOLEDO™ XS204 precision balance (note: METTLER TOLEDO™ is a kind of balance used in labs and industry)

Balance: METTLER TOLEDO™ XS6002S electronic balance (note: METTLER TOLEDO™ is a kind of balance used in labs and industry)

Plexiglass box: 25 cm length*15 cm width*15 cm height with one opaque side wall, custom made by Suzhou Fengshi Laboratory Animal Equipment Co., Ltd 3-channel timer: Oregon/Model NO.WB-388.

4.2.2 Test Animal Grouping

1) Vehicle/PTZ: 0.5% CMC-Na+1% Tween-80 (10 ml/kg, p.o.), administered 0.5 hr before the PTZ administration; PTZ (120 ml/kg, s.c.), administered before the test;

2) 3 mg/kg of the compounds of Examples/PTZ: the compounds of Example 3, Example 60, Example 61 and Example 74 (3 mg/kg, 10 ml/kg, p.o.), administered 0.5 hr before the PTZ administration; PTZ (120 ml/kg, s.c.), administered before the test.

4.3 Experimental Procedures 4.3.1 Solvent Formulation 1) 0.5% CMC-Na+1% Tween-80 (Administration Volume: 10 mL/Kg):

1 g of sodium carboxymethyl cellulose was precisely weighed and added to a 250 mL solvent bottle, then 150 mL of double-distilled water was added. The mixture was stirred at room temperature for 4 hours with a magnetic stirrer to obtain a uniform and clear solution. 2 mL of Tween-80 was slowly added, and the mixture was stirred at room temperature for 3 hours to obtain a uniform and clear solution. The solution was slowly transferred to a 200 mL volumetric flask, and double distilled water was added to the constant volume of 200 mL. The solution was transferred to a 250 mL solvent bottle, and stirred for 1 hour with a magnetic stirrer to obtain a uniform and clear solution.

2) 30% Hydroxypropyl-β-cyclodextrin:

30.6122 g of hydroxypropyl-β-cyclodextrin (purity: 98%) was precisely weighed and added to a 100 mL solvent bottle, then 60 mL of double-distilled water was added.

The mixture was mixed by vortex for 3 minutes, and treated by ultrasound at room temperature for 15 minutes to obtain a uniform and clear solution. Double distilled water was added to the constant volume of 100 mL, mixed by vortex for 1 minute, and treated by ultrasound at room temperature for 5 minutes to obtain a uniform and clear solution.

4.3.2 Test Compound Formulation 1) 12 mg/mL PTZ (Dose: 120 mg/kg; Administration Volume: 10 mL/kg):

248 mg of PTZ was precisely weighed and added to a 40 mL brown flask, then 20.667 mL of physiological saline was added. The mixture was mixed by vortex for 2 minutes, and treated by ultrasound at room temperature for 2 minutes to obtain a uniform and clear solution (concentration: 12 mg/mL).

2) 0.3 mg/mL of the Compounds of Example 5 or Example 23 (Dose: 3 mg/kg; Administration Volume: 10 mL/kg):

A certain amount of 0.5% CMC-Na+1% Tween-80 was taken and added to a flask containing a certain amount of the compounds of Example 5 or Example 23. The mixture was mixed by vortex for 3 minutes, and treated by ultrasound at room temperature for 15 minutes to obtain a uniform suspension (concentration: 0.3 mg/mL).

4.3.3 Test Method

1) The test animals were transferred to the operating room to adapt to the environment 1 hour before the test;

2) The animals were randomly grouped, marked and weighed;

3) The compounds of Example 3, Example 60, Example 61 and Example 74 were administered respectively 1 hour before the PTZ administration, or 0.5% CMC-Na+1% Tween-80, the compounds of Example 3, Example 60, Example 61 and Example 74 were administered respectively 0.5 hour before the PTZ administration;

4) PTZ (120 mg/kg) was administered subcutaneously before the test observation, and this time point was recorded as the observation start point;
5) After the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died, 6) if the animal did not have seizures during the 30-minute observation period, the incubation period was recorded as 1800 sec and the number of seizures was recorded as 0.

Clonic seizure: generalized clonic seizure in animals lasts for more than 3 seconds, and is accompanied by a fall;
Tonic seizure: the limbs straightens 900 to the body;
6) The possible side effects induced by the drug after the administration were observed and recorded, which can be divided into four levels:
None: normal
Mild sedation
Moderate sedation
Severe sedation
7) The test was carried out from 12:00 am to 16:30 pm.

4.4 Adaptation to the Environment

The test animals were transferred to the operating room to adapt to the environment 1 hour before the test.

4.5 Grouping and Administration

The mice were randomly grouped, marked and weighed; 10 mice per group. The test compound was administered orally at an administration volume of 10 mL/kg 30-60 minutes before the PTZ administration.

4.6 PTZ Modeling and Testing

PTZ (120 mg/kg) was administered subcutaneously before the test observation, and this time point was recorded as the observation start point; after the administration of PTZ, the animal was immediately placed in the observation box and observed for 30 minutes, and the followings were recorded: a) the incubation period of the first clonic seizure, b) the incubation period of the first generalized tonic seizure, c) the number of clonic seizures, d) the number of generalized tonic seizures, e) the time when the animal died. If the animal did not have seizures during the 30-minute observation period, the incubation period was recorded as 1800 sec and the number of seizures was recorded as 0.

4.7 Data Analysis

All measurement data were expressed as Mean±SEM, and analysed with Prism 6.0 statistical software.

4.7 Test Data:

| Example No. | Dose (mpk) | Incubation period of the clonic seizure (sec) Mean ± SEM | Number of clonic seizures Mean | Incubation period of the generalized tonic seizure (sec) Mean | Number of generalized tonic seizures Mean | Time when the animal died (sec) Mean | Mortality rate (%) |
|---|---|---|---|---|---|---|---|
| Vehicle | / | 331.4 ± 61.2 | 2.1 ± 0.2 | 821.6 ± 107.7 | 1.0 ± 0.0 | 839.8 ± 108.0 | 100% |
| 3 | 3 | 902.9 ± 200.8 | 1.3 ± 0.3 | 1736.0 ± 63.2 | 0.1 ± 0.1 | 1739.8 ± 60.2 | 10% |
| 60 | 3 | 1308.1 ± 170.1 | 0.5 ± 0.2 | 1800.0 ± 0.0 | 0.0 ± 0.0 | 1800.0 ± 0.0 | 0% |
| 61 | 3 | 841.6 ± 179.8 | 1.9 ± 0.4 | 1497.4 ± 124.3 | 0.5 ± 0.2 | 1573.1 ± 117.9 | 40% |
| 74 | 3 | 635.4 ± 149.9 | 1.8 ± 0.3 | 1506.8 ± 149.8 | 0.3 ± 0.2 | 1618.1 ± 121.3 | 30% |

4.9 Test Results

The compounds of the examples significantly prolonged the incubation period of clonic seizure and generalized tonic seizure and reduced the number of clonic seizures and generalized tonic seizures compared with the control group. The compounds of the examples can protect 60%-100% of animals from death, significantly prolong the incubation period of death, and have a good antiepileptic effect.

What is claimed is:

1. A compound of

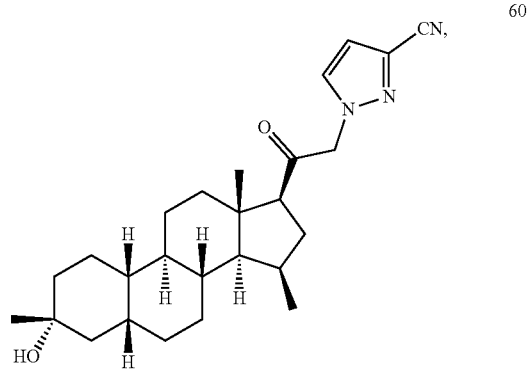

or a stereoisomer thereof, or a pharmaceutically acceptable salt thereof.

2. A pharmaceutical composition, comprising a therapeutically effective amount of the compound according to claim 1, the stereoisomer thereof, or the pharmaceutically acceptable salt thereof, and one or more pharmaceutically acceptable carriers, diluents or excipients.

3. A method of treating depression or epilepsy in a subject in need thereof, comprising administering the pharmaceutical composition according to claim 2 to the subject.

* * * * *